US012559566B2

(12) United States Patent
Deckert et al.

(10) Patent No.: US 12,559,566 B2

(45) **Date of Patent: *Feb. 24, 2026**

(54) CD37-BINDING MOLECULES IMMUNOCONJUGATES THEREOF

(71) Applicant: Debiopharm International SA, Lausanne (CH)

(72) Inventors: Jutta Deckert, Lexington, MA (US); Peter Park, Somerville, MA (US); Daniel Tavares, Natick, MA (US); Lingyun Rui, Weston, MA (US)

(73) Assignee: DEBIOPHARM INTERNATIONAL, S.A., Lausanne (CH)

( * ) Notice: Subject to any disclaimer, the term of this patent is extended or adjusted under 35 U.S.C. 154(b) by 691 days.

This patent is subject to a terminal disclaimer.

(21) Appl. No.: 17/938,886

(22) Filed: Oct. 7, 2022

(65) Prior Publication Data

US 2023/0287137 A1 Sep. 14, 2023

Related U.S. Application Data

(60) Continuation of application No. 16/221,747, filed on Dec. 17, 2018, now Pat. No. 11,466,095, which is a division of application No. 15/130,667, filed on Apr. 15, 2016, now Pat. No. 10,202,460, which is a division of application No. 13/796,768, filed on Mar. 12, 2013, now Pat. No. 9,346,887, which is a division of application No. 13/045,693, filed on Mar. 11, 2011, now Pat. No. 8,765,917.

(60) Provisional application No. 61/412,644, filed on Nov. 11, 2010, provisional application No. 61/327,314, filed on Apr. 23, 2010, provisional application No. 61/313,628, filed on Mar. 12, 2010.

(51) Int. Cl.

| | |
|---|---|
| ***C07K 16/28*** | (2006.01) |
| ***A61K 47/60*** | (2017.01) |
| ***A61K 47/68*** | (2017.01) |
| ***C07K 16/30*** | (2006.01) |
| ***G01N 33/566*** | (2006.01) |
| *A61K 39/00* | (2006.01) |

(52) U.S. Cl.

CPC .......... *C07K 16/2896* (2013.01); *A61K 47/60* (2017.08); *A61K 47/68033* (2023.08); *A61K 47/6817* (2017.08); *A61K 47/6849* (2017.08); *A61K 47/6867* (2017.08); *C07K 16/30* (2013.01); *G01N 33/566* (2013.01); *A61K 2039/505* (2013.01); *C07K 2317/24* (2013.01); *C07K 2317/33* (2013.01); *C07K 2317/56* (2013.01); *C07K 2317/565* (2013.01); *C07K 2317/60* (2013.01); *C07K 2317/73* (2013.01); *C07K 2317/732* (2013.01); *C07K 2317/734* (2013.01); *C07K 2317/92* (2013.01); *G01N 2333/70596* (2013.01)

(58) Field of Classification Search
None
See application file for complete search history.

(56) References Cited

U.S. PATENT DOCUMENTS

| | | | |
|---|---|---|---|
| 5,122,368 A | 6/1992 | Greenfield et al. | |
| 5,595,756 A | 1/1997 | Bally | |
| 7,303,749 B1 | 12/2007 | Chari | |
| 7,585,491 B2 | 9/2009 | Govindan | |
| 7,601,354 B2 | 10/2009 | Chari et al. | |
| 7,989,598 B2 | 8/2011 | Steeves et al. | |
| 8,088,387 B2 | 1/2012 | Steeves et al. | |
| 8,765,917 B2 | 7/2014 | Deckert et al. | |
| 9,346,887 B2 | 5/2016 | Deckert et al. | |
| 9,447,189 B2 | 9/2016 | Deckert et al. | |
| 10,202,460 B2 | 2/2019 | Deckert et al. | |
| 10,556,958 B2 | 2/2020 | Deckert et al. | |
| 11,395,796 B2 | 7/2022 | Romanelli et al. | |
| 11,466,095 B2 * | 10/2022 | Deckert | A61P 35/02 |
| 2003/0114398 A1 | 6/2003 | Chatterjee et al. | |
| 2004/0166115 A1 | 8/2004 | Griffiths et al. | |
| 2005/0136049 A1 | 6/2005 | Ledbetter et al. | |
| 2005/0287538 A1 | 12/2005 | Cheung et al. | |
| 2006/0039913 A1 | 2/2006 | Das et al. | |
| 2006/0233822 A1 | 10/2006 | Xia et al. | |
| 2006/0263349 A1 | 11/2006 | Mccutcheon et al. | |
| 2007/0009519 A1 | 1/2007 | Hariharan et al. | |
| 2007/0059306 A1 | 3/2007 | Grosmaire et al. | |
| 2007/0237779 A1 | 10/2007 | Ledbetter et al. | |
| 2007/0270585 A1 | 11/2007 | Chari et al. | |

(Continued)

FOREIGN PATENT DOCUMENTS

| | | |
|---|---|---|
| CN | 1446104 A | 10/2003 |
| CN | 1494433 A | 5/2004 |

(Continued)

OTHER PUBLICATIONS

Altschuler, E.P., et al., “Method for Obtaining Recombinant Antibodies and for Improving Affinities Thereof,” Uspehi biologicheskoi himii 50: 203-258, Pleiades Publishing Ltd., Russia (Dec. 2010).

Altshuler, E.P., et al., “Generation of Recombinant Antibodies and Means for Increasing Their Affinity,” Biochemistry 75(13):1584-1605, Pleiades Publishing, Ltd., United States (Dec. 2010).

Angeletti, R.H., “Design of Useful Peptide Antigens,” Journal of Biomolecular Techniques 10(1):2-10, Association of Biomolecular Resource Facilities, United States (1999).

Angelisova, P., et al., “Association of Four Antigens of the Tetraspans Family (CD37, CD53, TAPA-1, and R2/C33) with MHC Class II Glycoproteins,” Immunogenetics 39(4):249-256, Springer-Verlag, Germany (1994).

(Continued)

*Primary Examiner* — Brad Duffy

(74) *Attorney, Agent, or Firm* — Sterne, Kessler, Goldstein & Fox P.L.L.C.

(57) ABSTRACT

Novel anti-cancer agents, including, but not limited to, antibodies and immunoconjugates, that bind to CD37 are provided. Methods of using the agents, antibodies, or immunoconjugates, such as methods of inhibiting tumor growth are further provided.

20 Claims, 32 Drawing Sheets

Specification includes a Sequence Listing.

(56) References Cited

U.S. PATENT DOCUMENTS

2008/0075726 A1 3/2008 Smith et al.
2008/0226626 A1 9/2008 Hariharan et al.
2008/0227198 A1 9/2008 Hariharan et al.
2008/0279850 A1 11/2008 Brady et al.
2008/0311676 A1* 12/2008 Brate ............... G01N 33/54393 436/501
2009/0041783 A1 2/2009 Takayama et al.
2009/0136516 A1 5/2009 Tedder et al.
2009/0148447 A1 6/2009 Ledbetter et al.
2009/0175867 A1 7/2009 Thompson et al.
2009/0269336 A1 10/2009 Hong et al.
2009/0274692 A1 11/2009 Tan et al.
2009/0274713 A1 11/2009 Chari et al.
2010/0034820 A1 2/2010 Ledbetter et al.
2010/0135900 A1 6/2010 Cerveny et al.
2010/0189722 A1 7/2010 Heider et al.
2011/0256056 A1 10/2011 Alper et al.
2011/0256153 A1 10/2011 Deckert et al.
2012/0020963 A1 1/2012 Banchereau et al.
2012/0020983 A9 1/2012 Braun et al.
2012/0276119 A1 11/2012 Deckert et al.
2013/0058947 A1 3/2013 Stull et al.
2013/0295104 A1 11/2013 Deckert et al.
2014/0120083 A1 5/2014 Stern et al.
2014/0170063 A1 6/2014 Govindan et al.
2014/0348745 A1 11/2014 Larsen et al.
2015/0093397 A1 4/2015 Carrigan
2015/0343077 A1 12/2015 Deckert et al.
2016/0326258 A1 11/2016 Deckert et al.
2016/0340438 A1 11/2016 Deckert et al.
2017/0000900 A1 1/2017 Romanelli et al.
2018/0244795 A1 8/2018 Deckert et al.
2019/0183788 A1 6/2019 Romanelli et al.
2020/0054763 A1 2/2020 Bertoni et al.
2020/0270361 A1 8/2020 Deckert et al.
2020/0330604 A1 10/2020 Li et al.
2021/0196835 A1 7/2021 Rouits et al.

FOREIGN PATENT DOCUMENTS

CN 1568198 A 1/2005
EP 0328147 B1 5/1994
JP 2006513203 A 4/2006
JP 2016536298 A 11/2016
WO WO-0124763 A2 4/2001
WO WO-0204021 A1 1/2002
WO WO-02060484 A1 8/2002
WO WO-02060485 A2 8/2002
WO WO-02102972 A2 12/2002
WO WO-03048306 A2 6/2003
WO WO-03083069 A2 10/2003
WO WO-2004058298 A1 7/2004
WO WO-2005017148 A1 2/2005
WO WO-2005037989 A2 4/2005
WO WO-2005037992 A2 4/2005
WO WO-2006074397 A2 7/2006
WO WO-2006133450 A2 12/2006
WO WO-2007014278 A2 2/2007
WO WO-2007077173 A1 7/2007
WO WO-2007140371 A2 12/2007
WO WO-2007146968 A2 12/2007
WO WO-2008052030 A2 5/2008
WO WO-2008119567 A2 10/2008
WO WO-2009019312 A2 2/2009
WO WO-2009065576 A1 5/2009
WO WO-2009085576 A2 7/2009
WO WO-2009126858 A2 10/2009
WO WO-2009126944 A1 10/2009
WO WO-2009134977 A1 11/2009
WO WO-2010008726 A1 1/2010
WO WO-2010009124 A2 1/2010
WO WO-2010126551 A1 11/2010
WO WO-2011090754 A1 7/2011
WO WO-2011090762 A1 7/2011
WO WO-2011100398 A1 8/2011
WO WO-2011100403 A1 8/2011
WO WO-2011112978 A1 9/2011
WO WO-2012135740 A2 10/2012
WO WO-2013149171 A2 10/2013
WO WO-2013171289 A1 11/2013
WO WO-2014143807 A2 9/2014
WO WO-2014195460 A1 12/2014
WO WO-2014197411 A1 12/2014
WO WO-2015038777 A1 3/2015
WO WO-2015067586 A2 5/2015
WO WO-2015116729 A2 8/2015
WO WO-2015175533 A2 11/2015
WO WO-2016200676 A1 12/2016
WO WO-2017040247 A1 3/2017
WO WO-2018083633 A1 5/2018
WO WO-2019229677 A1 12/2019

OTHER PUBLICATIONS

Awan, F., et al., "Phase 1 Study of TRU-016, an Anti-CD37 SMIP Protein in Naive and Relapsed and/or Refractory CLL Patients," ASH Annual Meeting 642: Abstract #1792 poster, p. 1, United States (Nov. 2011). Accessed at: URL:[https://ash.confex.com/ash/2011/webprogram/Paper39421.html] on Jul. 20, 2015.

Awan, F.T., et al., "Phase 1 Study of TRU-016, an Anti-CD37 SMIP™ Protein in Naive and Relapsed and/or Refractory CLL Patients," Blood (ASH Annual Meeting Abstracts) 118(21): Abstract 1792, pp. 1-2, United States (Nov. 2011), Accessed at URL:[http://www.bloodjournal.org/content/118/21/1792.full.pdf] on Dec. 2, 2015.

Barrena, S., et al., "Aberrant Expression of Tetraspanin Molecules in B-cell Chronic Lymphoproliferative Disorders and its Correlation with Normal B-cell Maturation," Leukemia 19(8):1376-1383, Nature Publishing Group, United Kingdom (2005).

Beckwith, K.A., et al.,"The CD37-Targeted Antibody-Drug Conjugate IMGN529 is Highly Active against Human CLL and in a Novel CD37 Transgenic Murine Leukemia Model," Leukemia 28(7):1501-1510, Nature Publishing Group, United Kingdom (Jul. 2014).

Bernstein, I.D., et al., "High Dose Radiolabeled Antibody Therapy of Lymphoma," Cancer Research 50(3 Suppl):1017s-1021s, American Association for Cancer Research, United States (1990).

Blanc, V., et al., "SAR3419: An Anti-CD19-Maytansinoid Immunoconjugate for the Treatment of B-Cell Malignancies," Clinical Cancer Research 17(20):6448-6458, American Association for Cancer Research, United States (2011).

Braslawsky, G.R., et al., "Antitumor Activity of Adriamycin (hydrazone-linked) Immunoconjugates Compared with Free Adriamycin and Specificity of Tumor Cell Killing," Cancer Research 50(20):6608-6614, American Association for Cancer Research, United States (1990).

Business Wire, "ImmunoGen, Inc. Announces Presentations at the 102nd Annual Meeting of the American Associated for Cancer Research," May 30, 2011, accessed at URL:[http://files.shareholder.cornjdownloads/ABEA-5VU3S1/0x0x500536/b6f7f6a6-1853-4476-93cf-2f2f895241d7/1MGN News_2011330_General_Releases.pdf], accessed on Dec. 8, 2014.

Cragg, M.S., et al., "Complement-mediated Lysis by Anti-CD20 mAb Correlates with Segregation into Lipid Rafts," Blood 101(3):1045-1052, American Society of Hematology, United States (Feb. 2003).

Dahle, J., et al., "Evaluating Antigen Targeting and Anti-tumor Activity of a New Anti-CD37 Radioimmunoconjugate Against Non-Hodgkin's Lymphoma," Anticancer Research 33(1):85-96, International Institute of Anticancer Research, Greece (2013).

Daniel, C., et al., "Mapping of Linear Antigenic Sites on the S Glycoprotein of a Neurotropic Murine Coronavirus with Synthetic Peptides: A Combination of Nine Prediction Algorithms Fails To Identify Relevant Episodes and Peptide Immunogenicity Is Drastically Influenced by the Nature of the Protein Carrier," Virology 202:540-549, Elsevier Inc., Netherlands (1994).

De Pascalis, R., et al., "Grafting of 'Abbreviated' Complementarity-determining Regions Containing Specificity-determining Residues Essential for Ligand Contact to Engineer a Less Immunogenic

(56) References Cited

OTHER PUBLICATIONS

Humanized Monoclonal Antibody," Journal of Immunology 169(6):3076-3084, The American Association of Immunologists, United States (Sep. 2002).
Deckert, J., et al., "A Novel Anti-CD37 Antibody-Drug Conjugate with Multiple Anti-tumor Mechanisms for the Treatment of B-Cell Malignancies," Blood 122(20):3500-3510 American Society of Hematology, United States (2013).
Deckert, J., et al., "IMGN529: A Therapeutic Maytansinoid Conjugate of an Anti-CD37 Antibody with Multiple Mechanisms of Action for B-cell Lymphoma and Leukemia," AACR Poster Abstract #2, United States, Apr. 2-6, 2011.
Deckert, J., et al., "IMGN529: An Anti-CD37 Antibody-Maytansinoid Conjugate with Multiple Mechanisms of Actions for B-Cell Malignancies," Keystone Symphosis—B Cells: New Insights into Normal versus Dysregulated Function, Apr. 12-16, 2011, Poster #306, United States (Apr. 2011).
Deckert, J., et al., "Potent B-Cell Depletion by IMGN529, a CD37-Targeting Antibody-Maytansinoid Conjugate for the Treatment of B-Cell Malignancies," ASH 2011, Abstract #3726, United States (Nov. 2011).
Dijoseph, J.F., et al., "CD20-specific Antibody-targeted Chemotherapy of Non-Hodgkin's B-cell Lymphoma Using Calicheamicin-conjugated Rituximab," Cancer Immunol Immunother 56(7):1107-1117, Springer-Verlag, Germany (2007).
Ducry, L., et al., "Antibody-Drug Conjugates: Linking Cytotoxic Payloads to Monoclonal Antibodies," Bioconjugate 21:5-13, American Chemical Society, United States (2009).
Extended European Search Report and Written Opinion for EP Application No. 13 77 0074, The Hague, Netherlands, completed on Oct. 20, 2015, pp. 1-9.
Greenfield, R.S., et al., "Evaluation in Vitro of Adriamycin Immunoconjugates Synthesized Using an Acid-sensitive Hydrazone Linker," Cancer Research 50(20):6600-6607, American Association for Cancer Research, United States (1990).
Greenspan, N.S. and Di Cera, E., "Defining Epitopes: It's not as Easy as it Seems," Nature Biotechnology 17(10):936-937, Nature Publishing Group, United States (1999).
Gussow, D. and Seemann, G., "Humanization of Monoclonal Antibodies," Methods in Enzymology 203:99-121, Elsevier Science, United States (1991).
Harris, C.L., et al., "Tumour Cell Killing Using Chemically Engineered Antibody Constructs Specific for Tumour Cells and the Complement Inhibitor CD59," Clinical & Experimental Immunology 107(2):364-371, Blackwell Publishing, United Kingdom (1997).
Heider, K.H., et al., "A Novel Fc-engineered Monoclonal Antibody to CD37 with Enhanced ADCC and High Proapoptotic Activity for Treatment of B-cell Malignancies," Blood 118(15):4159-4168, The American Society of Hematology, United States (2011).
International Preliminary Report on Patentability for International Application No. PCT/US2012/031648, The International Bureau of WIPO, Switzerland, mailed Oct. 2, 2013, pp. 1-9.
International Search Report and Written Opinion for International Application No. PCT/US11/28172, International Searching Authority, United States, mailed Jul. 13, 2011, pp. 1-9.
International Search Report and Written Opinion for International Application No. PCT/US12/31648, Commissioner for Patents, United States, mailed Sep. 20, 2012, 17 pages.
International Search Report and Written Opinion for International Application No. PCT/US15/30371, Commissioner for Patents, United States, mailed on Nov. 2, 2015, pp. 1-10.
International Search Report and Written Opinion for International Application No. PCT/US2013/034646, Commissioner for Patents, United States, mailed on Sep. 16, 2013.
International Search Report and Written Opinion for International Application No. PCT/US2016/035558, Commissioner for Patents, United States, mailed on Sep. 7, 2016, 11 pages.
International Search Report and Written Opinion for International Application No. PCT/US2016/048887, Commissioner for Patents, United States, mailed on Nov. 29, 2016, 8 pages.
Kaminski, M.S., et al., "Imaging, Dosimetry, and Radioimmunotherapy with Iodine 131-labeled Anti-CD37 Antibody in B-cell Lymphoma," Journal of Clinical Oncology 10(11):1696-1711, American Society of Clinical Oncology, United States (1992).
Knobeloch, K.P., et al., "Targeted Inactivation of the Tetraspanin CD37 Impairs T-cell-dependent B-cell Response Under Suboptimal Costimulatory Conditions," Molecular and Cellular Biology 20(15):5363-5369, American Society for Microbiology, United States (2000).
Kovtun, Y., et al., "Antibody-Maytansinoid Conjugates Designed to Bypass Multidrug Resistance," Cancer Research 70(6):2528-2537, American Association for Cancer Research, United States (Mar. 2010).
Lai, K.C., et al., "The CD37-targeting ADC IMGN529 Combines the Potent Anti-cancer Activity of K7153A Antibody with Efficient Maytansinoid Delivery," AACR-EORTC-NCI 2011, Poster Abstract #B209, p. 1, United States (Nov. 2011).Accessed at: URL:[http://mct.aacrjournals.org/content/10/11_Supplement/B209.short] on Jul. 20, 2015.
Lai, K.C., et al., "The CD37-targeting ADC IMGN529 Combines the Potent Anti-cancer Activity of K7153A Antibody with Efficient Maytansinoid Delivery," Oasis, The Online Abstract Submission System, Abstract 11-A-226-AACR:pp. 1-2, Molecular Targets and Cancer Therapeutics, Nov. 12-16, 2011, San Francisco, United States (Nov. 2011). Accessed at URL:[http://www.abstractsonline.com/plan/viewabstract.aspx?mid=2889&skey=946d141d-1376-4bec-8e3f-a54580b89072&ckey=5af84375-1153-46e6-974c-e95ea6225aef&mkey=%7Ba57ff86d-d414-4079-bcbd-157746574f37%7D] on Jul. 16, 2015.
Lambert, J.M., "Antibody-Maytansinoid Conjugates: A New Strategy for the Treatment of Cancer," Drugs of the Future 35(6):471-480, Prous Science, S.A.U., Spain (Jun. 2010).
Lapalombella, R., et al., "Tetraspanin CD37 Directly Mediates Transduction of Survival and Apoptotic Signals," Cancer Cell 21(5):694-708, Elsevier Inc., United States (2012).
Link, M.P., et al., "A Unique Antigen on Mature B Cells Defined by a Monoclonal Antibody," The Journal of Immunology 137(9):3013-3018, The American Association of Immunologists, United States (1986).
Lippincott-Schwartz, J., "Antibodies as Cell Biological Tools," Current Protocols in Cell Biology, 16.0.1-16.0.2, John Wiley & Sons, United States (2002).
MacCallum, R.M., et al., "Antibody-antigen Interactions: Contact Analysis and Binding Site Topography," Journal of Molecular Biology 262(5):732-745, Academic Press, United Kingdom (Oct. 1996).
Maecker, H.T., et al., "The Tetraspanin Superfamily: Molecular Facilitators," FASEB Journal 11(6):428-442, The Federation, United States (1997).
Mariuzza, R.A., et al., "The Structural Basis of Antigen-antibody Recognition," Annual Review of Biophysics and Biomolecular Structure 16:139-159, Annual Reviews, United States (1987).
Marken, J.S., et al., "Membrane Topology of the L6 Antigen and Identification of the Protein Epitope Recognized by the L6 Monoclonal Antibody," The Journal of Biological Chemistry 269(10):7397-7401, American Society for Biochemistry and Molecular Biology, United States (1994).
Meyer-Wentrup, F., et al., "Dectin-1 Interaction with Tetraspanin CD37 Inhibits IL-6 Production," The Journal of Immunology 178(1):154-162, The American Association of Immunologists, Inc., United States (2007).
Moore, K., et al., "Use of the Monoclonal Antibody WR17, Identifying the CD37 gp40-45 Kd Antigen Complex, in the Diagnosis of B-lymphoid Malignancy," Journal of Pathology 152(1):13-21, John Wiley & Sons, Ltd., United Kingdom (1987).
Morris, G.E., "Epitope Mapping of Protein Antigens by Competition ELISA," The Protein Protocols Handbook 1:595-600, Humana Press, United States (1996).
Office Action dated Oct. 8, 2015 in Russian Patent Application No. 2012139045, filed Mar. 11, 2011, Applicant: Immunogen, Inc, US, pp. 1-12.
Pagel, J.M, et al., "Phase 1 Study of TRU-016, An Anti-CD37 SMIPTM Protein in Relapsed and/or Refractory NHL Patients,"

(56) References Cited

OTHER PUBLICATIONS

Blood (ASH Annual Meeting Abstracts) 118(21): Abstract 1636, The American Society of Hematology, United States (2011).
Park, P.U., et al., "Antibody and Linker Selection for the Anti-CD37 Antibody-maytansinoid Conjugate IMGN529 for the Treatment of B-cell Malignancies," Experimental and Molecular Therapeutics Session, AACR Annual Meeting 2011, Experimental and Molecular Therapeutics session, Abstract #2830:1-24, United States (Apr. 2011). Accessed at URL:[http://cancerres.accrjournals.org/content/71/8_Supplement/2830.abstract] on Jul. 20, 2015.
Paul, W.E., "Immunogenicity and Antigen Structure," in *Fundamental Immunology*, Third Edition, pp. 242, Raven Press, United States (1993).
Pinkas, J., "Antibody Maytansinoid Conjugates for the Treatment of Cancer," Protein Therapeutics Forum 2012:1-23, United States (Jan. 30, 2012).
Polson, A.G., et al., "Antibody-drug Conjugates For the Treatment of Non-Hodgkin's Lymphoma: Target and Linker-drug Selection," Cancer Research 69(6):2358-2364, American Association for Cancer Research, United States (2009).
Preissuance Submission by Third Party under 37 C.F.R. § 1.290 in U.S. Appl. No. 13/045,693 (inventors Deckert et al., filed Mar. 11, 2011) dated May 30, 2013, 14 pages.
Preissuance Submission by Third Party under 37 C.F.R. § 1.290 in U.S. Appl. No. 13/436,528 (inventors Deckert et al., filed Mar. 30, 2012), dated Aug. 26, 2013, 15 pages.
Preissuance Submission by Third Party under 37 C.F.R. § 1.290 in U.S. Appl. No. 13/796,768 (inventors Deckert et al., filed Mar. 12, 2013), dated Apr. 1, 2014, 18 pages.
Press, O.W., et al., "Endocytosis and Degradation of Monoclonal Antibodies Targeting Human B-cell Malignancies," Cancer Research 49(17):4906-4912, American Association for Cancer Research, United States (1989).
Press, O.W., et al., "Radiolabeled-antibody Therapy of B-cell Lymphoma with Autologous Bone Marrow Support," The New England Journal of Medicine 329(17):1219-1224, Massachusetts Medical Society, United States (1993).
Press, O.W., et al., "Retention of B-cell-specific Monoclonal Antibodies by Human Lymphoma Cells," Blood 83(5):1390-1397, The American Society of Hematology, United States (1994).
Press, O.W., et al., "Treatment of Refractory Non-Hodgkin's Lymphoma with Radiolabeled MB-1 (anti-CD37) Antibody," Journal of Clinical Oncology 7(8):1027-1038, American Society of Clinical Oncology, United States (1989).
Robak, T., et al., "TRU-016, a Humanized Anti-CD37 IgG Fusion Protein for the Potential Treatment of B-cell Malignancies," Current Opinion in Investigational Drugs 10(12):1383-1390, Thomson Reuters Ltd., United Kingdom (2009).
Roguska, M.A., et al., "A Comparison of Two Murine Monoclonal Antibodies Humanized by CDR-grafting and Variable Domain Resurfacing," Protein Engineering 9(10):895-904, Oxford University Press, United Kingdom (1996).
Roguska, M.A., et al., "Humanization of Murine Monoclonal Antibodies through Variable Domain Resurfacing," Proceedings of the National Academy of Sciences USA 91(3):969-973, National Academy of Sciences, United States (Feb. 1994).
Rops, A.L., et al., "The Tetraspanin CD37 Protects Against Glomerular IgA Deposition and Renal Pathology," American Journal of Pathology 176(5):2188-2197, American Society for Investigative Pathology, United States (May 2010).
Rudikoff, S., et al., "Single Amino Acid Substitution Altering Antigen-binding Specificity," Proceedings of the National Academy of Sciences of the United States of America 79(6):1979-1983, National Academy of Sciences, United States (Mar. 1982).
Schwartz-Albiez, R., et al., "The B Cell-associated CD37 Antigen (gp40-52). Structure and Subcellular Expression of an Extensively Glycosylated Glycoprotein," The Journal of Immunology 140(3):905-914, The American Association of Immunologists, United States (1988).
Sheng, K-C., et al., "Tetraspanins CD37 and CD151 Differentially Regulate Ag Presentation and T-cell co-stimulation by DC," European Journal of Immunology 39(1):50-55, Wiley-VCH Verlag GmbH & Co. KGaA, Germany (2009).
Supplementary European Search Report for Application No. EP11754195, mailed on Sep. 10, 2013, 7 pages.
Tedder, T.F., et al., "Structure of the Gene Encoding the Human B Lymphocyte Differentiation Antigen CD20 (B1)," The Journal of Immunology 142(7):2560-2568, The American Association of Immunologists, United States (1989).
Teicher, B.A. and Chari, R.V.J., "Antibody Conjugate Therapeutics: Challenges and Potential," Clinical Cancer Research 17(20):6389-6397, American Association for Cancer Research, United States (Oct. 2011).
Van Spriel, A.B., et al., "A Regulatory Role for CD37 in T Cell Proliferation," The Journal of Immunology 172 (5):2953-2961, The American Association of Immunologists, United States (2004).
Van Spriel, A.B., et al., "The Tetraspanin Protein CD37 Regulates IgA Responses and Anti-Fungal Immunity," PLoS Pathogens 5(3) e1000338:1-11, Public Library of Science, United States (2009).
Written Opinion for Singapore Patent Application No. 10201501803Y, dated Sep. 4, 2018, Intellectual Property Office of Singapore, Singapore, 6 pages.
Yu, B., et al., "Targeted Drug Delivery and Cross-Linking Induced Apoptosis with Anti-CD37 based Dual-Ligand Immunoliposomes in B Chronic Lymphocytic Leukemia Cells," Biomaterials 34(26):6185-6193, Elsevier Science, Netherlands (2013).
Zhao, X., et al., "CD37 is a Potential Therapeutic Target for B-Cell Non-Hodgkin Lymphoma," Blood 116(21), 1 page, American Society of Hematology, United States (Nov. 2011); 52nd Annual Meeting of the American Society of Hematology; United States; (Dec. 4-7, 2010), accessed at URL:[https://ash.confex.com/ash/2010/webprogram/Paper28315.html], on Nov. 13, 2015.
Zhao, X., "Targeting CD37 and folate receptor for cancer therapy: strategies based on engineered proteins and liposomes," Europe PubMed Central, accessed at URL:[http://europepmc.org/theses/ETH/6183], accessed on Dec. 9, 2014 (2007) [Thesis 6183], pp. 1-296.
Zhao, X.B., et al., "Novel Anti-CD37 Small Modular Immunopharmaceutical (SMP) Induces B-Cell-Specific, Caspase-Independent Apoptosis in Human CLIJ Cells," Blood 104, Abstract 2515, 1 page, ASII Annual Meeting, American Society of Hematology, United States (2004). Accessed at URL:[http://abstracts.hematologylibrary.org/cgi/content/short/104/11/2515] on Jul. 16, 2015.
Zhao, X.B. et al., "Targeting CD37-positive Lymphoid Malignancies with a Novel Engineered Small Modular Immunopharmaceutical," Blood 110(7):2569-2577, The American Society of Hematology, United States (2007).
Office Action mailed May 16, 2018, in U.S. Appl. No. 15/130,667, inventor Deckert; Jutta, et al., filed Apr. 15, 2016, 6 pages.
Office Action mailed Oct. 31, 2017, in U.S. Appl. No. 15/130,667, inventor Deckert; Jutta, et al., filed Apr. 15, 2016, 19 pages.
Office Action mailed Apr. 28, 2017, in U.S. Appl. No. 15/130,667, inventor Deckert; Jutta, et al., filed Apr. 15, 2016, 15 pages.
Smith, S.M., et al., "The Impact of MYC Expression in Lymphoma Biology: Beyond Burkitt Lymphoma," Blood Cells, Molecules and Diseases 45(4):317-323, Academic Press, United States (Dec. 2010).
Ackler, S., et al., "The Bcl-2 Inhibitor ABT-263 Enhances the Response of Multiple Chemotherapeutic Regimens in Hematologic Tumors in Vivo," Cancer Chemotherapy and Pharmacology 66(5):869-880, Springer Verlag, Germany (2010).
Algate, P., et al., "TRU-016, An Anti-CD37 SMIP (TM) Biologic, In combination with Other therapeutic Drugs in Models of Non-Hodgkin's Lymphoma," Blood 116(21):3931, American Society of Hematology, United States (2010), 5 pages.
Alley, S.C., et al., "Antibody-drug Conjugates: Targeted Drug Delivery for Cancer," Current Opinion in Chemical Biology 14(4):529-537, Elsevier, United Kingdom (2010).
Awan, F., et al., "Phase 1 Study of TRU-016, an Anti-CD37 SMIP Protein in Naïve and Relapsed and/or Refractory CLL Patients," Poster 1792, 1 page, 2011 American Society of Hematology Annual Meeting (Dec. 10, 2011), San Diego, United States (2011).

(56) References Cited

OTHER PUBLICATIONS

Beers, S.A., et al., "Type II (Tositumomab) Anti-CD20 Monoclonal Antibody Out Performs Type I (Rituximab-Like) Reagents in B-Cell Depletion Regardless of Complement Activation," Blood 112(10):4170-4177, American Society of Hematology, United States (2008).
Bissery, M., et al., "Experimental Antitumor Activity of Taxotere (RP 56976, NSC 628503), a Taxol Analogue," Cancer Research 51(18):4845-4852, American Association for Cancer Research, United States (1991).
Boross, P. and Leusen, J.H., "Mechanisms of Action of CD20 Antibodies," American Journal of Cancer Research 2(6):676-690, e-Century Publishing Corporation, United States (2012).
Chen, R., et al., "A Phase II Study of Vorinostat and Rituximab for Treatment of Newly Diagnosed and Relapsed/refractory Indolent Non-hodgkin Lymphoma," Haematologica 100(3):357-362, Ferrata Storti Foundation, Italy (Mar. 2015).
Cheson, B.D., et al., "Revised Response Criteria for Malignant Lymphoma," Journal of Clinical Oncology 25(5):579-586, American Society of Clinical Oncology, United States (2007).
Deckert, et al, "Preclinical Mechanistic Studies Investigating Neutrophil and Lymphoid Cell Depletion by IMGN529, a CD37-Targeting Antibody-Drug Conjugate (ADC), " Poster #3119, 2 pages, 57th ASH Annual Meeting and Exposition (Dec. 6-9, 2014), San Francisco, United States.
Deckert, J., et al., "IMGN529, a Novel Antibody-Drug Conjugate (ADC) Targeting CD37 Shows Synergistic Activity with Rituximab in Non-Hodgkin Lymphoma (NHL) Models," Blood 126(23):1548, 4 pages American Society of Hematology, United States (2015).
Deckert, J., et al., "Preclinical Mechanistic Studies Investigating Neutrophil and Lymphoid Cell Depletion by IMGN529, a CD37-Targeting Antibody-Drug Conjugate (ADC)," 56th ASH Annual Meeting and Exposition: Abstract #3119, 1 page, United States (Dec. 2014) Accessed at URL:[https://ash.confex.com/ash/2014/webprogram/Paper70777.html] on Aug. 26, 2015.
Tomayko. M.M. and Reynolds, C.P., "Determination of Subcutaneous Tumor Size in Athymic (Nude) Mice," Cancer Chemotherapy and Pharmacology 24(3):148-154, Springer Verlag, Germany (1989).
Epstein, A.L., et al., "Two new monoclonal antibodies (LN-1, LN-2) reactive in B5 formalin-fixed, paraffin-embedded tissues with follicular center and mantle zone human B lymphocytes and derived tumors," The Journal of Immunology, 133:1028-1036, The American Association of Immunologists, United States (1984).
Gaudio, E., et al., "Identification Of Anti-Lymphoma Biomarkers Of Response To The Anti-CD37 Antibody Drug Conjugate (ADC) IMGN529," presented at 58th Annual Meeting and Exposition of the American Society of Hematology 128, 1 page (Dec. 2, 2016).
Friedberg, J.W., "Double-Hit Diffuse Large B-cell Lymphoma," Journal of Clinical Oncology 30(28):3439-3443, American Society of Clinical Oncology, United States (2012).
Goel, M., et al., "Plasticity Within the Antigen-combining Site May Manifest as Molecular Mimicry in the Humoral Immune Response," Journal of Immunology 173(12):7358-7367, American Association of Immunologists, United States (Dec. 2004).
Gopal, A., et al., "Phase 1b Study of otlertuzumab (TRU-016), an Anti-CD37 monospecific ADAPTIR™ therapeutic protein, in Combination with Rituximab and Bendamustine in Relapsed Indolent Lymphoma patients," Investigational New Drugs 32(6):1213-1225, Presented at ASH Annual Meeting 2012, Springer Science+ Business Media, United States, 13 pages.
Green, T.M., et al., "Immunohistochemical Double-Hit Score Is a Strong Predictor of Outcome in Patients with Diffuse Large B-cell Lymphoma Treated with Rituximab Plus Cyclophosphamide, Doxorubicin, Vincristine, and Prednisone," Journal of Clinical Oncology 30(28):3460-3467, American Society of Clinical Oncology, United States (2012).
Gross, J., "3333: Evaluation of Otlertuzumab (TRU-016), an Anti-CD37 ADAPTIR™M Therapeutic in Preclinical Combination Studies with Kinase Inhibitors and a Next Generation Anti-CD20 Mab in Vitro and in Animal Models of Non-Hodgkin's Lymphoma," Blood 124(21):3333, 2 pages, American Society of Hematology, United States (2014).
Hicks, S.W., et al., "The Antitumor Activity of IMGN529, a CD37-targeting Antibody-drug Conjugate, Is Potentiated by Rituximab in Non-Hodgkin Lymphoma Models," Neoplasia 19(9):661-671, Neoplasia Press, United States (Sep. 2017).
Hu, S., et al., "MYC/BCL2 Protein Coexpression Contributes to the Inferior Survival of Activated B-Cell Subtype of Diffuse Large B-Cell Lymphoma and Demonstrates High-Risk Gene Expression Signatures: a Report from The International DLBCL Rituximab-CHOP Consortium Program," Blood 121(20):4021-4031, American Society of Hematology, United States (2013).
International Preliminary report on patentability for International Application No. PCT/US2016/035558, International search authority, Switzerland, mailed on Dec. 12, 2017, 8 pages.
International Search Report with Written Opinion for International Application No. PCT/IB2017/056841, International Searching Authority, Netherlands, mailed Feb. 2, 2018, 10 pages.
Khan, T and Salunke, D.M, "Adjustable Locks and Flexible Keys: Plasticity of Epitope-paratope Interactions in Germline Antibodies," Journal of Immunology 192(11):5398-5405, American Association of Immunologists, United States (Jun. 2014).
Konig, A., et al., "Basic Fibroblast Growth Factor (bFGF) Upregulates the Expression of bcl-2 in B Cell Chronic Lymphocytic Leukemia Cell Lines Resulting in Delaying Apoptosis," Leukemia 11(2):258-265, Nature Publishing Group, United Kingdom (1997).
Lai, K.C., et al., "Evaluation of Targets for Maytansinoid ADC Therapy Using a Novel Radiochemical Assay," Pharmaceutical Research 32(11):3593-3603, Kluwer Academic, United States (2015).
Lai, K.C., et al., "The CD37-targeting ADC IMGN529 Combines the Potent Anti-cancer Activity of K7153A Antibody with Efficient Maytansinoid Delivery," AACR-EORTC-NCI 2011, Poster, 1 page, United States (Nov. 2011).
Lim, S.H., et al., "Anti-CD20 Monoclonal Antibodies: Historical and Future Perspectives," Haematologica 95(1):135-143, Ferrata Storti Foundation, Italy (Jan. 2010).
NCT01534715, "IMGN529 in Treating Patients with Relapsed or Refractory Non-Hodgkin's Lymphoma," retrieved from URL:[https://clinical.gov/archive/NCT01534715/2012_02_16], retrieved on Sep. 6, 2016, 2 pages.
Oki, Y., et al., "Pegylated Liposomal Doxorubicin Replacing Conventional Doxorubicin in Standard R-chop Chemotherapy for Elderly Patients With Diffuse Large B-cell Lymphoma: an Open Label, Single Arm, Phase II Trial," Clinical Lymphoma, Myeloma & Leukemia 152-158, Elsevier, United States (Mar. 2015).
Pers, J.O., et al., "Anti-CD20 Antibody-Mediated Apoptosis of B Cells Is a Lipid Raft-Dependent Process," Annals of the Rheumatic Diseases 70(Suppl 2):A73, BMJ Publishing Group Ltd., United Kingdom (Feb. 2011).
Poosarla, V.G., et al., "Computational De Novo Design of Antibodies Binding to a Peptide With High Affinity," Biotechnology and Bioengineering 114(6):1331-1342, Wiley, United States (Jun. 2017).
Zhao, X., "Targeting CD37 and folate receptor for cancer therapy: strategies based on engineered proteins and liposomes," Ohio Link Electronic Theses & Dissertations Center, document number osul 174678307, pp. 1-314, The Ohio State University, United States (2007). Accessed at URL:[https://etd.ohiolink.edu/ap/10?0::NO:10:P10ACCESSION_NUM:osu1174678307] on Oct. 2, 2015.
Robak, T. and Robak, E., "New Anti-CD20 Monoclonal Antibodies for the Treatment of B-cell Lymphoid Malignancies," BioDrugs 25(1):13-25, Springer International, New Zealand (Feb. 2011).
Romanelli, A., et al., Novel CD37-Targeting Antibody-Drug Conjugate (ADC), IMGN529, Has Synergistic Activity in Combination with Rituximab in Non-Hodgkin Lymphoma (NHL) Models, presented at 13th International Conference on Malignant Lymphoma, Jun. 17-20, 2015, 1 page (2015).
Rudolph, C., et al., "Molecular Cytogenetic Characterization of the Mantle Cell Lymphoma Cell Line GRANTA-519," Cancer Genetics and Cytogenetics 153(2):144-150, Elsevier, United States (2004).
Smith, T.J., et al., "2006 Update of Recommendations for the Use of White Blood Cell Growth Factors: An Evidence-based Clinical

(56) References Cited

OTHER PUBLICATIONS

Practice Guideline," Journal of Clinical Oncology 24(19):3187-3205, American Society of Clinical Oncology, United States (2006).
Smolewski, P., et al., "Pro-apoptotic Effect of an Anti-CD37 scFv-Fc Fusion Protein, in Combination With the Anti-CD20 Antibody, Ofatumumab, on Tumour Cells From B-cell Malignancies," European Journal of Cancer 50(15):2677-2684, Elsevier, Netherlands (Oct. 2014).
Stathis, A et al., "Preliminary Findings from a Phase I, Multi-center, Open-label Study of the anti-CD37 Antibody-Drug Conjugate (ADC), IMGN529, in Adult Patients with Relapsed or Refractory Non-Hodgkin Lymphoma (NHL)," 2014 ASCO Annual Meeting, Poster, Abstract #8526, United States (May 2014), 1 page, Accessed at URL:[http://www.immunogen.com/documents/Publications/IMGN529%20first%20clin%20ASCO%202014.pdf] on Aug. 26, 2015.
Stathis, A. et al., "A Phase I Study Of IMGN529, An Antibody-Drug Conjugate (ADC) Targeting CD37, In Adult Patients With Relapsed Or Refractory Non-Hodgkin Lymphoma (NHL)," 56th ASH Annual Meeting and Exposition: Abstract #1760, United States (Dec. 2014), 1 page Accessed at URL:[https://ash.confex.com/ash/2014/webprogram/Paper70219.html], on Aug. 26, 2015.
Stathis, A et al., "A Phase I Study Of IMGN529, An Antibody-Drug Conjugate (ADC) Targeting CD37, In Adult Patients With Relapsed Or Refractory Non-Hodgkin Lymphoma (NHL)," Abstract #1760, ASH Annual Meeting, San Francisco, California, United States (Dec. 2014), 2 pages, accessed at URL:[http://www.immunogen.com/documents/Publications/IMGN529_PhI_ASH12-2014.pdf], accessed on Aug. 26, 2015.
Stathis, A., et al., "Safety, tolerability, and preliminary activity of IMGN529, a CD37-targeted antibody-drug conjugate, in patients with relapsed or refractory B-cell non-Hodgkin lymphoma: a dose escalation phase I study," Invest New Drugs, 36:869-876, e-pub Feb. 17, 2018, Springer US, United States (2018).
Tedoldi, S., et al., "Selective Loss of B-Cell Phenotype in Lymphocyte Predominant Hodgkin Lymphoma," Pathology 213(4):429-440, John Wiley and Sons, United Kingdom (Dec. 2007).
Co, M.S., et al., "Chimeric and Humanized Antibodies With Specificity for the CD33 Antigen," Journal of immunology (Baltimore, MD.:1950), 148(4):1149-1154, American Association of Immunologists, United States (Feb. 1992).
Deckert, J., et al., "IMGN529, a Novel Antibody-Drug Conjugate (ADC) Targeting CD37 Shows Synergistic Activity with Rituximab in Non-Hodgkin Lymphoma (NHL) Models," poster #1548. 1 page, 57th ASH Annual Meeting and Exposition, Dec. 6-9, 2014, San Francisco, United States.
Gershoni, J.M., et al., "Epitope Mapping: the First Step in Developing Epitope-based Vaccines," BioDrugs 21(3):145-156, Springer International, New Zealand (2007).
Tutt, A., et al., "Trispecific F(ab')3 Derivatives that use Cooperative Signaling via the TCR/CD3 Complex and CD2 to Activate and Redirect Resting Cytotoxic T Cells," The Journal of Immunology 147:60-69, The American Association of Immunologists, United States (Jul. 1991).
Wang, L., et al., "Structural Characterization of the Maytansinoid-Monoclonal Antibody Immunoconjugate, huN901-DM1, by mass spectrometry," Protein Science, 14(9):2436-2446, Cold Spring Harbor Laboratory Press, United States (Sep. 2005).
Wang, Z., et al., "Universal PCR Amplification of Mouse Immunoglobulin Gene Variable Regions: the Design of Degenerate Primers and an Assessment of the Effect of DNA Polymerase 3' to 5' Exonuclease Activity," Journal of Immunological Methods 233(1-2):167-177, Elsevier, Netherlands (Jan. 2000).
Zenz, T., et al., "Exceptional In Vitro Activity of CD37 Antibodies in CLL," Blood 116(21):1021-1022, 2010 ASH Annual Meeting Abstracts (Abstract 2460), 5 pages, American Society of Hematology, United States (Nov. 2010), accessed at URL:[https://ashconfex.com/ash/2010/webprogram/Paper29401.html], accessed on Apr. 4, 2016.
Colman, P.M., "Effects of Amino Acid Sequence Changes on Antibody-Antigen Interactions," Research in Immunology 145(1):33-36, Elsevier, France (Jan. 1994).
Office Action mailed Jan. 21, 2016 in U.S. Appl. No. 13/436,528, inventors Deckert, J., et al., filing date Mar. 30, 2012, 8 pages.
Office Action mailed Mar. 30, 2015 in U.S. Appl. No. 13/436,528, inventors Deckert, J., et al., filing date Mar. 30, 2012, 10 pages.
Office Action mailed Mar. 7, 2014 in U.S. Appl. No. 13/436,528, inventors Deckert, J., et al., filing date Mar. 30, 2012, 14 pages.
Office Action mailed Sep. 8, 2015 in U.S. Appl. No. 13/436,528, inventors Deckert, J., et al., filing date Mar. 30, 2012, 8 pages.
Heppner, G.H., et al., "Tumor heterogeneity: biological implications and therapeutic consequences," Cancer Metastasis Rev. 2(1):5-23, Martinus Nihoff Publishers, Netherlands (1983).
International Search Report and Written Opinion mailed Aug. 21, 2019, in International Application No. PCT/IB2019/054457, European Patent Office, Netherlands, 11 pages.
Jain, R.K., "Barriers to Drug Delivery in Solid Tumors," Scientific American 271(1):58-65, Scientific American Inc., United States (Jul. 1994).
Zhao, X., et al., "CD37 Is a Potential Therapeutic Target for B-Cell Non-Hodgkin Lymphoma," Blood: 2010 ASH Annual Meeting Abstracts 116(21):1277-1278, Abstract #3098, 2 pages, American Society of Hematology, United States (Nov. 19, 2010).
Deckert, J., et al., "IMGN529, a Novel Antibody-Drug Conjugate (ADC) Targeting CD37 Shows Synergistic Activity with Rituximab in Non-Hodgkin Lymphoma (NHL) Models," poster #1548, 1 page, 57th ASH Annual Meeting and Exposition, Dec. 5, 2015, Orlando, United States.
Deckert, J., et al., "Preclinical Mechanistic Studies Investigating Neutrophil and Lymphoid Cell Depletion by IMGN529, a CD37-Targeting Antibody-Drug Conjugate (ADC)," 56th ASH Annual Meeting and Exposition: Poster, 1 page, Abstract #3119, Accessed at URL:[http://www.immunogen.com/documents/Publications/IMGN529%20preclinical%20ASH% 2012-2014.pdf] on Aug. 26, 2015.
Epstein, A.L., et al., "Two New Monoclonal Antibodies, Lym-1 and Lym-2, Reactive With Human B-lymphocytes and Derived Tumors, With Immunodiagnostic and Immunotherapeutic Potential," Cancer Research 47(3):830-840, American Association for Cancer Research, United States (Feb. 1987).
International Preliminary Report on Patentability for International Application No. PCT/US2016/048887, International Searching Authority, United States, issued Mar. 6, 2018, 5 pages.
Levy, M. Y., et al., "Safety and efficacy of CD37-Targeting Naratuximab Emtansine plus Rituximab in Diffuse Large B-cell Lymphoma and Other Non-Hodgkin's B-cell Lymphomas—a Phase 2 Study," Poster #244, presented at the 16th International Conference on Malignant Lymphoma (Virtual Edition), Debiopharm International S.A., Switzerland, accessed at URL:[https://www.debiopharm.com/drug-development/publications/safety-and-efficacy-of-cd37-targeting-naratuximab-emtansine-plus-rituximab-in-diffuse-large-b-cell-lymphoma-and-other-non-hodgkins-b-cell-lymphomas-a-phase-2-study/] on Jul. 16, 2021, 1 page (Jun. 2021).
Malia, T. J., et al., "Epitope mapping and structural basis for the recognition of phosphorylated tau by the anti-tau antibody AT8," Proteins 84(4):427-434, John Wiley & Sons, United States (Apr. 2016).
De Genst, E., et al., "Antibody repertoire development in camelids," Developmental and Comparative Immunology 30(1-2):187-198, Elsevier, Netherlands (2006).
Ward, E. S., et al., "Binding activities of a repertoire of single immunoglobulin variable domains secreted from *Escherichia coli*," Nature 341(6242):544-546, Nature Publishing Group, United Kingdom (Oct. 1989).
Barthelemy, P. A., et al., "Comprehensive analysis of the factors contributing to the stability and solubility of autonomous human VH domains," Journal of Biological Chemistry 283(6):3639-3654, Elsevier, Netherlands (Feb. 2008).
Choi, Y., and Deane, C. M., "Predicting antibody complementarity determining region structures without classification," Molecular BioSystems 7(12):3327-3334, Royal Society of Chemistry, United Kingdom (Dec. 2011).

(56) References Cited

OTHER PUBLICATIONS

Griffiths, A. D., et al., "Human anti-self antibodies with high specificity from phage display libraries," EMBO J 12(2):725-734, European Molecular Biology Organization, Germany (Feb. 1993).
Klimka, A., et al., "Human anti-CD30 recombinant antibodies by guided phage antibody selection using cell panning," British Journal of Cancer 83(2):252-260, Nature Publishing Group, United Kingdom (Jul. 2000).
Beiboer, S. H., et al., "Guided selection of a pan carcinoma specific antibody reveals similar binding characteristics yet structural divergence between the original murine antibody and its human equivalent," Journal of Molecular Biology 296(3): 833-849, Elsevier, Netherlands (Feb. 2000).

* cited by examiner

Figure 4
A
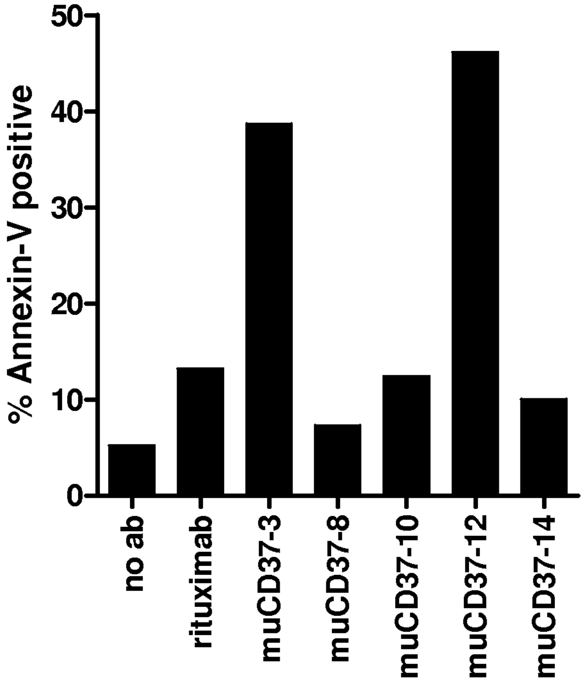
B
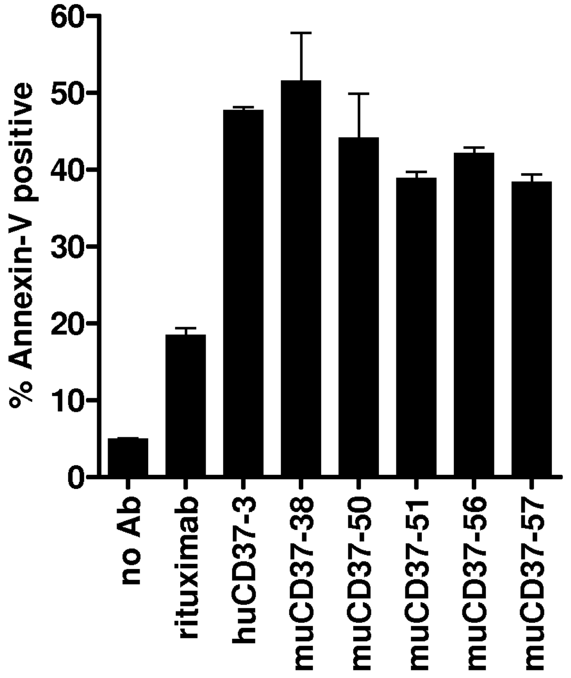

| CD37-3 $V_L$ | | |
|---|---|---|
| Kabat position | Murine residue | Human residue |
| 1 | D | D |
| 3 | Q | Q |
| **9** | **A** | ***S*** |
| 15 | V | V |
| **18** | **T** | ***R*** |
| **40** | **Q** | ***P*** |
| 41 | G | G |
| 42 | K | K |
| **45** | **Q** | ***K*** |
| 57 | G | G |
| 60 | S | S |
| 67 | S | S |
| **70** | **Q** | ***D*** |
| **80** | **S** | ***P*** |
| 81 | E | E |
| **100** | **G** | ***Q*** |
| 103 | K | K |
| 107 | K | K |
| 108 | R | R |

B

| CD37-3 $V_H$ | | | |
|---|---|---|---|
| Kabat position | Murine residue | Human v1.00 residue | Human v1.01 residue |
| 1 | Q | Q | Q |
| 3 | Q | Q | Q |
| **5** | **K** | ***Q*** | ***Q*** |
| 11 | L | L | L |
| 15 | S | S | S |
| 16 | Q | Q | Q |
| **17** | **S** | ***T*** | ***T*** |
| 28 | S | S | S |
| 41 | P | P | P |
| 42 | G | G | G |
| 43 | K | K | K |
| **61** | **S** | ***P*** | **S** |
| **62** | **A** | ***S*** | ***S*** |
| 64 | K | K | K |
| 65 | S | S | S |
| 74 | S | S | S |
| 75 | K | K | K |
| **83** | **Q** | ***T*** | ***T*** |
| **84** | **T** | ***A*** | ***A*** |
| **85** | **D** | ***A*** | ***A*** |
| 105 | Q | Q | Q |
| 108 | L | L | L |
| 112 | S | S | S |

| CD37-50 $V_L$ | | |
|---|---|---|
| Kabat position | Murine residue | Human residue |
| **1** | **D** | ***E*** |
| 3 | V | V |
| 5 | T | T |
| 9 | A | A |
| **10** | **I** | ***T*** |
| 15 | P | P |
| **18** | **K** | ***R*** |
| **40** | **S** | ***P*** |
| 41 | G | G |
| **42** | **T** | ***Q*** |
| 57 | G | G |
| **60** | **G** | ***A*** |
| 67 | S | S |
| 77 | S | S |
| 81 | E | E |
| **100** | **S** | ***Q*** |
| 107 | K | K |
| 108 | R | R |

B

| CD37-50 $V_H$ | | |
|---|---|---|
| Kabat position | Murine residue | Human residue |
| 1 | Q | Q |
| 3 | Q | Q |
| 5 | Q | Q |
| **10** | **D** | ***G*** |
| 11 | L | L |
| 13 | K | K |
| 15 | S | S |
| 16 | Q | Q |
| **25** | **T** | ***S*** |
| 39 | Q | Q |
| **40** | **F** | ***H*** |
| 61 | P | P |
| 62 | S | S |
| 64 | K | K |
| 65 | S | S |
| 74 | S | S |
| 75 | K | K |
| **84** | **T** | ***A*** |
| **85** | **E** | ***A*** |
| 105 | Q | Q |
| 108 | L | L |
| 112 | S | S |

```
                   1                                                          60
     muCD37-3 VL   DIQMTQSPASLSVSVGETVTITCRASENIRSNLAWYQQKQGKSPQLLVNVATNLADGVPS
huCD37-3 VLv1.00   --------S--------R---------------------P----K---------------
                   61                                             108
     muCD37-3 VL   RFSGSGSGTQYSLKINSLQSEDFGTYYCQHYWGTTWTFGGGTKLEIKR
huCD37-3 VLv1.00   ---------D---------P-------------------Q--------
```

B

```
                   1                                                          60
     muCD37-3 VH   QVQVKESGPGLVAPSQSLSITCTVSGFSLTTSGVSWVRQPPGKGLEWLGVIWGDGSTNYH
huCD37-3 VHv1.00   ----Q-----------T-------------------------------------------
huCD37-3 VHv1.01   ----Q-----------T-------------------------------------------
                   61                                                    115
     muCD37-3 VH   SALKSRLSIKKDHSKSQVFLKLNSLQTDDTATYYCAKGGYSLAHWGQGTLVTVSS
huCD37-3 VHv1.00   PS-----------------------TAA---------------------------
huCD37-3 VHv1.01   -S-----------------------TAA---------------------------
```

C

```
                   1                                                          60
muCD37-50 VL       QIVLTQSPAIMSASPGEKVTMTCSATSSVTYMHWYQQKSGTSPKRWIYDTSKLPYGVPGR
huCD37-50 VL       E--------T-------R--------------------P-Q----------N------A-
                   61                                            107
muCD37-50 VL       FSGSGSGTSYSLTISSMEAEDAATYYCQQWSDNPPTFGSGTKLEIKR
huCD37-50 VL       --------------------------------------Q--------
```

D

```
                   1                                                          60
muCD37-50 VH       QVQLQESGPDLLKPSQSLSLTCTVTGYSITSGFAWHWIRQFPGNKLEWMGYILYSGSTVY
huCD37-50 VH       ---------G--------------S---------------H-------------------
                   61                                                        120
muCD37-50 VH       SPSLKSRISITRDTSKNHFFLQLNSVTTEDTATYYCARGYYGYGAWFAYWGQGTLVTVSA
huCD37-50 VH       ---------------------------AA-------------------------------
```

Figure 9
A
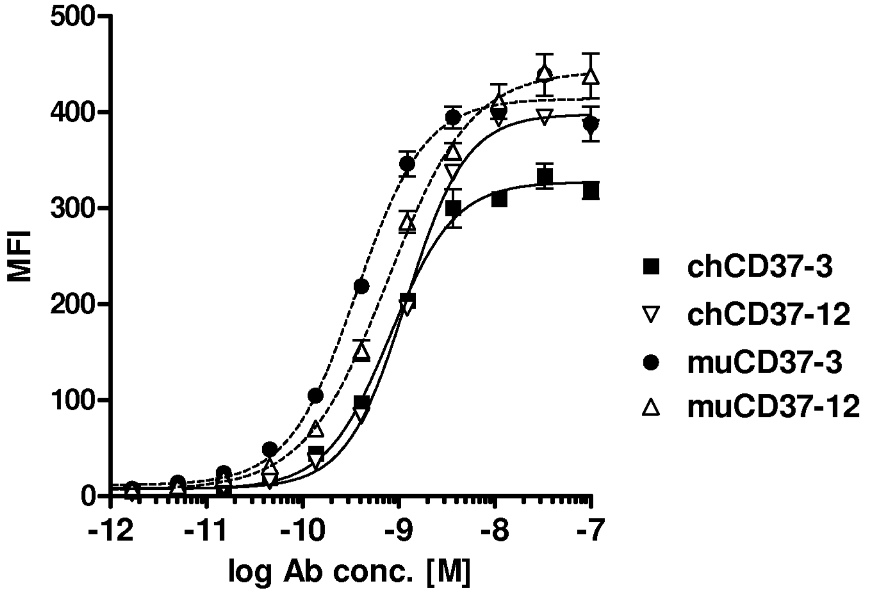
B
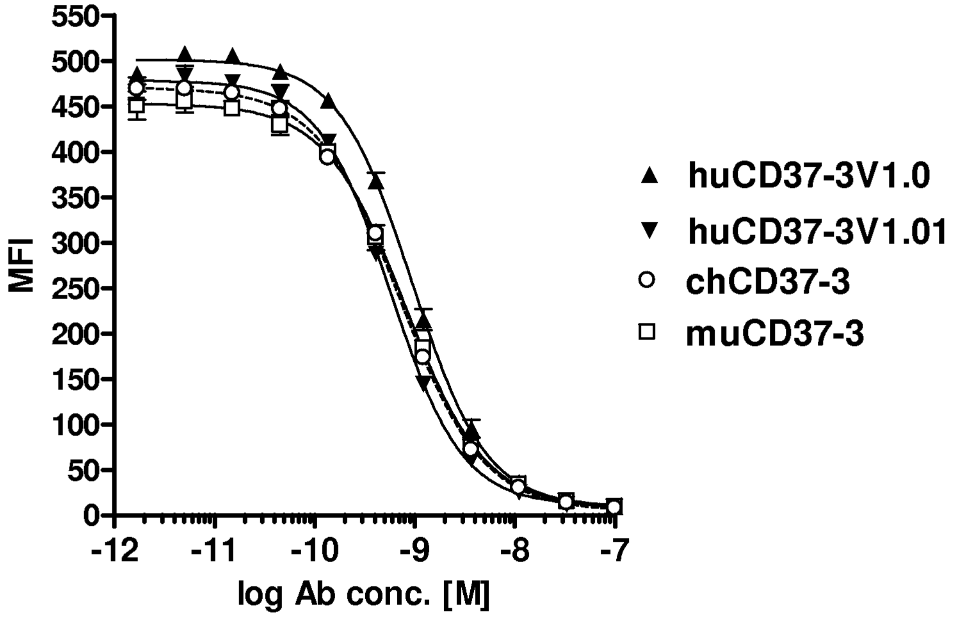

Figure 14
A
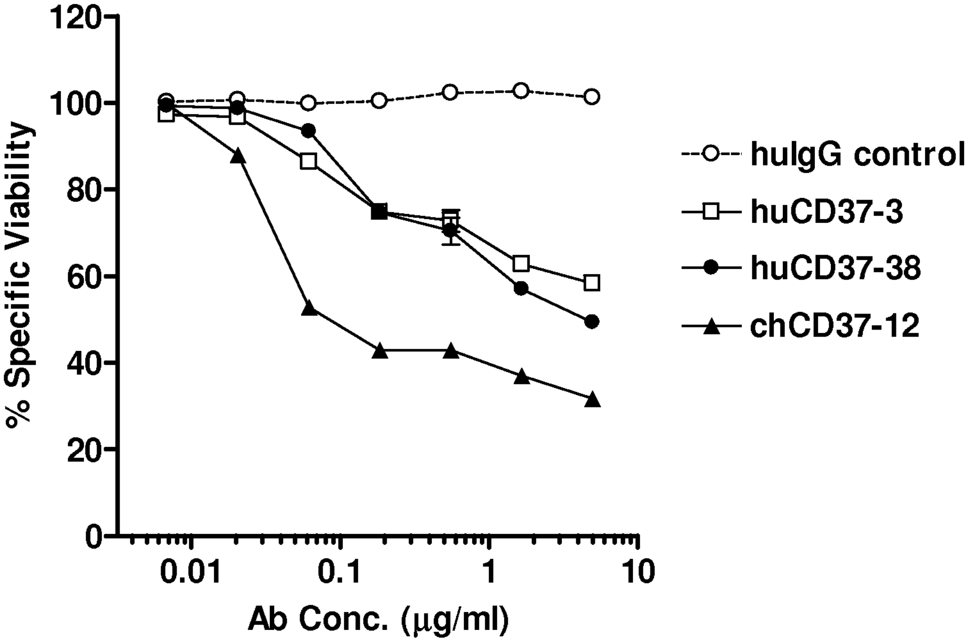
B
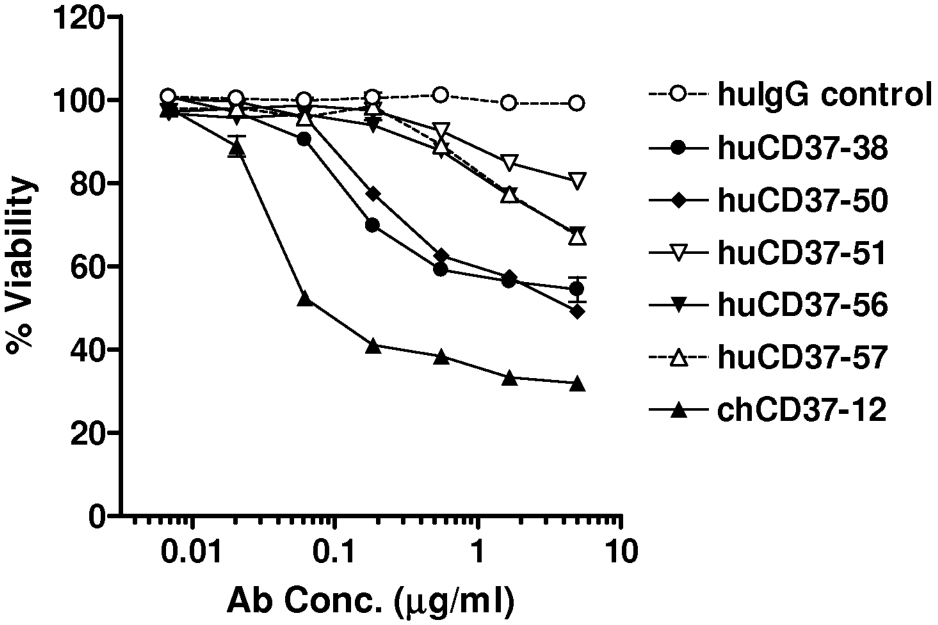

Figure 15
A
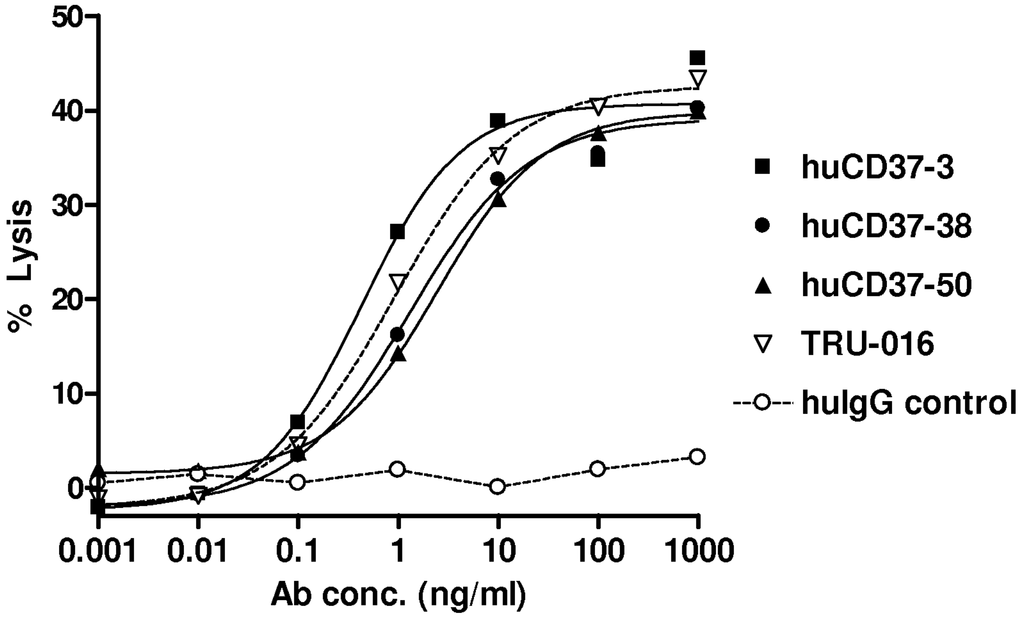
B
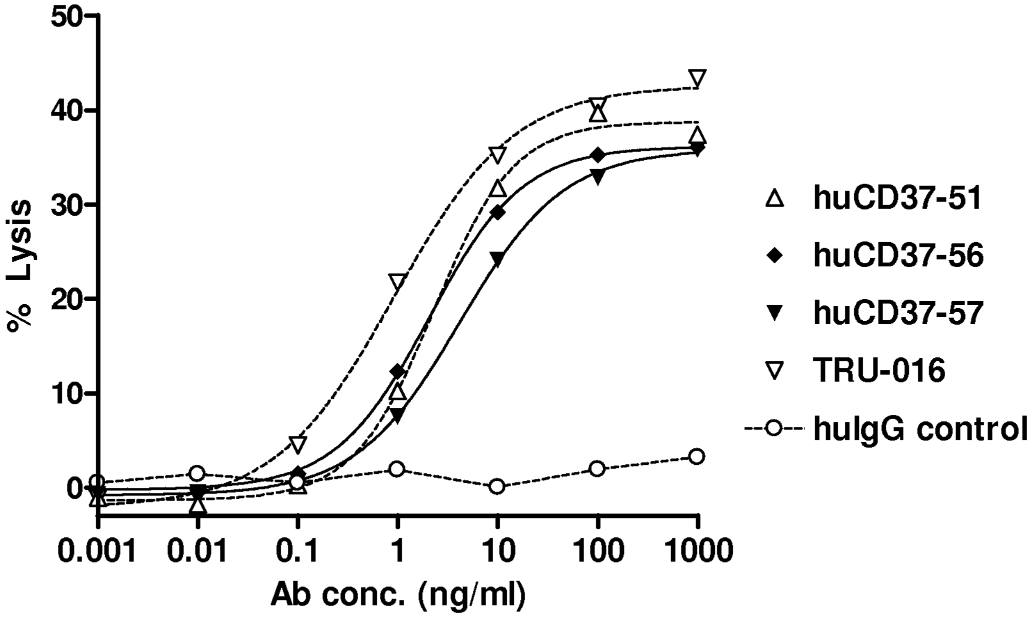

Figure 16

```
         1                                                Small ECD   60
muCD37   MSAQESCLSLIKYFLFVFNLFFFV.LGGLIFCFGTWILIDKTSFVSFVGLSFVPLQTWSK
huCD37   ------------------------.--S------I---------------A-----I---
macCD37  ------------------------I--S------I---------------A-----I---

         61                                                        120
muCD37   VLAVSGVLTMALALLGCVGALKELRCLLGLYFGMLLLLFATQITLGILISTQRVLERRV
huCD37   ---I--IF--GI-----------------------------------------AQ---SL
macCD37  ---I---F--G------------------------------------------AQ---SL

         121                        Large ECD                      180
muCD37   QELVLRTIQSYRTNPDETAAEESWDYAQFQLRCCGWQSPRDWNKAQMLKANESEEPFVPC
huCD37   RDV-EK---K-G---E----------V---------HY-Q--FQVLI-RG-G--AHR---
macCD37  -DI-EK---R-H---E----------V---------HS-Q--FQVLT-RG-G--AHR---

         181                        Large ECD                      240
muCD37   SCYNSTATNDSTVFDKLFFSQLSRLGPRAKLRQTADICALPAKAHIYREGCAQSLQKWLH
huCD37   ----LS------IL--VILP------HL-RS-HS-----V--ES---------G------
macCD37  ----LS------IL--VILP------QL-RS-HST----V--NS--------R-------

         241                                     282
muCD37   NNIISIVGICLGVGLLELGFMTLSIFLCRNLDHVYDRLARYR
huCD37   --L--------------------------------N------
macCD37  --L--------------------------------N------
```

Figure 17

```
             100    EcoRV                                 SacII       149
      huCD37 TQITLGILISTQRAQLERSLRDVVEKTIQKYGTNPEETAAEESWDYVQFQ
   huCD37-M1 -------------VR---RVQEL-LR---S-R---D--------------
   huCD37-M2 ----------------------------------------------A---
   huCD37-M3 --------------------------------------------------
  huCD37-M45 --------------------------------------------------
 muCD37-R176 -------------VR---RVQEL-LR---S-R---D----------A---
      muCD37 -------------VR---RVQEL-LR---S-R---D----------A---

             150                      Kpn1                        199
      huCD37 LRCCGWHYPQDWFQVLILRGNGSEAHRVPCSCYNLSATNDSTILDKVILP
   huCD37-M1 --------------------------------------------------
   huCD37-M2 ------QS-R--NKAQM-KA-E--EP------------------------
   huCD37-M3 ----------------------------------ST------VF--LFFS
  huCD37-M45 --------------------------------------------------
 muCD37-R176 ------QS-R--NKAQM-KA-E--EP--------ST------VF--LFFS
      muCD37 ------QS-R--NKAQM-KA-E--EPF-------ST------VF--LFFS

             Blp1          Nde1                Pst1           249
      huCD37 QLSRLGHLARSRHSADICAVPAESHIYREGCAQGLQKWLHNNLISIVGIC
   huCD37-M1 --------------------------------------------------
   huCD37-M2 --------------------------------------------------
   huCD37-M3 --------------------------------------------------
  huCD37-M45 ------PR-KL-QT-----L--KA---------S----------------
 muCD37-R176 ------PR-KL-QT-----L--KA---------S----------------
      muCD37 ------PR-KL-QT-----L--KA---------S--------I-------
```

Figure 18
A
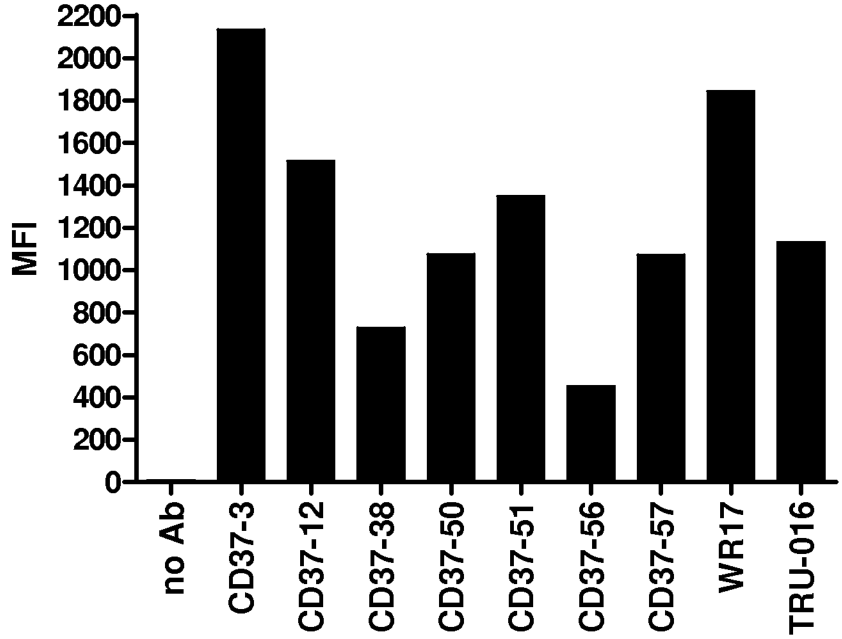
B
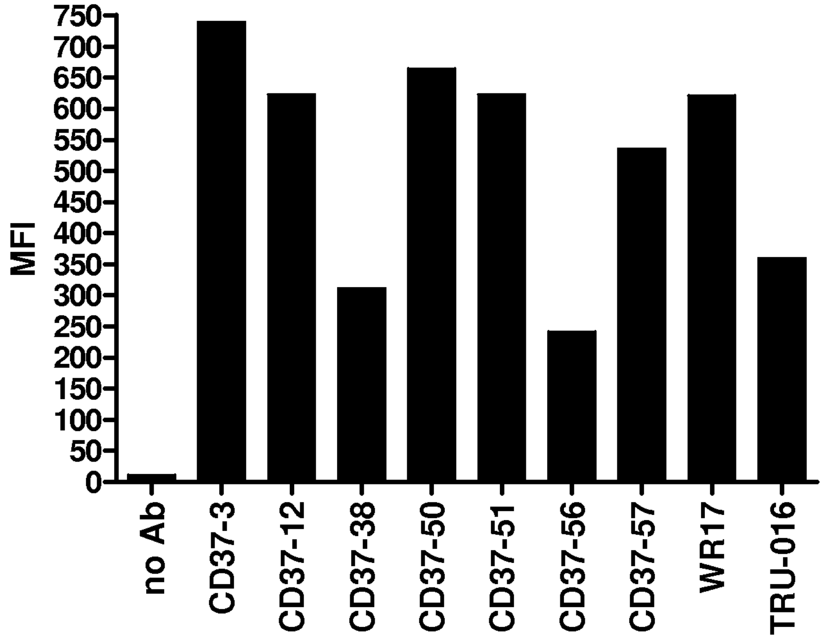

Figure 20
A
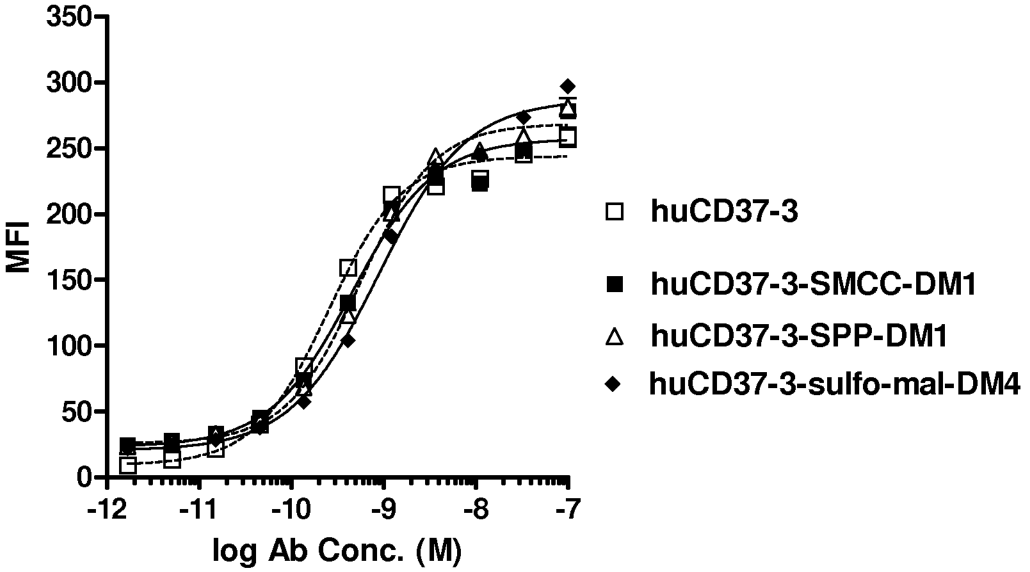
B
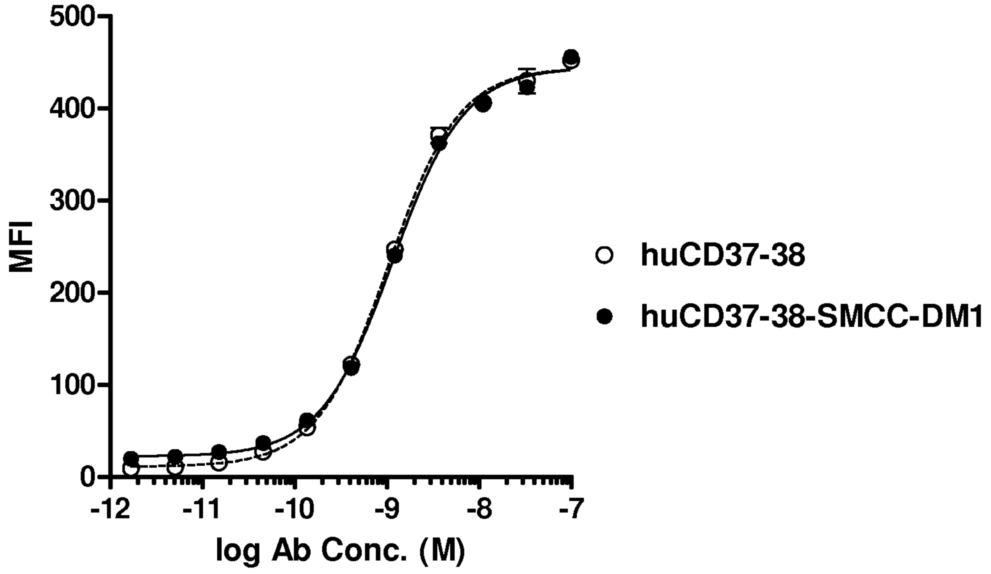

Figure 21
A
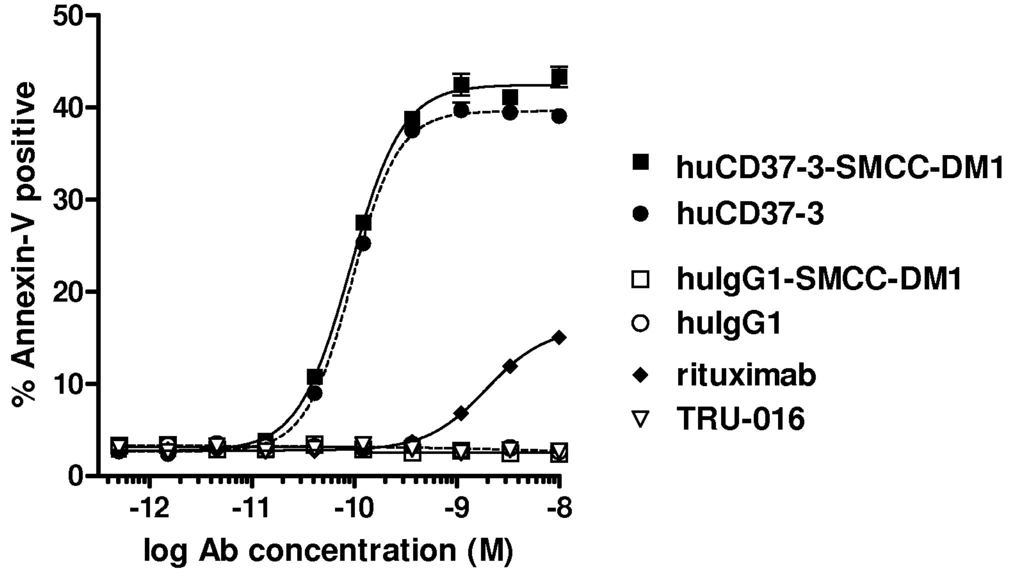
B
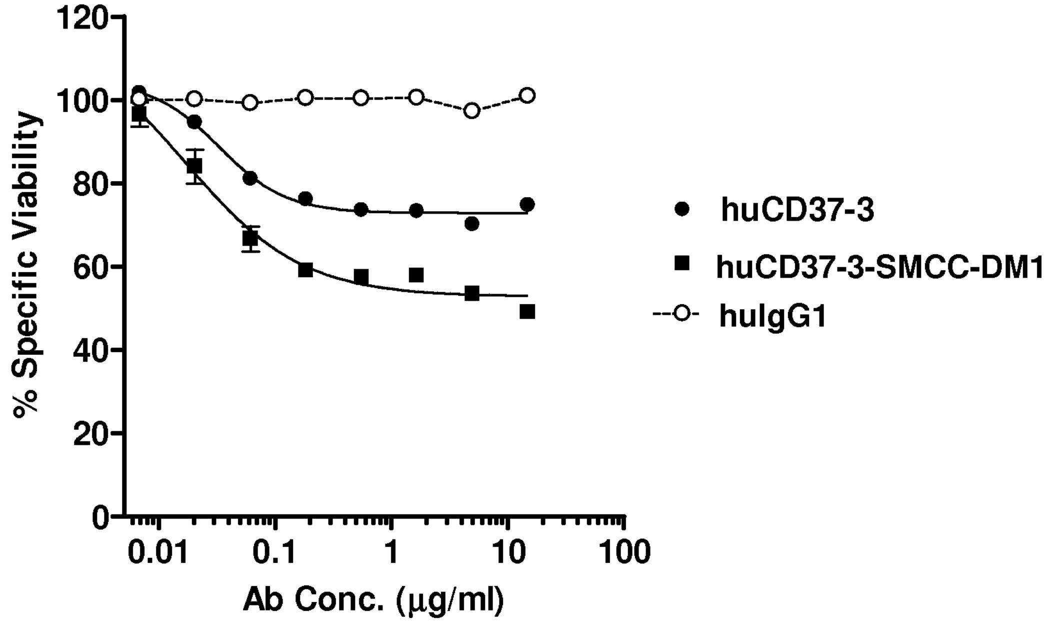

Figure 22
A
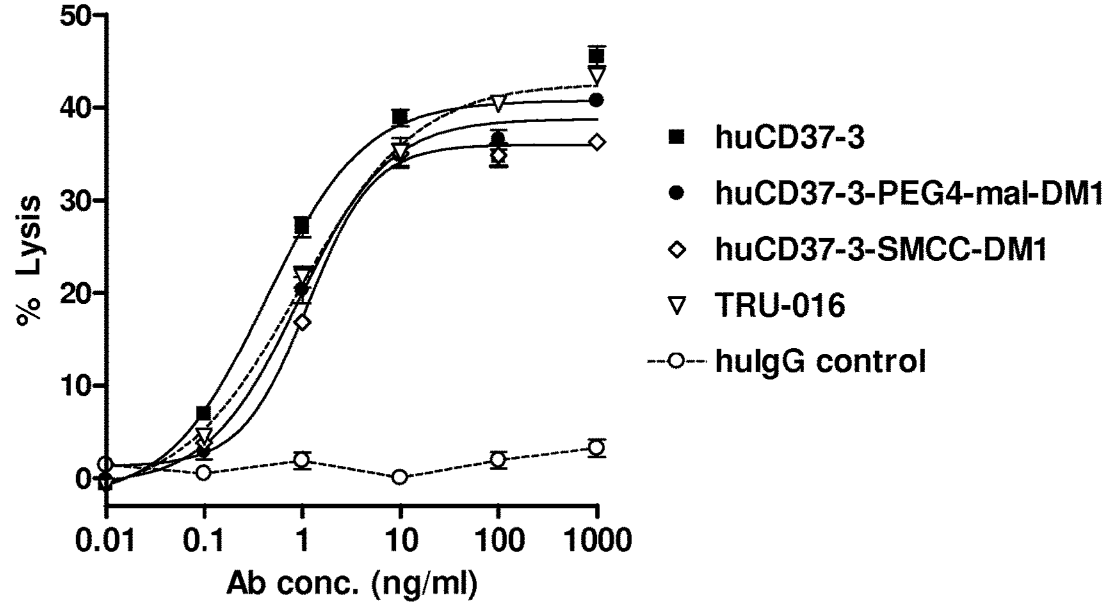
B
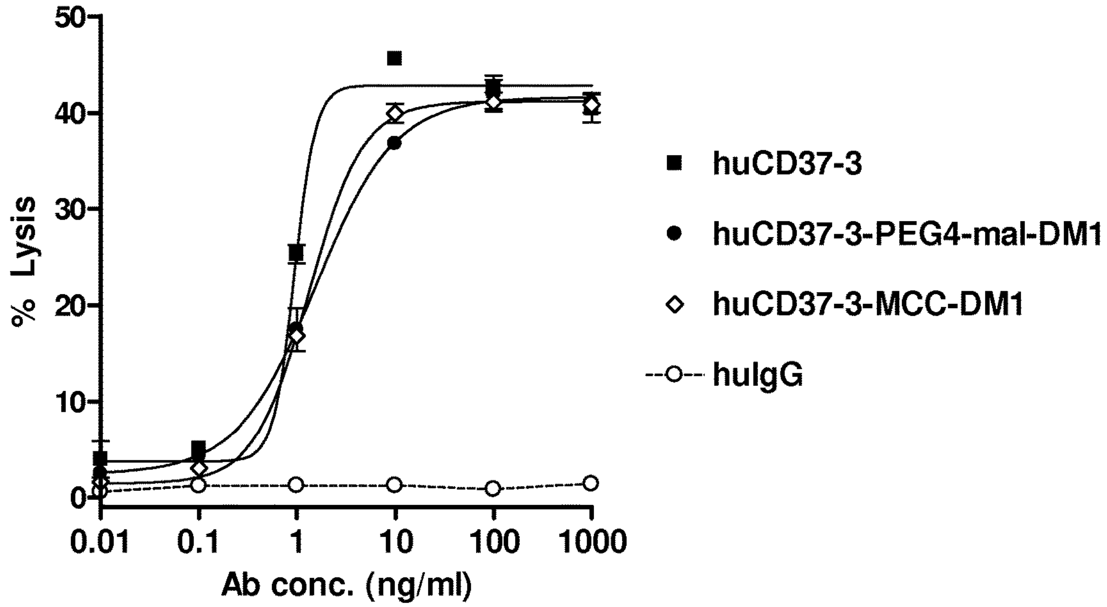

Figure 23
A
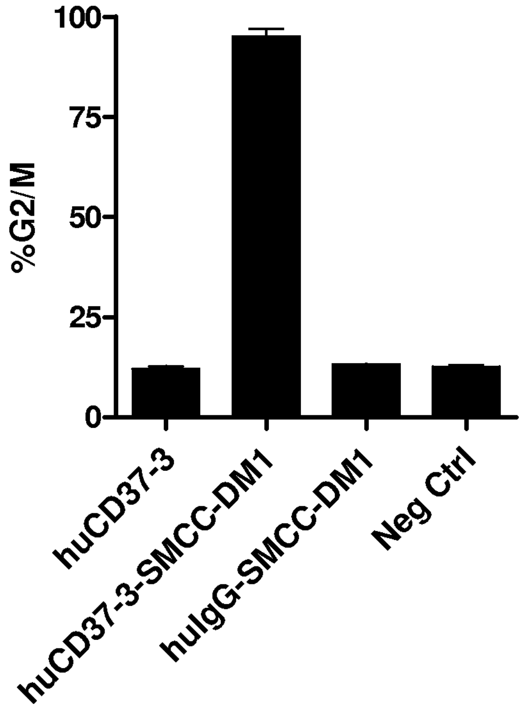
B
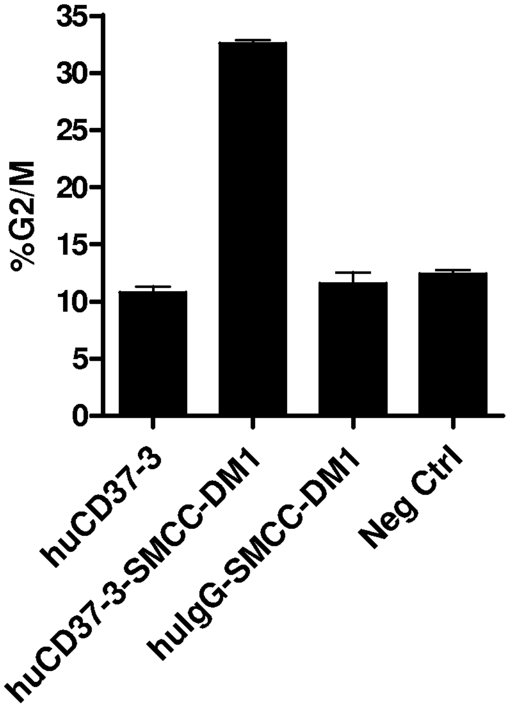

1

CD37-BINDING MOLECULES IMMUNOCONJUGATES THEREOF

CROSS-REFERENCE TO RELATED APPLICATIONS

This application is a continuation of U.S. application Ser. No. 16/221,747, filed Dec. 17, 2018, which is a divisional of U.S. application Ser. No. 15/130,667, filed Apr. 15, 2016, now U.S. Pat. No. 10,202,460, issued Feb. 12, 2019, which is a divisional of U.S. application Ser. No. 13/796,768, filed Mar. 12, 2013, now U.S. Pat. No. 9,346,887, issued May 24, 2016, which is a divisional of U.S. application Ser. No. 13/045,693, filed Mar. 11, 2011, now U.S. Pat. No. 8,765, 917, issued Jul. 1, 2014, which claims the benefit of U.S. Provisional Patent Application No. 61/412,644, filed Nov. 11, 2010, U.S. Provisional Patent Application No. 61/327, 314, filed Apr. 23, 2010, and U.S. Provisional Patent Application No. 61/313,628, filed Mar. 12, 2010, each of which is incorporated herein by reference in its entirety.

FIELD OF THE INVENTION

The field of the invention generally relates to antibodies, antigen-binding fragments thereof, polypeptides, and immunoconjugates that bind to CD37, as well as to methods of using such CD37-binding molecules for the treatment of diseases, such as B-cell malignancies.

REFERENCE TO A SEQUENCE LISTING SUBMITTED ELECTRONICALLY VIA EFS-WEB

The content of the electronically submitted sequence listing (Name: 4018_0010007_Seglisting_ST26; Size 273, 088 bytes; and Date of Creation: Mar. 15, 2023) is herein incorporated by reference in its entirety.

BACKGROUND OF THE INVENTION

Leukocyte antigen CD37 ("CD37"), also known as GP52-40, tetraspanin-26, or TSPAN26, is a transmembrane protein of the tetraspanin superfamily (Maecker et al., 1997 FASEB J. 11:428-442). It is a heavily glycosylated protein with four transmembrane domains that is expressed on B cells during the pre-B to peripheral mature B-cell stages, but is absent on terminal differentiation to plasma cells. (Link et al., 1987, J Pathol. 152:12-21). The CD37 antigen is only weakly expressed on T-cells, myeloid cells and granulocytes (Schwartz-Albiez et al. 1988, J. Immunol., 140(3)905-914). However, CD37 is also expressed on malignant B-cells such as those founding non-Hodgkin's lymphoma (NHL) and chronic lymphoid leukemia (CLL) (Moore et al. 1986, J Immunol. 137(9):3013-8). This expression profile suggests that CD37 represents a promising therapeutic target for B-cell malignancies.

While the exact physiological role of CD37 in unclear, studies suggest a potential role in T-cell proliferation (van Spriel et al. 2004, J Immunol., 172(5):2953-61) As part of the tetraspanin family of cell surface glycoproteins, CD37 may also complex with other surface proteins (Angelisová 1994, Immunogenetics., 39(4):249-56). Mice deficient in CD37 expression were developed and revealed no changes in development and cellular composition of lymphoid organs. Only reduced levels of IgG1 and alterations of responses to T-cell dependent antigens were observed (Knobeloch et al. 2000, Mol Cell Biol., 20(15):5363-9).

2

Antibodies are emerging as a promising method to treat such cancers. In particular, antibodies that are able to induce apoptosis in target cells are desirable. In addition, antibodies having complement-dependent cytotoxicity (CDC) activity and antibody-dependent cytotoxicity (ADCC) are also desirable.

Currently, an anti-CD20 antibody called rituximab is being used to treat B-cell malignancies (Leget et al., 1998, Curr. Opin. Oncol., 10:548-551). However, only a subset of patients respond to rituximab treatment, and even responding patients taking rituximab eventually relapse and often develop resistance to rituximab treatment. In addition, CD37-binding agents are also being tested as potential therapeutics for B-cell malignancies. Trubion Pharmaceuticals developed the CD37-binding agents SMIP-016 and TRU-016 (Zhao et al., 2007, Blood, 110:2569-2577). SMIP-016 is a single chain polypeptide that includes variable regions from a hybridoma and engineered human constant regions. TRU-016 is a humanized version of the anti-CD37 SMIP protein. See e.g. U.S. Published Application No. 2007/0009519. TRU-016 is being tested clinically for the treatment of chronic lyphocytic leukemia (CLL). Boehringer Ingelheim has also disclosed a CD37 binding agent in International Published Application No. WO 2009/019312. However, no CDC activity has been described for any of these binding agents and no in vitro pro-apoptotic activity has been described in the absence of cross-linking agents.

Radio-immunotherapy (RIT) has been attempted using a radio-labeled anti-CD37 antibody MB-1 in two separate trials. Therapeutic doses of $^{1311}$-MB-1 were administered to six relapsed NHL patients (Press et al. 1989 J Clin Oncol. 7(8):1027-38, Press at el. 1993, N Engl J Med. 329(17): 1219-24). All six patients achieved a complete remission (CR) with a duration of four to thirty-one months. In another trial, $^{1311}$-MB-1 was administered to ten relapsed NHL patients (Kaminski et al. 1992 J Clin Oncol. 10(11):1696-711). A total of four patients had a response ranging in duration from two to six months, although only one CR was reported. However, not all patients could be treated due to an unfavorable biodistribution of the radio-label which raised concern for radiation exposure of vital non-target organs. Indeed, RIT related toxicities were observed in these trials including severe myelosupression and cardiopulmonary toxicity. While these clinical data suggest that anti-CD37 radio-immunoconjugates may be effective, these therapies are cumbersome to administer, and at relapse post-RIT patients cannot be retreated with RIT due to the risks associated with high doses of radiation.

To overcome the limitations of RIT, antibody-cytotoxic agent conjugates (ACC), also called antibody-drug conjugates (ADC), have been developed. These are immunoconjugates that include a cytotoxic agent covalently linked to an antibody through a chemical linker which can allow for specific delivery of cytotoxic drugs to cells expressing a protein recognized by the antibody. However, proteins that are poorly internalized are not considered to be favorable targets for such therapeutics. CD37 is structurally similar to CD20 as both antigens contain four transmembrane domains, although CD20 is not part of the tetraspanin family (Tedder et al. 1989, J. Immun. 142: 2560-2568). Antibodies against several B-cell antigens including CD37 and CD20 have been studied for their ability to undergo endocytosis and degradation (Press et al. 1989, Cancer Res. 49(17): 4906-12, and Press et al. 1994, Blood. 83(5):1390-7). The anti-CD37 antibody MB-1 was retained on the cell surface and internalized slowly in Daudi lymphoma cells in vitro. The MB-1 antibody also had a low rate of endocytosis and intracellular metabolism in NHL patient cells in vitro. Similar results were obtained with the anti-CD20 antibody 1F5, which was also retained mainly on the lymphoma cell surface and internalized poorly. ADCs of CD20 antibodies have been studied previously but have not demonstrated significantly strong potency, especially when non-disulfide or acid stable linkers are used (see for example Polson et al., 2009, Cancer Res., 69(6):2358-2364). In light of these observations, CD37 has not been considered a favorable target for antibody-drug conjugates.

Therefore, there exists a need for CD37 binding agents including antibodies, antigen-binding fragments thereof, and antibody-drug conjugates (immunoconjugates) as a means to treat B-cell malignancies. The present invention addresses that need.

BRIEF SUMMARY OF THE INVENTION

Novel antibodies that bind to human CD37, immunoconjugates comprising these antibodies, and methods of their use are described herein. Novel polypeptides, such as antibodies that bind human CD37, fragments of such antibodies, and other polypeptides related to such antibodies are also provided. Polynucleotides comprising nucleic acid sequences encoding the polypeptides are also provided, as are vectors comprising the polynucleotides. Cells comprising the polypeptides and/or polynucleotides of the invention are further provided. Compositions (e.g., pharmaceutical compositions) comprising the novel CD37 antibodies or immunoconjugates are also provided. In addition, methods of making and using the novel CD37 antibodies or immunoconjugates are also provided, such as methods of using the novel CD37 antibodies or immunoconjugates to inhibit tumor growth and/or treat cancer.

Antibodies or antigen binding fragment thereof that specifically bind to CD37, and are capable of inducing complement dependent cytotoxicity (CDC) are provided. In some embodiments, the antibody is also capable of inducing apoptosis and/or antibody dependent cell mediated cytotoxicity (ADCC).

The antibody or antigen binding fragment thereof can be one that specifically binds to the same CD37 epitope as an antibody selected from the group consisting of: (a) an antibody comprising the polypeptide of SEQ ID NO:55 and the polypeptide of SEQ ID NO:72; (b) an antibody comprising the polypeptide of SEQ ID NO:59 and the polypeptide of SEQ ID NO:75; (c) an antibody comprising the polypeptide of SEQ ID NO:61 and the polypeptide of SEQ ID NO:77; (d) an antibody comprising the polypeptide of SEQ ID NO:64 and the polypeptide of SEQ ID NO:80; (e) an antibody comprising the polypeptide of SEQ ID NO:66 and the polypeptide of SEQ ID NO:82; (f) an antibody comprising the polypeptide of SEQ ID NO:68 and the polypeptide of SEQ ID NO: 84; and (g) an antibody comprising the polypeptide of SEQ ID NO:70 and the polypeptide of SEQ ID NO:86.

In some embodiments, the antibody or antigen binding fragment thereof specifically binds to CD37 and specifically binds to the polypeptide of SEQ ID NO: 180. In a certain embodiment, the antibody or antigen binding fragment thereof does not bind to the polypeptide of SEQ ID NO: 184.

In some embodiments, the antibody or antigen binding fragment thereof specifically binds to CD37, and the antibody or fragment thereof competitively inhibits an antibody selected from the group consisting of: (a) an antibody comprising the polypeptide of SEQ ID NO:55 and the polypeptide of SEQ ID NO:72; (b) an antibody comprising the polypeptide of SEQ ID NO:59 and the polypeptide of SEQ ID NO:75; (c) an antibody comprising the polypeptide of SEQ ID NO:61 and the polypeptide of SEQ ID NO:77; (d) an antibody comprising the polypeptide of SEQ ID NO:64 and the polypeptide of SEQ ID NO:80; (e) an antibody comprising the polypeptide of SEQ ID NO:66 and the polypeptide of SEQ ID NO:82; (f) an antibody comprising the polypeptide of SEQ ID NO:68 and the polypeptide of SEQ ID NO: 84; and (g) an antibody comprising the polypeptide of SEQ ID NO:70 and the polypeptide of SEQ ID NO:86.

In certain embodiments, the antibody or antigen binding fragment thereof is produced by hybridoma selected from the group consisting of ATCC Deposit Designation PTA-10664, deposited with the ATCC on Feb. 18, 2010, ATCC Deposit Designation PTA-10665, deposited with the ATCC on Feb. 18, 2010, ATCC Deposit Deisgnation PTA-10666, deposited with the ATCC on Feb. 18, 2010, ATCC Deposit Designation PTA-10667 deposited with the ATCC on Feb. 18, 2010, ATCC Deposit Designation PTA-10668, deposited with the ATCC on Feb. 18, 2010, ATCC Deposit Designation PTA-10669, deposited with the ATCC on Feb. 18, 2010, and ATCC Deposit Designation PTA-10670, deposited with the ATCC on Feb. 18, 2010.

In some embodiments, the antibody or antigen binding fragment thereof specifically binds to CD37, and the antibody comprises polypeptide sequences selected from the group consisting of: (a) SEQ ID NOs: 4, 5, and 6 and SEQ ID NOs: 28, 29, and 30; (b) SEQ ID NOs: 7, 8, and 9 and SEQ ID NOs: 31, 32, and 33; (c) SEQ ID NOs: 10, 11, and 12 and SEQ ID NOs: 34, 35, and 36; (d) SEQ ID NOs: 13, 14, and 15 and SEQ ID NOs: 37, 38, and 39; (e) SEQ ID NOs: 13, 14, and 15 and SEQ ID NOs: 37, 40, and 39; (f) SEQ ID NOs: 16, 17, and 18 and SEQ ID NOs: 41, 42, and 43; (g) SEQ ID NOs: 19, 20, and 21 and SEQ ID NOs: 44, 45, and 46; (h) SEQ ID NOs: 19, 20, and 21 and SEQ ID NOs: 44, 47, and 46; (i) SEQ ID NOs: 22, 23, and 24 and SEQ ID NOs: 48, 49, and 50; (j) SEQ ID NOs: 22, 23, and 24 and SEQ ID NOs: 48, 51, and 50; (k) SEQ ID NOs: 25, 26, and 27 and SEQ ID NOs: 52, 53, and 54; and (1) variants of (a) to (k) comprising 1, 2, 3, or 4 conservative amino acid substitutions.

In further embodiments, the antibody or antigen binding fragment thereof comprises polypeptide sequences that are at least 90% identical, at least 95% identical, at least 99% identical, or identical to polypeptide sequences selected from the group consisting of: (a) SEQ ID NO:55 and SEQ ID NO:72; (b) SEQ ID NO:56 and SEQ ID NO:73; (c) SEQ ID NO:57 and SEQ ID NO:74; (d) SEQ ID NO:58 and SEQ ID NO:74; (e) SEQ ID NO:59 and SEQ ID NO:75; (f) SEQ ID NO:60 and SEQ ID NO:76; (g) SEQ ID NO:61 and SEQ ID NO:77; (h) SEQ ID NO:62 and SEQ ID NO:78; (i) SEQ ID NO:63 and SEQ ID NO:79; (j) SEQ ID NO:64 and SEQ ID NO:80; (k) SEQ ID NO:65 and SEQ ID NO:81; (1) SEQ ID NO:66 and SEQ ID NO:82; (m) SEQ ID NO:67 and SEQ ID NO:83; (n) SEQ ID NO:68 and SEQ ID NO:84; (o) SEQ ID NO:69 and SEQ ID NO:85; (p) SEQ ID NO:70 and SEQ ID NO:86; and (q) SEQ ID NO:71 and SEQ ID NO:87.

In some embodiments, the antibody or antigen binding fragment thereof is murine, non-human, humanized, chimeric, resurfaced, or human.

In some embodiments, the antibody or antibody fragment is capable of inducing apoptosis of a cell expressing CD37 in vitro in the absence of cross-linking agents. In some embodiments, the antibody or antigen binding fragment is capable of inducing complement dependent cytotoxicity (CDC). In still further embodiments, the antibody or antigen binding fragment is capable of inducing antibody dependent cell mediated cytotoxicity (ADCC).

In other embodiments, the antibody or antigen binding fragment thereof is human or humanized, specifically binds to CD37, and is capable of inducing apoptosis of a cell expressing CD37 in vitro in the absence of cross-linking agents. In further embodiments, the human or humanized antibody or antigen binding fragment thereof is also capable of inducing complement dependent cytotoxicity (CDC) and/or capable of inducing antibody dependent cell mediated cytotoxicity (ADCC).

In still other embodiments, the antibody or antigen binding fragment thereof binds to human CD37 and macaque CD37.

In some embodiments, the antibody or antigen binding fragment thereof is a full length antibody or an antigen binding fragment. The antibody or antigen binding fragment thereof can comprise a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

In other embodiments, the CD37-binding agent is a polypeptide that specifically binds CD37, and the polypeptide comprises sequences selected from the group consisting of: (a) SEQ ID NOs: 4, 5, and 6 and SEQ ID NOs: 28, 29, and 30; (b) SEQ ID NOs: 7, 8, and 9 and SEQ ID NOs: 31, 32, and 33; (c) SEQ ID NOs: 10, 11, and 12 and SEQ ID NOs: 34, 35, and 36; (d) SEQ ID NOs: 13, 14, and 15 and SEQ ID NOs: 37, 38, and 39; (e) SEQ ID NOs: 13, 14, and 15 and SEQ ID NOs: 37, 40, and 39; (f) SEQ ID NOs: 16, 17, and 18 and SEQ ID NOs: 41, 42, and 43; (g) SEQ ID NOs: 19, 20, and 21 and SEQ ID NOs: 44, 45, and 46; (h) SEQ ID NOs: 19, 20, and 21 and SEQ ID NOs: 44, 47, and 46; (i) SEQ ID NOs: 22, 23, and 24 and SEQ ID NOs: 48, 49, and 50; (j) SEQ ID NOs: 22, 23, and 24 and SEQ ID NOs: 48, 51, and 50; (k) SEQ ID NOs: 25, 26, and 27 and SEQ ID NOs: 52, 53, and 54; and (1) variants of (a) to (k) comprising 1, 2, 3, or 4 conservative amino acid substitutions.

In other embodiments, the CD37-binding agent is a polypeptide that specifically binds CD37, and the polypetide comprises sequences that are at least 90% identical, at least 95% identical, at least 99% identical, or identical to sequences selected from the group consisting of: (a) SEQ ID NO:55 and SEQ ID NO:72; (b) SEQ ID NO:56 and SEQ ID NO:73; (c) SEQ ID NO:57 and SEQ ID NO:74; (d) SEQ ID NO:58 and SEQ ID NO:74; (e) SEQ ID NO:59 and SEQ ID NO:75; (f) SEQ ID NO:60 and SEQ ID NO:76; (g) SEQ ID NO:61 and SEQ ID NO:77; (h) SEQ ID NO:62 and SEQ ID NO:78; (i) SEQ ID NO:63 and SEQ ID NO:79; (j) SEQ ID NO:64 and SEQ ID NO:80; (k) SEQ ID NO:65 and SEQ ID NO:81; (1) SEQ ID NO:66 and SEQ ID NO:82; (m) SEQ ID NO:67 and SEQ ID NO:83; (n) SEQ ID NO:68 and SEQ ID NO:84; (o) SEQ ID NO:69 and SEQ ID NO:85; (p) SEQ ID NO:70 and SEQ ID NO:86; and (q) SEQ ID NO:71 and SEQ ID NO:87.

Cells producing the antibody or antigen binding fragment thereof or the polypeptide can also be made and used according to the methods described herein. The methods provide methods of making an antibody or antigen-binding fragment thereof or a polypeptide comprising (a) culturing a cell producing such a CD37-binding agent; and (b) isolating the antibody, antigen-binding fragment thereof, or polypeptide from the cultured cell.

In some embodiments, the CD37-binding agent is an immunoconjugate having the formula (A)-(L)-(C), wherein: (A) is a CD37-binding agent; (L) is a linker; and (C) is a cytotoxic agent; and wherein the linker (L) links (A) to (C).

In some embodiments, the CD37-binding agent is an immunoconjugate having the formula (A)-(L)-(C), wherein: (A) is an antibody or antigen binding fragment that specifically binds to CD37; (L) is a non-cleavable linker; and (C) is a cytotoxic agent; and wherein the linker (L) links (A) to (C).

In some embodiments, the CD37-binding agent is an immunoconjugate having the formula (A)-(L)-(C), wherein: (A) is an antibody or antigen binding fragment that specifically binds to CD37; (L) is a linker; and (C) is a maytansinoid; and wherein the linker (L) links (A) to (C).

The immunoconjugate linker can be a non-cleavable linker. The linker can be selected from a group consisting of a cleavable linker, a non-cleavable linker, a hydrophilic linker, and a dicarboxylic acid based linker. The linker can be selected from the group consisting of: N-succinimidyl 4-(2-pyridyldithio)pentanoate (SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl) cyclohexanecarboxylate (SMCC); N-sulfosuccinimidyl 4-(maleimidomethyl) cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol]ester (NHS-PEG4-maleimide). The linker can be N-succinimidyl-[(N-maleimidopropionamido)-tetraethyleneglycol]ester (NHS-PEG4-maleimide).

The cytotoxic agent can be selected from the group consisting of a maytansinoid, maytansinoid analog, doxorubicin, a modified doxorubicin, benzodiazepine, taxoid, CC-1065, CC-1065 analog, duocarmycin, duocarmycin analog, calicheamicin, dolastatin, dolastatin analog, aristatin, tomaymycin derivative, and leptomycin derivative or a prodrug of the agent. The cytotoxic agent can be a maytansinoid. The cytotoxic agent can be N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

Also provided herein is a pharmaceutical composition comprising a CD37-binding agent and a pharmaceutically acceptable carrier. The pharmaceutical composition can comprise a second anti-cancer agent.

A diagnostic reagent comprising a CD37-binding agent which is labeled is also provided herein. The label can be selected from the group consisting of a radiolabel, a fluorophore, a chromophore, an imaging agent and a metal ion.

Also provided herein is a kit comprising a CD37-binding agent.

The methods described herein include methods for inhibiting the growth of a cell expressing CD37 comprising contacting the cell with a CD37 binding agent or pharmaceutical composition comprising the same.

The methods also provide methods for treating a patient having cancer comprising administering to the patient a therapeutically effective amount of a CD37 binding agent or pharmaceutical composition comprising the same to the subject.

The methods can comprise administering a second anti-cancer agent to the subject. The second anti-cancer agent can be a chemotherapeutic agent.

The cancer can be a cancer selected from the group consisting of B cell lymphomas, NHL, precursor B cell lymphoblastic leukemia/lymphoma and mature B cell neoplasms, B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), low grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

Isolated polynucleotides comprising a sequence that encodes a polypeptide at least 90% identical, at least 95% identical, at least 99% identical, or identical to a sequence selected from the group consisting of SEQ ID NOs: 55-87 are also provided herein. The polynucleotide can comprise a sequence that is at least 90%, at lesat 95% identical, at least 99% identical, or identical to SEQ ID NOs: 121-151.

Vectors and host cells comprising such polynucleotides and vectors are also provided herein.

BRIEF DESCRIPTION OF THE DRAWINGS/FIGURES

FIG. 1 depicts the histograms for antibody binding to non-transfected 300-19 control cells (left panels) and CD37-expressing 300-19 cells (right panels). Histograms are shown for staining with 10 nM of muCD37-3, muCD37-12, muCD37-38 and the absence of primary antibody.

FIG. 2 depicts the histograms for antibody binding to non-transfected 300-19 control cells (left panels) and CD37-expressing 300-19 cells (right panels). Histograms are shown for staining with 10 nM muCD37-50, muCD37-51, muCD37-56 and muCD37-57.

FIG. 3 depicts the binding of (A) muCD37-3 and muCD37-12 and (B) muCD37-8, muCD37-10 and muCD37-14 to WSU-DLCL-2 cells as assayed by flow cytometry. Mean fluorescence intensity (MFI) is plotted for each antibody concentration used. The binding curves were used to determine the EC50 of antibody binding, which corresponds to the apparent Kd of each antibody.

FIG. 4 depicts results from an Annexin-V assay to measure induction of apoptosis using Ramos lymphoma cells incubated with a 10 nM concentration of (A) rituximab, muCD37-3, muCD37-8, muCD37-10, muCD37-12 or muCD37-14 and (B) rituximab, huCD37-3, muCD37-38, muCD37-50, muCD37-51, muCD37-56 or muCD37-57. Control samples of untreated cells in the absence of antibody (no Ab) are used in comparison.

FIG. 6 depicts a list of CD37-3 surface residues and substitutions in resurfaced versions for (A) CD37-3 VL and (B) CD37-3 VH.

FIG. 7 depicts a list of CD37-50 surface residues and substitutions in the resurfaced version for (A) CD37-50 VL and (B) CD37-50 VH.

FIG. 8 depicts alignments of resurfaced sequences for the CD37-3 and CD37-50 variable region with their murine counterparts: A) CD37-3 light chain variable domain; B) CD37-3 heavy chain variable domain. C) CD37-50 light chain variable domain; D) CD37-50 heavy chain variable domain. Dashes "-" denote identity with the murine sequence.

FIG. 9 depicts (A) direct binding assays of muCD37-3, chCD37-3, muCD37-12 and chCD37-12 to Ramos cells as assayed by flow cytometry and (B) competitive binding assays with muCD37-3, chCD37-3, huCD37-3v1.0 and huCD37-3v1.01 to BJAB cells in the presence of 2 nM concentration of muCD37-3-PE conjugates.

Figure 10:
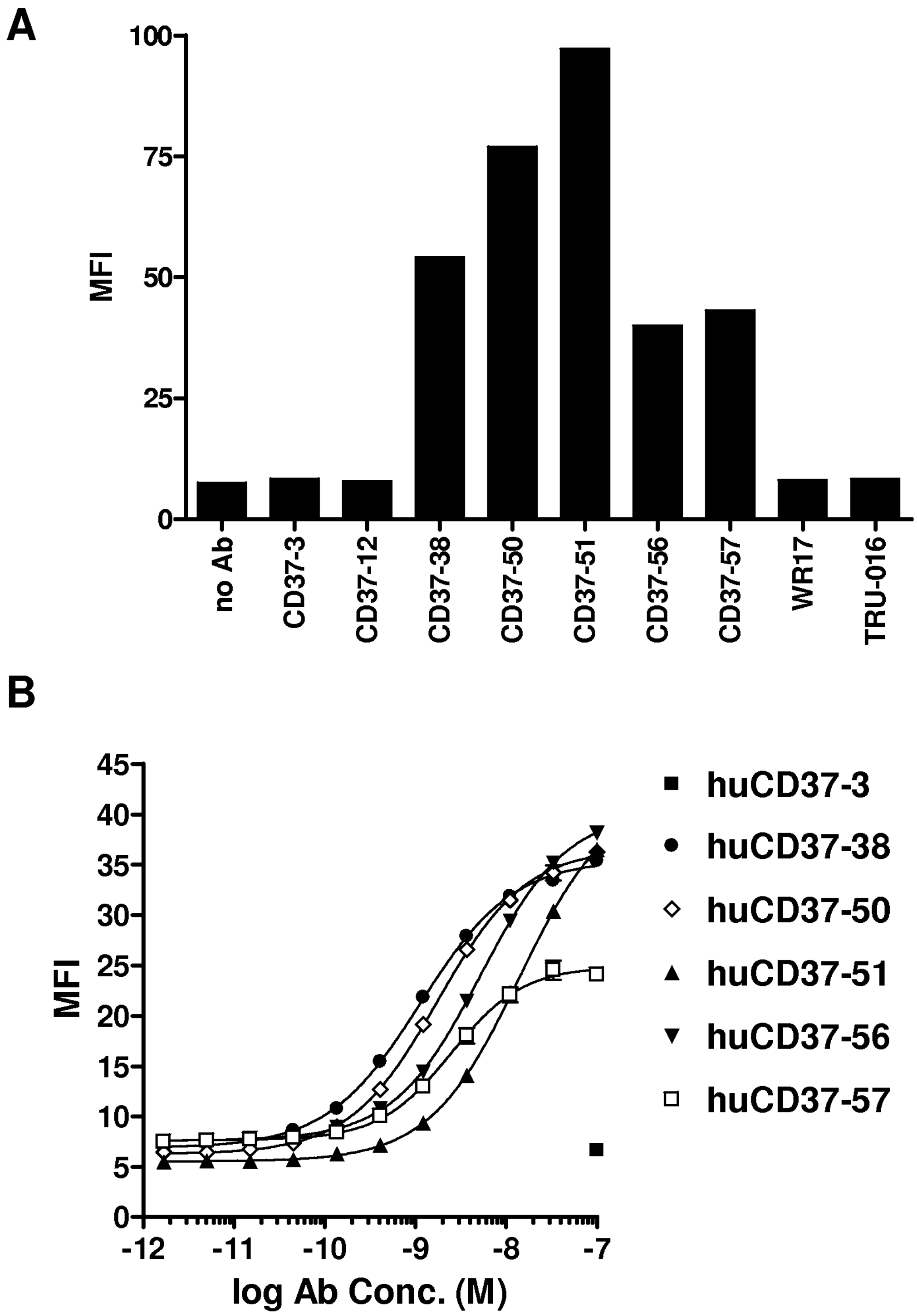

FIG. 10 depicts binding of anti-CD37 antibodies to 300-19 cells expressing the macaque CD37 antigen as assayed by flow cytometry: (A) binding of muCD37-3, muCD37-12, muCD37-38, muCD37-50, muCD37-51, muCD37-56, muCD37-57, WR17 and TRU-016 and (B) binding of huCD37-3, huCD37-38, huCD37-50, huCD37-51, huCD37-56 and huCD37-57. The binding curves were used to determine the EC50 of antibody binding, which corresponds to the apparent Kd of each antibody.

Figure 11:
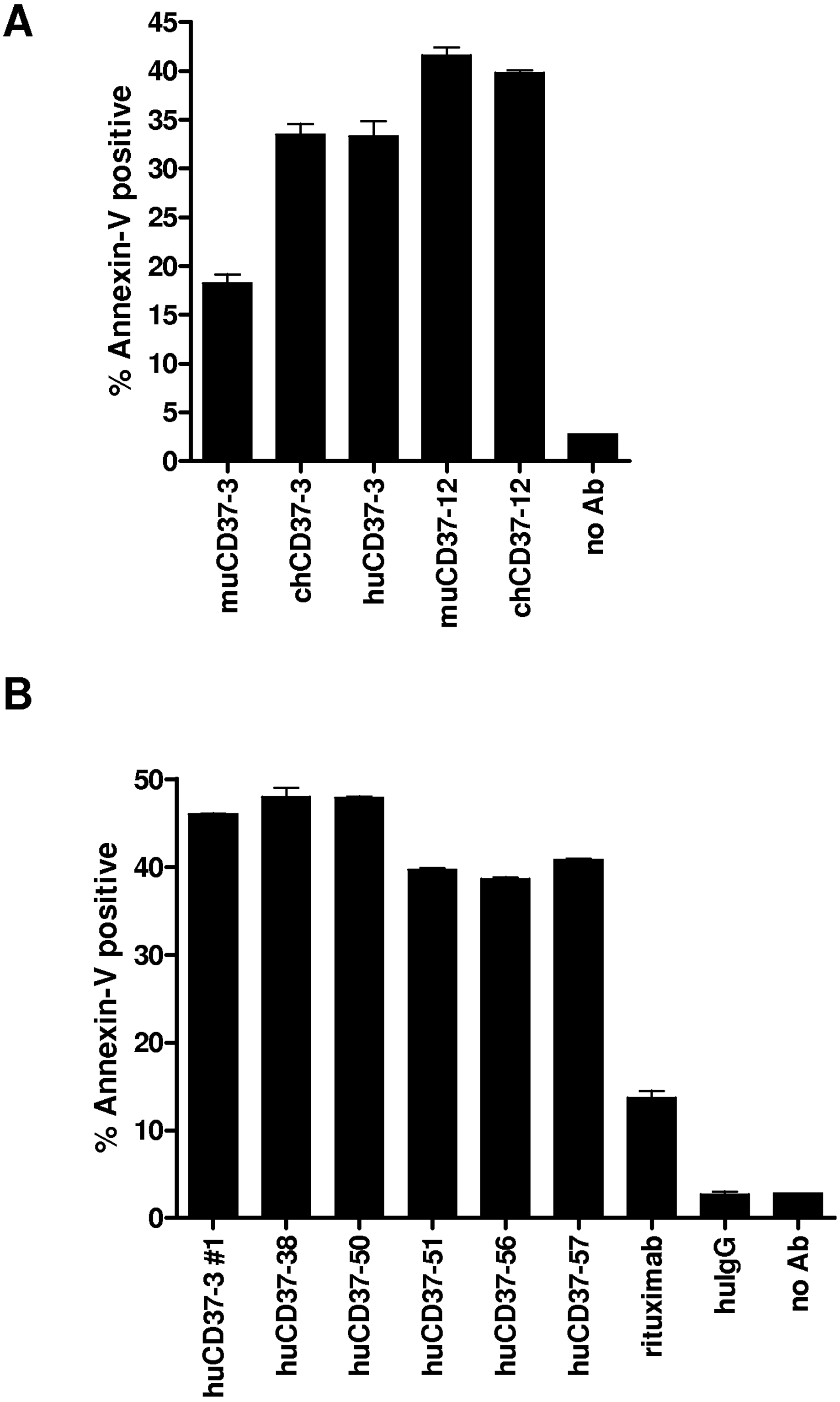

FIG. 11 depicts the results from an Annexin-V assay to measure induction of apoptosis on Ramos lymphoma cells incubated with varying concentration of (A) huCD37-3, huCD37-38, huCD37-50 and (B) huCD37-51, huCD37-56, huCD36-57 and rituximab. Control samples of cells treated with a human IgG1 isotype control antibody (huIgG control) are used in comparison.

Figure 12:
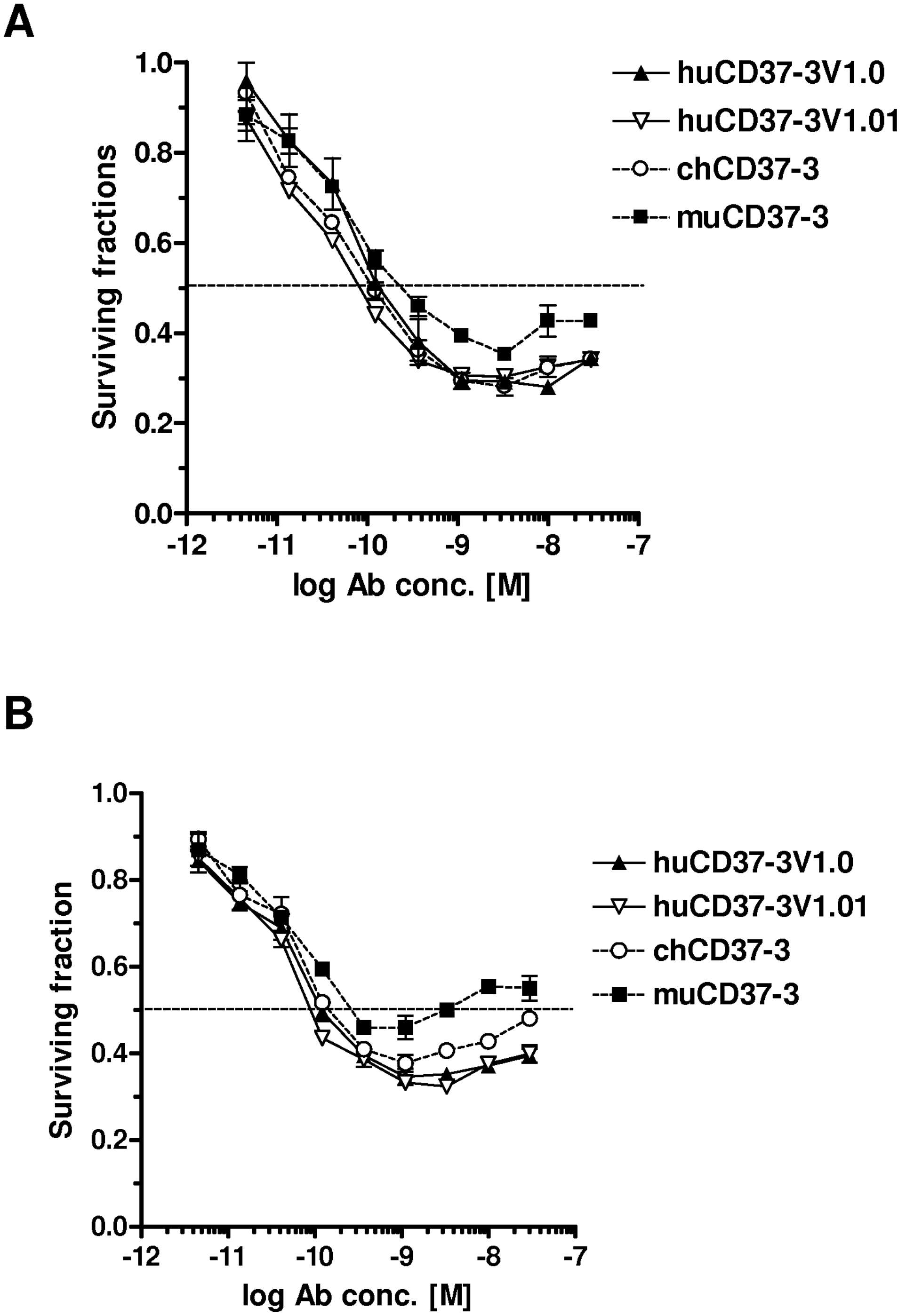

FIG. 12 depicts the results from WST-8 proliferation assays on (A) SU-DHL-4 and (B) DOHH-2 lymphoma cells incubated with varying concentrations of muCD37-3, chCD37-3, huCD37-3v1.0 and huCD37-3v1.01 antibodies for 5 days.

Figure 13:
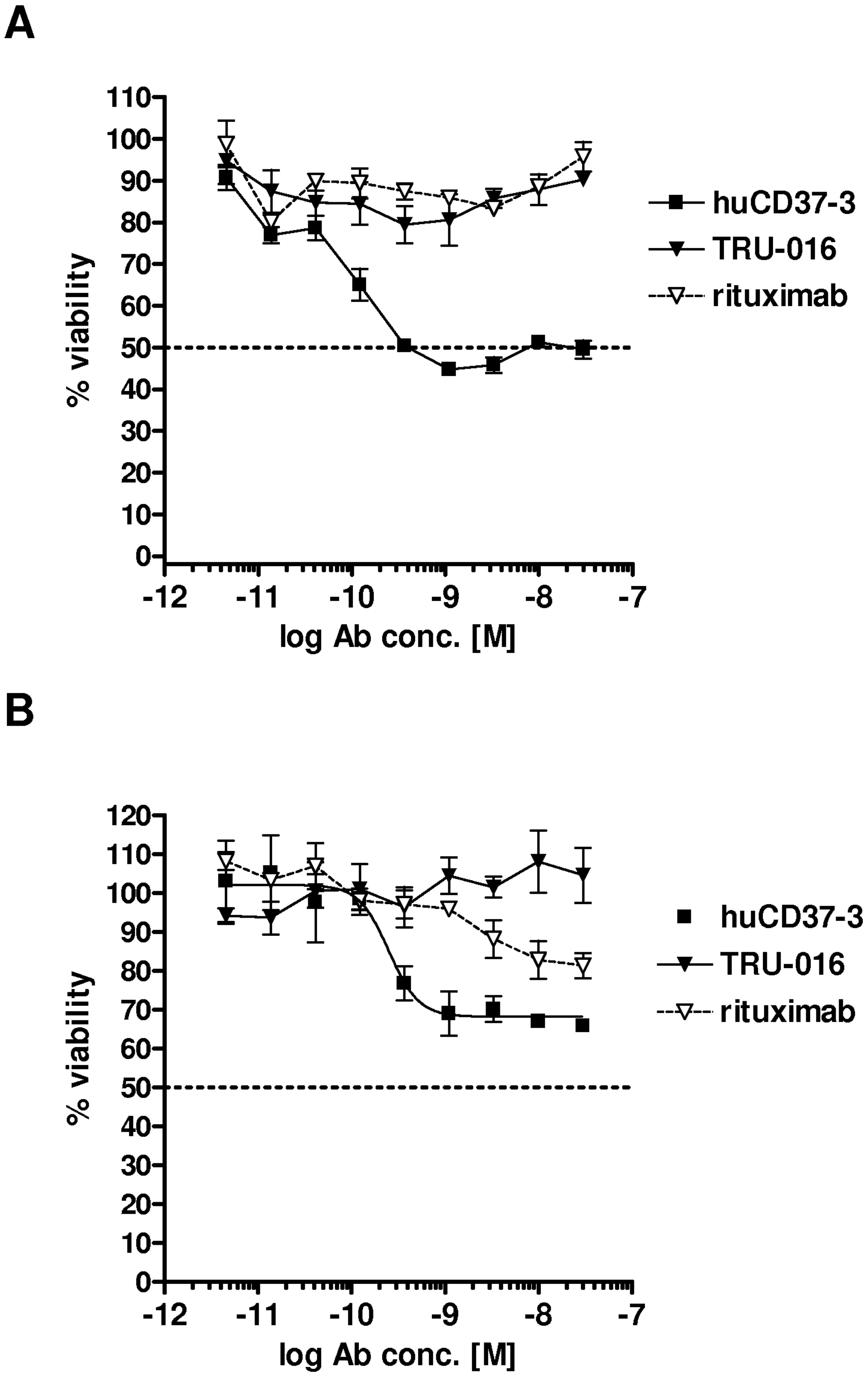

FIG. 13 depicts the results from WST-8 proliferation assays on (A) Granta-519 and (B) SU-DHL-4 lymphoma cells incubated with varying concentrations of huCD37-3, TRU-016 or rituximab antibodies for 5 days.

FIG. 14 depicts the results from CDC assays on Ramos lymphoma cells incubated with (A) huCD37-3, huCD37-38, chCD37-12 or a huIgG1 isotype control antibody and (B) huCD37-38, huCD37-50, huCD37-51, huCD37-56, huCD37-57, chCD37-12 or a huIgG1 isotype control antibody in the presence of 5% human serum as a source of complement.

FIG. 15 depicts the results from an ADCC assay on Daudi lymphoma cells incubated with (A) huCD37-3, huCD37-38, huCD37-50, TRU-016 and (B) huCD37-51, huCD37-56, huCD37-57, TRU-016 or a human IgG1 isotype control antibody in the presence of purified human NK cells as effector cells.

FIG. 16 depicts the alignment of the full length murine, human, and macaca CD37 amino acid sequences. Dashes "-" denote identity with the murine sequence. The small and large extracellular domains are marked with underlines.

FIG. 17 depicts the alignment of the large extracellular domain of human, recombinant and wild type murine, macaca and the chimeric CD37 sequences. Dashes "-" denote identity with the human sequence. The positions of the engineered restriction sites are given and the affected residues are underlined.

FIG. 18 depicts binding of a panel of CD37 antibodies to cells transfected with (A) human CD37 wildtype and (B) hCD37-M3 variant as assayed by flow cytometry using 1.5 g/mL of each antibody.

Figure 19:
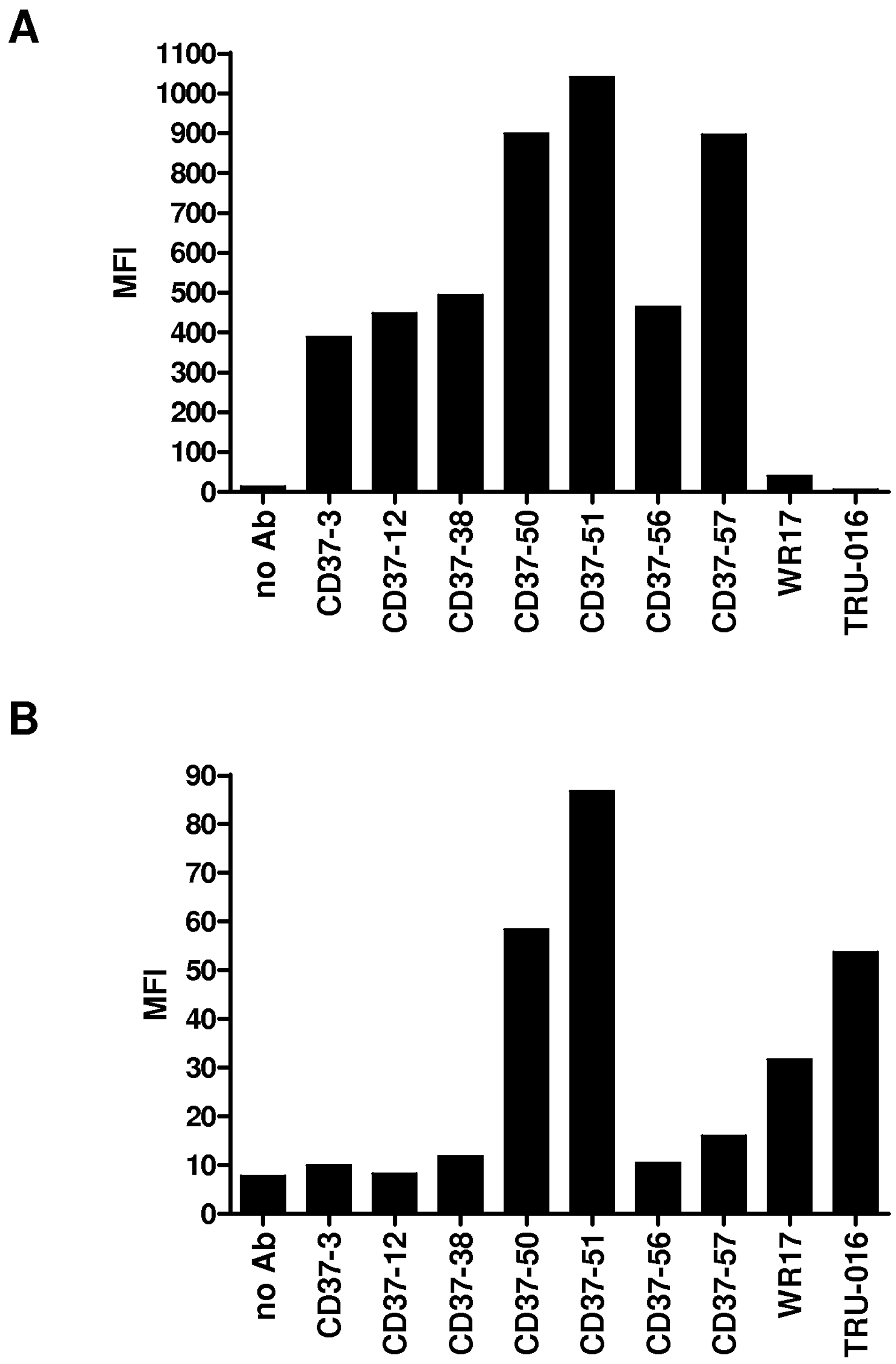

FIG. 19 depicts binding of a panel of CD37 antibodies to cells transfected with (A) the hCD37-M1 variant and (B) the hCD37-M45 variant as assayed by flow cytometry using 1.5 g/mL of each antibody.

FIG. 20 depicts binding of (A) huCD37-3 in comparison with huCD37-3-SMCC-DM1 huCD37-3-SPP-DM1 and huCD37-3-sulfo-mal-DM4 and (B) huCD37-38 in comparison with huCD37-38-SMCC-DM1 to BJAB cells as assayed by flow cytometry. The binding curves were used to determine the EC50 of antibody or conjugate binding, which corresponds to the apparent Kd of each.

FIG. 21 depicts the results of (A) an Annexin-V assay to measure induction of apoptosis and (B) the results from a CDC assay. Assays were performed on Ramos lymphoma cells incubated with varying concentrations of the huCD37-3, huCD37-3-SMCC-DM1, huIgG1 control antibody, huIgG1-SMCC-DM1 control conjugate, or rituximab. CDC assays were performed in the presence of 5% human serum as a source of complement.

FIG. 22 depicts the results from ADCC assays on (A) Daudi lymphoma cells incubated with huCD37-3, huCD37-3-SMCC-DM1, huCD37-3-PEG4-mal-DM1, TRU-016 or a huIgG1 isotype control antibody and (B) Ramos lymphoma cells incubated with huCD37-3, huCD37-3-SMCC-DM1, huCD37-3-PEG4-mal-DM1 or a huIgG1 isotype control antibody in the presence of purified human NK cells as effector cells.

FIG. 23 depicts the results from a cell cycle analysis using propridium iodide staining on (A) BJAB cells and (B) RL cells incubated with huCD37-3, huCD37-3-SMCC-DM1, or a non-binding huIgG1-SMCC-DM1 control conjugate at a 10 nM concentration for 20 hours.

Figure 24:
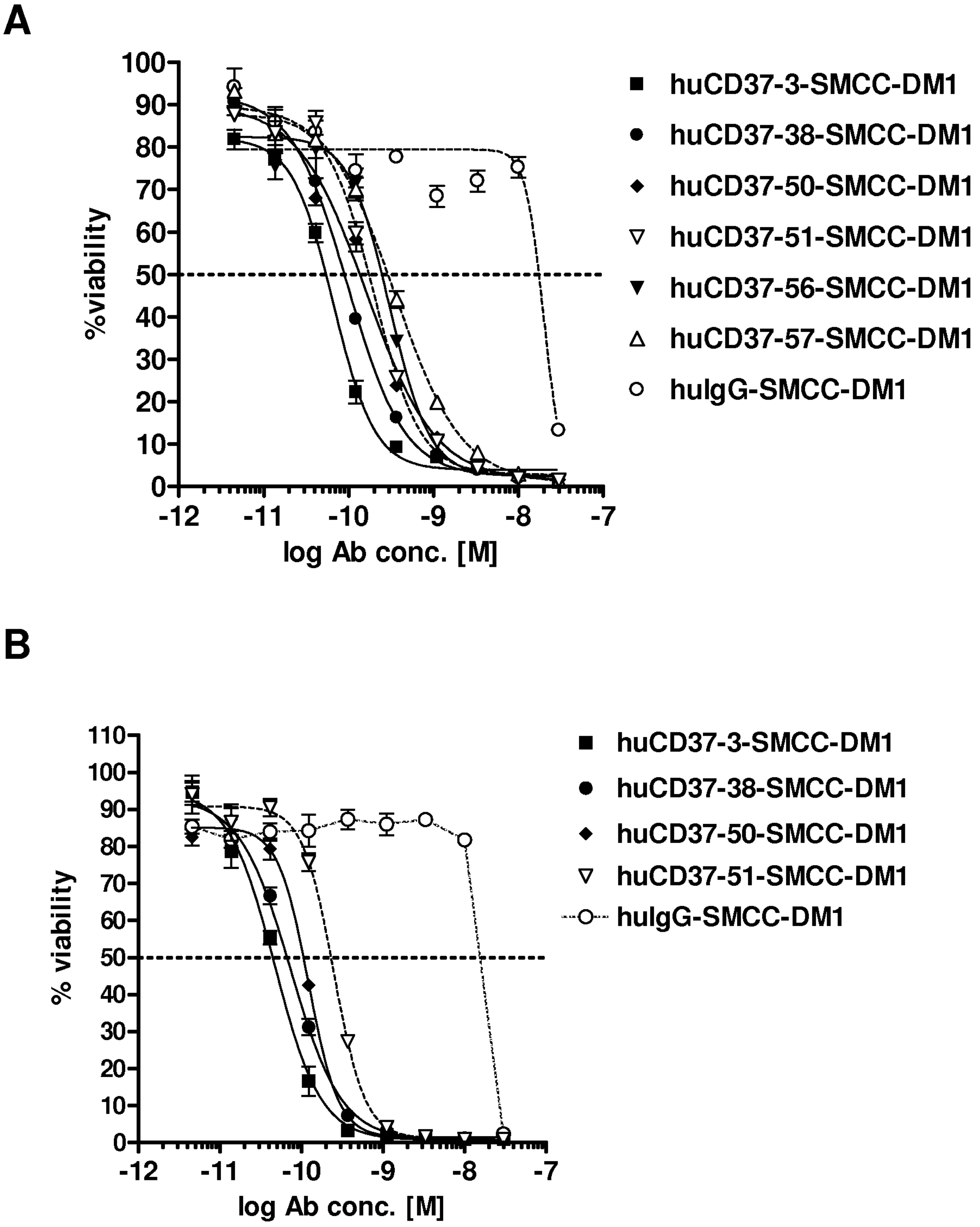

FIG. 24 depicts the results from a WST-8 cytotoxicity assay on (A) Daudi cells incubated with huCD37-3-SMCC-DM1, huCD37-38-SMCC-DM1, huCD37-50-SMCC-DM1, huCD37-51-SMCC-DM1, huCD37-56-SMCC-DM1, huCD37-57-SMCC-DM1, and (B) Granta-519 cells incubated with huCD37-3-SMCC-DM1, huCD37-38-SMCC-DM1, huCD37-50-SMCC-DM1, huCD37-51-SMCC-DM1, or a non-binding huIgG1-SMCC-DM1 control conjugate at concentrations ranging from $3\times10^{-8}$ M to $1\times10^{-11}$ M for 5 days.

Figure 25:
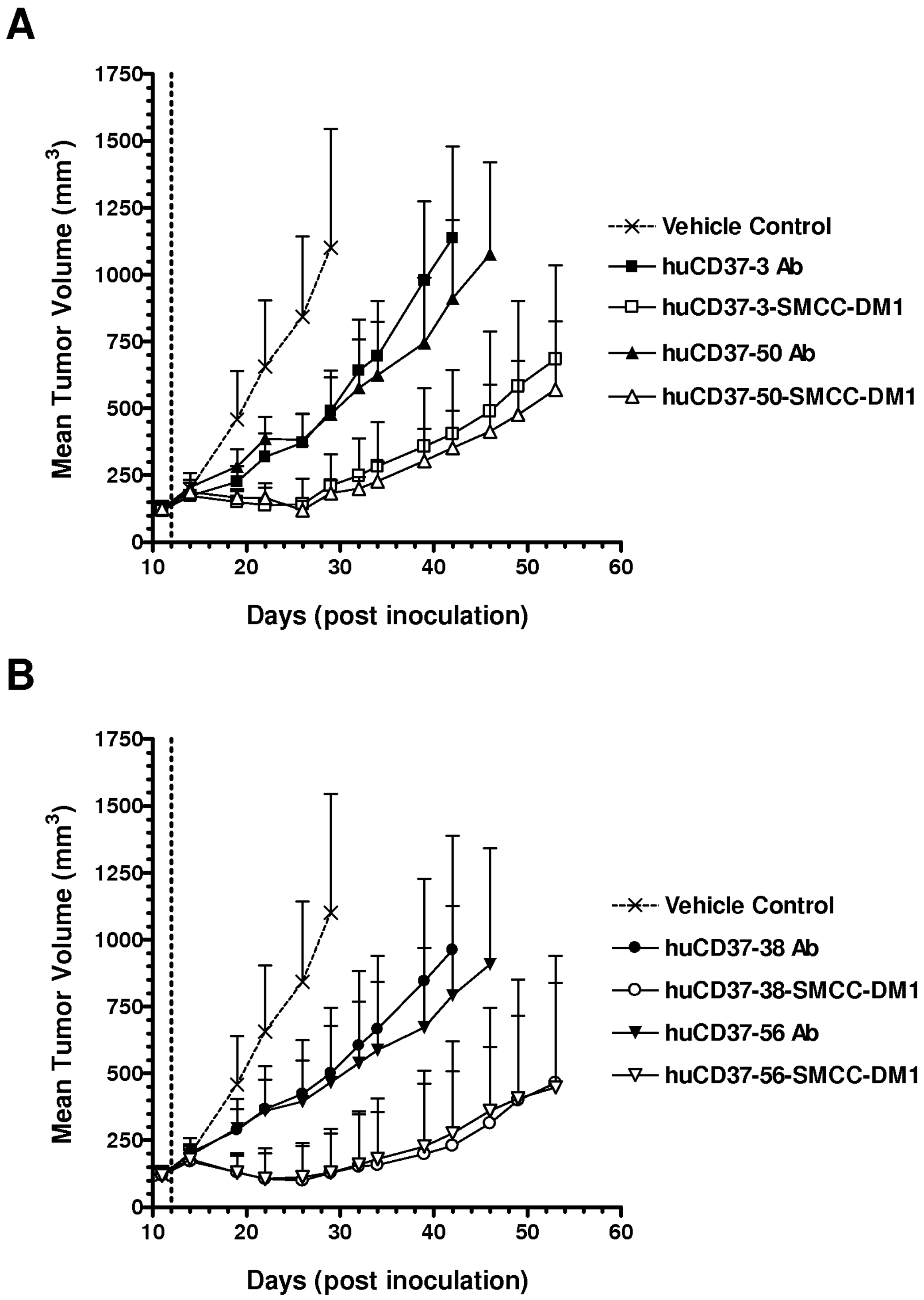

FIG. 25 depicts the results of an established xenograft model using BJAB lymphoma cells implanted subcutaneous into SCID mice. Animals were treated once on day 12 post cell inoculation with either 10 mg/kg of (A) huCD37-3 Ab, huCD37-3-SMCC-DM1, huCD37-50 Ab, huCD37-50-SMCC-DM1 or (B) huCD37-38 Ab, huCD37-38-SMCC-DM1, huCD37-56 Ab, huCD37-56-SMCC-DM1. The mean tumor volume of the different treatment groups is plotted against time post tumor cell inoculation.

Figure 26:
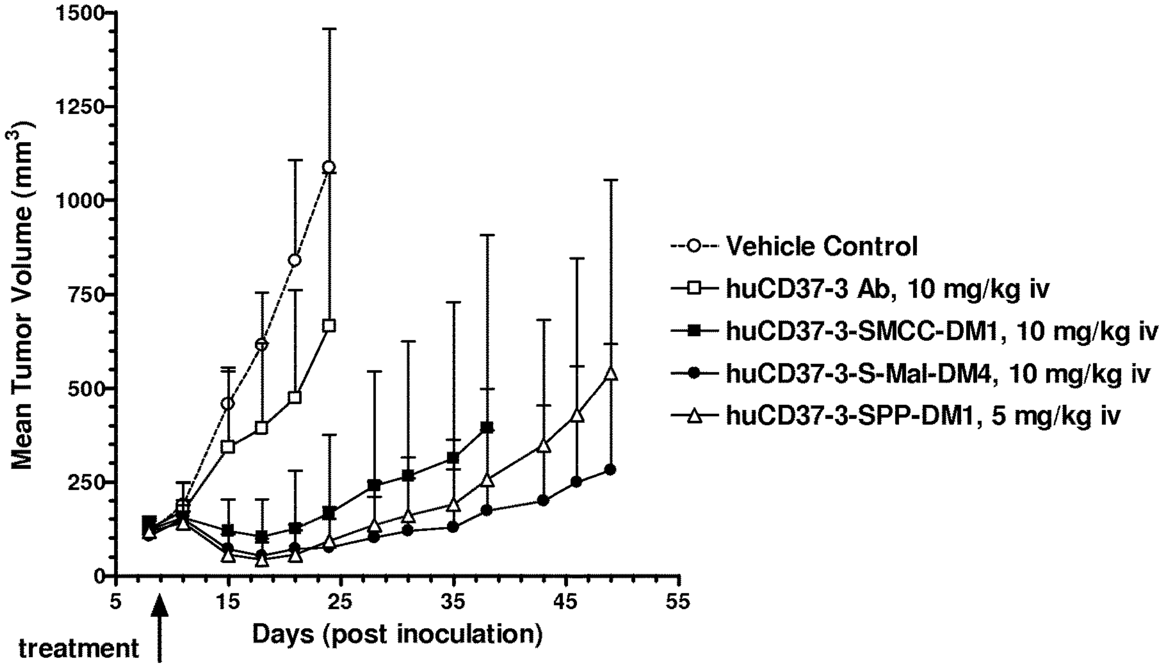

FIG. 26 depicts results from an established xenograft study using BJAB lymphoma cells implanted subcutaneous into SCID mice. Animals were treated once on day 9 post cell inoculation with either 10 mg/kg of huCD37-3 Ab, huCD37-3-SMCC-DM1, huCD37-3-sulfo-mal-DM4 or 5 mg/kg of huCD37-3-SPP-DM1. The mean tumor volume of the different treatment groups is plotted against time post tumor cell inoculation.

Figure 27:
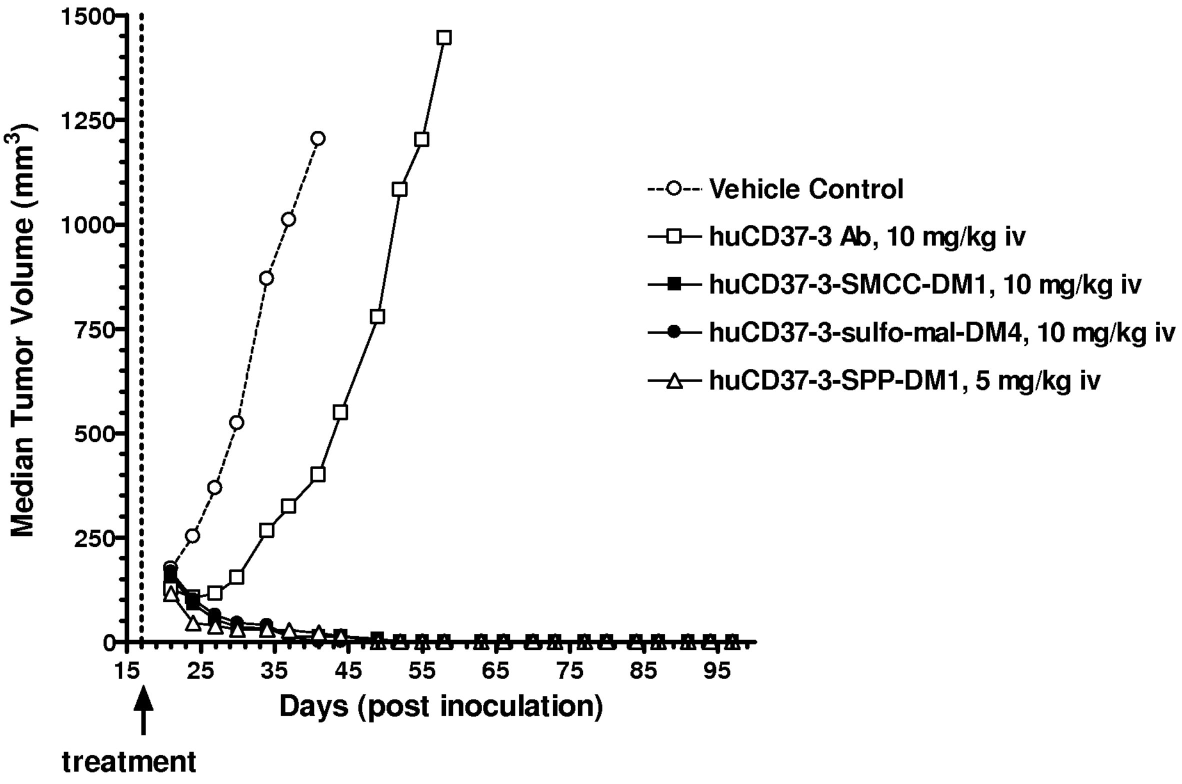

FIG. 27 depicts results from an established xenograft model using SU-DHL-4 diffuse large B-cell lymphoma cells implanted subcutaneous into SCID mice. Animals were treated once on day 17 post cell inoculation with either 10 mg/kg of huCD37-3 Ab, huCD37-3-SMCC-DM1, huCD37-3-sulfo-mal-DM4 or 5 mg/kg of huCD37-3-SPP-DM1. The median tumor volume of the different treatment groups is plotted against time post tumor cell inoculation.

Figure 28:
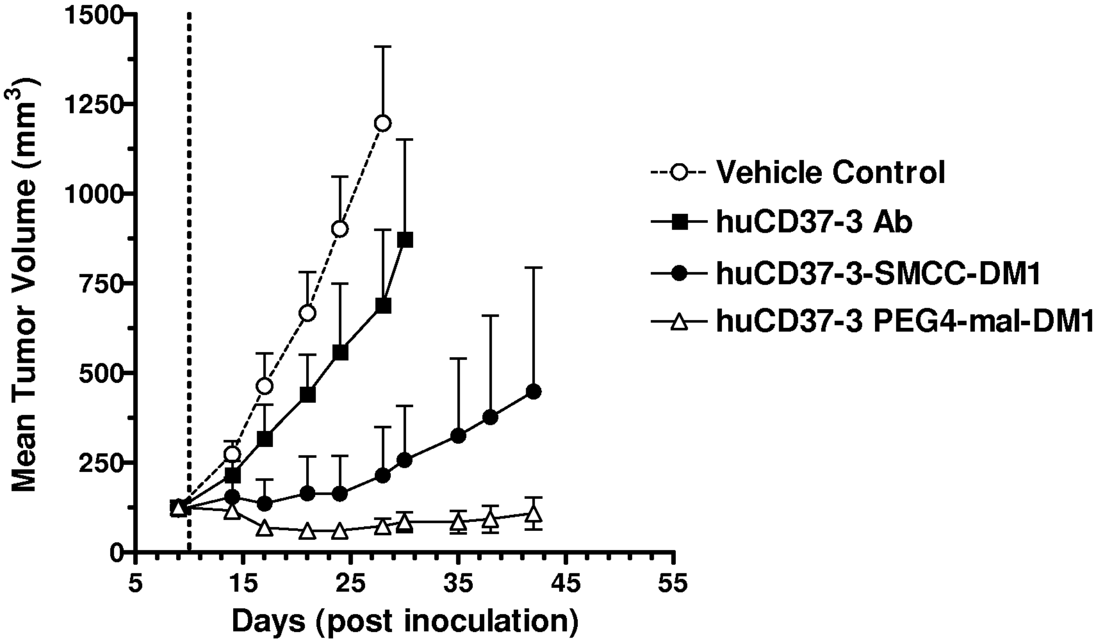

FIG. 28 depicts the results of an established xenograft model using BJAB lymphoma cells implanted subcutaneous into SCID mice. Animals were treated once on day 9 post cell inoculation with either 10 mg/kg of huCD37-3 Ab, huCD37-3-SMCC-DM1 or huCD37-3-PEG4-mal-DM1. The mean tumor volume of the different treatment groups is plotted against time post tumor cell inoculation.

Figure 29:
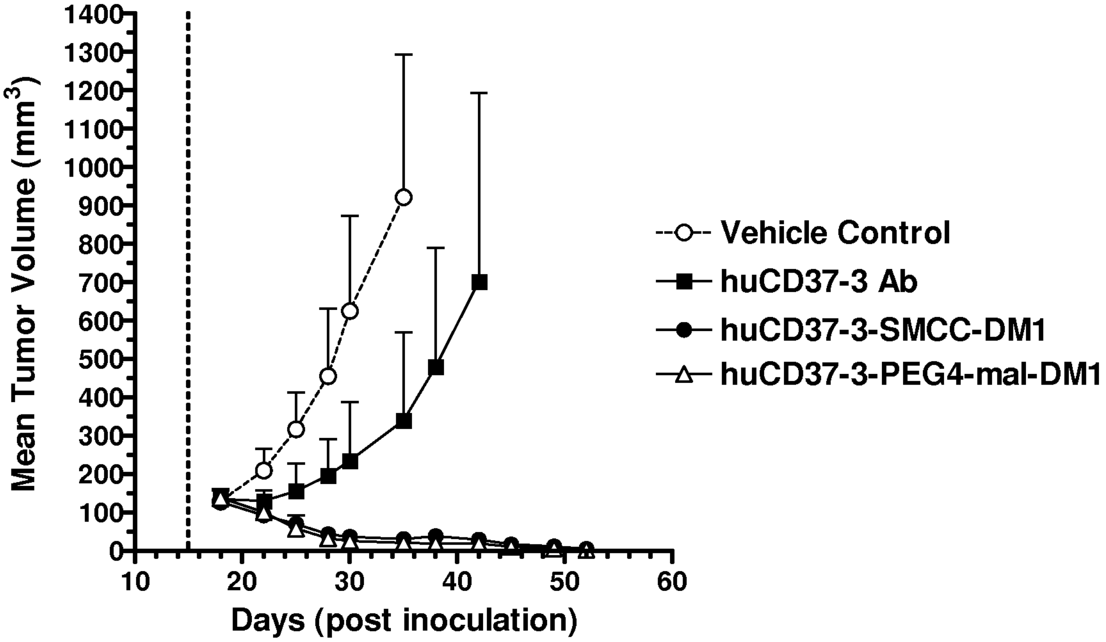

FIG. 29 depicts the results of an established xenograft model using SU-DHL-4 diffuse large B-cell lymphoma cells implanted subcutaneous into SCID mice. Animals were treated once on day 15 post cell inoculation with either 10 mg/kg of huCD37-3 Ab, huCD37-3-SMCC-DM1 or huCD37-3-PEG4-mal-DM1. The mean tumor volume of the different treatment groups is plotted against time post tumor cell inoculation.

Figure 30:
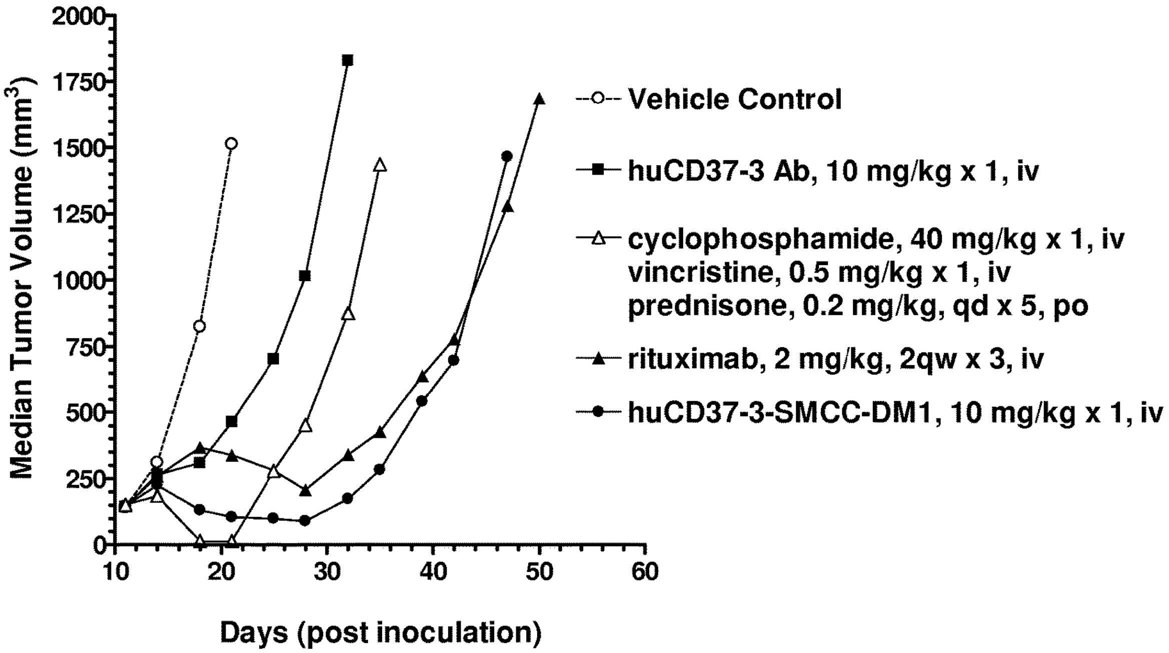

FIG. 30 depicts the results of an assay using an established xenograft model with DoHH2 follicular B-cell lymphoma cells implanted subcutaneously into SCID mice. Animals were treated starting on day 12 post inoculation with (i) a single dose of 10 mg/kg of huCD37-3 antibody, (ii) a single dose of 10 mg/kg of huCD37-3-SMCC-DM1 conjugate, (iii) six doses of 2 mg/kg of Rituximab twice per week for three weeks, (iv) a regimen of a single 40 mg/kg dose of cyclophosphamide and 0.5 mg/kg of vincristine, along with five daily 0.2 mg/kg doses of prednisone (CVP), or (v) a vehicle control. The median tumor volume of the different treatment groups is plotted against time post tumor cell inoculation.

Figure 31:
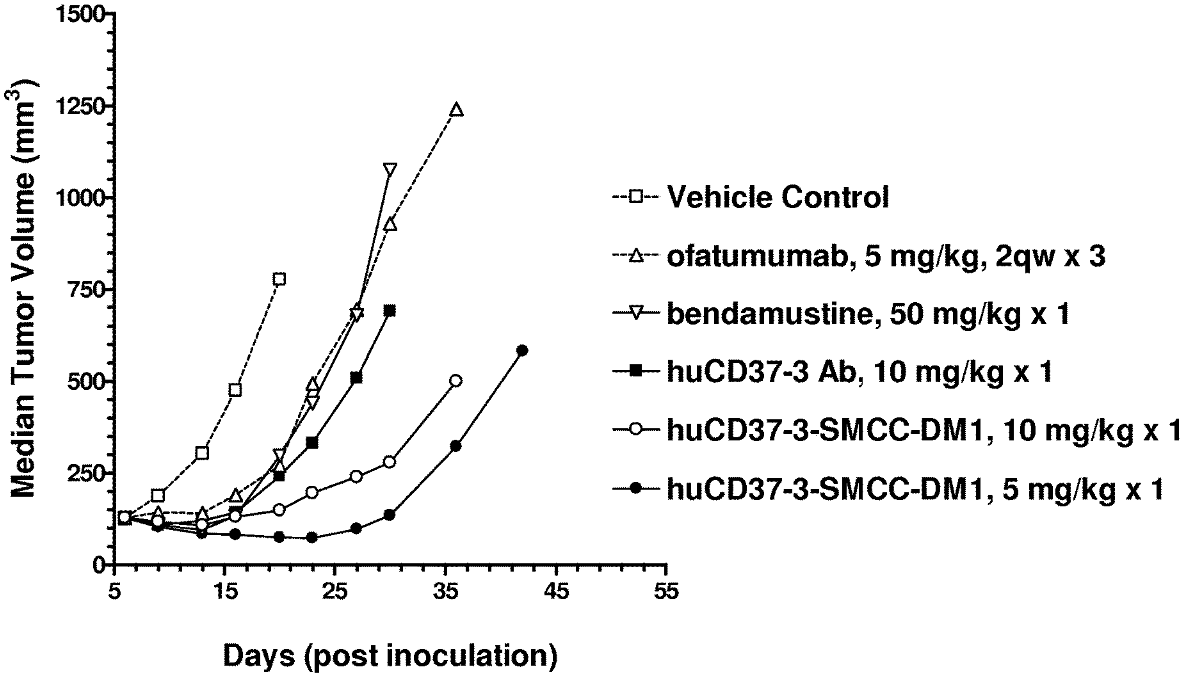

FIG. 31 depicts the results of an assay an using established xenograft model with JVM3 CLL cells implanted subcutaneous into SCID mice. Animals were treated starting on day 7 post inoculation with (i) a single dose of 10 mg/kg of huCD37-3 antibody, (ii) a 5 mg/kg dose of huCD37-3-SMCC-DM1 conjugate, (iii) a 10 mg/kg dose of huCD37-3-SMCC-DM1 conjugate, (iv) six doses of 5 mg/kg of ofatumumab twice per week for three weeks, (v) a single 50 mg/kg dose of bendamustine, or (vi) a vehicle control. The median tumor volume of the different treatment groups is plotted against time post tumor cell inoculation.

Figure 32:
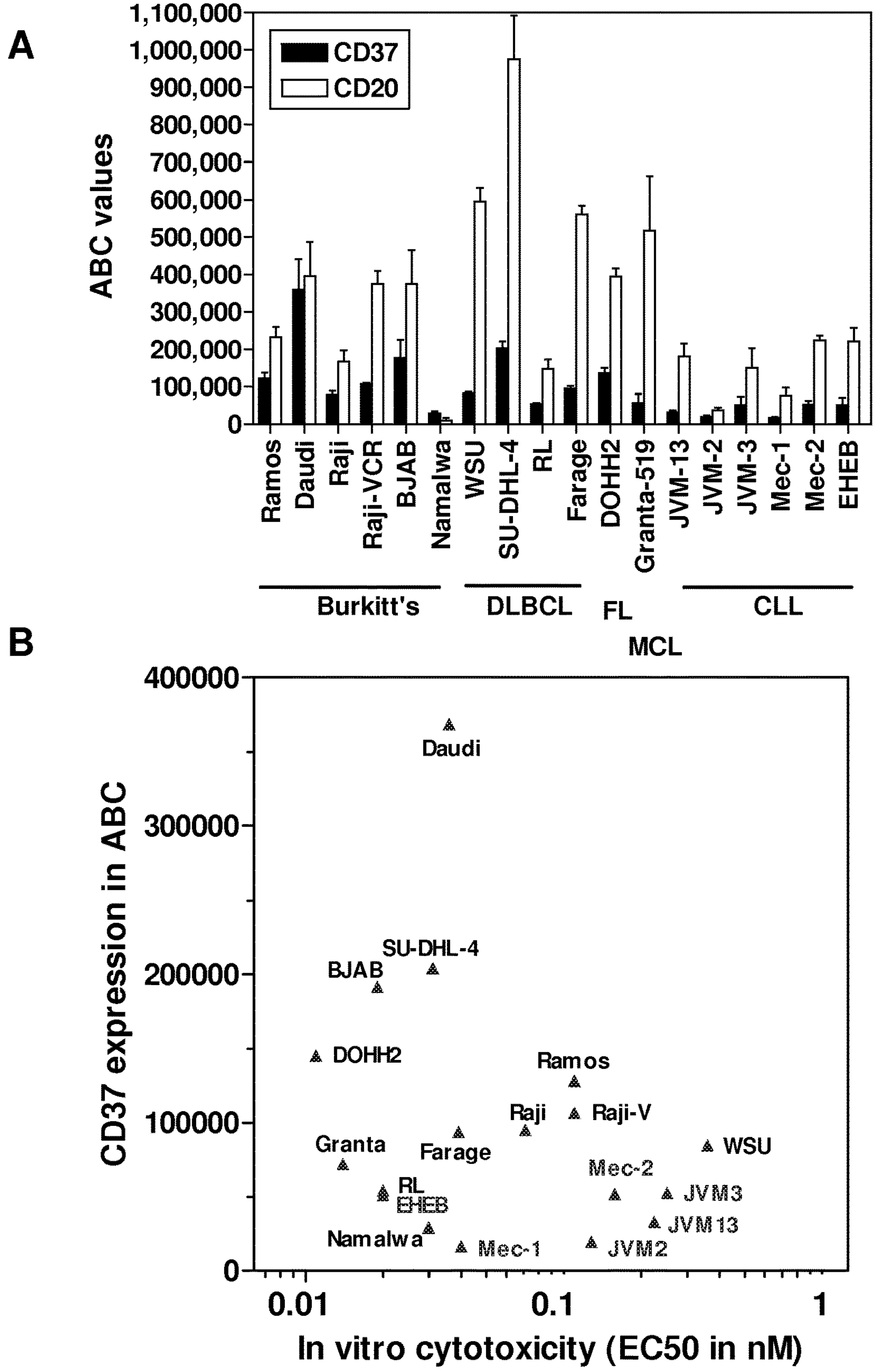

FIG. 32 depicts the CD37 and CD20 expression levels measured in various NHL and CLL tumor cell lines (A) and the in vitro cytotoxicty of huCD37-3-SMCC-DM1 measured in these cell lines (B).

DETAILED DESCRIPTION OF THE INVENTION

The present invention provides a new class of CD37 binding molecules having high potency in the following three cytotoxic activities against CD37 expressing (e.g., positive) cells: induction of apoptosis, ADCC, and CDC. Further, immunoconjugates of anti-CD37 antibodies kill CD37 expressing cells unexpectedly well, as demonstrated using in vivo tumor models.

I. Definitions

To facilitate an understanding of the present invention, a number of terms and phrases are defined below.

The term CD37 as used herein, refers to any native CD37, unless otherwise indicated. CD37 is also referred to as GP52-40, leukocyte antigen CD37, and Tetraspanin-26. The term "CD37" encompasses "full-length," unprocessed CD37 as well as any form of CD37 that results from processing in the cell. The term also encompasses naturally occurring variants of CD37, e.g., splice variants, allelic variants, and isoforms. The CD37 polypeptides described herein can be isolated from a variety of sources, such as from human tissue types or from another source, or prepared by recombinant or synthetic methods.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as CD37. In some embodiments, blocking antibodies or antagonist antibodies substantially or completely inhibit the biological activity of the antigen. The biological activity can be reduced by 10%, 20%, 30%, 50%, 70%, 80%, 90%, 95%, or even 100%.

The term "anti-CD37 antibody" or "an antibody that binds to CD37" refers to an antibody that is capable of binding CD37 with sufficient affinity such that the antibody is useful as a diagnostic and/or therapeutic agent in targeting CD37. The extent of binding of an anti-CD37 antibody to an unrelated, non-CD37 protein can be less than about 10% of the binding of the antibody to CD37 as measured, e.g., by a radioimmunoassay (RIA). In certain embodiments, an antibody that binds to CD37 has a dissociation constant (Kd) of ≤1 M, ≤100 nM, ≤10 nM, ≤1 nM, or ≤0.1 nM.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, *Nature,* 321:522-525; Riechmann et al., 1988, *Nature,* 332:323-327; Verhoeyen et al., 1988, *Science,* 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32..34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-CD37 antibody or fragment thereof) and is defined by a generic formula: C-L-A, wherein C=cytotoxin, L=linker, and A=cell binding agent or anti-CD37 antibody or antibody fragment. Immunoconjugates can also be defined by the generic formula in reverse order: A-L-C.

A "linker" is any chemical moiety that is capable of linking a compound, usually a drug, such as a maytansinoid, to a cell-binding agent such as an anti CD37 antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. "Tumor" and "neoplasm" refer to one or more cells that result from excessive cell growth or proliferation, either benign (noncancerous) or malignant (cancerous) including pre-cancerous lesions. Examples of "cancer" or "tumorigenic" diseases which can be treated and/or prevented include B-cell lymphomas including NHL, precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth; and/or relieve to some extent one or more of the symptoms associated with the cancer. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

A "chemotherapeutic agent" is a chemical compound useful in the treatment of cancer, regardless of mechanism of action. Chemotherapeutic agents include, for example, antagonists of CD20 such as Rituximab and cyclophosphamide, doxorubicin, vincristine, predinisone, fludarabine, etoposide, methotrexate, lenalidomide, chlorambucil, bentamustine and/or modified versions of such chemotherapeutics.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorgenic frequency, or tumorgenic capacity, of a tumor; reduction in the number or frequency of cancer stem cells in a tumor; differentiation of tumorigenic cells to a non-tumorigenic state; or some combination of effects. [00108]"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), "(O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and optionally expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells . . . .

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, Proc. Natl. Acad. Sci., 87:2264-2268, as modified in Karlin et al., 1993, Proc. Natl. Acad. Sci., 90:5873-5877, and incorporated into the NBLAST and XBLAST programs (Altschul et al., 1991, Nucleic Acids Res., 25:3389-3402). In certain embodiments, Gapped BLAST can be used as described in Altschul et al., 1997, Nucleic Acids Res. 25:3389-3402. BLAST-2, WU-BLAST-2 (Altschul et al., 1996, Methods in Enzymology, 266:460-480), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the invention do not abrogate the binding of the polypeptide or antibody containing the amino acid sequence, to the antigen(s), i.e., the CD37 to which the polypeptide or antibody binds. Methods of identifying nucleotide and amino acid conservative substitutions which do not eliminate antigen binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natd. Acad. Sci. USA* 94:.412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. CD37 Binding Agents

The present invention provides agents that specifically bind CD37. These agents are referred to herein as "CD37 binding agents." The full-length amino acid sequences for human, macaca, and murine CD37 are known in the art and also provided herein as represented by SEQ ID NOs:1-3, respectively.

```
Human CD37:
                                        (SEQ ID NO: 1)
MSAQESCLSLIKYFLFVFNLFFFVLGSLIFCFGIWILIDKTSFVSFVGL

AFVPLQIWSKVLAISGIFTMGIALLGCVGALKELRCLLGLYFGMLLLLF

ATQITLGILISTQRAQLERSLRDVVEKTIQKYGTNPEETAAEESWDYVQ

FQLRCCGWHYPQDWFQVLILRGNGSEAHRVPCSCYNLSATNDSTILDKV

ILPQLSRLGHLARSRHSADICAVPAESHIYREGCAQGLQKWLHNNLISI

VGICLGVGLLELGFMTLSIFLCRNLDHVYNRLAYR

Macaca CD37:
                                        (SEQ ID NO: 2)
MSAQESCLSLIKYFLFVFNLFFFVILGSLIFCFGIWILIDKTSFVSFVG

LAFVPLQIWSKVLAISGVFTMGLALLGCVGALKELRCLLGLYFGMLLLL

FATQITLGILISTQRAQLERSLQDIVEKTIQRYHTNPEETAAEESWDYV

QFQLRCCGWHSPQDWFQVLTLRGNGSEAHRVPCSCYNLSATNDSTILDK

VILPQLSRLGQLARSRHSTDICAVPANSHIYREGCARSLQKWLHNNLIS

IVGICLGVGLLELGFMTLSIFLCRNLDHVYNRLRYR

Murine CD37 (NP_031671):
                                        (SEQ ID NO: 3)
MSAQESCLSLIKYFLFVFNLFFFVLGGLIFCFGTWILIDKTSFVSFVGL

SFVPLQTWSKVLAVSGVLTMALALLGCVGALKELRCLLGLYFGMLLLLF

ATQITLGILISTQRVRLERRVQELVLRTIQSYRTNPDETAAEESWDYAQ

FQLRCCGWQSPRDWNKAQMLKANESEEPFVPCSCYNSTATNDSTVFDKL

FFSQLSRLGPRAKLRQTADICALPAKAHIYREGCAQSLQKWLHNNIISI

VGICLGVGLLELGFMTLSIFLCRNLDHVYDRLARYR
```

In certain embodiments, the CD37 binding agents are antibodies, immunoconjugates or polypeptides. In some embodiments, the CD37 binding agents are humanized antibodies.

In certain embodiments, the CD37-binding agents have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells.

In certain embodiments, the CD37-binding agents are capable of inducing complement dependent cytotoxicity. For example, treatment of cells with the CD37-binding agents can result in CDC activity that reduces cell viability to less than about 80%, less than about 70%, less than about 60%, less than about 50%, less than about 40% or less than about 35% of the cell viability of untreated cells. Treatment of cells with the CD37-binding agents can also result in CDC activity that reduces cell viability to about 70-80%, about 60-70%, about 50-60%, about 40-50%, or about 30-40% of the cell viability of untreated cells. In some particular embodiments, the CD37-binding agents are capable of inducing complement dependent cytotoxicity in Ramos cells.

In certain embodiments, the CD37-binding agents are capable of inducing antibody dependent cell mediated cytotoxicity (ADCC). For example, treatment of cells with the CD37-binding agents can result in ADCC activity that produces at least about 15%, at least about 20%, at least about 25%, at least about 30%, at least about 35%, at least about 40%, at least about 45%, at least about 50%, or at least about 60% cell lysis. Treatment of cells with the CD37-binding agents can result in ADCC activity that produces about 10-20%, about 20-30%, about 30-40%, or about 40-50% cell lysis. Treatment of cells with the CD37-binding agents can also result in ADCC activity that produces about 10-50%, about 20-50%, about 30-50%, or about 40-50% cell lysis. In some particular embodiments, the CD37-binding agents are capable of inducing ADCC in Daudi, Ramos, and/or Granata-519 cells.

In some embodiments, the CD37-binding agents are capable of inducing apoptosis. For example, treatment of cells with the CD37-binding agents can induce apoptosis in at least about 15%, at least about 20%, at least about 25%, at least about 30%, at least about 35%, at least about 40%, at least about 45%, at least about 50%, or at least about 55% of cells. In some particular embodiments, the CD37-binding agents are capable of inducing apoptosis in Ramos cells and/or Raji cells.

In some embodiments, the CD37-binding agents are capable of reducing tumor volume. The ability of a CD37-binding agent to reduce tumor volume can be assessed, for example, by measuring a % T/C value, which is the median tumor volume of treated subjects divided by the median tumor volume of the control subjects. In some embodiments, treatment with a CD37-binding agent results in a % T/C value that is less than about 55%, less than about 50%, less than about 45%, less than about 40%, less than about 35%, less than about 30%, less than about 25%, less than about 20%, less than about 15%, less than about 10%, or less than about 5%. In some particular embodiments, the CD37-binding agents can reduce tumor size in a BJAB xenograft model and/or a SU-DHL-4 xenograft model.

In certain embodiments, immunoconjugates or other agents that specifically bind human CD37 trigger cell death via a cytotoxic agent. For example, in certain embodiments, an antibody to a human CD37 antibody is conjugated to a maytansinoid that is activated in tumor cells expressing the CD37 by protein internalization. In certain alternative embodiments, the agent or antibody is not conjugated.

In certain embodiments, the CD37-binding agents are capable of inhibiting tumor growth. In certain embodiments, the CD37-binding agents are capable of inhibiting tumor growth in vivo (e.g., in a xenograft mouse model and/or in a human having cancer).

The CD37-binding agents include CD37 antibodies CD37-3, CD37-12, CD37-38, CD37-50, CD37-51, CD37-56 and CD37-57 and fragments, variants and derivatives thereof. The CD37-binding agents also include CD37-binding agents that specifically bind to the same CD37 epitope as an antibody selected from the group consisting of CD37-3, CD37-12, CD37-38, CD37-50, CD37-51, CD37-56 and CD37-57. The CD37-binding agents also include CD37-binding agents that competitively inhibit an antibody selected from the group consisting of CD37-3, CD37-12, CD37-38, CD37-50, CD37-51, CD37-56 and CD37-57.

In some particular embodiments, the binding of the CD37-binding agents to CD37 does not require human CD37 amino acids 109-138. Thus, some CD37-binding agents bind to a polypeptide comprising the amino acid sequence of SEQ ID NO: 180. In other embodiments, the binding of the CD37-binding agents to CD37 is disrupted by mutation of human CD37 amino acids 202-243. Thus, some CD37-binding agents do not bind to a polypeptide comprising the amino acid sequence of SEQ ID NO: 184.

In some embodiments, the CD37-binding agents bind to a polypeptide of SEQ ID NO: 180 and to a polypeptide of SEQ ID NO: 183, but do not bind to a polypeptide of SEQ ID NO: 184.

In some embodiments, the CD37-binding agents bind to a polypeptide of SEQ ID NO: 190. In some embodiments, the CD37-binding agents bind to a polypeptide of SEQ ID NO: 190 and a polypeptide of SEQ ID NO: 189. In some embodiments, the CD37-binding agents bind to a polypeptide of SEQ ID NO:190 and a polypeptide of SEQ ID NO:188.

In some embodiments, the CD37-binding agent binds to a polypeptide of SEQ ID NO: 192, but does not bind to a polypeptide of SEQ ID NO: 194. In some embodiments, the CD37-binding agent binds to a polypeptide of SEQ ID NO: 193, but does not bind to a polypeptide of SEQ ID NO:194.

CD37 peptide fragments to which certain CD37-binding agents bind to include, but are not limited to, CD37 fragments comprising, consisting essentially of, or consisting of amino acids 200-243 of SEQ ID NO: 1, amino acids 202-220 or SEQ ID NO:1, or amino acids 221-243 of SEQ ID NO:1. In some embodiments, the CD37-binding agent is specifically binds to a human CD37 epitope comprising amino acids 202-243 of SEQ ID NO: 1. In some embodiments, the binding of the CD37-binding agent to CD37 requires amino acids 202-243 of SEQ ID NO: 1. In some embodiments, the binding of the CD37-binding agent to CD37 requires amino acids 200-220 of SEQ ID NO: 1. In some embodiments, the binding of the CD37-binding agent to CD37 requires amino acids 221-243 of SEQ ID NO:1.

The CD37-binding agents also include CD37-binding agents that comprise the heavy and light chain CDR sequences of CD37-3, CD37-12, CD37-38, CD37-50, CD37-51, CD37-56 or CD37-57. The heavy and light chain CDRs of CD37-38, CD37-50, CD37-51, CD37-56 and CD37-57 contain related sequences. Therefore, the CD-37 binding agents can also comprise heavy and light chain CDR sequences that comprise a consensus sequence obtained by the alignment of CD37-38, CD37-50, CD37-51, CD37-56 and CD37-57. The CDR sequences of CD37-3, CD37-12, CD37-38, CD37-50, CD37-51, CD37-56 and CD37-57, as well as the consensus sequence of CD37-38, CD37-50, CD37-51, CD37-56 and CD37-57 are described in Tables 1 and 2 below.

TABLE 1

| Variable heavy chain CDR amino acid sequences | | | |
|---|---|---|---|
| Antibody | VH-CDR1 | VH-CDR2 | VH-CDR3 |
| CD37-3 | TSGVS (SEQ ID NO: 4) | VIWGDGSTN (SEQ ID NO: 5) | GGYSLAH (SEQ ID NO: 6) |
| CD37-12 | KYGMN (SEQ ID NO: 7) | WINTNTGESR (SEQ ID NO: 8) | GTVVAD (SEQ ID NO: 9) |
| CD37-38 | SGFGWH (SEQ ID NO: 10) | YILYSGGTD (SEQ ID NO: 11) | GYYGYGAWFVY (SEQ ID NO: 12) |
| CD37-50 | SGFAWH (SEQ ID NO: 13) | YILYSGSTV (SEQ ID NO: 14) | GYYGYGAWFAY (SEQ ID NO: 15) |
| CD37-51 | SGFAWH (SEQ ID NO: 16) | YIHYSGSTN (SEQ ID NO: 17) | GYYGFGAWFVY (SEQ ID NO: 18) |
| CD37-56 | SGFAWH (SEQ ID NO: 19) | YIHYSGGTN (SEQ ID NO: 20) | GYYGFGAWFAY (SEQ ID NO: 21) |
| CD37-57 | SGFAWH (SEQ ID NO: 22) | YILYSGSTV (SEQ ID NO: 23) | GYYGYGAWFAY (SEQ ID NO: 24) |
| CONSENSUS | SGF[A or G]WH (SEQ ID NO: 25) | YI[L or H]YSG[G or S]T[D, V, or N] (SEQ ID NO: 26) | GYYG[Y or F]GAWF[V or A]Y (SEQ ID NO: 27) |

TABLE 2

| Variable light chain CDR amino acid sequences | | | |
|---|---|---|---|
| Antibody | VL-CDR1 | VL-CDR2 | VL-CDR3 |
| CD37-3 | RASENIRSNLA (SEQ ID NO: 28) | VATNLAD (SEQ ID NO: 29) | QHYWGTTWT (SEQ ID NO: 30) |
| CD37-12 | RASQSVSTSSYSYLY (SEQ ID NO: 31) | YASNLAS (SEQ ID NO: 32) | QHSWEIPYT (SEQ ID NO: 33) |
| CD37-38 | SASSSVTYMH (SEQ ID NO: 34) | DTSKLAS (SEQ ID NO: 35) | QQWISNPPT (SEQ ID NO: 36) |
| CD37-50 | SATSSVTYMH (SEQ ID NO: 37) | DTSKLPY (SEQ ID NO: 38)<br>Humanized DTSNLPY (SEQ ID NO: 40) | QQWSDNPPT (SEQ ID NO: 39) |
| CD37-51 | SATSSVTYMH (SEQ ID NO: 41) | DTSKLAS (SEQ ID NO: 42) | QQWSSNPPT (SEQ ID NO: 43) |
| CD37-56 | SASSSVTYMH (SEQ ID NO: 44) | DTSKLAS (SEQ ID NO: 45)<br>Humanized DTSNLAS (SEQ ID NO: 47) | QQWISDPPT (SEQ ID NO: 46) |
| CD37-57 | SATSSVTYMH (SEQ ID NO: 48) | DTSKLAS (SEQ ID NO: 49)<br>Humanized DTSNLAS (SEQ ID NO: 51) | QQWSDNPPT (SEQ ID NO: 50) |
| CONSENSUS | SA[T or S]SSVTYMH (SEQ ID NO: 52) | DTS[K or N]L[A or P][S or Y] (SEQ ID NO: 53) | QQW[I or S][S or D][N or D]PPT (SEQ ID NO: 54) |

The CD37 binding molecules can be antibodies or antigen binding fragments that specifically bind to CD37 that comprise the CDRs of CD37-3, CD37-12, CD37-50, CD37-51, CD37-56, or CD37-57 with up to four (i.e. 0, 1, 2, 3, or 4) conservative amino acid substitutions per CDR.

Polypeptides an comprise one of the individual variable light chains or variable heavy chains described herein. Antibodies and polypeptides can also comprise both a variable light chain and a variable heavy chain. The variable light chain and variable heavy chain sequences of murine, chimeric, and humanized CD37-3, CD37-12, CD37-50, CD37-51, CD37-56, and CD37-57 antibodies are provided in Tables 3 and 4 below.

TABLE 3

Variable heavy chain amino acid sequences

| Antibody | VH Amino Acid Sequence (SEQ ID NO) |
|---|---|
| muCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSA (SEQ ID NO: 55) |
| chCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSA (SEQ ID NO: 56) |
| huCD37-3v1.0 | QVQVQESGPGLVAPSQTLSITCTVSGFSLTTSGVSWVRQPPGKGLEWLGVIW GDGSTNYHPSLKSRLSIKKDHSKSQVFLKLNSLTAADTATYYCAKGGYSLA HWGQGTLVTVSS (SEQ ID NO: 57) |
| huCD37-3v1.1 | QVQVQESGPGLVAPSQTLSITCTVSGFSLTTSGVSWVRQPPGKGLEWLGVIW GDGSTNYHSSLKSRLSIKKDHSKSQVFLKLNSLTAADTATYYCAKGGYSLA HWGQGTLVTVSS (SEQ ID NO: 58) |
| muCD37-12 | QIQLVQSGPELKKPGETVKISCKASGYTFTKYGMNWVKQAQGKGLKWMG WINTNTGESRNAEEFKGRFAFSLETSASTAYLQINNLKYEDTATYFCGRGTV VADWGQGTTLTVSS (SEQ ID NO: 59) |
| chCD37-12 | QIQLVQSGPELKKPGETVKISCKASGYTFTKYGMNWVKQAQGKGLKWMG WINTNTGESRNAEEFKGRFAFSLETSASTAYLQINNLKYEDTATYFCGRGTV VADWGQGTTLTVSS (SEQ ID NO: 60) |
| muCD37-38 | DVQLQESGPDLVKPSQSLSLTCTVTGYSITSGFGWHWIRQFPGNKLEWMAY ILYSGGTDYNPSLKSRISITRDTSKNQFFLRLSSVTTEDTATYYCARGYYGYG AWFVYWGQGTLVTVSA (SEQ ID NO: 61) |
| chCD37-38 | QVQLQESGPDLVKPSQSLSLTCTVTGYSITSGFGWHWIRQFPGNKLEWMAY ILYSGGTDYNPSLKSRISITRDTSKNQFFLRLSSVTTEDTATYYCARGYYGYG AWFVYWGQGTLVTVSA (SEQ ID NO: 62) |
| huCD37-38 | QVQLQESGPGLVKPSQSLSLTCTVSGYSITSGFGWHWIRQFPGKGLEWMAYI LYSGGTDYNPSLKSRISITRDTSKNQFFLRLSSVTAADTATYYCARGYYGYG AWFVYWGQGTLVTVSS (SEQ ID NO: 63) |
| muCD37-50 | DVQLQESGPDLLKPSQSLSLTCTVTGYSITSGFAWHWIRQFPGNKLE WMGYILYSGSTVYSPSLKSRISITRDTSKNHFFLQLNSVTTEDTATYY CARGYYGYGAWFAYWGQGTLVTVSA (SEQ ID NO: 64) |
| huCD37-50 | QVQLQESGPGLLKPSQSLSLTCTVSGYSITSGFAWHWIRQHPGNKLEWMGY ILYSGSTVYSPSLKSRISITRDTSKNHFFLQLNSVTAADTATYYCARGYYGYG AWFAYWGQGTLVTVSA (SEQ ID NO: 65) |
| muCD37-51 | DVQLQESGPDLLKPSQSLSLTCTVTGYSISSGFAWHWIRQFPGNKLEWMGYI HYSGSTNYSPSLKSRISITRDSSKNQFFLQLNSVTTEDTATYYCARGYYGFGA WFVYWGQGTLVTVSA (SEQ ID NO: 66) |
| huCD37-51 | EVQLVESGPEVLKPGESLSLTCTVSGYSISSGFAWHWIRQFPGKGLEWMGYI HYSGSTNYSPSLQGRISITRDSSINQFFLQLNSVTASDTATYYCARGYYGFGA WFVYWGQGTLVTVSA (SEQ ID NO: 67) |
| muCD37-56 | DVQLQESGPDLVKPSQSLSLTCTVTGYSITSGFAWHWIRQFPGNKLEWMGY IHYSGGTNYNPSLKSRVSITRDTSKNQFFLQLNSVTTEDTATYYCARGYYGF GAWFAYWGQGTLVPVSA (SEQ ID NO: 68) |
| huCD37-56 | QVQLQESGPGLVKPSQSLSLTCTVSGYSITSGFAWHWIRQFPGKGLEWMGYI HYSGGTNYNPSLKSRVSITRDTSKNQFFLQLNSVTAADTATYYCARGYYGF GAWFAYWGQGTLVPVSA (SEQ ID NO: 69) |
| muCD37-57 | DVQLQESGPDLLKPSQSLSLTCTVTGYSITSGFAWHWIRQFPGNKLEWMGYI LYSGSTVYSPSLKSRISITRDTSKNQFFLQLNSVTTEDTATYYCARGYYGYG AWFAYWGQGTLVTVSA (SEQ ID NO: 70) |

TABLE 3-continued

| Variable heavy chain amino acid sequences | |
|---|---|
| Antibody | VH Amino Acid Sequence (SEQ ID NO) |
| huCD37-57 | QVQLQESGPGLLKPSQSLSLTCTVSGYSITSGFAWHWIRQFPGKGLEWMGYI LYSGSTVYSPSLKSRISITRDTSKNQFFLQLNSVTAADTATYYCARGYYGYG AWFAYWGQGTLVTVSA (SEQ ID NO: 71) |

TABLE 4

| Variable light chain amino acid sequences | |
|---|---|
| Antibody | VL Amino Acid Sequence (SEQ ID NO) |
| muCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKR (SEQ ID NO: 72) |
| chCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKR (SEQ ID NO: 73) |
| huCD37-3 (1.0 and 1.1) | DIQMTQSPSSLSVSVGERVTITCRASENIRSNLAWYQQKPGKSPKLLV NVATNLADGVPSRFSGSGSGTDYSLKINSLQPEDFGTYYCQHYWGTT WTFGQGTKLEIKR (SEQ ID NO: 74) |
| muCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKR (SEQ ID NO: 75) |
| chCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKR (SEQ ID NO: 76) |
| muCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKR (SEQ ID NO: 77) |
| chCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKR (SEQ ID NO: 78) |
| huCD37-38 | DIVLTQSPASMSASPGERVTMTCSASSSVTYMHWYQQKPGTSPKRWIYDTS KLASGVPARFSGSGSGTSYSLTISSMEAEDAATYYCQQWISNPPTFGGGTKL EIKR (SEQ ID NO: 79) |
| muCD37-50 | QIVLTQSPAIMSASPGEKVTMTCSATSSVTYMHWYQQKSGTSPKRWIYDTS KLPYGVPGRFSGSGSGTSYSLTISSMEAEDAATYYCQQWSDNPPTFGSGTKL EIKR (SEQ ID NO: 80) |
| huCD37-50 | EIVLTQSPATMSASPGERVTMTCSATSSVTYMHWYQQKPGQSPKRWIYDTS NLPYGVPARFSGSGSGTSYSLTISSMEAEDAATYYCQQWSDNPPTFGQGTKL EIKR (SEQ ID NO: 81) |
| muCD37-51 | QIVLTQSPAIMSASPGEKVTMTCSATSSVTYMHWYQQKSGTSPKRWIYDTS KLASGVPARFSGSGSGTSYSLTISNMEAEDAATYYCQQWSSNPPTFGSGTKL EIKR (SEQ ID NO: 82) |
| huCD37-51 | EIVLTQSPATMSASPGERVTMTCSATSSVTYMHWYQQKPGQSPKRWIYDTS KLASGVPARFSGSGSGTSYSLTISSMEAEDAATYYCQQWSSNPPTFGQGTKL EIKR (SEQ ID NO: 83) |
| muCD37-56 | QIVLTQSPAFMSASPGDKVTMTCSASSSVTYMHWYQQKSGTSPKRWIYDTS KLASGVPARFSGGGSGTSYSLTISTMEAEDAATYYCQQWISDPPTFGGGTKL EIKR (SEQ ID NO: 84) |
| huCD37-56 | DIVLTQSPAFMSASPGEKVTMTCSASSSVTYMHWYQQKPDQSPKRWIYDTS NLASGVPSRFSGGGSGTDYSLTISSMEAEDAATYYCQQWISDPPTFGQGTKL EIKR (SEQ ID NO: 85) |
| muCD37-57 | QIVLTQSPAIMSASPGEKVTMTCSATSSVTYMHWYQQKSGTSPKRWIYDTS KLASGVPARFSGSGSGTSYSLTISSMEAEDAATYYCQQWSDNPPTFGSGTKL EIKR (SEQ ID NO: 86) |

TABLE 4-continued

| Variable light chain amino acid sequences | |
|---|---|
| Antibody | VL Amino Acid Sequence (SEQ ID NO) |
| huCD37-57 | EIVLTQSPATMSASPGERVTMTCSATSSVTYMHWYQQKPGQSPRRWIYDTS NLASGVPARFSGSGSGTSYSLTISSMEAEDAATYYCQQWSDNPPTFGQGTKL EIKR (SEQ ID NO: 87) |

Also provided are polypeptides that comprise: (a) a polypeptide having at least about 90% sequence identity to SEQ ID NOs:55-71; and/or (b) a polypeptide having at least about 90% sequence identity to SEQ ID NOs:72-87. In certain embodiments, the polypeptide comprises a polypeptide having at least about 95%, at least about 96%, at least about 97%, at least about 98%, or at least about 99% sequence identity to SEQ ID NOs:55-87. Thus, in certain embodiments, the polypeptide comprises (a) a polypeptide having at least about 95% sequence identity to SEQ ID NOs:55-71, and/or (b) a polypeptide having at least about 95% sequence identity to SEQ ID NOs:72-87. In certain embodiments, the polypeptide comprises (a) a polypeptide having the amino acid sequence of SEQ ID NOs:55-71; and/or (b) a polypeptide having the amino acid sequence of SEQ ID NOs:72-87. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NOs:55-87 differs from SEQ ID NOs:55-87 by conservative amino acid substitutions only.

Polypeptides can comprise one of the individual light chains or heavy chains described herein. Antibodies and polypeptides can also comprise both a light chain and a heavy chain. The light chain and variable chain sequences of murine, chimeric, and humanized CD37-3, CD37-12, CD37-50, CD37-51, CD37-56, and CD37-57 antibodies are provided in Tables 5 and 6 below.

TABLE 5

| Full-length heavy chain amino acid sequences | |
|---|---|
| Antibody | Full-Length Heavy Chain Amino Acid Sequence (SEQ ID NO) |
| muCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSAAKTTAPSVYPLAPVCGDTTGSSVTLGCLVKGYFPEPVTL TWNSGSLSSGVHTFPAVLQSDLYTLSSSVTVTSSTWPSQSITCNVAHPASSTK VDKKIEPRGPTIKPCPPCKCPAPNLLGGPSVFIFPPKIKDVLMISLSPIVTCVVV DVSEDDPDVQISWFVNNVEVHTAQTQTHREDYNSTLRVVSALPIQHQDWM SGKEFKCKVNNKDLPAPIERTISKPKGSVRAPQVYVLPPPEEEMTKKQVTLT CMVTDFMPEDIYVEWTNNGKTELNYKNTEPVLDSDGSYFMYSKLRVEKKN WVERNSYSCSVVHEGLHNHHTTKSFSRTPGK (SEQ ID NO: 88) |
| chCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSAASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPGK (SEQ ID NO: 89) |
| huCD37-3v1.0 | QVQVQESGPGLVAPSQTLSITCTVSGFSLTTSGVSWVRQPPGKGLEWLGVIW GDGSTNYHPSLKSRLSIKKDHSKSQVFLKLNSLTAADTATYYCAKGGYSLA HWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPG (SEQ ID NO: 90) |
| huCD37-3v1.1 | QVQVQESGPGLVAPSQTLSITCTVSGFSLTTSGVSWVRQPPGKGLEWLGVIW GDGSTNYHSSLKSRLSIKKDHSKSQVFLKLNSLTAADTATYYCAKGGYSLA HWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPG (SEQ ID NO: 91) |
| muCD37-12 | QIQLVQSGPELKKPGETVKISCKASGYTFTKYGMNWVKQAQGKGLKWMG WINTNTGESRNAEEFKGRFAFSLETSASTAYLQINNLKYEDTATYFCGRGTV VADWGQGTTLTVSSAKTTAPSVYPLAPVCGDTTGSSVTLGCLVKGYFPEPV |

TABLE 5-continued

Full-length heavy chain amino acid sequences

| Antibody | Full-Length Heavy Chain Amino Acid Sequence (SEQ ID NO) |
|---|---|
| | TLTWNSGSLSSGVHTFPAVLQSDLYTLSSSVTVTSSTWPSQSITCNVAHPASS<br>TKVDKKIEPRGPTIKPCPPCKCPAPNLLGGPSVFIFPPKIKDVLMISLSPIVTCV<br>VVDVSEDDPDVQISWFVNNVEVHTAQTQTHREDYNSTLRVVSALPIQHQD<br>WMSGKEFKCKVNNKDLPAPIERTISKPKGSVRAPQVYVLPPPEEEMTKKQV<br>TLTCMVTDFMPEDIYVEWTNNGKTELNYKNTEPVLDSDGSYFMYSKLRVE<br>KKNWVERNSYSCSVVHEGLHNHHTTKSFSRTPGK (SEQ ID NO: 92) |
| chCD37-12 | QIQLVQSGPELKKPGETVKISCKASGYTFTKYGMNWVKQAQGKGLKWMG<br>WINTNTGESRNAEEFKGRFAFSLETSASTAYLQINNLKYEDTATYFCGRGTV<br>VADWGQGTTLTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPS<br>NTKVDKKVEPKSCDKTHTCPPCPAPELLGGPSVFLFPPKPKDTLMISRTPEVT<br>CVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSRDELTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 93) |
| muCD37-38 | DVQLQESGPDLVKPSQSLSLTCTVTGYSITSGFGWHWIRQFPGNKLEWMAY<br>ILYSGGTDYNPSLKSRISITRDTSKNQFFLRLSSVTTEDTATYYCARGYYGYG<br>AWFVYWGQGTLVTVSAAKTTPPSVYPLAPGSAAQTNSMVTLGCLVKGYFP<br>EPVTVTWNSGSLSSGVHTFPAVLESDLYTLSSSVTVPSSMRPSETVTCNVAH<br>PASSTKVDKKIVPRDCGCKPCICTVPEVSSVFIFPPKPKDVLTITLTPKVTCVV<br>VDISKDDPEVQFSWFVDDVEVHTAQTQPREEQFNSTFRSVSELPIMHQDWL<br>NGKEFKCRVNSAAFPAPIEKTISKTKGRPKAPQVYTIPPPKEQMAKDKVSLT<br>CMITDFFPEDITVEWQWNGQPAENYKNTQPIMNTNGSYFVYSKLNVQKSN<br>WEAGNTFTCSVLHEGLHNHHTEKSLSHSPGK (SEQ ID NO: 94) |
| chCD37-38 | QVQLQESGPDLVKPSQSLSLTCTVTGYSITSGFGWHWIRQFPGNKLEWMAY<br>ILYSGGTDYNPSLKSRISITRDTSKNQFFLRLSSVTTEDTATYYCARGYYGYG<br>AWFVYWGQGTLVTVSAASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTLMISRTP<br>EVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 95) |
| huCD37-38 | QVQLQESGPGLVKPSQSLSLTCTVSGYSITSGFGWHWIRQFPGKGLEWMAYI<br>LYSGGTDYNPSLKSRISITRDTSKNQFFLRLSSVTAADTATYYCARGYYGYG<br>AWFVYWGQGTLVTVSSASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTLMISRTP<br>EVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 96) |
| muCD37-50 | DVQLQESGPDLLKPSQSLSLTCTVTGYSITSGFAWHWIRQFPGNKLEWMGYI<br>LYSGSTVYSPSLKSRISITRDTSKNHFFLQLNSVTTEDTATYYCARGYYGYG<br>AWFAYWGQGTLVTVSAAKTTAPSVYPLAPVCGDTTGSSVTLGCLVKGYFP<br>EPVTLTWNSGSLSSGVHTFPAVLQSDLYTLSSSVTVTSSTWPSQSITCNVAHP<br>ASSTKVDKKIEPRGPTIKPCPPCKCPAPNLLGGPSVFIFPPKIKDVLMISLSPIV<br>TCVVVDVSEDDPDVQISWFVNNVEVHTAQTQTHREDYNSTLRVVSALPIQH<br>QDWMSGKEFKCKVNNKDLPAPIERTISKPKGSVRAPQVYVLPPPEEEMTKK<br>QVTLTCMVTDFMPEDIYVEWTNNGKTELNYKNTEPVLDSDGSYFMYSKLR<br>VEKKNWVERNSYSCSVVHEGLHNHHTTKSFSRTPGK (SEQ ID NO: 97) |
| huCD37-50 | QVQLQESGPGLLKPSQSLSLTCTVSGYSITSGFAWHWIRQHPGNKLEWMGY<br>ILYSGSTVYSPSLKSRISITRDTSKNHFFLQLNSVTAADTATYYCARGYYGYG<br>AWFAYWGQGTLVTVSAASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTLMISRTP<br>EVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 98) |
| muCD37-51 | DVQLQESGPDLLKPSQSLSLTCTVTGYSISSGFAWHWIRQFPGNKLEWMGYI<br>HYSGSTNYSPSLKSRISITRDSSKNQFFLQLNSVTTEDTATYYCARGYYGFGA<br>WFVYWGQGTLVTVSAAKTTAPSVYPLAPVCGDTTGSSVTLGCLVKGYFPEP<br>VTLTWNSGSLSSGVHTFPAVLQSDLYTLSSSVTVTSSTWPSQSITCNVAHPAS<br>STKVDKKIEPRGPTIKPCPPCKCPAPNLLGGPSVFIFPPKIKDVLMISLSPIVTC<br>VVVDVSEDDPDVQISWFVNNVEVHTAQTQTHREDYNSTLRVVSALPIQHQD<br>WMSGKEFKCKVNNKDLPAPIERTISKPKGSVRAPQVYVLPPPEEEMTKKQV<br>TLTCMVTDFMPEDIYVEWTNNGKTELNYKNTEPVLDSDGSYFMYSKLRVE<br>KKNWVERNSYSCSVVHEGLHNHHTTKSFSRTPGK (SEQ ID NO: 99) |

TABLE 5-continued

Full-length heavy chain amino acid sequences

| Antibody | Full-Length Heavy Chain Amino Acid Sequence (SEQ ID NO) |
|---|---|
| huCD37-51 | EVQLVESGPEVLKPGESLSLTCTVSGYSISSGFAWHWIRQFPGKGLEWMGYI HYSGSTNYSPSLQGRISITRDSSINQFFLQLNSVTASDTATYYCARGYYGFGA WFVYWGQGTLVTVSAASTKGPSVFPLAPSSKSTSGGTAALGCLVKDYFPEP VTVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELT KNQVSLTCLVKGFYPSDIAVEWESNGQPENNYKTTPPVLDSDGSFFLYSKLT VDKSRWQQGNVFSCSVMHEALHNHYTQKSLSLSPG (SEQ ID NO: 100) |
| muCD37-56 | DVQLQESGPDLVKPSQSLSLTCTVTGYSITSGFAWHWIRQFPGNKLEWMGY IHYSGGTNYNPSLKSRVSITRDTSKNQFFLQLNSVTTEDTATYYCARGYYGF GAWFAYWGQGTLVPVSAAKTTPPSVYPLAPGSAAQTNSMVTLGCLVKGYF PEPVTVTWNSGSLSSGVHTFPAVLESDLYTLSSSVTVPSSMRPSETVTCNVA HPASSTKVDKKIVPRDCGCKPCICTVPEVSSVFIFPPKPKDVLTITLTPKVTCV VVDISKDDPEVQFSWFVDDVEVHTAQTQPREEQFNSTFRSVSELPIMHQDW LNGKEFKCRVNSAAFPAPIEKTISKTKGRPKAPQVYTIPPPKEQMAKDKVSL TCMITDFFPEDITVEWQWNGQPAENYKNTQPIMNTNGSYFVYSKLNVQKSN WEAGNTFTCSVLHEGLHNHHTEKSLSHSPGK (SEQ ID NO: 101) |
| huCD37-56 | QVQLQESGPGLVKPSQSLSLTCTVSGYSITSGFAWHWIRQFPGKGLEWMGYI HYSGGTNYNPSLKSRVSITRDTSKNQFFLQLNSVTAADTATYYCARGYYGF GAWFAYWGQGTLVPVSAASTKGPSVFPLAPSSKSTSGGTAALGCLVKDYFP EPVTVSWNSGALTSGVHTFPAVLQSSGLYSLSSVVTVPSSSLGTQTYICNVN HKPSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKL TVDKSRWQQGNVFSCSVMHEALHNHYTQKSLSLSPG (SEQ ID NO: 102) |
| muCD37-57 | DVQLQESGPDLLKPSQSLSLTCTVTGYSITSGFAWHWIRQFPGNKLEWMGYI LYSGSTVYSPSLKSRISITRDTSKNQFFLQLNSVTTEDTATYYCARGYYGYG AWFAYWGQGTLVTVSAAKTTAPSVYPLAPVCGDTTGSSVTLGCLVKGYFP EPVTLTWNSGSLSSGVHTFPAVLQSDLYTLSSSVTVTSSTWPSQSITCNVAHP ASSTKVDKKIEPRGPTIKPCPPCKCPAPNLLGGPSVFIFPPKIKDVLMISLSPIV TCVVVDVSEDDPDVQISWFVNNVEVHTAQTQTHREDYNSTLRVVSALPIQH QDWMSGKEFKCKVNNKDLPAPIERTISKPKGSVRAPQVYVLPPPEEEMTKK QVTLTCMVTDFMPEDIYVEWTNNGKTELNYKNTEPVLDSDGSYFMYSKLR VEKKNWVERNSYSCSVVHEGLHNHHTTKSFSRTPGK (SEQ ID NO: 103) |
| huCD37-57 | QVQLQESGPGLLKPSQSLSLTCTVSGYSITSGFAWHWIRQFPGKGLEWMGYI LYSGSTVYSPSLKSRISITRDTSKNQFFLQLNSVTAADTATYYCARGYYGYG AWFAYWGQGTLVTVSAASTKGPSVFPLAPSSKSTSGGTAALGCLVKDYFPE PVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELT KNQVSLTCLVKGFYPSDIAVEWESNGQPENNYKTTPPVLDSDGSFFLYSKLT VDKSRWQQGNVFSCSVMHEALHNHYTQKSLSLSPG (SEQ ID NO: 104) |

TABLE 6

Full-length light chain amino acid sequences

| Antibody | Full-length Light Chain Amino Acid Sequence (SEQ ID NO) |
|---|---|
| muCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKRADAAPTVSIFPPSSEQLTSGGASVVCFLNNFYPKDINVKWKIDGSERQ NGVLNSWTDQDSKDSTYSMSSTLTLTKDEYERHNSYTCEATHKTSTSPIVKS FNRNEC (SEQ ID NO: 105) |
| chCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC (SEQ ID NO: 106) |
| huCD37-3 (1.0 and 1.1) | DIQMTQSPSSLSVSVGERVTITCRASENIRSNLAWYQQKPGKSPKLLVNVAT NLADGVPSRFSGSGSGTDYSLKINSLQPEDFGTYYCQHYWGTTWTFGQGTK |

TABLE 6-continued

Full-length light chain amino acid sequences

| Antibody | Full-length Light Chain Amino Acid Sequence (SEQ ID NO) |
| --- | --- |
| | LEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC (SEQ ID NO: 107) |
| muCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKRADAAPTVSIFPPSSEQLTSGGASVVCFLNNFYPKDINVKWKIDGSE RQNGVLNSWTDQDSKDSTYSMSSTLTLTKDEYERHNSYTCEATHKTSTSPI VKSFNRNEC (SEQ ID NO: 108) |
| chCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPV TKSFNRGEC (SEQ ID NO: 109) |
| muCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 110) |
| chCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 111) |
| huCD37-38 | DIVLTQSPASMSASPGERVTMTCSASSSVTYMHWYQQKPGTSPKRWIYDTS KLASGVPARFSGSGSGTSYSLTISSMEAEDAATYYCQQWISNPPTFGGGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 112) |
| muCD37-50 | QIVLTQSPAIMSASPGEKVTMTCSATSSVTYMHWYQQKSGTSPKRWIYDTS KLPYGVPGRFSGSGSGTSYSLTISSMEAEDAATYYCQQWSDNPPTFGSGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 113) |
| huCD37-50 | EIVLTQSPATMSASPGERVTMTCSATSSVTYMHWYQQKPGQSPKRWIYDTS NLPYGVPARFSGSGSGTSYSLTISSMEAEDAATYYCQQWSDNPPTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 114) |
| muCD37-51 | QIVLTQSPAIMSASPGEKVTMTCSATSSVTYMHWYQQKSGTSPKRWIYDTS KLASGVPARFSGSGSGTSYSLTISNMEAEDAATYYCQQWSSNPPTFGSGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 115) |
| huCD37-51 | EIVLTQSPATMSASPGERVTMTCSATSSVTYMHWYQQKPGQSPKRWIYDTS KLASGVPARFSGSGSGTSYSLTISSMEAEDAATYYCQQWSSNPPTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 116) |
| muCD37-56 | QIVLTQSPAFMSASPGDKVTMTCSASSSVTYMHWYQQKSGTSPKRWIYDTS KLASGVPARFSGGGSGTSYSLTISTMEAEDAATYYCQQWISDPPTFGGGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 117) |
| huCD37-56 | DIVLTQSPAFMSASPGEKVTMTCSASSSVTYMHWYQQKPDQSPKRWIYDTS NLASGVPSRFSGGGSGTDYSLTISSMEAEDAATYYCQQWISDPPTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 118) |
| muCD37-57 | QIVLTQSPAIMSASPGEKVTMTCSATSSVTYMHWYQQKSGTSPKRWIYDTS KLASGVPARFSGSGSGTSYSLTISSMEAEDAATYYCQQWSDNPPTFGSGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 119) |

TABLE 6-continued

| Full-length light chain amino acid sequences | |
|---|---|
| Antibody | Full-length Light Chain Amino Acid Sequence (SEQ ID NO) |
| huCD37-57 | EIVLTQSPATMSASPGERVTMTCSATSSVTYMHWYQQKPGQSPRRWIYDTS NLASGVPARFSGSGSGTSYSLTISSMEAEDAATYYCQQWSDNPPTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 120) |

Also provided are polypeptides that comprise: (a) a polypeptide having at least about 90% sequence identity to SEQ ID NOs:88-104; and/or (b) a polypeptide having at least about 90% sequence identity to SEQ ID NOs:105-120. In certain embodiments, the polypeptide comprises a polypeptide having at least about 95%, at least about 96%, at least about 97%, at least about 98%, or at least about 99% sequence identity to SEQ ID NOs:88-120. Thus, in certain embodiments, the polypeptide comprises (a) a polypeptide having at least about 95% sequence identity to SEQ ID NOs:88-104, and/or (b) a polypeptide having at least about 95% sequence identity to SEQ ID NOs:105-120. In certain embodiments, the polypeptide comprises (a) a polypeptide having the amino acid sequence of SEQ ID NOs:88-104; and/or (b) a polypeptide having the amino acid sequence of SEQ ID NOs:105-120. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NOs:88-120 differs from SEQ ID NOs:88-120 by conservative amino acid substitutions only.

In certain embodiments, the CD37 antibody can be the antibody produced from a hybridoma selected from the group consisting of consisting of ATCC Deposit Designation PTA-10664, deposited with the ATCC on Feb. 18, 2010, ATCC Deposit Designation PTA-10665, deposited with the ATCC on Feb. 18, 2010, ATCC Deposit Deisgnation PTA-10666, deposited with the ATCC on Feb. 18, 2010, ATCC Deposit Designation PTA-10667 deposited with the ATCC on Feb. 18, 2010, ATCC Deposit Designation PTA-10668, deposited with the ATCC on Feb. 18, 2010, ATCC Deposit Designation PTA-10669, deposited with the ATCC on Feb. 18, 2010, and ATCC Deposit Designation PTA-10670, deposited with the ATCC on Feb. 18, 2010. In certain embodiments, the antibody comprises the VH-CDRs and the VL-CDRS of the antibody produced from a hydridoma selected from the group consisting of PTA-10665, PTA-10666, PTA-10667, PTA-10668, PTA-10669, and PTA-10670.

In certain embodiments, the CD37 antibody can comprise a light chain encoded by the recombinant plasmid DNA phuCD37-3LC (ATCC Deposit Designation PTA-10722, deposited with the ATCC on Mar. 18, 2010). In certain embodiments, the CD37 antibody can comprise a heavy chain encoded by the recombinant plasmid DNA phuCD37-3HCv.1.0 (ATCC Deposit Designation PTA-10723, deposited with the ATCC on Mar. 18, 2010). In certain embodiments, the CD37 antibody can comprise a light chain encoded by the recombinant plasmid DNA phuCD37-3LC (PTA-10722) and a heavy chain encoded by the recombinant plasmid DNA phuCD37-3HCv.1.0 (PTA-10723). In certain embodiments, the CD37 antibody can comprise the VL-CDRs encoded by the recombinant plasmid DNA phuCD37-3LC (PTA-10722) and the VH-CDRs encoded by the recombinant plasmid DNA phuCD37-3HCv.1.0 (PTA-10723).

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human CD37 is a humanized antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody to CD37is a human antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a CD37. Bispecific antibodies are antibodies that are capable of specifically recognizing and binding at least two different epitopes. The different epitopes can either be within the same molecule (e.g. the same CD37) or on different molecules such that both, for example, the antibodies can specifically recognize and bind a CD37 as well as, for example, 1) an effector molecule on a leukocyte such as a T-cell receptor (e.g. CD3) or Fc receptor (e.g. CD64, CD32, or CD16) or 2) a cytotoxic agent as described in detail below.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168). Antibodies with more than two valencies are also contemplated. For example, trispecific antibodies can be prepared (Tutt et al., J. Immunol. 147:60 (1991)). Thus, in certain embodiments the antibodies to CD37 are multispecific.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to CD37 (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for CD37, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of a human CD37. In this regard, the variable region can comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and possibly from an antibody from a different species. It is not alway necessary to replace all of the CDRs with the complete CDRs from the donor variable region to transfer the antigen binding capacity of one variable domain to another. Rather, in some cases it is only necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the CD37-binding antibodies provide for altered effector functions that, in turn, affect the biological profile of the administered antibody. For example, the deletion or inactivation (through point mutations or other means) of a constant region domain can reduce Fc receptor binding of the circulating modified antibody thereby increasing tumor localization. In other cases, it can be that constant region modifications, consistent with this invention, moderate complement binding and thus reduce the serum half life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well known biochemical or molecular engineering techniques well within the purview of the skilled artisan.

In certain embodiments, a CD37-binding agent that is an antibody does not have one or more effector functions. For instance, in some embodiments, the antibody has no antibody-dependent cellular cytotoxicity (ADCC) activity and/or no complement-dependent cytotoxicity (CDC) activity. In certain embodiments, the antibody does not bind to an Fc receptor and/or complement factors. In certain embodiments, the antibody has no effector function.

It will be noted that in certain embodiments, the modified antibodies can be engineered to fuse the CH3 domain directly to the hinge region of the respective modified antibodies. In other constructs it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies of the present invention can be provided by the partial deletion or substitution of a few or even a single amino acid. For example, the mutation of a single amino acid in selected areas of the CH2 domain can be enough to substantially reduce Fc binding and thereby increase tumor localization. Similarly, it can be desirable to simply delete that part of one or more constant region domains that control the effector function (e.g. complement CLQ binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it can be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides of the present invention can be recombinant polypeptides, natural polypeptides, or synthetic polypeptides comprising an antibody, or fragment thereof, against a human CD37. It will be recognized in the art that some amino acid sequences of the invention can be varied without significant effect of the structure or function of the protein. Thus, the invention further includes variations of the polypeptides which show substantial activity or which include regions of an antibody, or fragment thereof, against CD37 protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, PA (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human CD37. Recombinant expression vectors are replicable DNA constructs which have synthetic or cDNA-derived DNA fragments encoding a polypeptide chain of an anti-CD37 antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR 1, pBR322, pMB9 and their derivatives, wider host range plasmids, such as M13 and filamentous single-stranded DNA phages.

Suitable host cells for expression of a CD37-binding polypeptide or antibody (or a CD37 protein to use as an antigen) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a CD37-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication No. 2008/0312425, 2008/0177048, and 2009/0187005, each of which is hereby incorporated by reference herein in its entirety.

In certain embodiments, the CD37-binding agent is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275:2677-83 (2008), each of which is incorporated by reference herein in its entirety. In certain embodiments, phage display technology has been used to identify/produce the CD37-binding polypeptide. In certain embodiments, the polypeptide comprises a protein scaffold of a type selected from the group consisting of protein A, a lipocalin, a fibronectin domain, an ankyrin consensus repeat domain, and thioredoxin.

In some embodiments, the agent is a non-protein molecule. In certain embodiments, the agent is a small molecule. Combinatorial chemistry libraries and techniques useful in the identification of non-protein CD37-binding agents are known to those skilled in the art. See, e.g., Kennedy et al., J. Comb. Chem, 10:345-354 (2008), Dolle et al, J. Comb. Chem., 9:855-902 (2007), and Bhattacharyya, Curr. Med. Chem., 8:1383-404 (2001), each of which is incorporated by reference herein in its entirety. In certain further embodiments, the agent is a carbohydrate, a glycosaminoglycan, a glycoprotein, or a proteoglycan.

In certain embodiments, the agent is a nucleic acid aptamer. Aptamers are polynucleotide molecules that have been selected (e.g., from random or mutagenized pools) on the basis of their ability to bind to another molecule. In some embodiments, the aptamer comprises a DNA polynucleotide. In certain alternative embodiments, the aptamer comprises an RNA polynucleotide. In certain embodiments, the aptamer comprises one or more modified nucleic acid residues. Methods of generating and screening nucleic acid aptamers for binding to proteins are well known in the art. See, e.g., U.S. Pat. Nos. 5,270,163, 5,683,867, 5,763,595, 6,344,321, 7,368,236, 5,582,981, 5,756,291, 5,840,867, 7,312,325, 7,329,742, International Patent Publication No. WO 02/077262, International Patent Publication No. WO 03/070984, U.S. Patent Application Publication No. 2005/0239134, U.S. Patent Application Publication No. 2005/0124565, and U.S. Patent Application Publication No. 2008/0227735, each of which is incorporated by reference herein in its entirety.

III. Immunoconjugates

The present invention is also directed to conjugates (also referred to herein as immunoconjugates), comprising the anti-CD37 antibodies, antibody fragments, and their functional equivalents as disclosed herein, linked or conjugated to a drug or prodrug. Suitable drugs or prodrugs are known in the art. The drugs or prodrugs can be cytotoxic agents. The cytotoxic agent used in the cytotoxic conjugate of the present invention can be any compound that results in the death of a cell, or induces cell death, or in some manner decreases cell viability, and includes, for example, maytansinoids and maytansinoid analogs. Other suitable cytotoxic agents are for example benzodiazepines, taxoids, CC-1065 and CC-1065 analogs, duocarmycins and duocarmycin analogs, enediynes, such as calicheamicins, dolastatin and dolastatin analogs including auristatins, tomaymycin derivaties, leptomycin derivaties, methotrexate, cisplatin, carboplatin, daunorubicin, doxorubicin, vincristine, vinblastine, melphalan, mitomycin C, chlorambucil and morpholino doxorubicin.

Such conjugates can be prepared by using a linking group in order to link a drug or prodrug to the antibody or functional equivalent. Suitable linking groups are well known in the art and include, for example, disulfide groups, thioether groups, acid labile groups, photolabile groups, peptidase labile groups and esterase labile groups.

The drug or prodrug can, for example, be linked to the anti-CD37 antibody or fragment thereof through a disulfide bond. The linker molecule or crosslinking agent comprises a reactive chemical group that can react with the anti-CD37 antibody or fragment thereof. The reactive chemical groups for reaction with the cell-binding agent can be N-succinimidyl esters and N-sulfosuccinimidyl esters. Additionally the linker molecule comprises a reactive chemical group, which can be a dithiopyridyl group that can react with the drug to form a disulfide bond. Linker molecules include, for example, N-succinimidyl 3-(2-pyridyldithio) propionate (SPDP) (see, e.g., Carlsson et al., *Biochem*. J., 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)2-sulfobutanoate (sulfo-SPDB) (see US Publication No. 20090274713), N-succinimidyl 4-(2-pyridyldithio) pentanoate (SPP) (see, e.g., CAS Registry number 341498-08-6), 2-iminothiolane, or acetylsuccinic anhydride. For example, the antibody or cell binding agent can be modified with crosslinking reagents and the antibody or cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

In another aspect of the present invention, the anti-CD37 antibody is linked to cytotoxic drugs via disulfide bonds and a polyethylene glycol spacer in enhancing the potency, solubility or the efficacy of the immunoconjugate. Such cleavable hydrophilic linkers are described in W02009/0134976. The additional benefit of this linker design is the desired high monomer ratio and the minimal aggregation of the antibody-drug conjugate. Specifically contemplated in this aspect are conjugates of cell-binding agents and drugs linked via disulfide group (—S—S—) bearing polyethylene glycol spacers ($(CH_2CH_2O)_{n=1-14}$) with a narrow range of drug load of 2-8 are described that show relatively high potent biological activity toward cancer cells and have the desired biochemical properties of high conjugation yield and high monomer ratio with minimal protein aggregation.

Specifically contemplated in this aspect is an anti-CD37 antibody drug conjugate of formula (I) or a conjugate of formula (I'):

$$CB—[X_1—(—CH_2—CH_2O—)_n—Y\text{-}D]_m \quad (I)$$

$$[D\text{-}Y—(—CH_2—CH_2O—)_n—X_1]_m—CB \quad (I')$$

wherein:

CB represents an anti-CD37 antibody or fragment;

D represents a drug;

X represents an aliphatic, an aromatic or a heterocyclic unit attached to the cell-binding agent via a thioether bond, an amide bond, a carbamate bond, or an ether bond;

Y represents an aliphatic, an aromatic or a heterocyclic unit attached to the drug via a disulfide bond;

1 is 0 or 1;

m is an integer from 2 to 8; and n is an integer from 1 to 24.

In some embodiments, m is an integer from 2 to 6.

In some embodiments, m is an integer from 3 to 5.

In some embodiments, n is an integer form 2 to 8. Alternatively, as disclosed in, for example, U.S. Pat. Nos. 6,441,163 and 7,368,565, the drug can be first modified to introduce a reactive ester suitable to react with a cell-binding agent. Reaction of these drugs containing an activated linker moiety with a cell-binding agent provides another method of producing a cell-binding agent drug conjugate. Maytansinoids can also be linked to anti-CD37 antibody or fragment using PEG linking groups, as set forth for example in U.S. Pat. No. 6,716,821. These PEG non-cleavable linking groups are soluble both in water and in non-aqueous solvents, and can be used to join one or more cytotoxic agents to a cell binding agent. Exemplary PEG linking groups include heterobifunctional PEG linkers that react with cytotoxic agents and cell binding agents at opposite ends of the linkers through a functional sulfhydryl or disulfide group at one end, and an active ester at the other end. As a general example of the synthesis of a cytotoxic conjugate using a PEG linking group, reference is again made to U.S. Pat. No. 6,716,821 which is incorporated entirely by reference herein. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, to yield a cytotoxic conjugate comprising one or more cytotoxic agents covalently bonded to a cell binding agent through a PEG linking group. Alternatively, the cell binding can be modified with the bifunctional PEG crosslinker to introduce a reactive disulfide moiety (such as a pyridyldisulfide), which can then be treated with a thiol-containing maytansinoid to provide a conjugate. In another method, the cell binding can be modified with the bifunctional PEG crosslinker to introduce a thiol moiety which can then can be treated with a reactive disulfide-containing maytansinoid (such as a pyridyldisulfide), to provide a conjugate.

Antibody-maytansinoid conjugates with non-cleavable links can also be prepared. Such crosslinkers are described in the art (see US Publication No. 20050169933) and include but are not limited to, N-succinimidyl 4-(maleimidomethyl) cyclohexanecarboxylate (SMCC). In some embodiments, the antibody is modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephadex G25 column or by dialysis or tangential flow filtration. The modified antibodies are treated with the thiol-containing maytansinoid (1 to 2 molar equivalent/maleimido group) and antibody-maytansinoid conjugates are purified by gel filtration through a Sephadex G-25 column, chromatography on a ceramic hydroxyapatite column, dialysis or tangential flow filtration or a combination of methods thereof. Typically, an average of 1-10 maytansinoids per antibody are linked. One method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result. Maytansinoid conjugates of antibodies, antibody fragments, and other proteins are made in the same way.

In another aspect of the invention, the CD37 antibody is linked to the drug via a non-cleavable bond through the intermediacy of a PEG spacer. Suitable crosslinking reagents comprising hydrophilic PEG chains that form linkers between a drug and the anti-CD37 antibody or fragment are also well known in the art, or are commercially available (for example from Quanta Biodesign, Powell, Ohio). Suitable PEG-containing crosslinkers can also be synthesized from commercially available PEGs themselves using standard synthetic chemistry techniques known to one skilled in the art. The drugs can be reacted with bifunctional PEG-containing cross linkers to give compounds of the following formula, $Z—X_1—(—CH_2—CH_2—O—)_n—Y_p$-D, by methods described in detail in US Patent Publication 20090274713 and in W02009/0134976, which can then react with the cell binding agent to provide a conjugate. Alternatively, the cell binding can be modified with the bifunctional PEG crosslinker to introduce a thiol-reactive group (such as a maleimide or haloacetamide) which can then be treated with a thiol-containing maytansinoid to provide a conjugate. In another method, the cell binding can be modified with the bifunctional PEG crosslinker to introduce a thiol moiety which can then be treated with a thiol-reactive maytansinoid (such as a maytansinoid bearing a maleimide or haloacetamide), to provide a conjugate.

Accordingly, another aspect of the present invention is an anti-CD37 antibody drug conjugate of formula (II) or of formula (II'):

$$CB—[X_1—(—CH_2—CH_2—O—)_n—Y_p\text{-}D]_m \quad (II)$$

$$[D\text{-}Y_p(—CH_2—CH_2—O—)_n—X_1]_m—CB \quad (II')$$

wherein, CB represents an anti-CD37 antibody or fragment;

D represents a drug;

X represents an aliphatic, an aromatic or a heterocyclic unit bonded to the cell-binding agent via a thioether bond, an amide bond, a carbamate bond, or an ether bond;

Y represents an aliphatic, an aromatic, or a heterocyclic unit bonded to the drug via a covalent bond selected from the group consisting of a thioether bond, an amide bond, a carbamate bond, an ether bond, an amine bond, a carbon-carbon bond and a hydrazone bond;

1 is 0 or 1;

p is 0 or 1;

m is an integer from 2 to 15; and n is an integer from 1 to 2000.

In some embodiments, m is an integer from 2 to 8; and

In some embodiments, n is an integer from 1 to 24.

In some embodiments, m is an integer from 2 to 6.

In some embodiments, m is an integer from 3 to 5.

In some embodiments, n is an integer from 2 to 8. Examples of suitable PEG-containing linkers include linkers having an N-succinimidyl ester or N-sulfosuccinimidyl ester moiety for reaction with the anti-CD37 antibody or fragment thereof, as well as a maleimido- or haloacetyl-based moiety for reaction with the compound. A PEG spacer can be incorporated into any crosslinker known in the art by the methods described herein.

Many of the linkers disclosed herein are described in detail in U.S. Patent Publication Nos. 20050169933 and 20090274713, and in W02009/0134976; the contents of which are entirely incorporated herein by reference.

The present invention includes aspects wherein about 2 to about 8 drug molecules ("drug load"), for example, maytansinoid, are linked to an anti-CD37 antibody or fragment thereof, the anti-tumor effect of the conjugate is much more efficacious as compared to a drug load of a lesser or higher number of drugs linked to the same cell binding agent. "Drug load", as used herein, refers to the number of drug molecules (e.g., a maytansinoid) that can be attached to a cell binding agent (e.g., an anti-CD37 antibody or fragment thereof). In one aspect, the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). $N^{2'}$-deacetyl-$N^{2'}$-(3-mercapto-1-oxopropyl)-maytansine (DM1) and $N^{2'}$-deacetyl-$N^{2'}$-(4-mercapto-4-methyl-1-oxopentyl) maytansine (DM4) can be used.

Thus, in one aspect, an immunocongugate comprises 1 maytansinoid per antibody. In another aspect, an immunocongugate comprises 2 maytansinoids per antibody. In another aspect, an immunocongugate comprises 3 maytansinoids per antibody. In another aspect, an immunocongugate comprises 4 maytansinoids per antibody. In another aspect, an immunocongugate comprises 5 maytansinoids per antibody. In another aspect, an immunocongugate comprises 6 maytansinoids per antibody. In another aspect, an immunocongugate comprises 7 maytansinoids per antibody. In another aspect, an immunocongugate comprises 8 maytansinoids per antibody.

In one aspect, an immunoconjugate comprises about 1 to about 8 maytansinoids per antibody. In another aspect, an immunoconjugate comprises about 2 to about 7 maytansinoids per antibody. In another aspect, an immunoconjugate comprises about 2 to about 6 maytansinoids per antibody. In another aspect, an immunoconjugate comprises about 2 to about 5 maytansinoids per antibody. In another aspect, an immunoconjugate comprises about 3 to about 5 maytansinoids per antibody. In another aspect, an immunoconjugate comprises about 3 to about 4 maytansinoids per antibody.

In one aspect, a composition comprising immunoconjugates has an average of about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1) drug molecules (e.g., maytansinoids) attached per antibody. In one aspect, a composition comprising immunoconjugates has an average of about 1 to about 8 drug molecules (e.g., maytansinoids) per antibody. In one aspect, a composition comprising immunoconjugates has an average of about 2 to about 7 drug molecules (e.g., maytansinoids) per antibody. In one aspect, a composition comprising immunoconjugates has an average of about 2 to about 6 drug molecules (e.g., maytansinoids) per antibody. In one aspect, a composition comprising immunoconjugates has an average of about 2 to about 5 drug molecules (e.g., maytansinoids) per antibody. In one aspect, a composition comprising immunoconjugates has an average of about 3 to about 5 drug molecules (e.g., maytansinoids) per antibody. In one aspect, a composition comprising immunoconjugates has an average of about 3 to about 4 drug molecules (e.g., maytansinoids) per antibody.

In one aspect, a composition comprising immunoconjugates has an average of about 2±0.5, about 3±0.5, about 4±0.5, about 5±0.5, about 6±0.5, about 7±0.5, or about 8±0.5 drug molecules (e.g., maytansinoids) attached per antibody. In one aspect, a composition comprising immunoconjugates has an average of about 3.5±0.5 drug molecules (e.g., maytansinoids) per antibody.

The anti-CD37 antibody or fragment thereof can be modified by reacting a bifunctional crosslinking reagent with the anti-CD37 antibody or fragment thereof, thereby resulting in the covalent attachment of a linker molecule to the anti-CD37 antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

The drug molecules can also be linked to the antibody molecules through an intermediary carrier molecule such as serum albumin.

As used herein, the expression "linked to a cell-binding agent" or "linked to an anti-CD37 antibody or fragment" refers to the conjugate molecule comprising at least one drug derivative bound to a cell-binding agent anti-CD37 antibody or fragment via a suitable linking group, or a precursor thereof. One linking group is SMCC.

In certain embodiments, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain embodiment, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (III):

(III)

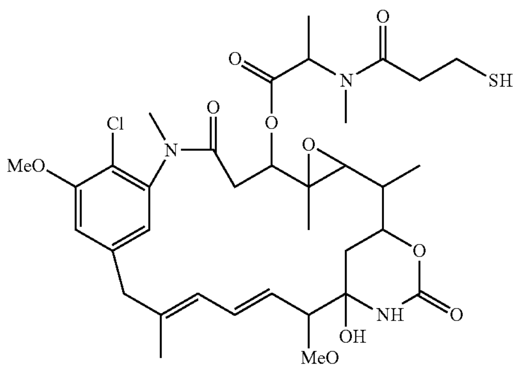

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula (IV):

(IV)

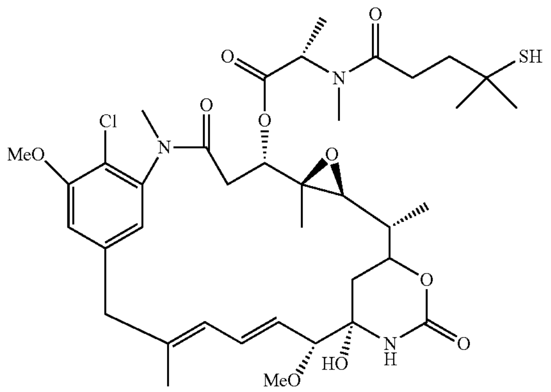

Another maytansinoid comprising a side chain that contains a sterically hindered thiol bond is $N^{2'}$-deacetyl-N-$^{2'}$(4-mercapto-1-oxopentyl)-maytansine (termed DM3), represented by the following structural formula (V):

(V)

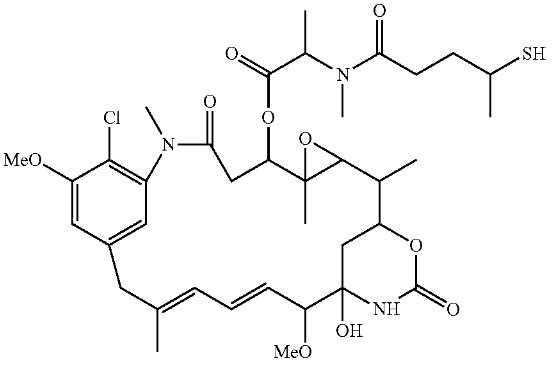

Each of the maytansinoids taught in U.S. Pat. Nos. 5,208,020 and 7,276,497, can also be used in the conjugate of the present invention. In this regard, the entire disclosure of U.S. Pat. Nos. 5,208,020 and 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety.

Structural representations of some conjugates are shown below:

(VI)

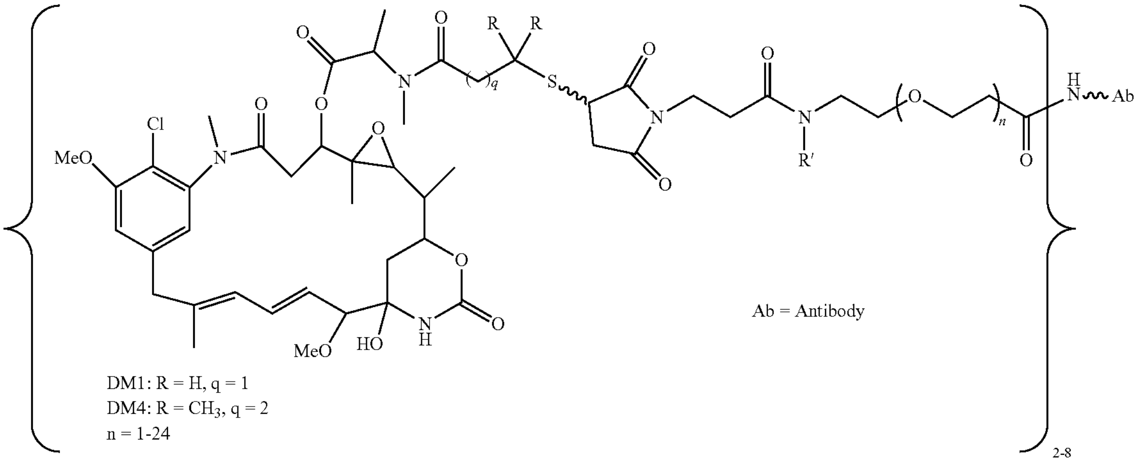

Ab = Antibody

DM1: R = H, q = 1
DM4: R = $CH_3$, q = 2
n = 1-24

Ab-PEG-Mal-DM1/DM4

(VII)

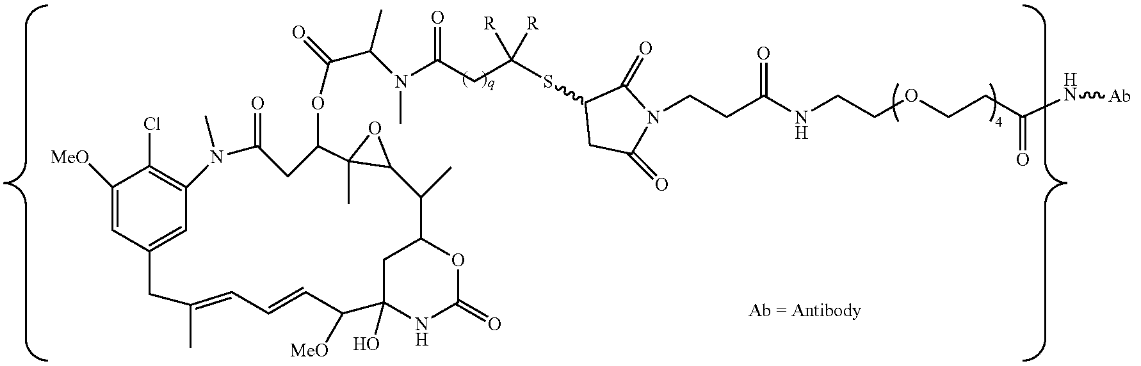

Ab = Antibody

Ab-PEG4-Mal-DM1

-continued
(VIII)
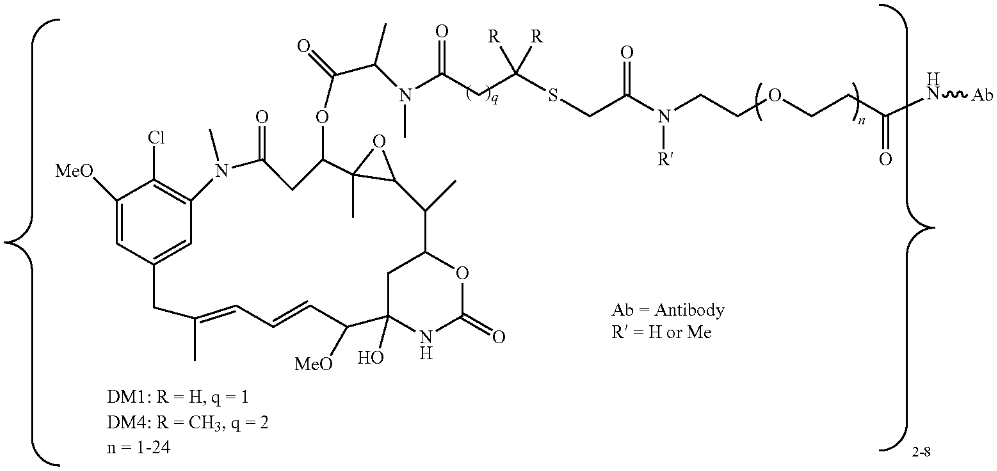
Ab = Antibody
R′ = H or Me
DM1: R = H, q = 1
DM4: R = $CH_3$, q = 2
n = 1-24
Ab-PEG-SIA-DM1/DM4
(IX)
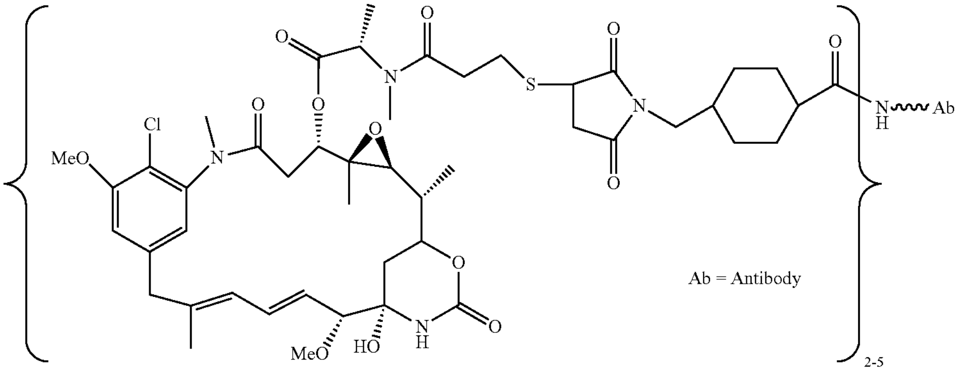
Ab = Antibody
Ab-SMCC-DM1
(X)
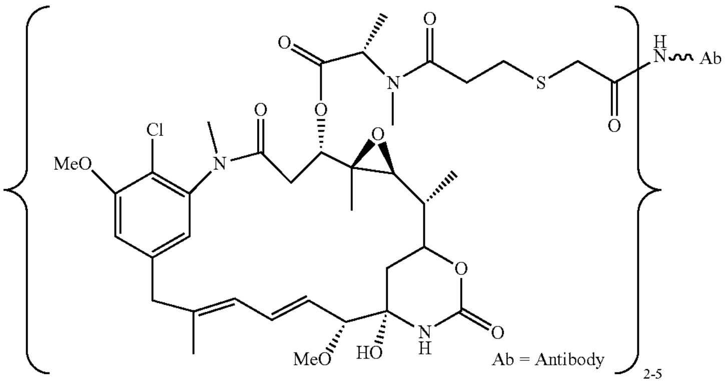
Ab = Antibody
Ab-SIA-DM1

-continued (XI)

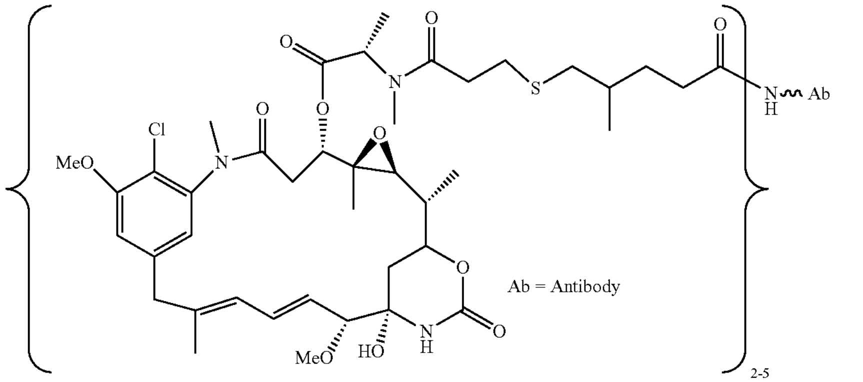

Ab-SPP-DM1

(XII)

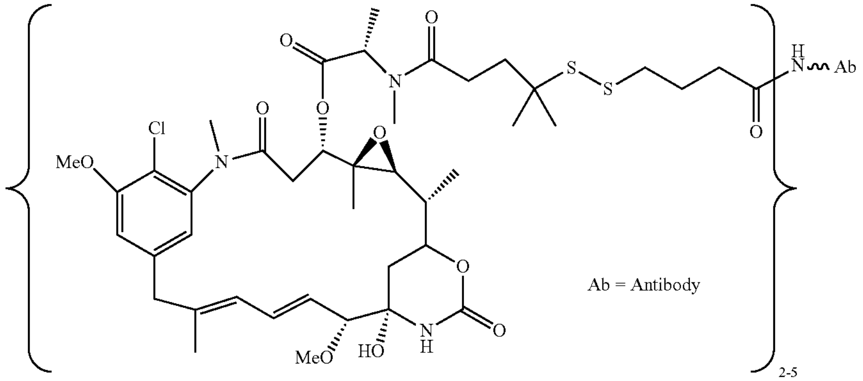

Ab-SPDB-DM4

(XIII)

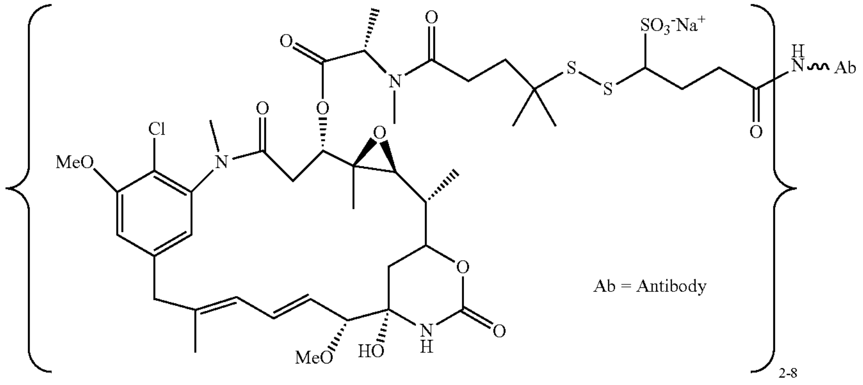

Ab-sulfo-SPDB-DM4

Several descriptions for producing such antibody-maytansinoid conjugates are provided in U.S. Pat. Nos. 6,333,410, 6,441,163, 6,716,821, and 7,368,565, each of which is incorporated herein in its entirety.

In general, a solution of an antibody in aqueous buffer can be incubated with a molar excess of maytansinoids having a disulfide moiety that bears a reactive group. The reaction mixture can be quenched by addition of excess amine (such as ethanolamine, taurine, etc.). The maytansinoid-antibody conjugate can then be purified by gel filtration.

The number of maytansinoid molecules bound per antibody molecule can be determined by measuring spectrophotometrically the ratio of the absorbance at 252 nm and 280 nm. The average number of maytansinoid molecules/antibody can be, for example, about 1-10, 2-5, 3-4, or about 3.5. In one aspect, the average number of maytansinoid molecules/antibody is about 3.5±0.5.

Anthracycline compounds, as well as derivatives, intermediates and modified versions thereof, can also be used to prepare anti-CD37 immunoconjugates. For example, doxorubicin, doxorubicin derivatives, doxorubicin intermediates, and modified doxorubicins can be used in anti-CD37 conjugates. Exemplary compounds are described in WO 2010/009124, which is herein incorporated by reference in its entirety. Such compounds include, for example, compounds of the following formula:

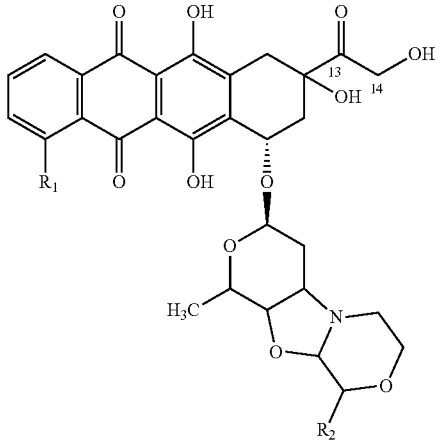

wherein $R_1$ is a hydrogen atom, hydroxy or methoxy group and $R_2$ is a $C_1$-$C_5$ alkoxy group, or a pharmaceutically acceptable salt thereof.

Conjugates of antibodies with maytansinoid or other drugs can be evaluated for their ability to suppress proliferation of various unwanted cell lines in vitro. For example, cell lines such as the human lymphoma cell line Daudi and the human lymphoma cell line Ramos, can easily be used for the assessment of cytotoxicity of these compounds. Cells to be evaluated can be exposed to the compounds for 4 to 5 days and the surviving fractions of cells measured in direct assays by known methods. $IC_5$s values can then be calculated from the results of the assays.

The immunoconjugates can, according to some embodiments described herein, be internalized into cells. The immunocongugate, therefore, can exert a therapeutic effect when it is taken up by, or internalized, by a CD37-expressing cell. In some particular embodiments, the immunoconjugate comprises an antibody, antibody fragment, or polypeptide, linked to a cytotoxic agent by a cleavable linker, and the cytotoxic agent is cleaved from the antibody, antibody fragment, or polypeptide, wherein it is internalized by a CD37-expressing cell.

In some embodiments, the immunoconjugates are capable of reducing tumor volume. For example, in some embodiments, treatment with an immunoconjugate results in a % T/C value that is less than about 50%, less than about 45%, less than about 40%, less than about 35%, less than about 30%, less than about 25%, less than about 20%, less than about 15%, less than about 10%, or less than about 5%. In some particular embodiments, the immunoconjugates can reduce tumor size in a BJAB xenograft model and/or a SU-DHL-4 xenograft model.

In another aspect of the invention siRNA molecules can be linked to the antibodies of the present invention instead of a drug. siRNAs can be linked to the antibodies of the present invention by methods commonly used for the modification of oligonucleotides (see, for example, US Patent Publications 20050107325 and 20070213292). Thus the siRNA in its 3' or 5'-phosphoromidite form can be reacted with one end of the crosslinker bearing a hydroxyl functionality to give an ester bond between the siRNA and the crosslinker. Similarly reaction of the siRNA phosphoramidite with a crosslinker bearing a terminal amino group results in linkage of the crosslinker to the siRNA through an amine. Alternatively, the siRNA can be derivatized by standard chemical methods to introduce a thiol group. This thiol-containing siRNA can be reacted with an antibody, that has been modified to introduce an active disulfide or maleimide moiety, to produce a cleavable or non cleavable conjugate. Between 1-20 siRNA molecules can be linked to an antibody by this method.

III. Polynucleotides

In certain embodiments, the invention encompasses polynucleotides comprising polynucleotides that encode a polypeptide that specifically binds CD37 or a fragment of such a polypeptide. For example, the invention provides a polynucleotide comprising a nucleic acid sequence that encodes an antibody to a human CD37 or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotides are isolated. In certain embodiments, the polynucleotides are substantially pure.

The invention provides a polynucleotide comprising a polynucleotide encoding a polypeptide comprising a sequence selected from the group consisting of SEQ ID NOs:4-120.

The invention further provides a polynucleotide comprising a sequence selected from those shown in Tables 7-10 below.

TABLE 7

Variable heavy chain polynucleotide sequences

| Antibody | VH Polynucleotide Sequence (SEQ ID NO) |
|---|---|
| muCD37-3 | caggtgcaggtgaaggagtcaggacctggcctggtggcgccctcacagagcctgtccattacatgcactg<br>tctcagggactcattaaccacctctggtgtaagctgggttcgccagcctccaggaaagggtctggagtg<br>gctgggagtaatatggggtgacgggagcacaaactatcattcagctctcaaatccagactgagcatcaag<br>aaggatcactccaagagccaagttacttaaaactgaacagtctgcaaactgatgacacagccacgtact<br>actgtgccaaaggaggctactcgaggctcactggggccaagggactctggtcacagtctctgca (SEQ ID<br>NO: 121) |
| chCD37-3 | aagcttgccaccatggctgtcctggcactgctcctctgcctggtgacatacccaagctgtgtcctatcacaggtgcaggtg<br>aaggagtcaggacctggcctggtggcgccctcacagagcctgtccattacatgcactgtctcagggttctcattaaccac<br>ctctggtgtaagctgggttcgccagcctccaggaaagggtctggagtggctgggagtaatatggggtgacgggagcac<br>aaactatcattcagctctcaaatccagactgagcatcaagaaggatcactccaagagccaagttacttaaaactgaacagt<br>ctgcaaactgatgacacagccacgtactactgtgccaaaggaggctactcgttggctcactggggccaagggactctgg<br>tcacagtctctgcagcctctacgaagggccc (SEQ ID NO: 122) |
| huCD37-3v1.0 | aagcttgccaccatgggttggagctgcattattctgtactggtggccaccgccaccggtgtgcactcacaagtccaagtc<br>caagaatctggtccaggtctggtggcccatcccaaactctgagcatcacctgtaccgtactggttttagccttaccacctc |

TABLE 7-continued

Variable heavy chain polynucleotide sequences

| Antibody | VH Polynucleotide Sequence (SEQ ID NO) |
|---|---|
| | tggtgtgagttgggtacgccaaccacccggtaagggtctcgaatggctgggtgtaatctggggtgatggttccacaaatt<br>accatccttccctcaagtcccgccttagcatcaaaaaggatcacagcaaaagtcaagttacctgaaactgaatagtctgac<br>agcagccgatacagccacctactattgcgccaagggtggttatagtcttgcacactggggtcaaggtaccctcgttaccgt<br>ctcctcagctagtaccaagggccc (SEQ ID NO: 123) |
| huCD37-3v1.1 | aagcttgccaccatgggctggagctgtatcattctgtactggtggcgacagctactggggtccactcccaagtgcaggta<br>caagagtccgggcctggattggtcgcaccaagccagaccctctctatcacttgtaccgttagcgggttctctctgacaacc<br>agtggagtgagttgggtgaggcagccaccaggaaagggactggagtggctgggggtgatttggggcgacggcagca<br>caaactatcattccagtcttaaatctcggttgtccattaaaaagaccatagtaaatctcaagttttcctgaaactcaatagcct<br>gacagccgcagacactgctacgtattactgcgccaaaggaggatacagtctggctcactggggacaggggaccctggt<br>gaccgtgtcatccgcatcaacaaagggccc (SEQ ID NO: 124) |
| muCD37-12 | cagatccagaggtgcagtctggacctgagctgaagaagcctggagagacagtcaagatctcctgcaagg<br>cttctgggtataccttcacaaagtatggaatgaactgggtgaagcaggctcaaggaaagggtttaaagtg<br>gatgggctggataaacaccaacactggagagtcaagaaatgctgaagaattcaagggacggtttgccttc<br>tctttggaaacctctgccagcactgcctatttgcagatcaacaacctcaaatatgaggacacggctacat<br>atttctgtggaaggggcacggtagtagcggactggggccaaggcaccactctcacagtctcctca (SEQ ID<br>NO: 125) |
| chCD37-12 | aagcttgccaccatggggtggtcatgcataatcctctttctggtcgctactgctaccggtgtgcactcacagattcagctgg<br>ttcaaagtggcccagagctgaaaaagccaggggaaacagtgaaaataagttgcaaggcatccggttacactttcacaaa<br>gtacggcatgaactgggtcaagcaggcccagggcaaggggctcaaatggatgggttggatcaataccaacactggcg<br>agtctaggaatgctgaggagtttaagggccggtttgccttcagcctggagacaagtgccagcacagcttacctgcaaatc<br>aacaatctgaagtatgaggatacagcaacctatttctgcggccgcggcactgtcgttgcagactggggacaaggtacca<br>ccttgactgtatccagtgccagcactaagggccc (SEQ ID NO: 126) |
| muCD37-38 | gatgtgcagcttcaggagtcaggacctgacctggtgaaaccttctcagtcactttcactcacctgcactg<br>tcactggctactccatcaccagtggttttggctggcactggatccggcagtttccaggaaacaagctgga<br>atggatggcctacatactctacagtggtggcactgactacaacccatctctcaaaagtcgaatctctatc<br>actcgagacacttccaagaaccagttcttcctgcggttgagttctgtgactactgaggacacagccacat<br>attactgtgcaagaggctactatggttacggggcctggtttgtttactggggccaagggactctggtcac<br>tgtctctgca (SEQ ID NO: 127) |
| chCD37-38 | aagcttgccaccatgggctggagttgtatcattctgtattggtggccaccgccactggagtccattcccaagtgcaactcc<br>aggaatctggccctgacctggttaagccatctcagagcctctccctgacctgcactgttacaggatactcaatcacatcag<br>gctttggctggcactggatcagacaatttcccgggaacaagttggaatggatggcttacattctgtatagcgggggtaccg<br>attacaatccttccctcaagagccgaatctctatcaccagggatacaagcaagaaccaattattctccgcctcagctctgtg<br>actaccgaagataccgctacttactattgtgccaggggctactatggatatggtgcatggttcgtctattggggccaggga<br>accctggtgactgtgagcgctgcctctaccaagggccc (SEQ ID NO: 128) |
| huCD37-38 | aagcttgccaccatgggttggagctgcatcattcttttcctggtcgctactgcaactggagtccactcacaggtccagctgc<br>aagagtccggtcctgggcttgtgaaacccagccagtccctcagtctcacctgtactgtctctggctactctattaccagtgg<br>gttcggctggcattggattaggcagtttcccggtaaggggctggagtggatggcatatatcctgtacagcggaggaacc<br>gattacaacccaagtctgaagagcaggatcagcattacccgggacacaagcaaaaaccagtttttccttcggctgtctagt<br>gttacagctgcagacaccgctacttactattgtgctcggggttactatggctatggggcttggtttgtgtattggggacaag<br>gcactcttgtgaccgtgagcagcgcctcaacaaagggccc (SEQ ID NO: 129) |
| muCD37-50 | gatgtgcagcttcaggagtcaggacctgacctgttgaaaccttctcagtcactttcactcacctgcactg<br>tcactggctactccatcaccagtggttttgcctggcactggatccggcagtttccaggaaacaaactgga<br>atggatgggctacatactctacagtggtagcactgtctacagcccatctctcaaaagtcgaatctctatc<br>actcgagacacatccaagaaccacttcttcctgcagttgaattctgtgactactgaggacacagccacat<br>attactgtgcaagagggtactatggttacggcgcctggtttgcttactggggccaagggactctggtcac<br>tgtctctgca (SEQ ID NO: 130) |
| huCD37-50 | aagcttgccaccatggggtggtcctgcataatccttacctggagctactgctaccggagtccattcacaggtgcagctgc<br>aggagtccggccccggcctgctcaagccttctcagagtctgagtctgacttgtactgtttctggctacagcataaccagcg<br>gtttcgcttggcactggatcagacagcatcccggcaacaaactggagtggatgggatacatactgtactcaggctcaact<br>gtctattccccctccctgaaatcccggatcagtattacccgtgacacttctaagaaccattlattctgcagctgaacagcgtt<br>accgcagctgacactgcaacctactactgtgcccggggatattatggatacggagcttggttcgcttactggggccaagg<br>caccctcgtaactgtgagtgctgcttccaccaagggccc (SEQ ID NO: 195) |
| muCD37-51 | gatgtgcagcttcaggagtcaggacctgacctgttgaaaccttctcagtcactttcactcacctgcactg<br>tcactggctactccatctccagtggttttgcctggcactggatccggcagtttccaggaaacaaactgga<br>atggatgggctacatacactacagtggtagcactaactacagcccatctctcaaaagtcgaatctctatc<br>actcgagactcatccaagaaccagttcttcctgcagttgaattctgtgactactgaggacacagccacat<br>attactgtgcaagaggatactatggtttcggcgcctggtttgtttactggggccaagggactctggtcac<br>tgtctctgca (SEQ ID NO: 131) |
| huCD37-51 | Aagcttgccaccatgggttggtcttgcatcatcctgttcctggtggccactgccactggcgtgcattcagaagttcagttgg<br>tggagtccggcccagaagtgctgaaacccggcgaatcactgtccctgacttgtaccgtgtcaggttatagcatcagcagc<br>ggctttgcttggcactggattcggcagtttccaggcaagggactggaatggatgggctacatccattacagtggctcaac<br>caattacagccctagcctgcagggccgaatctctattaccagggatagactattaaccagtattcctgcagcttaattccgt<br>gactgcctctgacacagcaacttactattgcgcccgtggctactacgggttcggagcctggtttgtatactggggtcaggg<br>caccctggtcactgtctcagccgcctctaccaagggccc (SEQ ID NO: 196) |

TABLE 7-continued

| Variable heavy chain polynucleotide sequences | |
|---|---|
| Antibody | VH Polynucleotide Sequence (SEQ ID NO) |
| muCD37-56 | gatgtgcagcttcaggagtcaggacctgacctggtgaaaccttctcagtcactttcactcacctgcactg tcactggctactccatcaccagtggttttgcctggcactggatccggcagtttccaggaaacaaactgga atggatgggctacatacactacagtggtggcactaactacaacccatctctcaaaagtcgagtctctatc actcgagacacatccaagaaccagttcttcctgcagttgaattctgtgactactgaggacacagccacatattactgtgcaa gaggctactatggtttcggggcctggtttgcttactggggccaagggactctggtccc tgtctctgca (SEQ ID NO: 132) |
| huCD37-56 | aagcttgccaccatggggtggagctgcattatcctgacctcgtcgccaccgcaaccggcgtccactcccaggtgcagct gcaagaaagcgggccaggattggtaaaaccttcccagtctctgagtcttacttgtaccgtatctggatacagtatcacatct ggcttcgcctggcattggattcgccagtttcccggcaaggggcttgagtggatggggtatattcattattctggaggtacca actacaacccttccctgaagagtcgagtctcaattaccagggacacttccaagaaccaattctattgcagcttaattcagtg accgctgccgacaccgctacttactactgcgcccggggctactatgggtttggtgcctggttcgcctactggggccaggg gaccctggtgcccgtgtctgctgcctccacaaagggccc (SEQ ID NO: 133) |
| muCD37-57 | gatgtgcagcttcaggagtcaggacctgacctgttgaaaccttctcagtcactttcactcacctgcactg tcactggctactccatcaccagtggttttgcctggcactggatccggcagtttccaggaaacaaactgga atggatgggctacatactctacagtggtagcactgtctacagcccatctctcaaaagtcgaatctctatc actcgagacacatccaagaaccagttcttcctgcagttgaattctgtgactactgaggacacagccacatattactgtgcaa gagggtactatggttacggcgcctggtttgcttactggggccaagggactctggtcactgtctctgca (SEQ ID NO: 134) |
| huCD37-57 | aagcttgccaccatgggctggagctgcatcattctgtttctggtggccacagcaactggcgttcacagtcaagtccaactg caggagagcggccccggactcctgaaaccatctcagtcactcagtctgacatgtactgtgagcggctacagcattacctc aggcttcgcttggcattggatcaggcagttccccggaaaaggtctggagtggatggggtacattctgtacagcggcagta cagtgtattcaccctccttgaaatctaggatatcaatcacacgtgatacaagcaaaaatcagttcttcctccagctgaactcc gtcaccgccgcagacacagcaacctattattgtgctcgcggatactacggatatggcgcatggttcgcctattggggcca ggggacactcgtgaccgtttccgccgcctccacaaagggccc (SEQ ID NO: 135) |

TABLE 8

| Variable light chain polynucleotide sequences | |
|---|---|
| Antibody | VL Polynucleotide Sequence (SEQ ID NO) |
| muCD37-3 | gacatccagatgactcagtctccagcctccctttctgtatctgtgggagaaactgtcaccatcacatgtc gagcaagtgagaatattcgcagtaatttagcatggtatcagcagaaacagggaaaatctcctcagctcct ggtcaatgttgcaacaaacttagcagatggtgtgccatcaaggttcagtggcagtggatcaggcacacag tattccctcaagatcaacagcctgcagtctgaagattttgggacttattactgtcaacattattggggta ctacgtggacgttcggtggaggcaccaagctggaaatcaaacgt (SEQ ID NO: 136) |
| chCD37-3 | gaattcgccaccatgagtgtgcccactcaggtcctggggttgctgctgctgtggcttacagatgccagatgtgacatccag atgactcagtctccagcctccctttctgtatctgtgggagaaactgtcaccatcacatgtcgagcaagtgagaatattcgca gtaatttagcatggtatcagcagaaacagggaaaatctcctcagctcctggtcaatgagcaacaaacttagcagatggtgt gccatcaaggttcagtggcagtggatcaggcacacagtattccctcaagatcaacagcctgcagtctgaagattttggga cttattactgtcaacattattggggtactacgtggacgttcggtggaggcaccaagctggaaatcaaacgtacg (SEQ ID NO: 137) |
| huCD37-3 (1.0 and 1.1) | gaattcgccaccatgggttggtcctgcatcatcttgtttctcgtggccacagccaccggtgttcactctgatatacaaatgac tcaaagcccttccagtttgagcgtaagtgtgggtgaacgcgtaacaatcacctgtagagctagtgaaaacatccgcagta atctcgcatggtaccaacaaaagccaggtaagtcacctaagctcctcgtgaatgagctaccaacctcgctgatggtgtgc cttcacgattctctggttcaggttccggtaccgattattcacttaagatcaactcactccaaccagaagatttcggtacatatta ctgtcaacactactggggtacgacctggacattcggtcaaggtactaagctggaaatcaagcgtacg (SEQ ID NO: 138) |
| muCD37-12 | gacattgtgctaacacagtctcctgcttccttagctgtatctctggggcagagggccaccatctcatgca gggccagccaaagtgtcagtacatctagctatagttatttgtactggttccagcagaaaccaggacagcc acccaaactcctcatcaagtatgcatccaacctagcatctggggtccctgccaggttcagtggcagtggg tctgggacagacttcaccctcaacatccatcctgtggaggaggaggatactgcaacatattactgtcaac acagttgggagattccgtacacgttcggagggggaccaaactggaaataaaacgg (SEQ ID NO: 139) |
| chCD37-12 | gaattcgccaccatgggttggtcctgtataatcctgttcttggtggccaccgctactggcgttcatagtgatattgtactcact cagtcaccagccagtctggcagtgtccctgggccagcgtgccaccatctcctgccgggcctcacagtccgtgagcacta gctcttattcctatctctactggtacaacagaagccaggacagccccctaagctgctgatcaagtacgcctccaacctcgc cagcggcgttcccgctagattctctggttccggtagcggaactgatttcactttgaacatccaccccgttgaggaagagga taccgccacttactattgtcaacactcttgggagattccttacacctaggaggaggaacaaagctcgaaattaagcgtacg (SEQ ID NO: 140) |
| muCD37-38 | caaattgttctcacccagtctccagcaatcatgtctgcatctccaggggagaaggtcaccatgacctgca gtgccagctcaagtgtaacttacatgcactggtaccagcagaagtcaggcacctcccccaaaagatggat ttatgacacatccaaactggcttctggagtccctgctcgcttcagtggcggtgggtctgggacctcttac tctctcacaatcagcagcatggaggctgaagatgctgccacttattactgccagcagtggattagtaacc cacccacgttcggaggggggaccaagctggaaattaaacgg (SEQ ID NO: 141) |

TABLE 8-continued

| Variable light chain polynucleotide sequences | |
|---|---|
| Antibody | VL Polynucleotide Sequence (SEQ ID NO) |
| chCD37-38 | gaattcgccaccatgggctggtcctgtatcatcctgtttctcgtggccacagctacaggtgttcattctcagattgtgctgac<br>ccaatcaccagctattatgtccgctagccccggcgagaaagtgacaatgacatgtagcgctagctcttctgtgacttacat<br>gcattggtatcaacagaagtcaggtaccagtcccaagcgttggatctacgacacatccaaactggcctccggagtccctg<br>ccaggttcagcggaggtgggtccggcaccagttattcactgaccatatcctctatggaagctgaagatgctgctacttatta<br>ttgtcaacaatggatttctaacccccccacctttggtggcggaacaaagctggagatcaagcgtacg (SEQ ID<br>NO: 142) |
| huCD37-38 | gaattcgccaccatgggatggtcctgcattattctgttcttggtcgccactgctactggcgttcactctgacattgtgctcaca<br>cagtctccagcctcaatgtctgcttcccccggtgagcgggtgaccatgacatgctctgccagttcctccgtgacatatatgc<br>attggtatcagcaaaaacccggtacctctccaaaaagatggatctacgacacttcaaagcttgcatcaggcgttcctgcca<br>gattttccgggtctgggtctggcacttcatacagtctgaccattagaccatggaagctgaagatgcagccacctattactgt<br>cagcagtggatttcaaatcctcctaccttcggcggcggaaccaaactggagataaagcgtacg (SEQ ID<br>NO: 143) |
| muCD37-50 | caaattgttctcacccagtctccagcaatcatgtctgcatctccaggggagaaggtcaccatgacctgca<br>gtgccacctcaagtgtgacttacatgcactggtaccagcagaagtcaggcacctcccccaaaagatggatttatgacaca<br>tccaaactgccttatggagtccctggtcgtttcagtggtagtgggtctgggacctcttactctctcacaatcagcagcatgg<br>aggctgaagatgctgccacttattactgccagcagtggagtgataacccacccacgttcggctcggggacaaagttgga<br>aataaagcgg (SEQ ID NO: 144) |
| huCD37-50 | gaattcgccaccatgggttggtcatgcattattctgttcctggttgctaccgcaacaggagtacatagtgagatagtcctcac<br>ccaaagtcctgctactatgtctgccagcccaggagagcgtgtgaccatgacttgctctgcaacctcaagtgtgacatacat<br>gcattggtatcagcaaaagcctggccaatcccctaaaaggtggatctacgatacttctaatctgccatacggtgtgcccgc<br>aaggttctccgggagtggcagtggcaccagttatagtctgaccatcagttcaatggaagcagaggatgcagcaacctatt<br>attgtcagcagtggtccgataatccccctacttttggtcagggtacaaagctggagattaagcgtacg (SEQ ID<br>NO: 145) |
| muCD37-51 | caaattgttctcacccagtctccagcaatcatgtctgcatctccaggggagaaggtcaccatgacctgca<br>gtgccacctcaagtgtgacttacatgcactggtaccagcagaagtcaggcacctcccccaaaagatggatttatgacaca<br>tccaaactggcttctggagtccctgctcgcttcagtggcagtgggtctgggacctcttactctctcacaatcagcaacatgg<br>aggctgaagatgctgccacttattactgccagcagtggagtagtaacccacccacgttcggctcggggacaaagttgga<br>aataaagcgg (SEQ ID NO: 146) |
| huCD37-51 | gaattcgccaccatgggatggagctgtattattctgttcctggttgctactgctactggcgtccattccgagatagtcctcac<br>ccagagccccgcaaccatgagtgcctcccctggggagcgagtgactatgacttgttccgccacttcttcagttacctatat<br>gcattggtatcagcagaaacctggacagtctccaaagcgttggatttacgacacctccaacctggcttcaggagttcctgc<br>taggttcagcggatctgggtctggcacaagttattcactcaccattagttccatggaggccgaagatgccgctacttactac<br>tgtcagcagtggagcagcaaccccctacattcgggcagggaactaagctggagatcaaacgtacg (SEQ ID<br>NO: 147) |
| muCD37-56 | caaattgttctcacccagtctccagcattcatgtctgcatctccaggggataaggtcaccatgacctgca<br>gtgccagttcaagtgttacttacatgcactggtatcagcagaagtcaggcacctcccccaaaagatggatttatgacacat<br>ccaaactggcttctggagtccctgctcgcttcagtggcggtgggtctgggacctcttac<br>tctctcacaatcagcaccatggaggctgaagatgctgccacttattactgccagcagtggattagtgacc<br>cacccacgttcggagggggggaccaagctggaaataaaacgg (SEQ ID NO: 148) |
| huCD37-56 | gaattcgccaccatgggctggtcctgtatcatcctgtttctggtggcaaccgctactggggttcactctgatattgtcctgac<br>acagagtccagccttcatgagtgcttctcccggagaaaaggtcacaatgacttgttcagcttcctcctccgtcacatacatg<br>cattggtaccagcagaagcctgaccagagtcctaagaggtggatctatgatacaagcaatctggcttccggtgtcccctc<br>ccgcttttcaggcggcggaagcggaactgactatagccttaccatctcctcaatggaagccgaggacgctgctacatatt<br>actgccagcaatggatcagcgaccctcctactttcggacagggaacaaaattggaaattaagcgtacg (SEQ ID<br>NO: 149) |
| muCD37-57 | caaattgttctcacccagtctccagcaatcatgtctgcatctccaggggagaaggtcaccatgacctgca<br>gtgccacctcaagtgtgacttacatgcactggtaccagcagaagtcaggcacctcccccaaaagatggatttatgacaca<br>tccaaactggcttctggagtccctgctcgcttcagtggcagtgggtctgggacctcttactctctcacaatcagcagcatgg<br>aggctgaagatgctgccacttattactgccagcagtggagtgataacccacccacgttcggctcggggacaaagttgga<br>aataaagcgg (SEQ ID NO: 150) |
| huCD37-57 | gaattcgccaccatggggtggtcctgtattatcctgttcctggtcgcaaccgccacaggcgttcactccgagatcgtgaga<br>ctcagagcccagccaccatgtccgcttcccccggggagagagtgacaatgacttgttccgccacaagttctgtaacctac<br>atgcattggtaccagcaaaaaccaggacagagtccccgtcgttggatttatgatacctctaacctggcttcaggcgttcctg<br>cccgcttttctggtagtggatctgggacttcctatagccttaccataagctctatggaagccgaggacgccgctacatacta<br>ctgccagcagtggagtgataaccccccaccttcgggcagggaaccaaattggagatcaaacgtacg (SEQ ID<br>NO: 151) |

TABLE 9

Full-length heavy chain polynucleotide sequences

| Antibody | Full-Length Heavy Chain Polynucleotide Sequence (SEQ ID NO) |
|---|---|
| chCD37-3 | aagcttgccaccatggctgtcctggcactgctcctctgcctggtgacatacccaagctgtgtcctatcacaggtgcaggtg<br>aaggagtcaggacctggcctggtggcgccctcacagagcctgtccattacatgcactgtctcagggttctcattaaccac<br>ctctggtgtaagctgggttcgccagcctccaggaaagggtctggagtggctgggagtaatatggggtgacgggagcac<br>aaactatcattcagctctcaaatccagactgagcatcaagaaggatcactccaagagccaagttttcttaaaactgaacagt<br>ctgcaaactgatgacacagccacgtactactgtgccaaaggaggctactcgttggctcactggggccaagggactctgg<br>tcacagtctctgcagcctctacgaagggcccatcagttttccccttggctccaagttctaaatccacaagcggtggaacag<br>ctgcactgggatgcctcgttaaagattatttccctgagcctgtgacagtgagctggaatagcggagcattgacttcaggtgt<br>gcacacttttcccgctgtgttgcagtcctccggtctgtactcactgtccagtgtcgtaaccgtcccttctagcagcttgggaa<br>cccagacctacatctgtaacgtcaaccataaaccatccaacacaaaggtggataagaaggttgaaccaaagagctgtga<br>taagacacatacatgccctccttgtcctgcaccagagctcctcggaggtccatctgtgttcctgtttccccccaaacccaag<br>gacactcttatgatctctcgtactccagaggtcacctgtgttgttgtcgacgtgagccatgaagatcccgaggttaaattcaa<br>ctggtacgtggatggagtcgaggttcacaatgccaagaccaagcccagggaggagcaatataattctacatatcgggta<br>gtgagcgttctgaccgtgctccaccaagattggctcaatggaaaagagtacaagtgcaaggtgtccaacaaggctcttcc<br>cgctcccattgagaaaactatctccaaagccaaggggcagccacgggaaccccaggtgtatacattgcccccatctaga<br>gacgagctgaccaagaaccaggtgagtctcacttgtctggtcaaggggttttacccttctgacattgctgtagagtgggag<br>tctaacggacagccagaaaacaactacaagacaactcccccagtgctggacagcgacgggagcttcttcctctactcca<br>agttgactgtagacaagtctagatggcagcaaggaaacgttttctcctgctcagtaatgcatgaggctctgcacaatcacta<br>tacccagaaatcactgtcccttagcccagggtgactcgag (SEQ ID NO: 152) |
| huCD37-3v1.0 | aagcttgccaccatgggttggagctgcattattctgtttctggtggccaccgccaccggtgtgcactcacaagtccaagtc<br>caagaatctggtccaggtctggtggccccttcccaaactctgagcatcacctgtaccgtttctggttttagccttaccacctc<br>tggtgtgagttgggtacgccaaccacccggtaagggtctcgaatggctgggtgtaatctggggtgatggttccacaaatt<br>accatccttccctcaagtcccgccttagcatcaaaaaggatcacagcaaaagtcaagttttcctgaaactgaatagtctgac<br>agcagccgatacagccacctactattgcgccaagggtggttatagtcttgcacactggggtcaaggtaccctcgttaccgt<br>ctcctcagctagtaccaagggcccatcagttttccccttggctccaagttctaaatccacaagcggtggaacagctgcact<br>gggatgcctcgttaaagattatttccctgagcctgtgacagtgagctggaatagcggagcattgacttcaggtgtgcacac<br>ttttcccgctgtgttgcagtcctccggtctgtactcactgtccagtgtcgtaaccgtcccttctagcagcttgggaacccaga<br>cctacatctgtaacgtcaaccataaaccatccaacacaaaggtggataagaaggttgaaccaaagagctgtgataagac<br>acatacatgccctccttgtcctgcaccagagctcctcggaggtccatctgtgttcctgtttccccccaaacccaaggacact<br>cttatgatctctcgtactccagaggtcacctgtgagttgtcgacgtgagccatgaagatcccgaggttaaattcaactggta<br>cgtggatggagtcgaggttcacaatgccaagaccaagcccagggaggagcaatataattctacatatcgggtagtgagc<br>gttctgaccgtgctccaccaagattggctcaatggaaaagagtacaagtgcaaggtgtccaacaaggctcttcccgctcc<br>cattgagaaaactatctccaaagccaaggggcagccacgggaaccccaggtgtatacattgcccccatctagagacga<br>gctgaccaagaaccaggtgagtctcacttgtctggtcaaggggttttacccttctgacattgctgtagagtgggagtctaac<br>ggacagccagaaaacaactacaagacaactcccccagtgctggacagcgacgggagcttcttcctctactccaagttga<br>ctgtagacaagtctagatggcagcaaggaaacgttttctcctgctcagtaatgcatgaggctctgcacaatcactataccc<br>agaaatcactgtcccttagcccagggtgactcgag (SEQ ID NO: 153) |
| huCD37-3v1.1 | aagcttgccaccatgggctggagctgtatcattctgtttctggtggcgacagctactggggtccactcccaagtgcaggta<br>caagagtccgggcctggattggtcgcaccaagccagaccctctctatcacttgtaccgttagcgggttctctctgacaacc<br>agtggagtgagttgggtgaggcagccaccaggaaagggactggagtggctgggggtgatttggggcgacggcagca<br>caaactatcattccagtcttaaatctcggttgtccattaaaaaagaccatagtaaatctcaagttttcctgaaactcaatagcct<br>gacagccgcagacactgctacgtattactgcgccaaaggaggatacagtctggctcactggggacaggggaccctggt<br>gaccgtgtcatccgcatcaacaaagggcccatcagttttccccttggctccaagttctaaatccacaagcggtggaacag<br>ctgcactgggatgcctcgttaaagattatttccctgagcctgtgacagtgagctggaatagcggagcattgacttcaggtgt<br>gcacacttttcccgctgtgttgcagtcctccggtctgtactcactgtccagtgtcgtaaccgtcccttctagcagcttgggaa<br>cccagacctacatctgtaacgtcaaccataaaccatccaacacaaaggtggataagaaggttgaaccaaagagctgtga<br>taagacacatacatgccctccttgtcctgcaccagagctcctcggaggtccatctgtgttcctgtaccccccaaacccaag<br>gacactcttatgatctctcgtactccagaggtcacctgtgttgttgtcgacgtgagccatgaagatcccgaggttaaattcaa<br>ctggtacgtggatggagtcgaggttcacaatgccaagaccaagcccagggaggagcaatataattctacatatcgggta<br>gtgagcgttctgaccgtgctccaccaagattggctcaatggaaaagagtacaagtgcaaggtgtccaacaaggctcttcc<br>cgctcccattgagaaaactatctccaaagccaaggggcagccacgggaaccccaggtgtatacattgcccccatctaga<br>gacgagctgaccaagaaccaggtgagtctcacttgtctggtcaaggggttttacccttctgacattgctgtagagtgggag<br>tctaacggacagccagaaaacaactacaagacaactcccccagtgctggacagcgacgggagcttcttcctctactcca<br>agttgactgtagacaagtctagatggcagcaaggaaacgttttctcctgctcagtaatgcatgaggctctgcacaatcacta<br>tacccagaaatcactgtcccttagcccagggtgactcgag (SEQ ID NO: 154) |
| chCD37-12 | aagcttgccaccatggggtggtcatgcataatcctctactggtcgctactgctaccggtgtgcactcacagattcagctgg<br>ttcaaagtggcccagagctgaaaaagccaggggaaacagtgaaaataagttgcaaggcatccggttacactttcacaaa<br>gtacggcatgaactgggtcaagcaggcccagggcaaggggctcaaatggatgggttggatcaataccaacactggcg<br>agtctaggaatgctgaggagtttaagggccggtagccttcagcctggagacaagtgccagcacagcttacctgcaaatc<br>aacaatctgaagtatgaggatacagcaacctatttctgcggccgcggcactgtcgttgcagactggggacaaggtacca<br>ccttgactgtatccagtgccagcactaagggcccatcagttttccccttggctccaagttctaaatccacaagcggtggaa<br>cagctgcactgggatgcctcgttaaagattatttccctgagcctgtgacagtgagctggaatagcggagcattgacttcag<br>gtgtgcacacttttcccgctgtgttgcagtcctccggtctgtactcactgtccagtgtcgtaaccgtcccttctagcagcttgg<br>gaacccagacctacatctgtaacgtcaaccataaaccatccaacacaaaggtggataagaaggttgaaccaaagagctg<br>tgataagacacatacatgccctccttgtcctgcaccagagctcctcggaggtccatctgtgttcctgtttccccccaaaccc<br>aaggacactcttatgatctctcgtactccagaggtcacctgtgttgttgtcgacgtgagccatgaagatcccgaggttaaatt<br>caactggtacgtggatggagtcgaggttcacaatgccaagaccaagcccagggaggagcaatataattctacatatcgg<br>gtagtgagcgttctgaccgtgctccaccaagattggctcaatggaaaagagtacaagtgcaaggtgtccaacaaggctct<br>tcccgctcccattgagaaaactatctccaaagccaaggggcagccacgggaaccccaggtgtatacattgcccccatct<br>agagacgagctgaccaagaaccaggtgagtctcacttgtctggtcaaggggattaccatctgacattgctgtagagtgg<br>gagtctaacggacagccagaaaacaactacaagacaactcccccagtgctggacagcgacgggagcttcttcctctact<br>ccaagttgactgtagacaagtctagatggcagcaaggaaacgttttctcctgctcagtaatgcatgaggctctgcacaatc<br>actatacccagaaatcactgtcccttagcccagggtgactcgag (SEQ ID NO: 155) |

TABLE 9-continued

| Full-length heavy chain polynucleotide sequences | |
|---|---|
| Antibody | Full-Length Heavy Chain Polynucleotide Sequence (SEQ ID NO) |
| chCD37-38 | aagcttgccaccatgggctggagttgtatcattctgtattggtggccaccgccactggagtccattcccaagtgcaactcc<br>aggaatctggccctgacctggttaagccatctcagagcctctccctgacctgcactgttacaggatactcaatcacatcag<br>gctttggctggcactggatcagacaatttcccgggaacaagttggaatggatggcttacattctgtatagcgggggtaccg<br>attacaatcatccctcaagagccgaatctctatcaccagggatacaagcaagaaccaattattctccgcctcagctctgtg<br>actaccgaagataccgctacttactattgtgccaggggctactatggatatggtgcatggttcgtctattggggccaggga<br>accctggtgactgtgagcgctgcctctaccaagggcccatcagttttccccttggctccaagttctaaatccacaagcggt<br>ggaacagctgcactgggatgcctcgttaaagattatttccctgagcctgtgacagtgagctggaatagcggagcattgact<br>tcaggtgtgcacacttacccgctgtgttgcagtcctccggtctgtactcactgtccagtgtcgtaaccgtccatctagcag<br>cttgggaacccagacctacatctgtaacgtcaaccataaaccatccaacacaaaggtggataagaaggttgaaccaaag<br>agctgtgataagacacatacatgccctccttgtcctgcaccagagctcctcggaggtccatctgtgttcctgtaccccca<br>aacccaaggacactcttatgatctctcgtactccagaggtcacctgtgttgttgtcgacgtgagccatgaagatcccgagg<br>ttaaattcaactggtacgtggatggagtcgaggttcacaatgccaagaccaagcccagggaggagcaatataattctaca<br>tatcgggtagtgagcgttctgaccgtgctccaccaagattggctcaatggaaaagagtacaagtgcaaggtgtccaacaa<br>ggctcttcccgctcccattgagaaaactatctccaaagccaaggggcagccacgggaaccccaggtgtatacattgccc<br>ccatctagagacgagctgaccaagaaccaggtgagtctcacttgtctggtcaaggggtttaccccttctgacattgctgtag<br>agtgggagtctaacggacagccagaaaacaactacaagacaactccccagtgctggacagcgacgggagcttcttcc<br>tctactccaagttgactgtagacaagtctagatggcagcaaggaaacgtttctcctgctcagtaatgcatgaggctctgca<br>caatcactatacccagaaatcactgtcccttagcccagggtgactcgag (SEQ ID NO: 156) |
| huCD37-38 | aagcttgccaccatgggttggagctgcatcattcttttcctggtcgctactgcaactggagtccactcacaggtccagctgc<br>aagagtccggtcctgggcttgtgaaacccagccagtccctcagtctcacctgtactgtctctggctactctattaccagtgg<br>gttcggctggcattggattaggcagtttcccggtaagggctggagtggatggcatatatcctgtacagcggaggaacc<br>gattacaacccaagtctgaagagcaggatcagcattacccgggacacaagcaaaaaccagttttccttcggctgtctagt<br>gttacagctgcagacaccgctacttactattgtgctcggggttactatggctatggggcttggtttgtgtattggggacaag<br>gcactcttgtgaccgtgagcagcgcctcaacaaagggcccatcagttttccccttggctccaagttctaaatccacaagcg<br>gtggaacagctgcactgggatgcctcgttaaagattatttccctgagcctgtgacagtgagctggaatagcggagcattg<br>acttcaggtgtgcacacttttcccgctgtgttgcagtcctccggtctgtactcactgtccagtgtcgtaaccgtcccttctagc<br>agcttgggaacccagacctacatctgtaacgtcaaccataaaccatccaacacaaaggtggataagaaggttgaaccaa<br>agagctgtgataagacacatacatgccctccttgtcctgcaccagagctcctcggaggtccatctgtgacctgtaccccc<br>caaacccaaggacactcttatgatctctcgtactccagaggtcacctgtgttgttgtcgacgtgagccatgaagatcccga<br>ggttaaattcaactggtacgtggatggagtcgaggttcacaatgccaagaccaagcccagggaggagcaatataattcta<br>catatcgggtagtgagcgttctgaccgtgctccaccaagattggctcaatggaaaagagtacaagtgcaaggtgtccaac<br>aaggctcttcccgctcccattgagaaaactatctccaaagccaaggggcagccacgggaaccccaggtgtatacattgc<br>ccccatctagagacgagctgaccaagaaccaggtgagtctcacttgtctggtcaaggggttttaccccttctgacattgctgt<br>agagtgggagtctaacggacagccagaaaacaactacaagacaactccccagtgctggacagcgacgggagcttctt<br>cctctactccaagttgactgtagacaagtctagatggcagcaaggaaacgttactcctgctcagtaatgcatgaggctctg<br>cacaatcactatacccagaaatcactgtcccttagcccagggtgactcgag (SEQ ID NO: 157) |
| huCD37-50 | aagcttgccaccatggggtggtcctgcataatccttacctggagctactgctaccggagtccattcacaggtgcagctgc<br>aggagtccggccccggcctgctcaagccttctcagagtctgagtctgacttgtactgtttctggctacagcataaccagcg<br>gtttcgcttggcactggatcagacagcatcccggcaacaaactggagtggatgggatacatactgtactcaggctcaact<br>gtctattccccctccctgaaatcccggatcagtattacccgtgacacttctaagaaccattlattctgcagctgaacagcgtt<br>accgcagctgacactgcaacctactactgtgcccggggatattatggatacggagcttggttcgcttactggggccaagg<br>caccctcgtaactgtgagtgctgcttccaccaagggcccatcagttttccccttggctccaagttctaaatccacaagcggt<br>ggaacagctgcactgggatgcctcgttaaagattatttccctgagcctgtgacagtgagctggaatagcggagcattgact<br>tcaggtgtgcacacttacccgctgtgttgcagtcctccggtctgtactcactgtccagtgtcgtaaccgtcccttctagcag<br>cttgggaacccagacctacatctgtaacgtcaaccataaaccatccaacacaaaggtggataagaaggttgaaccaaag<br>agctgtgataagacacatacatgccctccttgtcctgcaccagagctcctcggaggtccatctgtgttcctgtttcccccca<br>aacccaaggacactcttatgatctctcgtactccagaggtcacctgtgttgttgtcgacgtgagccatgaagatcccgagg<br>ttaaattcaactggtacgtggatggagtcgaggttcacaatgccaagaccaagcccagggaggagcaatataattctaca<br>tatcgggtagtgagcgttctgaccgtgctccaccaagattggctcaatggaaaagagtacaagtgcaaggtgtccaacaa<br>ggctcttcccgctcccattgagaaaactatctccaaagccaaggggcagccacgggaaccccaggtgtatacattgccc<br>ccatctagagacgagctgaccaagaaccaggtgagtctcacttgtctggtcaaggggtttaccccttctgacattgctgtag<br>agtgggagtctaacggacagccagaaaacaactacaagacaactccccagtgctggacagcgacgggagcttcttcc<br>tctactccaagttgactgtagacaagtctagatggcagcaaggaaacgttttctcctgctcagtaatgcatgaggctctgca<br>caatcactatacccagaaatcactgtcccttagcccagggtgactcgag (SEQ ID NO: 158) |
| huCD37-51 | aagcttgccaccatgggttggtcttgcatcatcctgttcctggtggccactgccactggcgtgcattcagaagttcagttggt<br>ggagtccggcccagaagtgctgaaacccggcgaatcactgtccctgacttgtaccgtgtcaggttatagcatcagcagc<br>ggctttgcttggcactggattcggcagtttccaggcaagggactggaatggatgggctacatccattacagtggctcaac<br>caattacagccctagcctgcagggccgaatctctattaccagggatagactattaaccagtattcctgcagcttaattccgt<br>gactgcctctgacacagcaacttactattgcgcccgtggctactacgggttcggagcctggtagtatactggggtcaggg<br>caccctggtcactgtctcagccgcctctaccaagggcccatcagttttccccttggctccaagttctaaatccacaagcggt<br>ggaacagctgcactgggatgcctcgttaaagattatttccctgagcctgtgacagtgagctggaatagcggagcattgact<br>tcaggtgtgcacacttttcccgctgtgttgcagtcctccggtctgtactcactgtccagtgtcgtaaccgtcccttctagcag<br>cttgggaacccagacctacatctgtaacgtcaaccataaaccatccaacacaaaggtggataagaaggttgaaccaaag<br>agctgtgataagacacatacatgccctccttgtcctgcaccagagctcctcggaggtccatctgtgttcctgtaccccca<br>aacccaaggacactcttatgatctctcgtactccagaggtcacctgtgttgttgtcgacgtgagccatgaagatcccgagg<br>ttaaattcaactggtacgtggatggagtcgaggttcacaatgccaagaccaagcccagggaggagcaatataattctaca<br>tatcgggtagtgagcgttctgaccgtgctccaccaagattggctcaatggaaaagagtacaagtgcaaggtgtccaacaa<br>ggctcttcccgctcccattgagaaaactatctccaaagccaaggggcagccacgggaaccccaggtgtatacattgccc<br>ccatctagagacgagctgaccaagaaccaggtgagtctcacttgtctggtcaaggggattaccatctgacattgctgtag<br>agtgggagtctaacggacagccagaaaacaactacaagacaactccccagtgctggacagcgacgggagcttcttcc<br>tctactccaagttgactgtagacaagtctagatggcagcaaggaaacgttttctcctgctcagtaatgcatgaggctctgca<br>caatcactatacccagaaatcactgtcccttagcccagggtgactcgag (SEQ ID NO: 159) |

TABLE 9-continued

| Full-length heavy chain polynucleotide sequences | |
|---|---|
| Antibody | Full-Length Heavy Chain Polynucleotide Sequence (SEQ ID NO) |
| huCD37-56 | aagcttgccaccatggggtggagctgcattatcctgacctcgtcgccaccgcaaccggcgtccactcccaggtgcagct<br>gcaagaaagcgggccaggattggtaaaaccttcccagtctctgagtcttacttgtaccgtatctggatacagtatcacatct<br>ggcttcgcctggcattggattcgccagtttcccggcaaggggcttgagtggatggggtatattcattattctggaggtacca<br>actacaacccttccctgaagagtcgagtctcaattaccagggacacttccaagaaccaattctattgcagcttaattcagtg<br>accgctgccgacaccgctacttactactgcgcccggggctactatgggtttggtgcctggttcgcctactggggccaggg<br>gaccctggtgcccgtgtctgctgcctccacaaagggcccatcagttttccccttggctccaagttctaaatccacaagcgg<br>tggaacagctgcactgggatgcctcgttaaagattatttccctgagcctgtgacagtgagctggaatagcggagcattgac<br>ttcaggtgtgcacacttacccgctgtgagcagtcctccggtctgtactcactgtccagtgtcgtaaccgtccatctagcag<br>cttgggaacccagacctacatctgtaacgtcaaccataaaccatccaacacaaaggtggataagaaggttgaaccaaag<br>agctgtgataagacacatacatgccctccttgtcctgcaccagagctcctcggaggtccatctgtgttcctgtacccccca<br>aacccaaggacactcttatgatctctcgtactccagaggtcacctgtgttgttgtcgacgtgagccatgaagatcccgagg<br>ttaaattcaactggtacgtggatggagtcgaggttcacaatgccaagaccaagcccagggaggagcaatataattctaca<br>tatcgggtagtgagcgttctgaccgtgctccaccaagattggctcaatggaaaagagtacaagtgcaaggtgtccaacaa<br>ggctcttcccgctcccattgagaaaactatctccaaagccaaggggcagccacgggaaccccaggtgtatacattgccc<br>ccatctagagacgagctgaccaagaaccaggtgagtctcacttgtctggtcaaggggattaccatctgacattgctgtag<br>agtgggagtctaacggacagccagaaaacaactacaagacaactcccccagtgctggacagcgacgggagcttcttcc<br>tctactccaagttgactgtagacaagtctagatggcagcaaggaaacgtttctcctgctcagtaatgcatgaggctctgca<br>caatcactatacccagaaatcactgtcccttagcccagggtgactcgag (SEQ ID NO: 160) |
| huCD37-57 | aagcttgccaccatgggctggagctgcatcattctgtttctggtggccacagcaactggcgttcacagtcaagtccaactg<br>caggagagcggccccggactcctgaaaccatctcagtcactcagtctgacatgtactgtgagcggctacagcattacctc<br>aggcttcgcttggcattggatcaggcagttccccggaaaaggtctggagtggatggggtacattctgtacagcggcagta<br>cagtgtattcaccctccttgaaatctaggatatcaatcacacgtgatacaagcaaaaatcagttcttcctccagctgaactcc<br>gtcaccgccgcagacacagcaacctattattgtgctcgcggatactacggatatggcgcatggttcgcctattggggcca<br>ggggacactcgtgaccgtttccgccgcctccacaaagggcccatcagttttccccttggctccaagttctaaatccacaag<br>cggtggaacagctgcactgggatgcctcgttaaagattatttccctgagcctgtgacagtgagctggaatagcggagcat<br>tgacttcaggtgtgcacacttacccgctgtgttgcagtcctccggtctgtactcactgtccagtgtcgtaaccgtcccttcta<br>gcagcttgggaacccagacctacatctgtaacgtcaaccataaaccatccaacacaaaggtggataagaaggttgaacc<br>aaagagctgtgataagacacatacatgccctccttgtcctgcaccagagctcctcggaggtccatctgtgttcctgtaccc<br>cccaaacccaaggacactcttatgatctctcgtactccagaggtcacctgtgttgttgtcgacgtgagccatgaagatccc<br>gaggttaaattcaactggtacgtggatggagtcgaggttcacaatgccaagaccaagcccagggaggagcaatataatt<br>ctacatatcgggtagtgagcgttctgaccgtgctccaccaagattggctcaatggaaaagagtacaagtgcaaggtgtcc<br>aacaaggctcttcccgctcccattgagaaaactatctccaaagccaaggggcagccacgggaaccccaggtgtatacat<br>tgcccccatctagagacgagctgaccaagaaccaggtgagtctcacttgtctggtcaaggggttttacccttctgacattg<br>ctgtagagtgggagtctaacggacagccagaaaacaactacaagacaactcccccagtgctggacagcgacgggagc<br>ttcttcctctactccaagttgactgtagacaagtctagatggcagcaaggaaacgttactcctgctcagtaatgcatgaggc<br>tctgcacaatcactatacccagaaatcactgtcccttagcccagggtgactcgag (SEQ ID NO: 161) |

TABLE 10

| Full-length light chain polynucleotide sequences | |
|---|---|
| Antibody | Full-length Light Chain Polynucleotide Sequence (SEQ ID NO) |
| chCD37-3 | gaattcgccaccatgagtgtgcccactcaggtcctggggttgctgctgctgtggcttacagatgccagatgtgacatccag<br>atgactcagtctccagcctccctttctgtatctgtgggagaaactgtcaccatcacatgtcgagcaagtgagaatattcgca<br>gtaatttagcatggtatcagcagaaacagggaaaatctcctcagctcctggtcaatgagcaacaaacttagcagatggtgt<br>gccatcaaggttcagtggcagtggatcaggcacacagtattccctcaagatcaacagcctgcagtctgaagattttggga<br>cttattactgtcaacattattggggtactacgtggacgttcggtggaggcaccaagctggaaatcaaacgtacggtggctg<br>caccatctgtcttcatcttcccgccatctgatgagcagttgaaatctggaactgcctctgttgtgtgcctgctgaataacttcta<br>tcccagagaggccaaagtacagtggaaggtggataacgccctccaatcgggtaactcccaggagagtgtcacagagc<br>aggacagcaaggacagcacctacagcctcagcagcaccctgacgctgagcaaagcagactacgagaaacacaaagt<br>ctacgcctgcgaagtcacccatcagggcctgagctcgcccgtcacaaagagcttcaacaggggagagtgttag<br>(SEQ ID NO: 162) |
| huCD37-3<br>(1.0 and 1.1) | gaattcgccaccatgggttggtcctgcatcatcttgtttctcgtggccacagccaccggtgttcactctgatatacaaatgac<br>tcaaagcccttccagtttgagcgtaagtgtgggtgaacgcgtaacaatcacctgtagagctagtgaaaacatccgcagta<br>atctcgcatggtaccaacaaaagccaggtaagtcacctaagctcctcgtgaatgagctaccaacctcgctgatggtgtgc<br>cttcacgattctctggttcaggttccggtaccgattattcacttaagatcaactcactccaaccagaagatttcggtacatatta<br>ctgtcaacactactggggtacgacctggacattcggtcaaggtactaagctggaaatcaagcgtacggtggctgcaccat<br>ctgtcttcatcttcccgccatctgatgagcagttgaaatctggaactgcctctgttgtgtgcctgctgaataacttctatccca<br>gagaggccaaagtacagtggaaggtggataacgccctccaatcgggtaactcccaggagagtgtcacagagcaggac<br>agcaaggacagcacctacagcctcagcagcaccctgacgctgagcaaagcagactacgagaaacacaaagtctacgc<br>ctgcgaagtcacccatcagggcctgagctcgcccgtcacaaagagcttcaacaggggagagtgttag (SEQ ID<br>NO: 163) |
| chCD37-12 | gaattcgccaccatgggttggtcctgtataatcctgttcttggtggccaccgctactggcgttcatagtgatattgtactcact<br>cagtcaccagccagtctggcagtgtccctgggccagcgtgccaccatctcctgccgggcctcacagtccgtgagcacta<br>gctcttattcctatctctactggtttcaacagaagccaggacagccccctaagctgctgatcaagtacgcctccaacctcgc<br>cagcggcgttcccgctagattctctggttccggtagcggaactgatttcactttgaacatccaccccgttgaggaagagga<br>taccgccacttactattgtcaacactcttgggagattccttacacctttggoggaggaacaaagctcgaaattaagcgtacg<br>gtggctgcaccatctgtcttcatcttcccgccatctgatgagcagttgaaatctggaactgcctctgttgtgtgcctgctgaat<br>aacttctatcccagagaggccaaagtacagtggaaggtggataacgccctccaatcgggtaactcccaggagagtgtca |

TABLE 10-continued

Full-length light chain polynucleotide sequences

| Antibody | Full-length Light Chain Polynucleotide Sequence (SEQ ID NO) |
|---|---|
| | cagagcaggacagcaaggacagcacctacagcctcagcagcaccctgacgctgagcaaagcagactacgagaaaca caaagtctacgcctgcgaagtcacccatcagggcctgagctcgcccgtcacaaagagcttcaacaggggagagtgtta g (SEQ ID NO: 164) |
| chCD37-38 | gaattcgccaccatgggctggtcctgtatcatcctgtttctcgtggccacagctacaggtgttcattctcagattgtgctgac ccaatcaccagctattatgtccgctagccccggcgagaaagtgacaatgacatgtagcgctagctcttctgtgacttacat gcattggtatcaacagaagtcaggtaccagtcccaagcgttggatctacgacacatccaaactggcctccggagtccctg ccaggttcagcggaggtgggtccggcaccagttattcactgaccatatcctctatggaagctgaagatgctgctacttatta ttgtcaacaatggatttctaaccccccccacctttggtggcggaacaaagctggagatcaagcgtacggtggctgcaccat ctgtcttcatcttcccgccatctgatgagcagttgaaatctggaactgcctctgttgtgtgcctgctgaataacttctatccca gagaggccaaagtacagtggaaggtggataacgccctccaatcgggtaactcccaggagagtgtcacagagcaggac agcaaggacagcacctacagcctcagcagcaccctgacgctgagcaaagcagactacgagaaacacaaagtctacgc ctgcgaagtcacccatcagggcctgagctcgcccgtcacaaagagcttcaacaggggagagtgttag (SEQ ID NO: 165) |
| huCD37-38 | gaattcgccaccatgggatggtcctgcattattctgttcttggtcgccactgctactggcgttcactctgacattgtgctcaca cagtctccagcctcaatgtctgcttccccggtgagcgggtgaccatgacatgctctgccagttcctccgtgacatatatgc attggtatcagcaaaaacccggtacctctccaaaaagatggatctacgacacttcaaagcttgcatcaggcgttcctgcca gattttccgggtctgggtctggcacttcatacagtctgaccattagttccatggaagctgaagatgcagccacctattactgt cagcagtggatttcaaatcctcctaccttcggcggcggaaccaaactggagataaagcgtacggtggctgcaccatctgt cttcatcttcccgccatctgatgagcagttgaaatctggaactgcctctgttgtgtgcctgctgaataacttctatcccagaga ggccaaagtacagtggaaggtggataacgccctccaatcgggtaactcccaggagagtgtcacagagcaggacagca aggacagcacctacagcctcagcagcaccctgacgctgagcaaagcagactacgagaaacacaaagtctacgcctgc gaagtcacccatcagggcctgagctcgcccgtcacaaagagcttcaacaggggagagtgttag (SEQ ID NO: 166) |
| huCD37-50 | gaattcgccaccatgggttggtcatgcattattctgttcctggttgctaccgcaacaggagtacatagtgagatagtcctcac ccaaagtcctgctactatgtctgccagcccaggagagcgtgtgaccatgacttgctctgcaacctcaagtgtgacatacat gcattggtatcagcaaaagcctggccaatcccctaaaaggtggatctacgatacttctaatctgccatacggtgtgcccgc aaggttctccgggagtggcagtggcaccagttatagtctgaccatcagttcaatggaagcagaggatgcagcaacctatt attgtcagcagtggtccgataatcccccctacttttggtcagggtacaaagctggagattaagcgtacggtggctgcaccat ctgtcttcatcttcccgccatctgatgagcagttgaaatctggaactgcctctgttgtgtgcctgctgaataacttctatccca gagaggccaaagtacagtggaaggtggataacgccctccaatcgggtaactcccaggagagtgtcacagagcaggac agcaaggacagcacctacagcctcagcagcaccctgacgctgagcaaagcagactacgagaaacacaaagtctacgc ctgcgaagtcacccatcagggcctgagctcgcccgtcacaaagagcttcaacaggggagagtgttag (SEQ ID NO: 167) |
| huCD37-51 | gaattcgccaccatgggatggagctgtattattctgttcctggttgctactgctactggcgtccattccgagatagtcctcac ccagagccccgcaaccatgagtgcctcccctggggagcgagtgactatgacttgttccgccacttcttcagttacctatat gcattggtatcagcagaaacctggacagtctccaaagcgttggatttacgacacctccaacctggcttcaggagttcctgc taggttcagcggatctgggtctggcacaagttattcactcaccattagttccatggaggccgaagatgccgctacttactac tgtcagcagtggagcagcaacccccctacattcgggcagggaactaagctggagatcaaacgtacggtggctgcacca tctgtcttcatcttcccgccatctgatgagcagttgaaatctggaactgcctctgttgtgtgcctgctgaataacttctatccca gagaggccaaagtacagtggaaggtggataacgccctccaatcgggtaactcccaggagagtgtcacagagcaggac agcaaggacagcacctacagcctcagcagcaccctgacgctgagcaaagcagactacgagaaacacaaagtctacgc ctgcgaagtcacccatcagggcctgagctcgcccgtcacaaagagcttcaacaggggagagtgttag (SEQ ID NO: 168) |
| huCD37-56 | gaattcgccaccatgggctggtcctgtatcatcctgtttctggtggcaaccgctactggggttcactctgatattgtcctgac acagagtccagccttcatgagtgcttctcccggagaaaaggtcacaatgacttgttcagcttcctcctccgtcacatacatg cattggtaccagcagaagcctgaccagagtcctaagaggtggatctatgatacaagcaatctggcttccggtgtcccctc ccgcttttcaggcggcggaagcggaactgactatagccttaccatctcctcaatggaagccgaggacgctgctacatatt actgccagcaatggatcagcgaccctcctactacggacagggaacaaaattggaaattaagcgtacggtggctgcacc atctgtcttcatcttcccgccatctgatgagcagttgaaatctggaactgcctctgttgtgtgcctgctgaataacttctatccc agagaggccaaagtacagtggaaggtggataacgccctccaatcgggtaactcccaggagagtgtcacagagcagga cagcaaggacagcacctacagcctcagcagcaccctgacgctgagcaaagcagactacgagaaacacaaagtctacg cctgcgaagtcacccatcagggcctgagctcgcccgtcacaaagagcttcaacaggggagagtgttag (SEQ ID NO: 169) |
| huCD37-57 | gaattcgccaccatggggtggtcctgtattatcctgttcctggtcgcaaccgccacaggcgttcactccgagatcgtgaga ctcagagcccagccaccatgtccgcttcccccggggagagagtgacaatgacttgttccgccacaagttctgtaacctac atgcattggtaccagcaaaaaccaggacagagtccccgtcgttggatttatgatacctctaacctggcttcaggcgttcctg cccgcttttctggtagtggatctgggacttcctatagccttaccataagctctatggaagccgaggacgccgctacatacta ctgccagcagtggagtgataaccccccccaccttcgggcagggaaccaaattggagatcaaacgtacggtggctgcacc atctgtcttcatcttcccgccatctgatgagcagttgaaatctggaactgcctctgttgtgtgcctgctgaataacttctatccc agagaggccaaagtacagtggaaggtggataacgccctccaatcgggtaactcccaggagagtgtcacagagcagga cagcaaggacagcacctacagcctcagcagcaccctgacgctgagcaaagcagactacgagaaacacaaagtctacg cctgcgaagtcacccatcagggcctgagctcgcccgtcacaaagagcttcaacaggggagagtgttag (SEQ ID NO: 170) |

Also provided is a polynucleotide having at least about 95%, at least about 96%, at least about 97%, at least about 98%, or at least about 99% sequence identity to SEQ ID NOs:121-170. Thus, in certain embodiments, the polypeptide comprises (a) a polypeptide having at least about 95% sequence identity to SEQ ID NOs:121-135 or 152-161, and/or (b) a polypeptide having at least about 95% sequence identity to SEQ ID NOs:136-151 or 162-170. In certain embodiments, the polypeptide comprises (a) a polypeptide having the amino acid sequence of SEQ ID NOs: 121-135 or 152-161; and/or (b) a polypeptide having the amino acid sequence of SEQ ID NOs: 136-151 or 162-170.

In some embodiments, the polynucleotide encodes the light chain encoded by the recombinant plasmid DNA phuCD37-3LC (ATCC Deposit Designation PTA-10722, deposited with the ATCC on Mar. 18, 2010) or a light chain that is at least about 85%, at least about 90%, at least about 95%, or at least about 99% to the light chain encoded by phuCD37-3LC (PTA-10722). In some embodiments, the polynucleotide encodes the heavy chain encoded by the recombinant plasmid DNA phuCD37-3HCv.1.0 (ATCC Deposit Designation PTA-10723, deposited with the ATCC on Mar. 18, 2010) or a heavy chain that is at least about 85%, at lesat about 90%, at least about 95%, or at least about 99% identical to the heavy chain encoded by phuCD37-3HCv.1.0 (PTA-10723). In certain embodiments the polynucleotide is the recombinant plasmid DNA phuCD37-3LC (PTA-10722) or the recombinant plasmid phuCD37-3HCv.1.0 (PTA-10723).

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

The present invention further relates to variants of the hereinabove described polynucleotides encoding, for example, fragments, analogs, and derivatives.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

Vectors and cells comprising the polynucleotides described herein are also provided.

IV. Methods of Use and Pharmaceutical Compositions

The CD37-binding agents (including antibodies, immunoconjugates, and polypeptides) of the invention are useful in a variety of applications including, but not limited to, therapeutic treatment methods, such as the treatment of cancer, such as B-cell malignancies. In certain embodiments, the agents are useful for inhibiting tumor growth, inducing differentiation, reducing tumor volume, and/or reducing the tumorigenicity of a tumor. The methods of use can be in vitro, ex vivo, or in vivo methods. In certain embodiments, the CD37-binding agent or antibody or immunoconjugate, or polypeptide is an antagonist of the human CD37 to which it binds.

In one aspect, anti-CD37 antibodies and immunoconjugates of the invention are useful for detecting the presence of CD37 in a biological sample. The term "detecting" as used herein encompasses quantitative or qualitative detection. In certain embodiments, a biological sample comprises a cell or tissue. In certain embodiments, such tissues include normal and/or cancerous tissues that express CD37 at higher levels relative to other tissues, for example, B cells and/or B cell associated tissues.

In one aspect, the invention provides a method of detecting the presence of CD37 in a biological sample. In certain embodiments, the method comprises contacting the biological sample with an anti-CD37 antibody under conditions permissive for binding of the anti-CD37 antibody to CD37, and detecting whether a complex is formed between the anti-CD37 antibody and CD37.

In one aspect, the invention provides a method of diagnosing a disorder associated with increased expression of CD37. In certain embodiments, the method comprises contacting a test cell with an anti-CD37 antibody; determining the level of expression (either quantitatively or qualitatively) of CD37 by the test cell by detecting binding of the anti-CD37 antibody to CD37; and comparing the level of expression of CD37 by the test cell with the level of expression of CD37 by a control cell (e.g., a normal cell of the same tissue origin as the test cell or a cell that expresses CD37 at levels comparable to such a normal cell), wherein a higher level of expression of CD37 by the test cell as compared to the control cell indicates the presence of a disorder associated with increased expression of CD37. In certain embodiments, the test cell is obtained from an individual suspected of having a disorder associated with increased expression of CD37. In certain embodiments, the disorder is a cell proliferative disorder, such as a cancer or a tumor.

In certain embodiments, a method of diagnosis or detection, such as those described above, comprises detecting binding of an anti-CD37 antibody to CD37 expressed on the surface of a cell or in a membrane preparation obtained from a cell expressing CD37 on its surface. In certain embodiments, the method comprises contacting a cell with an anti-CD37 antibody under conditions permissive for binding of the anti-CD37 antibody to CD37, and detecting whether a complex is formed between the anti-CD37 antibody and CD37 on the cell surface. An exemplary assay for detecting binding of an anti-CD37 antibody to CD37 expressed on the surface of a cell is a "FACS" assay.

Certain other methods can be used to detect binding of anti-CD37 antibodies to CD37. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-CD37 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-CD37 antibodies are immobilized on an insoluble matrix. Immobilization entails separating the anti-CD37 antibody from any CD37 that remains free in solution. This conventionally is accomplished by either insolubilizing the anti-CD37 antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-CD37 antibody after formation of a complex between the anti-CD37 antibody and CD37, e.g., by immunoprecipitation.

Any of the above embodiments of diagnosis or detection can be carried out using an immunoconjugate of the invention in place of or in addition to an anti-CD37 antibody.

In certain embodiments, the disease treated with the CD37-binding agent or antagonist (e.g., an anti-CD37 antibody) is a cancer. In certain embodiments, the cancer is characterized by CD37 expressing cells to which the CD37-binding agent (e.g., antibody) binds.

The present invention provides for methods of treating cancer comprising administering a therapeutically effective amount of a CD37-binding agent to a subject (e.g., a subject in need of treatment). In certain embodiments, the cancer is a B-cell malignancy. In certain embodiments, the cancer is selected from the group consisting of B cell lymphomas, NHL, precursor B cell lymphoblastic leukemia/lymphoma and mature B cell neoplasms, B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), low grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL). In certain embodiments, the subject is a human.

The present invention further provides methods for inhibiting tumor growth using the antibodies or other agents described herein. In certain embodiments, the method of inhibiting the tumor growth comprises contacting the cell with a CD37-binding agent (e.g., antibody) in vitro. For example, an immortalized cell line or a cancer cell line that expresses CD37 is cultured in medium to which is added the antibody or other agent to inhibit tumor growth. In some embodiments, tumor cells are isolated from a patient sample such as, for example, a tissue biopsy, pleural effusion, or blood sample and cultured in medium to which is added an CD37-binding agent to inhibit tumor growth.

In some embodiments, the method of inhibiting tumor growth comprises contacting the tumor or tumor cells with the CD37-binding agent (e.g., antibody) in vivo. In certain embodiments, contacting a tumor or tumor cell with a CD37-binding agent is undertaken in an animal model. For example, CD37-binding agents can be administered to xenografts expressing one or more CD37s that have been grown in immunocompromised mice (e.g. NOD/SCID mice) to inhibit tumor growth. In some embodiments, cancer stem cells are isolated from a patient sample such as, for example, a tissue biopsy, pleural effusion, or blood sample and injected into immunocompromised mice that are then administered a CD37-binding agent to inhibit tumor cell growth. In some embodiments, the CD37-binding agent is administered at the same time or shortly after introduction of tumorigenic cells into the animal to prevent tumor growth. In some embodiments, the CD37-binding agent is administered as a therapeutic after the tumorigenic cells have grown to a specified size.

In certain embodiments, the method of inhibiting tumor growth comprises administering to a subject a therapeutically effective amount of a CD37-binding agent. In certain embodiments, the subject is a human. In certain embodiments, the subject has a tumor or has had a tumor removed.

In certain embodiments, the tumor expresses the CD37 to which the CD37-binding agent or antibody binds. In certain embodiments, the tumor overexpresses the human CD37.

In addition, the invention provides a method of reducing the tumorigenicity of a tumor in a subject, comprising administering a therapeutically effective amount of a CD37-binding agent to the subject. In certain embodiments, the tumor comprises cancer stem cells. In certain embodiments, the frequency of cancer stem cells in the tumor is reduced by administration of the agent.

The invention further provides methods of differentiating tumorigenic cells into non-tumorigenic cells comprising contacting the tumorigenic cells with a CD37-binding agent (for example, by administering the CD37-binding agent to a subject that has a tumor comprising the tumorigenic cells or that has had such a tumor removed.

The use of the CD37-binding agents, polypeptides, or antibodies described herein to induce the differentiation of cells, including, but not limited to tumor cells, is also provided. For example, methods of inducing cells to differentiate comprising contacting the cells with an effective amount of a CD37-binding agent (e.g., an anti-CD37 antibody) described herein are envisioned. Methods of inducing cells in a tumor in a subject to differentiate comprising administering a therapeutically effective amount of a CD37-binding agent, polypeptide, or antibody to the subject are also provided. In certain embodiments, the tumor is a pancreatic tumor. In certain other embodiments, the tumor is a colon tumor. In some embodiments, the treatment methods comprise administering a therapeutically effective amount of the CD37-binding agent, polypeptide, or antibody to the subject.

The present invention further provides pharmaceutical compositions comprising one or more of the CD37-binding agents described herein. In certain embodiments, the pharmaceutical compositions further comprise a pharmaceutically acceptable vehicle. These pharmaceutical compositions find use in inhibiting tumor growth and treating cancer in human patients.

In certain embodiments, formulations are prepared for storage and use by combining a purified antibody or agent of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical compositions of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

An antibody or immunoconjugate of the invention can be combined in a pharmaceutical combination formulation, or dosing regimen as combination therapy, with a second compound having anti-cancer properties. The second compound of the pharmaceutical combination formulation or dosing regimen can have complementary activities to the ADC of the combination such that they do not adversely affect each other. Pharmaceutical compositions comprising the CD37-binding agent and the second anti-cancer agent are also provided. For example, CD37-binding agents can be administered in combination with CD20 antagonists, such as Rituximab.

For the treatment of the disease, the appropriate dosage of an antibody or agent of the present invention depends on the type of disease to be treated, the severity and course of the disease, the responsiveness of the disease, whether the antibody or agent is administered for therapeutic or preventative purposes, previous therapy, patient's clinical history, and so on all at the discretion of the treating physician. The antibody or agent can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody or agent. The administering physician can easily determine optimum dosages, dosing methodologies and repetition rates. In certain embodiments, dosage is from 0.01 μg to 100 mg per kg of body weight, and can be given once or more daily, weekly, monthly or yearly. In certain embodiments, the antibody or other CD37-binding agent is given once every two weeks or once every three weeks. In certain embodiments, the dosage of the antibody or other CD37-binding agent is from about 0.1 mg to about 20 mg per kg of body weight. The treating physician can estimate repetition rates for dosing based on measured residence times and concentrations of the drug in bodily fluids or tissues.

The combination therapy can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

VI. Kits Comprising CD37 Binding Agents

The present invention provides kits that comprise the antibodies, immunoconjugates or other agents described herein and that can be used to perform the methods described herein. In certain embodiments, a kit comprises at least one purified antibody against CD37 in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies, immunoconjugates or other agents of the present invention can be readily incorporated into one of the established kit formats which are well known in the art.

Further provided are kits comprising a CD37-binding agent (e.g., a CD37-binding antibody), as well as a second anti-cancer agent. In certain embodiments, the second anti-cancer agent is a chemotherapeutic agent (e.g., rituximab).

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application Cell lines and growth

| Cell line | Origin | Source |
|---|---|---|
| Ramos | Burkitt lymphoma | DSMZ (ACC 603) |
| Raji | Burkitt lymphoma | DSMZ (ACC 319) |
| Daudi | Burkitt lymphoma | DSMZ (ACC 78) |
| Namalwa | Burkitt lymphoma | ATCC (CRL-1432) |
| BJAB | B-NHL | A gift from Elliot Kieff (Harvard) |

-continued

| Cell lines and growth | | |
|---|---|---|
| Cell line | Origin | Source |
| WSU-DLCL-2 | B-NHL, diffuse large B-cell lymphoma | DSMZ (ACC 575) |
| RL | B-NHL, diffuse large B-cell lymphoma | DSMZ (ACC 613) |
| SU-DHL-4 | B-NHL, diffuse histiocytic lymphoma | DSMZ (ACC 495) |
| DOHH-2 | refractory immunoblastic B cell lymphoma, follicular lymphoma | DSMZ (ACC 47) |
| Granta-519 | B-NHL, mantle cell lymphoma | DSMZ (ACC 342) |

All cell lines were grown in RPMI-1640 media supplemented with 10% fetal bovine serum, 2 mM glutamine and 1% penicillin-streptomycin (all reagents from Invitrogen) at 37° C. in a humidified 5% $CO_2$ incubator. Cells were passaged by diluting into fresh media twice per week and maintained between 0.2 to $1\times10^6$ cells/ml.

Example 1

Production of Murine CD37 Antibodies

An expression plasmid pSRa-CD37 was constructed that contained the entire CD37 coding sequence (CDS) flanked by XbaI and BamHI restriction sites that allowed expression of human CD37. 300-19 cells, a pre-B cell line derived from a Balb/c mouse (M. G. Reth et al. 1985, Nature, 317: 353-355), were transfected with this expression plasmid to stably express high levels of human CD37 on the cell surface and used for immunization of Balb/c VAF mice. Mice were subcutaneously immunized with approximately $5\times10^6$ CD37-expressing 300-19 cells per mouse every 2-3 weeks by standard immunization protocols used at ImmunoGen, Inc. The immunized mice were boosted with another dose of antigen three days before being sacrificed for hybridoma generation. The spleen from the mouse was collected according to standard animal protocols and was ground between two sterile, frosted microscopic slides to obtain a single cell suspension in RPMI-1640 medium. The spleen cells were pelleted, washed, and fused with murine myeloma P3X63Ag8.653 cells (J. F. Kearney et al. 1979, J Immunol, 123: 1548-1550) by using polyethylene glycol-1500 (Roche 783 641). The fused cells were resuspended in RPMI-1640 selection medium containing hypoxanthine-aminopterin-thymidine (HAT) (Sigma H-0262) and selected for growth in 96-well flat-bottomed culture plates (Corning-Costar 3596, 200 μL of cell suspension per well) at 37° C. with 5% $CO_2$. After 5 days of incubation, 100 μL of culture supernatant were removed from each well and replaced with 100 μL of RPMI-1640 medium containing hypoxanthine-thymidine (HT) supplement (Sigma H-0137). Incubation at 37° C. with 5% $CO_2$ was continued until hydridoma clones were ready for antibody screening. Other techniques of immunization and hybridoma production can also be used, including those described in J. Langone and H. Vunakis (Eds., Methods in Enzymology, Vol. 121, “Immunochemical Techniques, Part I”; Academic Press, Florida) and E. Harlow and D. Lane (“Antibodies: A Laboratory Manual”;1988; Cold Spring Harbor Laboratory Press, New York).

Hybridoma Screening and Selection

Culture supernatants from the hybridoma were screened by flow cytometry for secretion of mouse monoclonal antibodies that bind to the CD37-expressing 300-19 cells, but not to the non-transfected 300-19 cells. 100 μl of hybridoma supernatants was incubated for 3 h with either CD37-expressing 300-19 cells or the non-transfected 300-19 cells ($1\times10^5$ cells per sample) in 100 μL FACS buffer (RPMI-1640 medium supplemented with 2% normal goat serum). Then, the cells were pelleted, washed, and incubated for 1 h with 100 μL of PE-conjugated goat anti-mouse IgG-antibody (Jackson Laboratory, 6 g/mL in FACS buffer). The cells were pelleted again, washed with FACS buffer and resuspended in 200 μL of PBS containing 1% formaldehyde. Samples were acquired using a FACSCalibur flow cytometer with the HTS multiwell sampler or a FACS array flow cytometer and analyzed using CellQuest Pro (all from BD Biosciences, San Diego, US).

The hybridoma clones that tested positive were subcloned by limiting dilution. One subclone from each hybridoma, which showed the same reactivity against CD37 as the parental cells by flow cytometry, was chosen for subsequent analysis. Stable subclones were cultured and the isotype of each secreted anti-CD37 antibody was identified using commercial isotyping reagents (Roche 1493027).

A total of 45 separate fusion experiments were conducted over the course of this investigation. A single fusion experiment routinely yielded approximately between 200 and 1000 hybridoma clones. All the resulting hybridoma clones were screened for CD37 binding by flow cytometry and a total of 184 hybridoma clones showed specific binding to CD37.

Antibody Purification

Antibodies were purified from hybridoma subclone supernatants using standard methods, such as, for example Protein A or G chromatography (HiTrap Protein A or G HP, 1 mL, Amersham Biosciences). Briefly, supernatant was prepared for chromatography by the addition of 1/10 volume of 1 M Tris/HCl buffer, pH 8.0. The pH-adjusted supernatant was filtered through a 0.22 μm filter membrane and loaded onto column equilibrated with binding buffer (PBS, pH 7.3). The column was washed with binding buffer until a stable baseline was obtained with no absorbance at 280 nm. Antibody was eluted with 0.1 M acetic acid buffer containing 0.15 M NaCl, pH 2.8, using a flow rate of 0.5 mL/min. Fractions of approximately 0.25 mL were collected and neutralized by the addition of 1/10 volume of 1M Tris/HCl, pH 8.0. The peak fraction(s) was dialyzed overnight twice against 1× PBS and sterilized by filtering through a 0.2 m filter membrane. Purified antibody was quantified by absorbance at A280.

Protein A purified fractions were further polished using ion exchange chromatography (IEX) with quaternary ammonium (Q) chromatography for murine antibodies. Briefly, samples from protein A purification were buffer exchanged into binding buffer (10 mM Tris, 10 mM sodium chloride, pH 8.0) and filtered through 0.22 m filer. The prepared sample was then loaded onto a Q fast flow resin (GE Lifesciences) that was equilibrated with binding buffer at a flow rate of 120 cm/hr. Column size was chosen to have sufficient capacity to bind all the MAb in the sample. The column was then washed with binding buffer until a stable baseline was obtained with no absorbance at 280 nm. Antibody was eluted by initiating a gradient from 10 mM to 500 mM sodium chloride in 20 column volume (CV). Peak fractions were collected based on absorbance measurement at 280 nm (A280). The percentage of monomer was assessed with size exclusion chromatography (SEC) on a TSK gel G3000SWXL, 7.8×300 mm with a SWXL guard column, 6.0×40 mm (Tosoh Bioscience, Montgomeryville, PA) using an Agilent HPLC 1100 system (Agilent, Santa Clara, CA). Fractions with monomer content above 95% were pooled, buffer exchanged to PBS (pH 7.4) using a TFF system, and sterilized by filtering through a 0.2 m filter membrane. The IgG concentration of purified antibody was determined by A280 using an extinction coefficient of 1.47. Alternative methods such as ceramic hydroxyapatite (CHT) were also used to polish antibodies with good selectivity. Type II CHT resin with 40 m particle size (Bio-Rad Laboratories) were used with a similar protocol as described for IEX chromatography. The binding buffer for CHT corresponds to 20 mM sodium phosphate, pH 7.0 and antibody was eluted with a gradient of 20-160 mM sodium phosphate over 20 CV.

Example 2

Binding Characterization by Flow Cytometry

Figure 1:
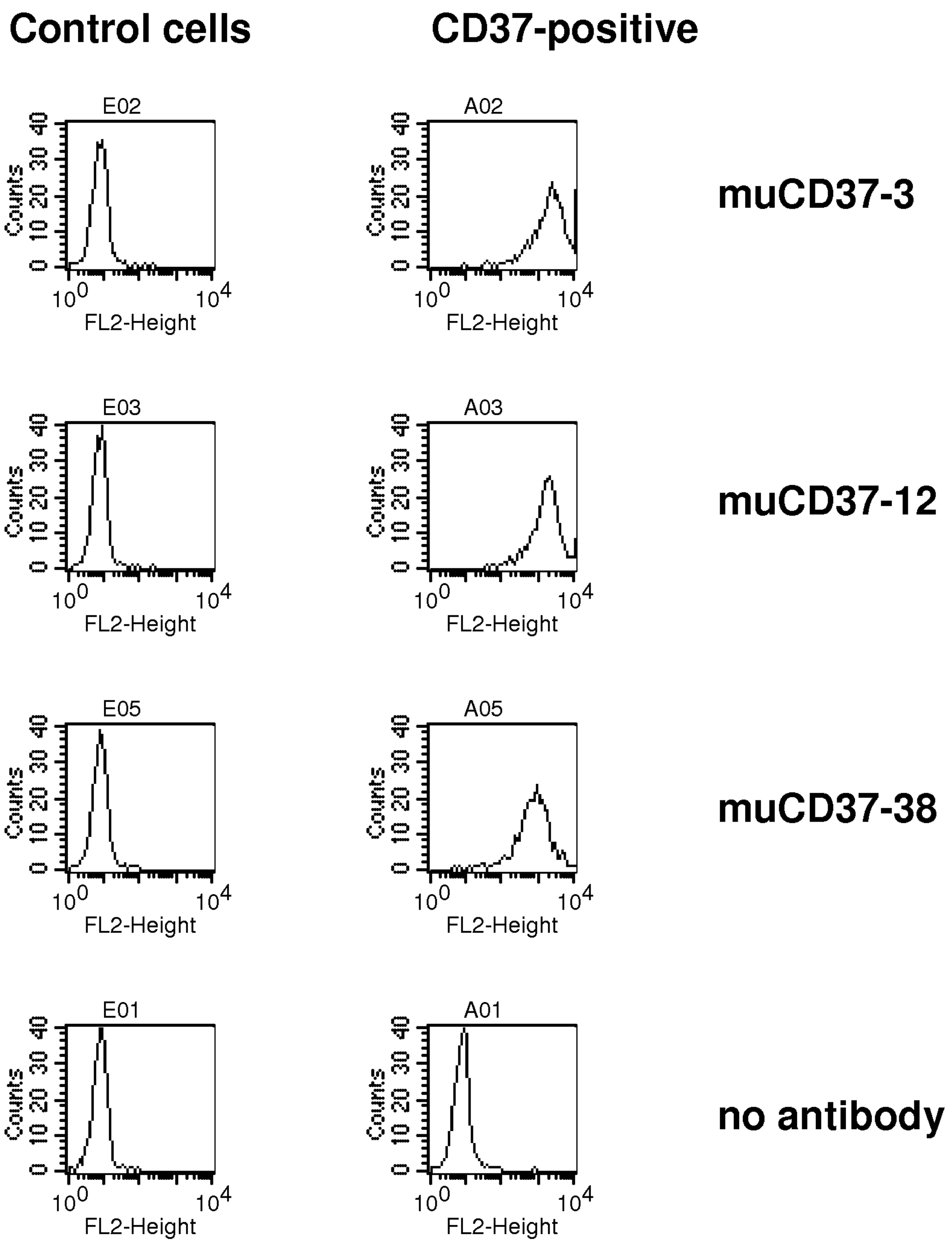
Figure 2:
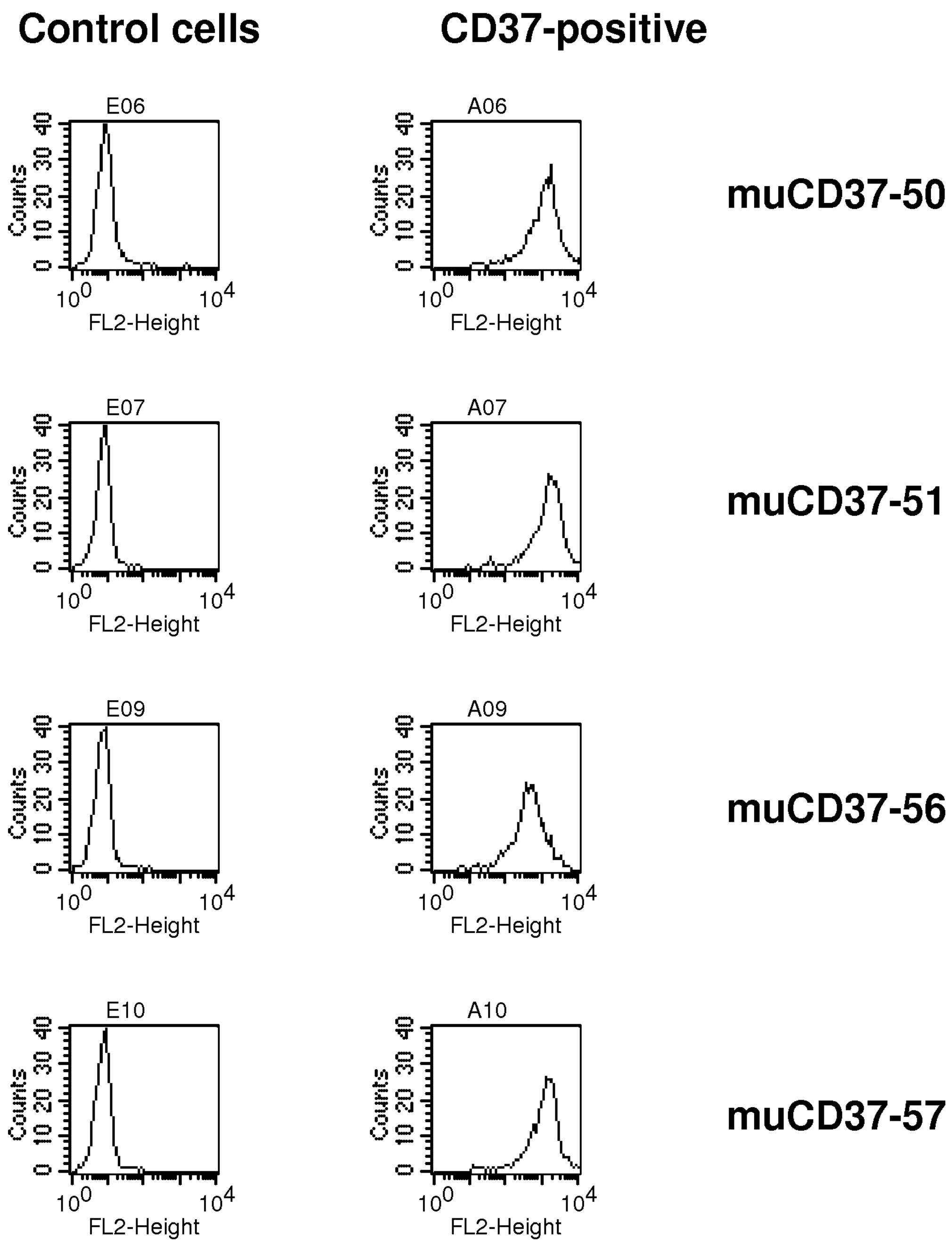

Binding specificity was tested by flow cytometry using purified antibodies. FACS histograms demonstrating the binding of muCD37-3, muCD37-12, muCD37-38, muCD37-50, muCD37-51, muCD37-56 and muCD37-57 to CD37-expressing 300-19 cells and the absence of binding to the parental 300-19 cells are shown in FIG. 1 and FIG. 2. All murine antibodies were incubated for 3 h with either CD37-expressing 300-19 cells or the non-transfected 300-19 cells ($1\times10^5$ cells per sample) in 100 μL FACS buffer (RPMI-1640 medium supplemented with 2% normal goat serum). Then, the cells were pelleted, washed, and incubated for 1 h with 100 μL of FITC-conjugated goat anti-mouse IgG-antibody (Jackson Laboratory, 6 g/mL in FACS buffer). The cells were pelleted again, washed with FACS buffer and resuspended in 200 μL of PBS containing 1% formaldehyde. Samples were acquired using a FACSCalibur flow cytometer with the HTS multiwell sampler or a FACS array flow cytometer and analyzed using CellQuest Pro (all from BD Biosciences, San Diego, US).

The FACS histograms of CD37-expressing 300-19 cells incubated with muCD37-3, muCD37-12, muCD37-38, muCD37-50, muCD37-51, muCD37-56 or muCD37-57 showed a fluorescence shift, while parental 300-19 cells did not. Also, no significant fluorescence shift was detected when either cell lines was incubated only with FITC-conjugated goat anti-mouse IgG-antibody alone (FIG. 1 bottom).

Figure 3:
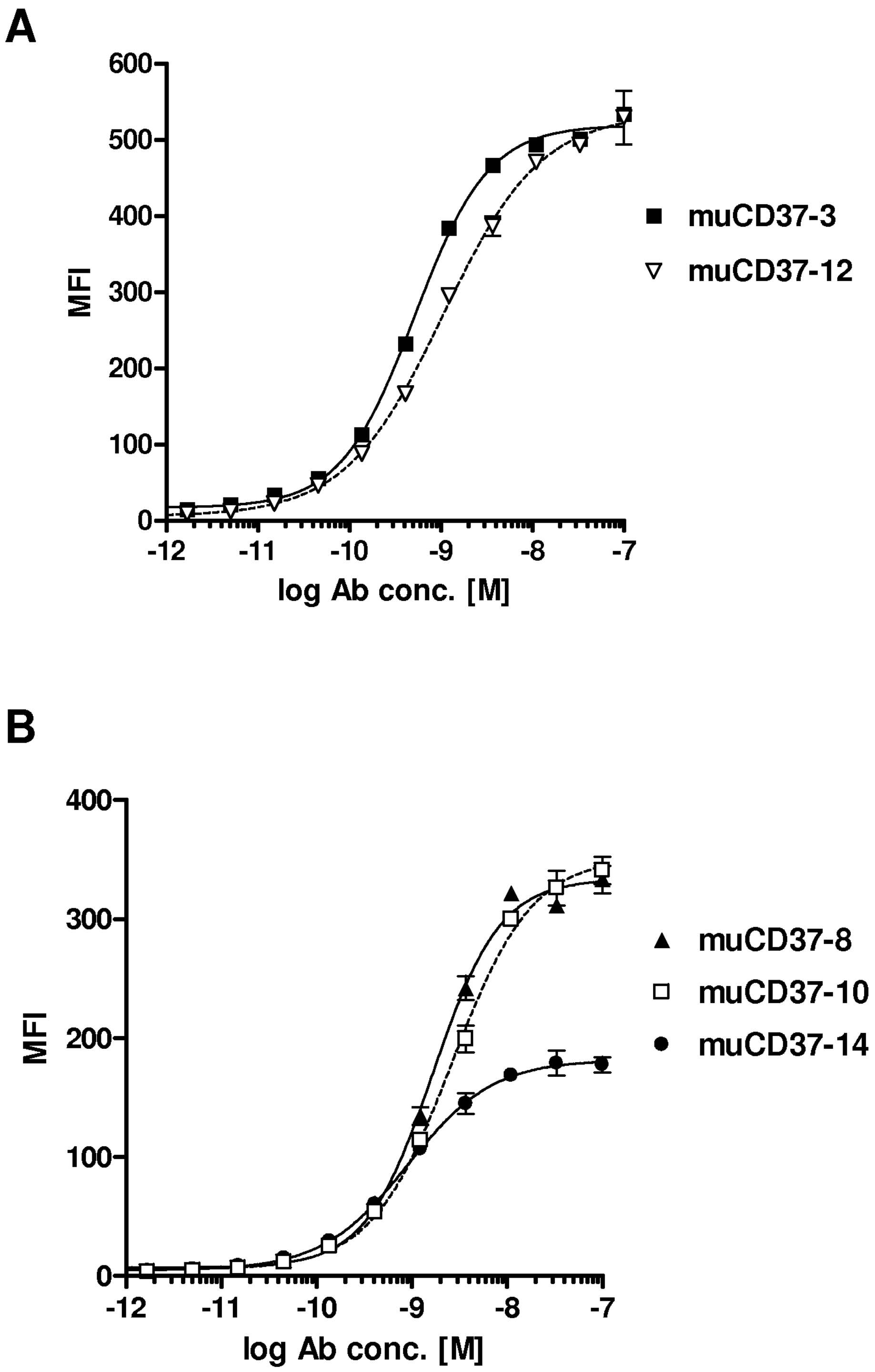

To verify that the antibodies can also bind to endogenously expressed CD37, binding experiments were performed with CD37-positive WSU-DLCL-2 lymphoma cells and the muCD37-3, muCD37-12, muCD37-8, muCD37-10 or muCD37-14 antibodies. WSU-DLCL-2 cells were incubated with varying concentrations of murine antibodies and processed as described above for flow cytometry analysis. Data analysis was performed using CellQuest Pro (BD Biosciences, San Diego, US) and for each sample the mean fluorescence intensity for FL1 (MFI) was exported and plotted against the antibody concentration in a semi-log plot (FIG. 3). A dose-response curve was generated by non-linear regression and the EC50 value of each curve, which corresponds to the apparent dissociation constant (Kd) of each antibody, was calculated using GraphPad Prism v4 (GraphPad software, San Diego, CA). A strong shift in fluorescence was observed for all antibodies tested and the Kd values correspond to 0.52 nM, 1.7 nM, 2.7 nM,1.1 nM or 0.91 nM for muCD37-3, muCD37-8, muCD37-10, muCD37-12 or muCD37-14 antibodies, respectively.

Likewise, strong binding was also observed when CD37-positive BJAB lymphoma cells were used for the same flow cytometry assay described above. The Kd values were calculated as described above and correspond to 0.2 nM, 0.4 nM, 0.6 nM, 0.4 nM and 1 nM for muCD37-3, muCD37-38, muCD37-50, muCD37-51, muCD37-56 and muCD37-57, respectively.

Example 3

Pro-Apoptotic Activity of Murine Antibodies

The murine anti-CD37 antibodies induced apoptosis of Ramos and Raji lymphoma cell lines. The degree of apoptosis was measured by flow cytometry analysis after staining with FITC conjugates of Annexin-V (Invitrogen) and with TO-PRO-3 (Invitrogen). In healthy, normal cells, phosphatidylserine is expressed on the inside of the membrane bilayer, and the transition of phosphatidylserine from the inner to the outer leaflet of the plasma membrane is one of the earliest detectable signals of apoptosis. Annexin V binds phosphatidylserine on the outside but not on the inside of the cell membrane bilayer of intact cells. The degree of Annexin V binding is therefore an indicator of the induction of apoptosis. TO-PRO-3 is a monomeric cyanine nucleic acid stain that can only penetrate the plasma membrane when the membrane integrity is breached, as occurs in the later stages of apoptosis. Three populations of cells are distinguishable in two-color flow cytometry: Non-apoptotic cells (Annexin-V negative and TO-PRO-3 negative), early apoptotic cells (Annexin-V positive and TO-PRO-3 negative) and necrotic cells or late apoptotic cells (Annexin-V positive and TO-PRO-3 positive).

Exponentially growing cells were plated at about $2\times10^5$ cells/mL in 24-well plates in RMPI-1640 medium supplemented with 10% fetal bovine serum (FBS), 2 mM L glutamine, and 50 g/mL gentamycin (denoted below as complete RMPI-1640 medium). Cells were generally grown in complete RMPI-1640 medium, unless stated otherwise. Cells were incubated with 10 nM of anti-CD37 antibodies for 20 to 24 h at 37° C. in a humidified 5% $CO_2$ incubator. The cells were then pelleted, washed twice with 500 μl PBS, resuspended in 100 μL binding buffer (10 mM Hepes-NaOH, pH 7.4, 140 mM NaCl, 2.5 mM $CaCl_2$)), and stained with 5 L of Annexin V-FITC for 15 min on ice. Then, 400 μL of binding buffer with 1 M of TO-PRO-3 was added to the mix, and the cell-associated fluorescence of FITC and TO-PRO-3 was immediately measured by flow cytometry. Five thousand events were collected for each sample. The dot plots for fluorescence of TO-PRO-3 (FL4-H; y-axis) and fluorescence of Annexin V-FITC (FL1-H; x-axis) were generated using BD CellQuest software.

The percentage of Annexin-V positive cells (includes both TO-PRO-3 positive and negative cells) were determined for each sample from these plots and are shown in FIG. 4 for Ramos cells. Several antibodies isolated from our antibody screen were tested for pro-apoptotic activity in comparison to rituximab. Unexpectedly, some of the isolated murine anti-CD37 antibodies, such as muCD37-3 and muCD37-12, showed very strong pro-apoptotic activity. Approximately 39% of Ramos cells exposed to muCD37-3 and 46% of Ramos cells exposed to muCD37-12 were Annexin-V positive. In contrast, treatment with the anti-CD20 antibody rituximab resulted in only 13% of Annexin-V positive cells, while untreated control samples contained 5% Annexin-V positive cells. Several of the isolated murine anti-CD37 antibodies did not show any pro-apoptotic activity. For example, treatment of Ramos cells with muCD37-8, muCD37-10 or muCD37-14 resulted in a minor or no increase in the percentage of Annexin-V positive as compared to untreated cells. This is in spite of their comparable binding affinity to CD37 as seen in FIG. 3.

Additional antibodies were isolated and screened for their ability to induce apoptosis in Ramos cells. Of many antibodies isolated that bound CD37 with high affinity, only some had pro-apoptotic activity. The results of a Annexin-V assay are shown in FIG. 4B. The murine antibodies muCD37-38, muCD37-50, muCD37-51, muCD37-56 and muCD37-57 were able to induce apoptosis and resulted in 38-45% of Annexin-V positive Ramos cells as compared with 5% in untreated control samples. Similar to the previous assay, treatment with the anti-CD20 antibody rituximab resulted in only 18% Annexin-V positive cells.

In addition, the murine antibodies were tested their ability to induce apoptosis in Raji lymphoma cells. As seen for Ramos cells, of the many antibodies isolated that bound CD37 with high affinity, only some had pro-apoptotic activity. Treatment with muCD37-3 or muCD37-12 resulted in 36% or 49% Annexin-V positive cells, respectively. In contrast, treatment with the anti-CD20 antibody rituximab resulted in only 20% of Annexin-V positive cells, while untreated control samples contained 4% Annexin-V positive cells.

Likewise, approximately 60% of Raji cells treated with muCD37-3, muCD37-38, muCD37-50, muCD37-51, muCD37-56 or muCD37-57 were Annexin-V positive cells compared to 15% of untreated cells.

Example 4

Proliferation Assays

The ability of anti-CD37 antibodies to inhibit cell growth was measured using in vitro cytotoxicity assays. Target cells were plated at 5,000 cells per well in 100 μL in complete RPMI media (RPMI-1640, 10% fetal bovine serum, 2 mM glutamine,1% penicillin-streptomycin, all reagents from Invitrogen). Antibodies were diluted into complete RPMI media using 3-fold dilution series and 100 μL were added per well. The final concentration typically ranged from $3\times10^{-8}$ M to $4.6\times10^{-12}$ M. Cells were incubated at 37° C. in a humidified 5% $CO_2$ incubator for 4 to 5 days. Viability of remaining cells was determined by colorimetric WST-8 assay (Dojindo Molecular Technologies, Inc., Rockville, MD, US). WST-8 is reduced by dehydrogenases in living cells to an orange formazan product that is soluble in tissue culture medium. The amount of formazan produced is directly proportional to the number of living cells. WST-8 was added to 10% of the final volume and plates were incubated at 37° C. in a humidified 5% CO2 incubator for an additional 2-4 hours. Plates were analyzed by measuring the absorbance at 450 nm (A450) in a multiwell plate reader. Background A450 absorbance of wells with media and WST-8 only was subtracted from all values. The percent viability was calculated by dividing each treated sample value by the average value of wells with untreated cells. Percent viability=100*(A450 treated sample −A450 background)/(A450 untreated sample −A450 background). The percent viability value was plotted against the antibody concentration in a semi-log plot for each treatment.

Figure 5:
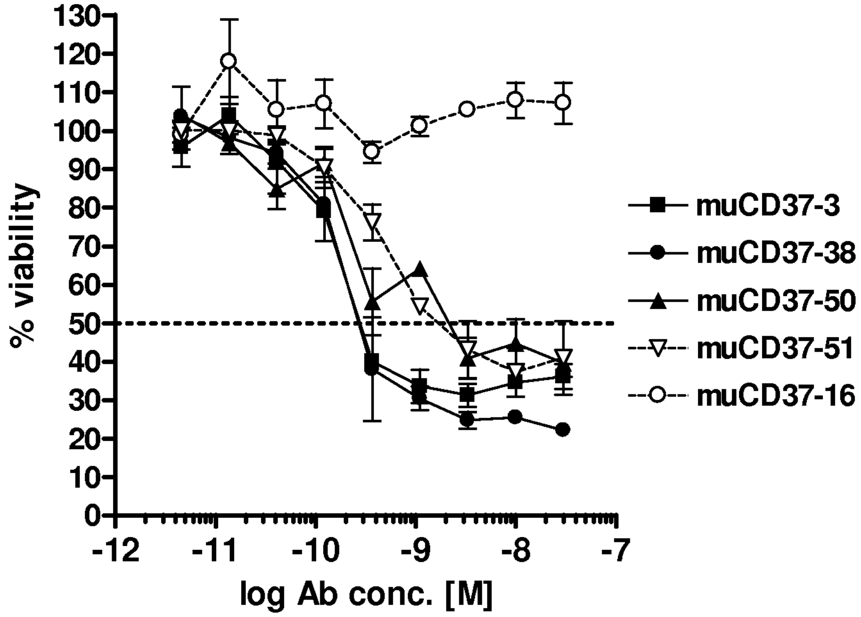
FIG. 5 depicts the results from WST-8 proliferation assays on SU-DHL-4 lymphoma cells incubated with varying concentrations of muCD37-3, muCD37-38, muCD37-50, muCD37-51 and muCD37-16 antibodies for 5 days.

The results from a typical proliferation assay using murine CD37 antibodies and SU-DHL-4 lymphoma cells are presented in FIG. 5. It is apparent, that several murine antibodies were able to inhibit proliferation of SU-DHL-4 cells substantially and in a dose-dependent manner, while others had no such effect. For example, treatment with muCD37-3 reduced the cell viability to 34% at the highest antibody concentration tested with an EC50 of 0.17 nM. Similarly, treatment with muCD37-38 reduced the cell viability to 25% at the highest antibody concentration tested with an EC50 of 0.19 nM. Likewise, treatment with muCD37-50 or muCD37-51 reduced the cell viability to 38% at the highest antibody concentration tested with an EC50 of 0.25 nM or 0.5 nM, respectively. In contrast, treatment with for example CD37-16 did not reduce cell viability in a dose-dependent manner.

Example 5

Cloning and Sequencing of the VL and VH Regions of the CD37-3 Antibody

Total cellular RNA was prepared from $5\times10^{6}$ cells of the CD37-3 hybridoma using an RNeasy kit (QIAgen) according to the manufacturer's protocol. cDNA was subsequently synthesized from total RNA using the SuperScript II cDNA synthesis kit (Invitrogen).

The procedure for the first round degenerate PCR reaction on the cDNA derived from hybridoma cells was based on methods described in Wang et al. ((2000) *J Immunol Methods.* 233:167-77) and Co et al. ((1992) *J Immunol.* 148: 1149-54). VH sequences were amplified by PCR using the following degenerate primers: EcoMH1 CTTCCGGAATTCSARGTNMAGCTGSAGSAGTC (SEQ ID NO: 171), EcoMH2 CTTCCGGAATTCSARGTNMAGCTGSAGSAGTCWGG (SEQ ID NO: 172) and BamIgG1 GGAGGATCCATAGACAGATGGGGGTGTCGTTTTGGC (SEQ ID NO: 173). VL sequences were amplified by PCR using the following degenerate primers: SacIMK GGAGCTCGAYATTGTGMTSACMCARWCTMCA (SEQ ID NO: 174) and HindKL TATAGAGCTCAAGCTTGGATGGTGGGAAGATGGATACAGTTGGTGC (SEQ ID NO: 175). (Mixed bases are defined as follows: N=G+A+T+C, S=G+C, Y=C+T, M=A+C, R=A+G, W=A+T). The PCR reaction mixtures were then run on a 1% low melt agarose gel, the 300 to 400 bp bands were excised, purified using Zymo DNA mini columns, and sent to Agencourt Biosciences for sequencing. The respective 5' and 3' PCR primers were used as sequencing primers to generate the variable region cDNAs from both directions. The amino acid sequences of VH and VL regions were predicted from the DNA sequencing results.

Since the degenerate primers used to clone the VL and VH cDNA sequences alters the 5' end sequences, additional sequencing efforts were needed to verify the complete sequences. The preliminary cDNA sequences were used to search the NCBI IgBlast site (http://www.ncbi.nlm.nih.gov/igblast/) for the murine germline sequences from which the antibody sequences are derived. PCR primers were then designed to anneal to the germline linked leader sequence of the murine antibody so that this new PCR reaction would yield a complete variable region cDNA sequence, unaltered by the PCR primers. The PCR reactions, band purifications, and sequencing were performed as described above.

Mass Determination for Sequence Confirmation

The cDNA sequence information for the variable region was combined with the germline constant region sequence to obtain full length antibody cDNA sequences. The molecular weights of the heavy chain and light chain were then calculated and compared with the molecular weights obtained by LC/MS analyses of the murine CD37-3 antibody. The molecular weight measurements are consistent with the cDNA sequences for both the CD37-3 light and heavy chain.

Chimerization

The variable sequence for the light chain variable region is cloned into EcoRI and BsiWI sites in the pchCD37-3LCZ plasmid. The heavy chain variable region is cloned into the HindIII and Apa1 sites in the pchCD37-3HCN plasmid. Equivalent plasmids were constructed for chCD37-12. These plasmids were used to express chimeric antibodies in HEK-293T cells using a standard calcium phosphate procedure (BD Biosciences, CalPhos Mammalian Transfection Kit, Cat #631312). Supernatant was purified using standard Protein A chromatography procedures as described above, but the polishing chromatography steps were performed using either carboxymethyl (CM) fast flow ion exchange (IEX) resin (GE Lifesciences) and 10 mM potassium phosphate, 10 mM sodium chloride binding buffer (pH 7.5) or the alternative CHT methods described above.

Example 6

Antibody Humanization

The CD37-3 and huCD37-50 antibodies were humanized following resurfacing methods previously described, such as, for example in Roguska et al., Proc. Natl. Acad. Sci., USA, 91(3):969-973 (1994) and Roguska et al., Protein Eng. 9(10):895-904 (1996), which are incorporated in their entirety herein by reference. Resurfacing generally involves identification of the variable region framework surface residues in both light and heavy chains and replacing them with human equivalents. The murine CDR's are preserved in the resurfaced antibody. Exemplary CDRs of CD37-3 and CD37-50 are defined as indicated in Table 11. In addition to the heavy chain CDR2 definition employed for resurfacing, the table provides exemplary Kabat defined heavy chain CDR2's for both the murine and human CD37-3 and CD37-50. The underlined sequence marks the portion of the Kabat heavy chain CDR2 not considered a CDR for resurfacing.

TABLE 11

| CD37-3 CDR's | CD37-50 CDR's |
|---|---|
| Light Chain | Light Chain |
| CDRLRASENIRSNLA (SEQ ID NO: 28) | CDRLSATSSVTYMH (SEQ ID NO: 37) |
| CDR2: VATNLAD (SEQ ID NO: 29) | MurineCDR2: DTSKLPY (SEQ ID NO: 38)<br>HumanCDR2: DTSNLPY (SEQ ID NO: 40) |
| CDR3: YWGTTWT (SEQ ID NO: 30) | CDR3: QQWSDNPPT (SEQ ID NO: 39) |
| Heavy Chain | Heavy Chain |
| CDR1: TSGVS (SEQ ID NO: 4) | CDR1: SGFAWH (SEQ ID NO: 13) |
| CDR2: VIWGDGSTN(SEQ ID NO: 5) | CDR2: YILYSGSTV (SEQ ID NO: 14) |
| CDR3: GGYSLAH (SEQ ID NO: 6) | CDR3: GYYGYGAWFAY (SEQ ID NO: 15) |
| Kabat Defined CD37-3 HC CDR2 | Kabat Defined CD37-50 HC CDR2 |
| Murine HC CDR2: VIWGDGSTNYHSALKS (SEQ ID NO: 176) | Murine HC CDR2: YILYSGSTVYSPSLKS (SEQ ID NO: 178) |
| Human HC CDR2: VIWGDGSTNYHPSLKS (SEQ ID NO: 177) | Human HC CDR2: YILYSGSTVYSPSLKS (SEQ ID NO: 179) |

The CD37-3 and CD7-50 light and heavy chain CDR's as defined for the resurfacing are given by way of example in Table 11. Lysine 53 in murine CD37-50 light chain CDR2 was replaced with asparagine in humanized CD37-50 (shown in italic) so both versions of the LC CDR2 are given. The Kabat definition for heavy chain CDR2 is also given for both the murine and human CD37-3. The underlined sequence marks the portion of the Kabat heavy chain CDR2 not considered a CDR for resurfacing.

Surface residue positions are defined as any position with its relative accessibility of 30% or greater (Pedersen J. T. et. Al, J. Mol. Biol. 1994; 235: 959-973). Surface residues are then aligned with human germline surface sequences to identify the most homologous human surface sequence. For CD37-3, the human germline sequences used as the replacement surfaces were IGKV1/OR2-0*01 and IGHV4-34*09 for VL and VH, respectively. For CD37-50, the human germline sequences used as the replacement surfaces were IGKV3/OR2-268*01 and IGHV4-31*03 for VL and VH, respectively. As can be seen from the lists in FIG. 6, a total of seven surface residues in the light chain and seven in the heavy chain were replaced with the human counterparts in CD37-3. As seen in FIG. 7 for CD37-50, the total surface residues that were replaced with human counterparts are seven and five in VL and VH, respectively. In CD37-3, the heavy chain residue 61 is in close proximity to CDR-H2 and since its substitution to the human residue proline might result in reduced binding affinity, a second resurfaced version was generated with murine serine residue retained. Since these antibodies were being tested as cytotoxic conjugates, the CD37-50 light chain CDR2 lysine 53 was replaced with an asparagine to avoid the concerns that lysine conjugation could impact binding affinity. FIG. 8 shows the alignment of the resurfaced sequences for the CD37-3 and CD37-50 variable domain of both light chain and heavy chain with their murine counterparts.

Recombinant Expression of huCD37-3 Antibody

The variable region sequences for huCD37-3 and CD37-50 were codon-optimized and synthesized by Blue Heron Biotechnology. The sequences are flanked by restriction enzyme sites for cloning in-frame with the respective constant sequences in single chain mammalian expression plasmids. The light chain variable region is cloned into EcoRI and BsiWI sites in the pAbKZeo plasmid. The heavy chain variable region is cloned into the HindIII and Apa1 sites in the pAbG1Neo plasmid. These plasmids can be used to express the recombinant antibodies in either transient or stable mammalian cell transfections. Transient transfections to express recombinant antibodies in HEK 293T cells were performed using a modified PEI procedure (Durocher, Y. et al., Nucleic Acids Res. 30:E9 (2002)). Supernatant was purified by Protein A and polishing chromatography steps using standard procedures as described above for chimerized antibodies.

Expression of TRU-016

In order to compare the activity of the isolated anti-CD37 antibodies, previously identified anti-CD37 antibodies were cloned and expressed. The DNA sequence for the anti-CD37 SMIP was drawn from US2007/0059306 using SEQ ID 51. The sequence was flanked by HindIII and XhoI restriction enzyme sites for cloning into the pAbG1Neo mammalian expression plasmids. Expression and purification was carried out as described for huCD37-3 above.

Example 7

Binding Affinity of Chimeric Antibodies

The chimeric antibodies chCD37-3 and chCD37-12 were assayed for their binding affinity to Ramos cells in comparison to their murine counterparts. Flow cytometry binding assays using Ramos cells and muCD37-3, chCD37-3, muCD37-12 and chCD37-12 antibodies were carried out and analyzed as described in Example 2 using secondary FITC-conjugated goat-anti-murine and-anti-human antibodies. FIG. 9A depicts the dose-response curves generated by non-linear regression for each antibody. The value for the apparent dissociation constant (Kd) of each antibody was calculated using GraphPad Prism v4 (GraphPad software, San Diego, CA). It is apparent that chimerization did not greatly affect the binding affinity of either antibody as the Kd for muCD37-3, chCD37-3, muCD37-12 and chCD37-12 corresponds to 0.4 nM, 0.8 nM, 0.8 nM and 1.2 nM, respectively.

Binding affinity of huCD37-3v1.0 and huCD37-3v1.01

Flow cytometry binding assays using BJAB cells and a competitive binding format were used to evaluate binding affinity of chimeric and humanized versions of CD37-3. BJAB cells were incubated with a 1 nM concentration of PE-labeled muCD37-3 antibody and competition was measured by adding varying amounts of muCD37-3, chCD37-3, huCD37-3v1.0 or huCD37-3v1.01. The samples were incubated for 3 hrs at 4° C. Then, the cells were pelleted, washed with FACS buffer and resuspended in 200 μL of PBS containing 1% formaldehyde. Samples were acquired using a FACSCalibur flow cytometer with the HTS multiwell sampler and analyzed using CellQuest Pro (all from BD Biosciences, San Diego, US). The resulting mean PE fluorescence was plotted against the amount of competing antibody used in a semi-log plot. FIG. 9B depicts the dose-response curves generated by non-linear regression for each antibody. The value for the apparent dissociation constant (Kd) of each antibody was calculated using GraphPad Prism v4 (GraphPad software, San Diego, CA). It is apparent that chimerization or humanization did not affect the binding affinity of CD37-3 as all version compete equally well for binding with the murine parent antibody. The EC50 of competition binding for muCD37-3, chCD37-3, huCD37-3v1.0 or huCD37-3v1.01 corresponds to 0.8 nM, 0.7 nM, 1 nM and 0.6 nM, respectively.

Binding Affinity of Humanized Antibodies

The humanized antibodies huCD37-38, huCD37-50, huCD37-51, huCD37-56 and chCD37-57 were assayed for their binding affinity to BJAB cells in comparison to their murine counterparts. Flow cytometry binding assays were carried out using secondary FITC-conjugated goat-anti-murine and-anti-human antibodies, analyzed as described in Example 2 and dose-response curves were generated by non-linear regression for each antibody. The value for the apparent dissociation constant (Kd) of each antibody was calculated using GraphPad Prism v4 (GraphPad software, San Diego, CA). It is apparent that humanization did not greatly affect the binding affinity of any antibody. The Kd for muCD37-3 and huCD37-3 corresponds to 0.2 nM, while the Kd for muCD37-38 and huCD37-38 corresponds to 0.4 nM and 0.3 nM, respectively. Similarly, the Kd for muCD37-50 and huCD37-50 corresponds to 0.6 nM and 0.2 nM, respectively, while the Kd for muCD37-51 and huCD37-51 corresponds to 0.6 nM and 0.8 nM, respectively. Finally, the Kd for muCD37-56 and huCD37-56 corresponds to 0.4 nM and 0.2 nM, respectively, while the Kd for muCD37-57 and huCD37-57 corresponds to 1.0 nM and 0.3 nM, respectively.

Example 8

Expression of Macaque CD37

The CD37 AA sequence of macaque CD37 was obtained from Genbank (GI: 718718). The sequence was codon-optimized and synthesized by Blue Heron Biotechnology. An expression plasmid pSRa-CD37mac was constructed that contained the entire CD37 coding sequence (CDS) from macaque flanked by XbaI and BamHI restriction sites that allowed expression of macaque CD37. 300-19 cells, a pre-B cell line derived from a Balb/c mouse (M. G. Reth et al. 1985, *Nature,* 317: 353-355), was transfected with this expression plasmid to stably express macaque CD37 on the cell surface.

Binding Affinity of Murine Antibodies to Macaque CD37

The murine antibodies muCD37-3, muCD37-12, muCD37-38, huCD37-50, muCD37-51, muCD37-56 and muCD37-57 were assayed for their ability to bind to 300-19/CD37mac cells expressing macaque CD37. Flow cytometry binding assays were carried out using secondary FITC-conjugated goat-anti-murine or goat-anti-human antibodies, analyzed as described in Example 2. Binding was compared to the previously described anti-CD37 antibody WR17 and the anti-CD37 SMIP TRU-016. As can be seen from FIG. 10A, several isolated anti-CD37 antibodies, muCD37-38, huCD37-50, muCD37-51, muCD37-56 and muCD37-57 can bind to the macaque derived CD37 antigen. In contrast, muCD37-3, muCD37-12, the previously described anti-CD37 antibody WR17 and the anti-CD37 SMIP TRU-016 are unable to bind the macaque derived CD37 antigen.

Binding Affinity of Humanized Antibodies to Macaque CD37

The humanized antibodies huCD37-38, huCD37-50, huCD37-51, huCD37-56 and huCD37-57 were assayed for their binding affinity to 300-19/CD37mac cells expressing macaque CD37. Flow cytometry binding assays were carried out using secondary FITC-conjugated goat-anti-human antibodies, analyzed as described in Example 2 and dose-response curves were generated by non-linear regression for each antibody. The value for the apparent dissociation constant (Kd) of each antibody was calculated using GraphPad Prism v4 (GraphPad software, San Diego, CA). It is apparent from FIG. 10B, that several isolated humanized antibodies bind to macaque CD37 while huCD37-3 does not. The Kd value for huCD37-38, huCD37-50, huCD37-51, huCD37-56 and huCD37-57 correspond to 1.1 nM, 1.8 nM, 14 nM, 5 nM, and 2 nM, respectively. Therefore, humanization does not affect the binding specificity of the isolated antibodies.

Example 9

Pro-Apoptotic Activity of Chimeric and Humanized Antibodies

The pro-apoptotic activity of chimeric and humanized antibodies was evaluated on Ramos cells. Cells were incubated with 10 nM concentration of antibodies or an huIgG isotype control antibody for 20 hrs followed by Annexin-V-FITC and TO-PRO-3 staining and flow cytometry analysis. ChCD37-12 retained strong pro-apoptotic activity of muCD37-12. Approximately 40% of Ramos cells are Annexin-V positive after treatment with either muCD37-12 or chCD37-12 antibody as compared to 4% of untreated control cells. Similarly, approximately 40% of Ramos cells are Annexin-V positive after treatment with huCD37-3, huCD37-38, huCD37-50, huCD37-51, huCD37-56 or huCD37-57 antibody as compared to 4% of isotype control treated or untreated cells. In contrast, treatment with the anti-CD20 antibody rituximab resulted in only 13% of Annexin-V positive cells. This result demonstrates that the strong pro-apoptotic activity of the murine anti-CD37 antibodies isolated here is retained by the chimeric or humanized antibodies derived from them. Therefore, the unique functional property of this group of anti-CD37 antibodies, strong pro-apoptotic activity in the absence of cross-linking, is not negatively affected by chimerization or humanization.

Pro-Apoptotic Activity of huCD37-3 and TRU-016

The pro-apoptotic activity of huCD37-3 against Ramos and Raji lymphoma cells was compared to the anti-CD37 SMIP TRU-016. TRU-016 has been described as a compound with no pro-apoptotic activity unless cross-linked with a secondary antibody. It is apparent that exemplary anti-CD37 antibodies huCD37-3 and chCD37-38 have much stronger pro-apoptotic activity against both lymphoma cell lines. Treatment with huCD37-3 or chCD37-38 resulted in 40% or 49% Annexin-V positive Ramos cells, as compared to 3% of untreated control cells. Rituximab treatment resulted in only 15% Annexin-V positive Ramos cells. In contrast, TRU-016 treatment did not increase the percentage of Annexin-V positive Ramos cells. Likewise, Treatment with huCD37-3 or chCD37-38 resulted in 34% or 30% Annexin-V positive Raji cells, as compared to 7% of untreated control cells. Rituximab treatment resulted in only 19% Annexin-V positive Raji cells. In contrast, TRU-016 treatment did not increase the percentage of Annexin-V positive Ramos cells.

Dose Response for Pro-Apoptotic Activity of Humanized Antibodies

Varying amounts of each antibody were incubated with Ramos cells for 20 hrs followed by Annexin-V-FITC and TO-PRO-3 staining and flow cytometry analysis. The percentage of Annexin-V positive cells was plotted against the antibody concentration in a semi-log plot, and EC50 values were calculated from curves fitted using non-linear regression analysis. It is apparent that all humanized antibodies have strong pro-apoptotic activity with a maximum percentage of Annexin-V positive cells of at least 40%. FIG. 11. The EC50 for this activity corresponds to 0.08, 0.08 and 0.11 nM for huCD37-3, huCD37-38 and huCD37-50, respectively. In addition, the EC50 for this activity corresponds to 0.41, 0.57 and 1.01 nM for huCD37-51, huCD37-56 and huCD37-57, respectively. In contrast, treatment with the anti-CD20 antibody rituximab resulted in a maximum percentage of Annexin-V positive cells of only 15% compared with 4% of cells treated with isotype control antibody.

Example 10

Proliferation Assays for Chimeric and Humanized Anti-CD37 Antibodies

The ability of chimeric and humanized anti-CD37 antibodies to inhibit cell growth was measured using in vitro cytotoxicity assays as described in Example 4. The results from a typical proliferation assay using SU-DHL-4 and DOHH-2 lymphoma cells are presented in FIG. 12. It is apparent, that all antibodies were able to inhibit proliferation of SU-DHL-4 cells substantially and in a dose-dependent manner. For example, treatment with muCD37-3 reduced the viability of SU-DHL-4 cells to 35% with an EC50 of 0.07 nM. Similarly, treatment with chCD37-3, huCD37-3v1.0 or huCD37-3v1.01 reduced the viability of SU-DHL-4 cells to approximately 30% at the highest antibody concentration tested with an EC50 of 0.03 nM, 0.06 nM or 0.03 nM, respectively. Likewise, all antibodies were able to inhibit proliferation of DOHH-2 follicular lymphoma cells substantially and in a dose-dependent manner. For example, treatment with muCD37-3 reduced the viability of DOHH-2 cells to 45% with an EC50 of 0.05 nM. Similarly, treatment with chCD37-3, huCD37-3v1.0 or huCD37-3v1.01 reduced the viability of DOHH-2 cells to approximately 35% with an EC50 of 0.06 nM, 0.07 nM or 0.05 nM, respectively. This result demonstrates that the various version of the CD37-3 antibody have similar anti-proliferative activity that is not affected by chimerization or humanization.

Additional humanized anti-CD37 antibodies were tested in similar in vitro cytotoxicity assays. All humanized antibodies tested were able to inhibit proliferation of SU-DHL-4 cells substantially and in a dose-dependent manner. For example, treatment with huCD37-38 reduced the viability of SU-DHL-4 cells to 24% with an EC50 of 0.42 nM, while treatment with huCD37-50 reduced the viability of SU-DHL-4 cells to 31% with an EC50 of 0.39 nM. In contrast, treatment with the anti-CD20 antibody rituximab reduced the viability of SU-DHL-4 cells to 35% with an EC50 of 1.6 nM. In addition, treatment with huCD37-51 or huCD37-56 reduced the viability of SU-DHL-4 cells to 24% with an EC50 of 0.60 nM or 0.68 nM, respectively. Furthermore, treatment with huCD37-57 reduced the viability of SU-DHL-4 cells to 31% with an EC50 of 0.42 nM. Treatment with an isotype control antibody did not have an effect on the viability of SU-DHL-4 cells.

Anti-Proliferative Activity of huCD37-3 in Comparison to Other Antibodies

To further characterize the anti-proliferative activity of the isolated anti-CD37 antibodies, we compared the effect of the exemplary huCD37-3 antibody to that of the anti-CD37 SMIP TRU-16 compound. Immunohistochemistry using tumor microarrays confirmed that CD37 and CD20 exhibited similar expression patterns and prevalances in subtypes of NHL. See Table 12 below. Thus, comparisons were also made to the anti-CD20 antibody rituximab. The panel of cell lines included Granta-519, SU-DHL-4, Namalwa and Daudi lymphoma cells. FIG. 13.

TABLE 12

CD37 staining on lymphoma tumor microarrays in comparison to CD20 staining.

| Tumor histology | # of pos. cores (≥1 hetero) CD37 | CD20 | # total cores |
|---|---|---|---|
| T-cell lymphoma | 0 | 0 | 4 |
| Multiple myeloma | 0 | 0 | 10 |
| Hodgkin's B-cell lymphoma | 1 (8%) | 1 (8%) | 12 |
| Non-Hodgkin B cell lymphoma (unspecified) | 21 (95%) | 21 (95%) | 22 |
| Follicular lymphoma | 3 (100%) | 3 (100%) | 3 |
| MALT lymphoma | 3 (100%) | 3 (100%) | 3 |
| Diffuse large B cell lymphoma | 13 (93%) | 13 (93%) | 14 |
| Burkitt's lymphoma | 6 (75%) | 7 (88%) | 8 |
| Mantle cell lymphoma | 3 (50%) | 6 (100%) | 6 |

In all case, huCD37-3 treatment resulted in a reduction in cell viability in a dose-dependent manner. For example, treatment with huCD37-3 reduced the viability of Granta-519 cells to approximately 37% with an EC50 of 0.062 nM. Rituximab treatment reduced the viability of Granta-519 cells to approximately 47% with an EC50 of 0.36 nM. Treatment with huCD37-3 reduced the viability of SU-DHL-4 cells to approximately 17% with an EC50 of 0.053 nM. Rituximab treatment reduced the viability of SU-DHL-4 cells to approximately 20% with an EC50 of 0.2 nM. In striking contrast, treatment with TRU-016 did not reduce the viability of Granta-519 or SU-DHL-4 cells to a significant degree or in a dose-dependent manner. In further examples, treatment with huCD37-3 reduced the viability of Namalwa cells to approximately 47% with an EC50 of 0.1 nM and reduced the viability of Daudi cells to approximately 68% with an EC50 of 0.25 nM. Rituximab treatment did not have an effect on Namalwa cells but reduced the viability of Daudi cells to approximately 69% with an EC50 of 2.6 nM. In striking contrast, treatment with TRU-016 did not reduce the viability of Namalwa or Daudi cells to a significant degree or in a dose-dependent manner. Finally, treatment with huCD37-3 reduced the viability of Ramos cells to approximately 53% with an EC50 of 0.08 nM, while neither TRU-016 nor rituximab treatment had any effect on Ramos cell viability. This result underscores the uniqueness of the anti-proliferative activity of the isolated anti-CD37 antibodies.

Example 11

CDC Activity of CD37 Antibodies

To assess complement-dependent cytotoxicity (CDC) activities of chimeric and humanized anti-CD37 antibodies, cell based assays were performed according to a published method (Gazzano-Santoro H, *J Immunol Methods.* 1997 202(2):163-71). Antibodies were aliquoted in duplicate at 50 μL/well into a flat-bottom 96-well tissue culture plate at various concentrations typically ranging from 5 g/mL (=3.3×$10^{-8}$ M) to 2.3 ng/mL (=1.5×$10^{-11}$ M) in RHBP (RPMI-1640, 20 mM HEPES, 0.1% BSA, 1% penicillin-streptomycin) medium. Target cells were added to the antibodies at 5×$10^4$ cells in 100 μL of RHBP medium per well. Lyophilized human complement (Sigma-Aldrich, St. Louis, US) was reconstituted with 1 mL sterile purified water per vial and diluted 5-fold to a 20% stock with RHBP media immediately before use. 50 μL/well of complement solution was added to each well for a final concentration of 5%. Plates were incubated for 2 h at 37° C. in 5% $CO_2$ humidified incubator to allow for complement mediated lysis. After this incubation time, Alamar Blue reagent (Invitrogen) was added to each well at a final concentration of 10% to measure the viability of the remaining cells. The plate was incubated for 16 to 20 hours at 37° C. before measuring the fluorescence (in relative fluorescence units, RFU) at EX540/EM590 nm. Controls included triplicate wells with media and complement but without cells (media only, 0% viability) and wells with cells and complement but without antibody (cells only, 100% viability). The percentage of specific cell viability for each sample was determined by to the following formula: Percent viability=(sample−media only)/(cells only−media only).

The result of an exemplary CDC assay using Ramos cells is presented in FIG. 14. Strikingly, chCD37-12 has potent CDC activity against Ramos cells. It reduced the viability of Ramos cells to 32% at the highest antibody concentration tested with an EC50 of 0.037 g/mL. In addition, several isolated antibodies showed CDC activity against Ramos to a varying degree. Treatment with huCD37-3, huCD37-38, huCD37-50 resulted in a reduction in cell viability to 59%, 50% and 45%, respectively. Treatment with huCD37-51, huCD37-56 or huCD37-56 moderately reduced cell viability of Ramos cells to approximately 70-80% at the highest antibody concentration tested.

Example 12

ADCC Activity of CD37 Antibodies

A lactate dehydrogenase (LDH) release assay was used to measure antibody-dependent cell mediated cytotoxicity (ADCC) of tumor cells lines using freshly isolated human natural killer (NK) cells as effector cells (Shields RL, J Biol Chem. 2001 276(9):6591-604). The NK cells were first isolated from human blood from a normal donor (Research Blood Components, Inc., Brighton, MA) using a modified protocol for the NK Isolation Kit II (Miltenyi Biotech, 130-091-152). Blood was diluted 2-fold with 1× PBS. 25 mL of diluted blood was carefully layered over 25 mL of Ficoll Paque in a 50 mL conical tube and centrifuged at 400 g for 45 min at RT. The peripheral blood mononuclear cells (PBMC) were collected from the interface, transferred into a new conical 50 mL tube, and washed once with 1× PBS. The PBMC were resuspended in 2 mL of NK-isolation buffer (lx PBS, 0.5% BSA, 2 mM EDTA), and then 500 μL of Biotin-Antibody Cocktail were added to the cell suspension. The Biotin-Antibody Cocktail contains biotinylated antibodies that bind to the lymphocytes, except for NK cells, resulting in a negative selection of NK cells. The mixture was incubated at 4° C. for 10 min, and then 1.5 mL of NK-isolation buffer and 1 mL of Anti-Biotin Micro Beads were added. The cell-antibody mixture was incubated for another 15 min at 4° C. Next, cells were washed once with 50 mL of NK-isolation buffer and resuspended in 3 mL of NK-isolation buffer. Then, a MACS LS column was mounted on the autoMACS separator (Miltenyi Biotech) and pre-washed with 3 mL of NK-isolation Buffer. The cell suspension was automatically applied onto the column, washed and the effluent fraction with unlabeled NK cells was collected into a new 50-mL conical tube. The resulting NK cells were plated into 30 mL of complete RPMI media (RPMI-1640 supplemented with 5% fetal bovine serum, 1% penicillin-streptomycin, 1 mM HEPES, 1 mM Sodium Pyruvate, 1% 100× MEM non-essential Amino Acid Solution) overnight. The subsequent assay and all dilutions were carried out in RHBP medium (RPMI-1640 medium supplemented with 20 mM HEPES, pH 7.4, 0.1% BSA and 1% penicillin-streptomycin).

Various concentrations of antibodies in RHBP medium were aliquoted in duplicate at 50 μL/well into a round bottom 96-well plate. The target cells were resuspended at 106 cells/mL in RHBP medium and added at 100 μL/well to each well containing antibody dilutions. The plate containing target cells and antibody dilutions was incubated for 30 min at 37° C. NK cells were then added to the wells containing the target cells at 50 μL/well. The typical ratio was 1 target cell to 3-4 NK cells. The following controls were set up for each experiment: NK cells alone, target cells alone (spontaneous LDH release), target cells with NK cells (antibody independent LDH release), target cells with 10% Triton X-100 (maximum LDH release). The mixtures were incubated at 37° C. for 4 h to allow for cell lysis. Plates were centrifuged for 10 min at 1200 rpm, and 100 μL of the supernatant was carefully transferred to a new flat-bottom 96-well plate. LDH reaction mixture (100 μL/well) from the Cytotoxicity Detection Kit (Roche 1 644 793) was added to each well and incubated at room temperature for 5 to 30 min. The optical density of samples was measured at 490 nm (OD490). The percent specific lysis of each sample was determined using the following formula: percent specific lysis=(sample value −spontaneous release)/(maximum release −spontaneous release)*100.

Incubation with humanized antibodies lead to good ADCC activity against Daudi, Ramos and Granta-519 lymphoma cells in the presence of human NK effector cells. Their ADCC activity against Daudi lymphoma cells was compared with the ADCC activity of TRU-016 (FIG. 15).

Treatment with huCD37-3, huCD37-38 or huCD37-50 antibodies resulted in approximately 41%, 39% or 40% Daudi cell lysis with an EC50 value of 0.42 ng/mL, 1.31 ng/mL, or 2.42 ng/mL, respectively. This activity was similar to that resulting from TRU-016 treatment with 42% Daudi cell lysis observed and an EC50 value of 0.93 ng/mL. In addition, treatment with huCD37-51, huCD37-56 and huCD37-57 resulted in approximately 39%, 36% or 36% of Daudi cell lysis with an EC50 value of 5.7 ng/mL, 4.3 ng/mL, or 7.9 ng/mL, respectively.

The ADCC activity of the isolated antibodies against Ramos lymphoma cells was compared with the ADCC activity of TRU-016. Treatment with huCD37-3, huCD37-38 or huCD37-50 antibodies resulted in approximately 43%, 42% or 46% Ramos cell lysis with an EC50 value of 0.95 ng/mL, 2.0 ng/mL, or 3.0 ng/mL respectively. This activity was similar to that resulting from TRU-016 treatment with 59% Ramos cell lysis observed and an EC50 value of 1.53 ng/mL. In addition, treatment with huCD37-51, huCD37-56 and huCD37-57 resulted in approximately 53%, 43% or 44% of Ramos cell lysis with an EC50 value of 5.7 ng/mL, 4.3 ng/mL, or 7.9 ng/mL, respectively.

In additional experiments the ADCC activity of huCD37-3 and chCD37-38 against Granta-519 cells was compared with the ADCC activity of TRU-016. Treatment with huCD37-3 or chCD37-38 antibodies resulted in approximately 19% or 18% Granta-519 cell lysis with an EC50 value of 0.13 ng/mL, or 0.73 ng/mL respectively. TRU-016 treatment resulted in 16% Granta-519 cell lysis observed and an EC50 value of 0.83 ng/mL.

Example 13

Epitope Mapping

The localization of amino acid requirements for the epitopes of different CD37 antibodies can help tie common or unique functional characteristics to specific molecular interactions. The extracellular domain of CD37 contains two extracellular loops, a small loop of about 18 residues, and a larger one consisting of approximately 135 amino acids. Epitope requirements have not been described for previously published CD37 antibodies. To further characterize the isolated CD37 antibodies of this invention, we constructed several CD37 antigen variants with AA substitution in the larger extracellular loop.

CD37 Variant Cloning and Expression

Mammalian expression plasmids were built containing either the entire human or macaca CD37 cDNA sequences, codon optimized and synthesized by Blue Heron Biotechnologies, and flanked by XbaI and BamHI restriction sites to facilitate cloning into the pSRa vector multiple cloning site. Since the human and macaca CD37 sequences are highly homologous (FIG. 16), the expression of these constructs could distinguish the human and macaca cross reactive antibodies from those that recognize epitopes requiring at least one of the 11 extracellular CD37 amino acid differences between in these two species as described in Example 8.

To further characterize the CD37 antibody epitopes, a series of murine and human chimeric CD37 constructs were built. Because of the size and high homology of the small CD37 extracellular loop, epitope localization efforts were limited to the large extracellular loop. An EcoRV to Pst1 cassette encoding residues 1108 to Q235 of the large extracellular loop was redesigned to be further segmented into 5 sections by incorporating 4 unique restriction sites that could be conserved between the human, murine, and macaca CD37 sequences (FIG. 17). The following human and mouse chimeric CD37 constructs were created:

```
hCD37-M1
                                        (SEQ ID NO: 180)
MSAQESCLSLIKYFLFVFNLFFFVLGSLIFCFGIWILIDKTSFVSFVGLA

FVPLQIWSKVLAISGIFTMGIALLGCVGALKELRCLLGLYFGMLLLLFAT

QITLGILISTQRVRLERRVQELVLRTIQSYRTNPDETAAEESWDYVQFQL

RCCGWHYPQDWFQVLILRGNGSEAHRVPCSCYNLSATNDSTILDKVILPQ

LSRLGHLARSRHSADICAVPAESHIYREGCAQGLQKWLHNNLISIVGICL

GVGLLELGFMTLSIFLCRNLDHVYNRLARYR

hCD37-M2
                                        (SEQ ID NO: 181)
MSAQESCLSLIKYFLFVFNLFFFVLGSLIFCFGIWILIDKTSFVSFVGLA

FVPLQIWSKVLAISGIFTMGIALLGCVGALKELRCLLGLYFGMLLLLFAT

QITLGILISTQRAQLERSLRDVVEKTIQKYGTNPEETAAEESWDYAQFQL

RCCGWQSPRDWNKAQMLKANESEEPRVPCSCYNLSATNDSTILDKVILPQ

LSRLGHLARSRHSADICAVPAESHIYREGCAQGLQKWLHNNLISIVGICL

GVGLLELGFMTLSIFLCRNLDHVYNRLARYR

hCD37-M3
                                        (SEQ ID NO: 182)
MSAQESCLSLIKYFLFVFNLFFFVLGSLIFCFGIWILIDKTSFVSFVGLA

FVPLQIWSKVLAISGIFTMGIALLGCVGALKELRCLLGLYFGMLLLLFAT

QITLGILISTQRAQLERSLRDVVEKTIQKYGTNPEETAAEESWDYVQFQL

RCCGWHYPQDWFQVLILRGNGSEAHRVPCSCYNSTATNDSTVFDKLFFSQ

LSRLGHLARSRHSADICAVPAESHIYREGCAQGLQKWLHNNLISIVGICL

GVGLLELGFMTLSIFLCRNLDHVYNRLARYR

hCD37-M45
                                        (SEQ ID NO: 183)
MSAQESCLSLIKYFLFVFNLFFFVLGSLIFCFGIWILIDKTSFVSFVGLA

FVPLQIWSKVLAISGIFTMGIALLGCVGALKELRCLLGLYFGMLLLLFAT

QITLGILISTQRAQLERSLRDVVEKTIQKYGTNPEETAAEESWDYVQFQL

RCCGWHYPQDWFQVLILRGNGSEAHRVPCSCYNLSATNDSTILDKVILPQ

LSRLGPRAKLRQTADICALPAKAHIYREGCAQSLQKWLHNNLISIVGICL

GVGLLELGFMTLSIFLCRNLDHVYNRLARYR

muCD37-R176
                                        (SEQ ID NO: 184)
ISTQRVRLERRVQELVLRTIQSYRTNPDETAAEESWDYAQFQLRCCGWQS

PRDWNKAQMLKANESEEPRVPCSCYNSTATNDSTVFDKLFFSQLSRLGPR

AKLRQTADICALPAKAHIYREGCAQSLQ.
```

In order to preserve one such restriction site, Kpn1, the human R176 was included in all of the murine/human chimeric constructs. The murine and human CD37 cassettes were ordered from Blue Heron and cloned into the pSRa vector together with a 5' end fragment of the original human CD37 construct generated by PCR to incorporate the EcoRV site and the 3' end Pst1 to Xba1 restriction fragment taken from the original macaca CD37 construct. The murine and human chimeric CD37 cassettes were then built using standard restriction digests and ligations taking advantage of the common unique restriction sites.

The hCD37-M1 variant was created by inserting a EcoRV-SacII restriction fragment encoding the AA S109 to A138 of the analogous murine CD37 sequence. Likewise the hCD37-M3 variant was created by inserting a KpnI-Blp1 restriction fragment encoding the AA V177 to L201 of the analogous murine CD37 sequence. The hCD37-M45 variant was created by inserting a Blp1-PstI restriction fragment encoding the AA S202 to 1243 of the analogous murine CD37 sequence. The resulting clones were verified by restriction enzyme digestion followed by DNA sequencing.

Stable cell lines were obtained by transfection of the murine and human chimeric CD37 variant expression plasmids into 300-19 cells using standard electroporation procedures. Briefly, $5\times10^6$ 300-19 cells were electroporated in cold RPMI-1640 media using a BioRad Gene Pulser set at 260V and 960 μF. Subsequently, cells were diluted and plated into 96-well plates in RPMI-1640 media supplemented with 10% FBS and 50 μM β3-mercaptoethanol. After 24 hours G418 (Invitrogen) was added at a final concentration of 2 mg/mL to select for transfected cells. After 2 weeks, single colonies were isolated, analyzed for CD37 surface expression by flow cytometry and expanded.

Antibody Binding to CD37 Variants

Binding of various CD37 antibodies to cells expressing human CD37 wildtype and variants was analyzed by flow cytometry using 1.5 g/mL of each antibody. The isolated antibodies of this invention were compared to commercially available CD37 antibody WR17, as well as the TRU-016 SMIP. As can be seen in FIG. 18A, all antibodies bound to wild type CD37 expressing cells. Likewise, all antibodies tested bound the hCD37-M3 variant (FIG. 18B). In contrast, the isolated antibodies of this invention bound the hCD37-M1 variant, while TRU-016 and WR17 were unable to bind hCD37-M1 variant (FIG. 19A). The CD37-50 and CD37-51 antibodies and TRU-016 were also able to bind the hCD37-M45 variant. WR17 showed partial binding to the hCD37-M45 variant, while the other antibodies CD37-3, CD37-12, CD37-38, CD37-56 and CD37-57 were unable to bind (FIG. 19B). This suggests that all of the isolated antibodies of this invention do not require the 12 AA residues in the hCD37-M1 variant that were changed to the corresponding murine AA residues for binding to the CD37 antigen. In contrast, the CD37-3, CD37-12, CD37-38, CD37-56 and CD37-57 antibodies require at least one of the 10 AA residues in the hCD37-M45 variant that were changed to the corresponding murine AA residues for binding to the CD37 antigen.

This unexpected result indicates that the isolated antibodies of this invention represent a novel class of CD37 antibodies with a unique combination of functional characteristics.

In addition, similar constructs are built following the same design. The constructs contain various combinations of murine, human and/or macaca sequences encoding the large extracellular loop of CD37 (see FIG. 17). Examples of constructs with a single human section inserted into the murine large extracellular loop sequence are:

hCD37mECD-H1:
(SEQ ID NO: 185)
MSAQESCLSLIKYFLFVFNLFFFVLGSLIFCFGIWILIDKTSFVSFVGLA
FVPLQIWSKVLAISGIFTMGIALLGCVGALKELRCLLGLYFGMLLLLFAT

-continued

QITLGILISTQRAQLERSLRDVVEKTIQKYGTNPEETAAEESWDYAQFQL
RCCGWQSPRDWNKAQMLKANESEEPRVPCSCYNSTATNDSTVFDKLFFSQ
LSRLGPRAKLRQTADICALPAKAHIYREGCAQSLQKWLHNNLISIVGICL
GVGLLELGFMTLSIFLCRNLDHVYNRLARY hCD37mECD-H2:
(SEQ ID NO: 186)
MSAQESCLSLIKYFLFVFNLFFFVLGSLIFCFGIWILIDKTSFVSFVGLF
AVPLQIWSKVLAISGIFTMGIALLGCVGALKELRCLLGLYFGMLLLLFAT
QITLGILISTQRVRLERRVQELVLRTIQSYRTNPDETAAEESWDYVQFQL
RCCGWHYPQDWFQVLILRGNGSEAHRVPCSCYNSTATNDSTVFDKLFFSQ
LSRLGPRAKLRQTADICALPAKAHIYREGCAQSLQKWLHNNLISIVGICL
GVGLLELGFMTLSIFLCRNLDHVYNRLARYR hCD37mECD-H3:
(SEQ ID NO: 187)
MSAQESCLSLIKYFLFVFNLFFFVLGSLIFCFGIWILIDKTSFVSFVGLA
FVPLQIWSKVLAISGIFTMGIALLGCVGALKELRCLLGLYFGMLLLLFAT
QITLGILISTQRVRLERRVQELVLRTIQSYRTNPDETAAEESWDYAQFQL
RCCGWQSPRDWNKAQMLKANESEEPRVPCSCYNLSATNDSTILDKVILPQ
LSRLGPRAKLRQTADICALPAKAHIYREGCAQSLQKWLHNNLISIVGICL
GVGLLELGFMTLSIFLCRNLDHVYNRLARYR hCD37mECD-H4:
(SEQ ID NO: 188)
MSAQESCLSLIKYFLFVFNLFFFVLGSLIFCFGIWILIDKTSFVSFVGLA
FVPLQIWSKVLAISGIFTMGIALLGCVGALKELRCLLGLYFGMLLLLFAT
QITLGILISTQRVRLERRVQELVLRTIQSYRTNPDETAAEESWDYAQFQL
RCCGWQSPRDWNKAQMLKANESEEPRVPCSCYNSTATNDSTVFDKLFFSQ
LSRLGHLARSRHSADICALPAKAHIYREGCAQSLQKWLHNNLISIVGICL
GVGLLELGFMTLSIFLCRNLDHVYNRLARYR hCD37mECD-H5
(SEQ ID NO: 189)
MSAQESCLSLIKYFLFVFNLFFFVLGSLIFCFGIWILIDKTSFVSFVGLA
FVPLQIWSKVLAISGIFTMGIALLGCVGALKELRCLLGLYFGMLLLLFAT
QITLGILISTQRVRLERRVQELVLRTIQSYRTNPDETAAEESWDYAQFQL
RCCGWQSPRDWNKAQMLKANESEEPRVPCSCYNSTATNDSTVFDKLFFSQ
LSRLGPRAKLRQTADICAVPAESHIYREGCAQGLQKWLHNNLISIVGICL
GVGLLELGFMTLSIFLCRNLDHVYNRLARYR
and hCD37mECD-H45
(SEQ ID NO: 190)
MSAQESCLSLIKYFLFVFNLFFFVLGSLIFCFGIWILIDKTSFVSFVGLA
FVPLQIWSKVLAISGIFTMGIALLGCVGALKELRCLLGLYFGMLLLLFAT
QITLGILISTQRVRLERRVQELVLRTIQSYRTNPDETAAEESWDYAQFQL
RCCGWQSPRDWNKAQMLKANESEEPRVPCSCYNSTATNDSTVFDKLFFSQ
LSRLGHLARSRHSADICAVPAESHIYREGCAQGLQKWLHNNLISIVGICL
GVGLLELGFMTLSIFLCRNLDHVYNRLARYR.

-continued hCD37-Mac12:

(SEQ ID NO: 191)

MSAQESCLSLIKYFLFVFNLFFFVLGSLIFCFGIWILIDKTSFVSFVGLA

FVPLQIWSKVLAISGIFTMGIALLGCVGALKELRCLLGLYFGMLLLLFAT

QITLGILISTQRAQLERSLQDIVEKTIQRYHTNPEETAAEESWDYVQFQL

RCCGWHSPQDWFQVLTLRGNGSEAHRVPCSCYNLSATNDSTILDKVILPQ

LSRLGHLARSRHSADICAVPAESHIYREGCAQGLQKWLHNNLISIVGICL

GVGLLELGFMTLSIFLCRNLDHVYNRLARYR hCD37-Mac4:

(SEQ ID NO: 192)

MSAQESCLSLIKYFLFVFNLFFFVLGSLIFCFGIWILIDKTSFVSFVGLA

FVPLQIWSKVLAISGIFTMGIALLGCVGALKELRCLLGLYFGMLLLLFAT

QITLGILISTQRAQLERSLRDVVEKTIQKYGTNPEETAAEESWDYVQFQL

RCCGWHYPQDWFQVLILRGNGSEAHRVPCSCYNLSATNDSTILDKVILPQ

LSRLGQLARSRHSTDICAVPAESHIYREGCAQGLQKWLHNNLISIVGICL

GVGLLELGFMTLSIFLCRNLDHVYNRLARYR hCD37-Mac5:

(SEQ ID NO: 193)

MSAQESCLSLIKYFLFVFNLFFFVLGSLIFCFGIWILIDKTSFVSFVGLA

FVPLQIWSKVLAISGIFTMGIALLGCVGALKELRCLLGLYFGMLLLLFAT

QITLGILISTQRAQLERSLRDVVEKTIQKYGTNPEETAAEESWDYVQFQL

RCCGWHYPQDWFQVLILRGNGSEAHRVPCSCYNLSATNDSTILDKVILPQ

LSRLGHLARSRHSADICAVPANSHIYREGCARSLQKWLHNNLISIVGICL

GVGLLELGFMTLSIFLCRNLDHVYNRLARYR and hCD37-Mac45:

(SEQ ID NO: 194)

MSAQESCLSLIKYFLFVFNLFFFVLGSLIFCFGIWILIDKTSFVSFVGLA

FVPLQIWSKVLAISGIFTMGIALLGCVGALKELRCLLGLYFGMLLLLFAT

QITLGILISTQRAQLERSLRDVVEKTIQKYGTNPEETAAEESWDYVQFQL

RCCGWHYPQDWFQVLILRGNGSEAHRVPCSCYNLSATNDSTILDKVILPQ

LSRLGQLARSRHSTDICAVPANSHIYREGCARSLQKWLHNNLISIVGICL

GVGLLELGFMTLSIFLCRNLDHVYNRLARY.

Furthermore, single point mutations are generated in the human large extracellular loop sequence to identify residues important for antibody binding.

Binding of CD37 binding agents to cells expressing SEQ ID NOs: 185-194 is analyzed by flow cytometry as described above.

Example 14

Preparation of huCD37-3-SPP-DM1

The N-succinimidyl 4-(2-pyridyldithio)pentanoate (SPP) linker was dissolved in ethanol. The huCD37-3 antibody was incubated at 5 mg/mL with a 7 fold molar excess of SPP linker for approximately 100 minutes at room temperature in 50 mM potassium phosphate buffer (pH 6.5) containing 50 mM NaCl, 2 mM EDTA, and 5% ethanol. The reaction mixture was purified using a SEPHADEX™ G25F column equilibrated with the aforementioned potassium phosphate buffer. Antibody containing fractions were pooled and used for subsequent steps.

The maytansinoid DM1 was dissolved in dimethylacetamide (DMA, final concentration is 3%) and a 1.7 fold molar excess relative to the linker was added drop wise to the SPP modified antibody. After overnight incubation at room temperature, the conjugated antibody was purified by chromatography on SEPHADEX™ G25F equilibrated in phosphate buffered saline (PBS), pH 6.5. The huCD37-3-SPP-DM1 conjugate was then dialyzed into buffer containing 10 mM histidine, 250 mM glycine, 1% sucrose pH 5.5. The number of DM1 molecules linked per antibody molecule was determined using the previously reported extinction coefficients for antibody and DM1 (Liu et al., *Proc. Natd. Acad. Sci. USA,* 93, 8618-8623 (1996)). The percentage of free maytansinoid present after the conjugation reaction was determined by injecting 20-50 μg conjugate onto a HiSep column equilibrated in 25% acetonitrile in 100 mM ammonium acetate buffer, pH 7.0, and eluting in acetonitrile. The peak area of total free maytansinoid species (eluted in the gradient and identified by comparison of elution time with known standards) was measured using an absorbance detector set to a wavelength of 252 nm and compared with the peak area related to bound maytansinoid (eluted in the conjugate peak in the column flow-through fractions) to calculate the percentage of total free maytansinoid species. Conjugates with 3.5-4 DM1 molecules per huCD37-3 antibody were obtained with <1% present as unconjugated maytansinoid.

Preparation of huCD37-3-SMCC-DM1

The (Succinimidyl 4-(N-maleimidomethyl)cyclohexane-1-carboxylate (SMCC, Pierce Biotechnology, Inc) linker was dissolved in DMA. The huCD37-3 antibody was modified with SMCC to introduce maleimides into the antibody by incubating the antibody at 5 mg/mL in 50 mM potassium phosphate, 50 mM NaCl, 2 mM EDTA, pH 6.5 with a 10 molar excess of SMCC. After approximately 100 minutes at ambient temperature, the reaction mixture was purified using a SEPHADEX™ G25 column equilibrated with the same potassium phosphate buffer. Antibody containing fractions were pooled and used for subsequent steps.

The SMCC-modified antibody was reacted with a 10 mM solution of DM1 at a 1.7 molar excess relative to the maleimide linker. The reaction was stirred at ambient temperature under for approximately 18 hours. The conjugation reaction mixture was filtered through a SEPHADEX™ G25 gel filtration column equilibrated with 1×PBS at pH 6.5. The huCD37-3-SMCC-DM1 conjugate was then dialyzed into buffer containing 10 mM histidine, 250 mM glycine, 1% sucrose pH 5.5. The number of DM1 molecules linked per antibody molecule and the percentage of total free maytansinoid species were determined as described above. Conjugates with 3.5-4 DM1 molecules per huCD37-3 antibody were obtained with <1% present as unconjugated maytansinoid.

Preparation of huCD37-3-sulfo-mal-DM4

Solutions of DM4 thiol and the heterobifunctional linker 1-(2,5-dioxo-2,5-dihydro-1H-pyrrol-1-yl)-4-(2,5-dioxopyrrolidin-1-yloxy)-4-oxobutane-2-sulfonic acid (3-sulfo-mal) were made up in N,N-dimethylacetamide (DMA) at concentrations of 30-60 mM. The linker and DM4 were mixed together in DMA containing up to 40% v/v of 200 mM succinate buffer, 2 mM EDTA, pH 5.0 to give a ratio of DM4 to linker of 1.6 and a final concentration of DM4 equal to 15 mM. After mixing, the reaction was left for 2 h added to a mixture of huCD37-3 antibody in phosphate buffer (pH 7.5) under final conjugation conditions of 4 mg/ml Ab, 90% phosphate buffer/10% DMA, pH 7.5. The conjugation reaction was allowed to proceed at ambient temperature for 2 h. The huCD37-3-sulfo-mal-DM4 conjugate was purified from excess unreacted DM4 and unconjugated linker products dialysis in PBS, followed by a final dialysis into buffer containing 10 mM histidine, 250 mM glycine, 1% sucrose pH 5.5. The conjugate was filtered through a 0.22 m filter for final storage. The number of DM4 molecules per huCD37-3 antibody molecule (average) in the final conjugate the percentage of total free maytansinoid species were determined as described above. Conjugates with 3.5-4 DM4 molecules per huCD37-3 antibody were obtained with <1% present as unconjugated maytansinoid.

Preparation of huCD37-3-PEG4-mal-DM1

The N-hydroxysuccinimidyl-(polyethylene glycol)4-(N-maleimidomethyl)-DM1 (NHS-PEG4-mal-DM1) reagent was dissolved in DMA. The huCD37-3 antibody was incubated at 5 mg/mL in 50 mM potassium phosphate, 150 mM NaCl, 2 mM EDTA, pH 7.5 with a 7 fold molar excess of NHS-PEG4-mal-DM1 (10% DMA total). After approximately 2 hours at ambient temperature, the reaction mixture was purified using a SEPHADEX™ G25 column equilibrated in 1× PBS, pH 7.4. Antibody containing fractions were pooled and dialyzed into buffer containing 10 mM histidine, 250 mM glycine, 1% sucrose, pH 5.5. The number of DM1 molecules linked per antibody and the percentage of total free maytansinoid species were determined as described above. Conjugates with 3.5-4 DM4 molecules per huCD37-3 antibody were obtained with <1% present as unconjugated maytansinoid.

Example 15

Binding Affinity of Maytansinoid Conjugates

Binding affinity of the exemplary huCD37-3 after conjugation to SMCC-DM1, SPP-DM1 or sulfo-mal-DM4 was assayed by flow cytometry as described in the above example. The value for the apparent dissociation constants (Kd) were calculated from the binding curves shown in FIG. 20A and correspond to 0.26 nM for huCD37-3, 0.46 for huCD37-3-SMCC-DM1, 0.56 nM for huCD37-3-SPP-DM1, and 0.89 nM for huCD37-3-sulfo-mal-DM4 conjugates. This result demonstrates that SMCC-DM1, SPP-DM1 or sulfo-mal-DM4 conjugation does not notably alter the affinity of the exemplary huCD37-3 antibody.

Binding affinity of huCD37-38 after conjugation to SMCC-DM1 was assayed by flow cytometry as described in the above example. The value for the apparent dissociation constants (Kd) were calculated from the binding curves shown in FIG. 20B and correspond to 1.04 nM for huCD37-38 and 1.2 nM for huCD37-38-SMCC-DM1 conjugates. This result demonstrates that SMCC-DM1 conjugation does not notably alter the affinity of the huCD38 antibody. Likewise, binding affinity of huCD37-50, huCD37-51, huCD37-56 and huCD37-57 after conjugation to SMCC-DM1 was assayed by flow cytometry. The value for the apparent dissociation constants (Kd) were calculated from binding curves and correspond to 0.43 nM for huCD37-50, 0.70 nM for huCD37-50-SMCC-DM1, 2.0 nM for huCD37-51, 1.6 nM for huCD37-51-SMCC-DM1, 0.3 nM for huCD37-56, 0.34 nM for huCD37-56-SMCC-DM1, 0.30 for huCD37-57 and 0.34 for huCD37-57-SMCC-DM1. This result demonstrates that SMCC-DM1 conjugation also does not notably alter the affinity of the huCD37-50, huCD37-51, huCD37-56 or huCD37-57 antibodies.

Binding Affinity of PEG4-Mal-DM1 Conjugates

Binding affinity of the exemplary huCD37-3 and huCD37-50 antibodies after conjugation to PEG4-mal-DM1 was assayed by flow cytometry as described in the above example. The value for the apparent dissociation constants (Kd) were calculated from binding curves and correspond to 0.28 nM for huCD37-3, 0.35 nM for huCD37-3-PEG4-mal-DM1, 0.68 nM for huCD37-50 and 1.1 nM for huCD37-50-PEG4-mal-DM1 conjugates. This result demonstrates that PEG4-mal-DM1 conjugation does not notably alter the affinity of the exemplary huCD37-3 or huCD50 antibodies.

Pro-apoptotic activity of huCD37-3-SMCC-DM1 conjugates

Pro-apoptotic activity of huCD37-3 after conjugation to SMCC-DM1 was evaluated by Annexin-V staining on Ramos cells as described above. Treatment with either huCD37-3 antibody or huCD37-3-SMCC-DM1 conjugate resulted in approximately 40% Annexin-V positive Ramos cells with an EC50 value of approximately 0.09 nM (FIG. 21A). Ramos cells treated with a non-binding control antibody or a non-binding SMCC-DM1 control conjugate contained only up to 4% Annexin-V positive cells. In comparison, treatment with the anti-CD20 antibody rituximab resulted in only 16% Annexin-V positive cells with an EC50 value of approximately 2 nM. In contrast, TRU-016 treatment did not increase the percentage of Annexin-V positive Ramos cells. This demonstrates that the strong pro-apoptotic activity of the human anti-CD37 antibody huCD37-3 is retained after conjugation to SMCC-DM1.

CDC Activity of huCD37-3-SMCC-DM1 Conjugates

CDC activity of huCD37-3 after conjugation to SMCC-DM1 was evaluated on Ramos cells in the presence of 5% human complement. Treatment with huCD37-3 or huCD37-3-SMCC-DM1 resulted in a reduction in cell viability to 53% and 73%, respectively (FIG. 21B). Therefore, the CDC activity of the exemplary huCD37-3 antibody is maintained after maytansinoid conjugation.

ADCC Activity of Conjugates

ADCC activity of huCD37-3 after conjugation to SMCC-DM1 or PEG4-mal-DM1 was evaluated on Daudi and Ramos cells in the presence of human NK effector cells by LDH release assay as described above. As can be seen in FIG. 22A, huCD37-3-SMCC-DM1 or huCD37-3-PEG4-mal-DM1 conjugates have similar ADCC activity as the unconjugated huCD37-3 antibody on Daudi cells. Treatment with huCD37-3, huCD37-3 SMCC-DM1 or huCD37-3-PEG4-mal-DM1 resulted in approximately 41%, 39% or 36% Daudi cell lysis with an EC50 value of 0.42 ng/mL, 1.13 ng/mL, or 0.91 ng/mL, respectively. Similar results were obtained using Ramos cells as target cells. As before, huCD37-3-SMCC-DM1 or huCD37-3-PEG4-mal-DM1 conjugates have comparable ADCC activity to the unconjugated huCD37-3 antibody on Ramos cells (FIG. 22B). Treatment with huCD37-3, huCD37-3 SMCC-DM1 or huCD37-3-PEG4-mal-DM1 resulted in approximately 43%, 41% or 42% Ramos cell lysis with an EC50 value of 0.95 ng/mL, 1.33 ng/mL, or 1.57 ng/mL, respectively. Therefore, the potent ADCC activity of the exemplary huCD37-3 antibody is maintained after maytansinoid conjugation.

Induction of Cell Cycle Arrest by huCD37-3-SMCC-DM1

The potential of anti-CD37 antibodies and conjugates to induce cell cycle arrest in cell lines was evaluated by propridium iodide (PI) staining followed by flow cytometry analysis. Exponentially growing cells were harvested by centrifugation at 1,300 rpm for 5 minutes at RT and resuspended at 0.5×106 cells/mL in complete RPMI media. Cells were transferred at 1 mL per well to a 24-well plate (Falcon 3077) to equal $0.5\times10^6$ cells/assay. The test compounds were added to each well in a final concentration of 10 nM. Complete RPMI media was added to untreated control wells. Cells were incubated overnight for 16 to 20 hrs at 37° C. in a humidified 5% $CO_2$ incubator. The next day, cells were harvested by transferring into 5 mL polystyrene tubes, washed once with 3 mL PBS, and fixed in 1 mL 70% ethanol for 30 minutes on ice. The samples were then washed again with 3 mL PBS once and resuspended in 0.5 mL PBS. RNase was added to the sample at 5 L/mL and incubated at 37° C. for 30 minutes. The samples were then stained with propidium iodide at a final concentration of 50 g/mL. Samples were acquired within 24 hours of PI staining. Samples were run on a FACS Calibur (BD Biosciences, San Diego). The FL2-A parameter was set to linear scale and the FL2 PTM was adjusted to position the G1 peak around 200. Samples were acquired at a low flow rate and 10,000 events were collected per sample. Distribution of cells in the different phases of the cell cycle was determined using ModFit software (Version 5.11, Verity Software House Inc., USA). This program utilizes peak fitting techniques to automatically model the PI data and provides the desired quantitative data. The data was analyzed with standard program settings.

The effect of huCD37-3 and huCD37-3-SMCC-DM1 on cell cycle arrest of BJAB and RL lymphoma cells was evaluated after a 16-20 hour incubation with either compound at a 10 nM concentration followed by propridium iodide (PI) staining and flow cytometry analysis. Incubation with huCD37-3-SMCC-DM1 resulted in an increase in the percentage of cells in G2/M phase from 13% for untreated BJAB lymphoma cells to 95% for huCD37-3-SMCC-DM1 treated cells (FIG. 23A). Similarly, incubation with huCD37-3-SMCC-DM1 resulted in an increase in the percentage of cells in G2/M phase from 12% for untreated RL lymphoma cells to 33% for huCD37-3-SMCC-DM1 treated cells (FIG. 23B). In contrast, the huCD37-3 antibody had no effect on the cell cycles of either BJAB or RL cells. In addition, a non-binding SMCC-DM1 conjugate tested at the same concentration also had no effect on the cell cycle of either cell type. This demonstrated that maytansinoid conjugates made with isolated anti-CD37 antibodies caused specific cell cycle arrest of CD37-positive lymphoma cell lines.

Example 16

In Vitro Cytotoxicity Assays

The ability of antiCD37 antibody-conjugates to inhibit cell growth was measured using in vitro cytotoxicity assays as described in Example 10 for antibodies. Briefly, target cells were plated at 5,000 cells per well in 100 μL in complete RPMI media (RPMI-1640, 10% fetal bovine serum, 2 mM glutamine, 1% penicillin-streptomycin, all reagents from Invitrogen). Conjugates were diluted into complete RPMI media using 3-fold dilution series and 100 μL were added per well. The final concentration typically ranged from $3\times10^{-8}$ M to $4.6\times10^{-12}$ M. Cells were incubated at 37° C. in a humidified 5% $CO_2$ incubator for 4 to 5 days. Viability of remaining cells was determined by colorimetric WST-8 assay as described for antibody assays and the absorbance at 450 nm (A450) was measured in a multiwell plate reader (Dojindo Molecular Technologies, Inc., Rockville, MD, US). The percent viability was calculated by dividing each treated sample value by the average value of wells with untreated cells. The percent viability value was plotted against the antibody-conjugate concentration in a semi-log plot for each treatment.

In Vitro Cytotoxicity of SMCC-DM1 Conjugates of Various Antibodies

The in vitro cytotoxicity of SMCC-DM1 conjugates made with various anti-CD37 antibodies was compared to the activity of a non-specific huIgG-SMCC-DM1 conjugate. The results from a typical cytotoxicity assay are shown in FIG. 24A for Daudi cells incubated with huCD37-3-SMCC-DM1, huCD37-38-SMCC-DM1, huCD37-50-SMCC-DM1, huCD37-51-SMCC-DM1, huCD37-56-SMCC-DM1, huCD37-57-SMCC-DM1, or a non-binding huIgG1-SMCC-DM1 control conjugate. All specific conjugates resulted in specific cell killing as compared to the control conjugate and reduced the cell viability completely at the highest concentration tested. The EC50 values correspond to 0.067 nM, 0.098 nM, 0.13 nM, 0.20 nM, 0.31 nM and 0.35 nM for SMCC-DM1 conjugates of huCD37-3, huCD37-38, huCD37-50, huCD37-51, huCD37-56 and huCD37-57, respectively. In contrast, SMCC-DM1 conjugates of a non-binding isotype control antibody resulted in cell killing with an EC50 value of only 20 nM.

Likewise, FIG. 24B shows the results of a typical cytotoxicity assay using Granta-519 cells incubated with huCD37-3-SMCC-DM1, huCD37-38-SMCC-DM1, huCD37-50-SMCC-DM1, huCD37-51-SMCC-DM1, or a non-binding huIgG1-SMCC-DM1 control conjugate for 5 days. Treatment with all specific SMCC-DM1 completely reduced viability at the highest concentration tested with an EC50 of 0.047 nM, 0.074 nM, 0.12 nM and 0.25 nM for SMCC-DM1 conjugates of huCD37-3, huCD37-38, huCD37-50, and huCD37-51, respectively. In contrast, SMCC-DM1 conjugates of a non-binding isotype control antibody resulted in cell killing with an EC50 value of only 20 nM.

In Vitro Cytotoxicity of huCD37-3-SMCC-DM1, -SPP-DM1 and Sulfo-Mal-DM4 Conjugates The in vitro cytotoxicity of huCD37-3-SMCC-DM1, -SPP-DM1 and sulfo-mal-DM4 conjugates against Daudi, Granta-519 and BJAB cells was compared to the activity of a non-specific huIgG-MCC-DM1 conjugate. All conjugates tested reduced viability of Daudi cells completely at the highest concentration tested with an EC50 value of 0.065 nM, 0.12 nM and 0.14 nM for huCD37-3-SMCC-DM1, huCD37-3-SPP-DM1 and huCD37-3-sulfo-mal-DM4, respectively. In contrast, the non-specific huIgG-SMCC-DM1 conjugate had an EC50 of 19 nM. Likewise, all conjugates tested reduced viability of Granta-519 cells completely at the highest concentration tested with an EC50 value of 0.047 nM, 0.13 nM and 0.088 nM for huCD37-3-SMCC-DM1, huCD37-3-SPP-DM1 and huCD37-3-sulfo-mal-DM4, respectively. In contrast, the non-specific huIgG-SMCC-DM1 conjugate had an EC50 of 19 nM. Finally, all conjugates tested reduced viability of BJAB cells completely at the highest concentration tested with an EC50 value of 0.041 nM, 0.11 nM and 0.11 nM for huCD37-3-SMCC-DM1, huCD37-3-SPP-DM1 and huCD37-3-sulfo-mal-DM4, respectively. In contrast, the non-specific huIgG-SMCC-DM1 conjugate had an EC50 of 16 nM.

In Vitro Cytotoxicity of huCD37-3-SMCC-DM1 and huCD37-3-PEG4-Mal-DM1 Conjugates

The in vitro cytotoxicity of huCD37-3-SMCC-DM1 and huCD37-3-PEG4-mal-DM1 conjugates against a panel of lymphoma cell lines was compared to the activity of a non-specific huIgG-SMCC-DM1 conjugate. Treatment with huCD37-3 conjugates completely reduced Daudi cell viability at the highest concentration tested with an EC50 of 0.036 nM or 0.018 nM for huCD37-3-SMCC-DM1 or huCD37-3-PEG4-mal-DM1 conjugates, respectively. In contrast, the non-binding isotype control conjugates reduced viability with an EC50 of 16 nM or greater than 30 nM for huIgG-SMCC-DM1 or huIgG-PEG4-mal-DM1, respectively. Likewise, treatment with huCD37-3 conjugates completely reduced Granta-519 cell viability at the highest concentration tested with an EC50 of 0.014 nM or 0.012 nM for huCD37-3-SMCC-DM1 or huCD37-3-PEG4-mal-DM1 conjugates, respectively. In contrast, the non-binding isotype control conjugates reduced viability with an EC50 of 6.5 nM or greater than 12 nM for huIgG-SMCC-DM1 or huIgG-PEG4-mal-DM1, respectively.

The in vitro cytotoxicity of huCD37-3-SMCC-DM1 and huCD37-3-PEG4-mal-DM1 conjugates against a panel of lymphoma cell lines was compared to the activity of a non-specific huIgG-SMCC-DM1 conjugate. Treatment with huCD37-3 conjugates completely reduced BJAB cell viability at the highest concentration tested with an EC50 of 0.019 nM or 0.010 nM for huCD37-3-SMCC-DM1 or huCD37-3-PEG4-mal-DM1 conjugates, respectively. In contrast, the non-binding isotype control conjugates reduced viability with an EC50 of 13 nM or 17 nM for huIgG-SMCC-DM1 or huIgG-PEG4-mal-DM1, respectively. Likewise, treatment with huCD37-3 conjugates completely reduced SU-DHL-4 cell viability at the highest concentration tested with an EC50 of 0.031 nM or 0.024 nM for huCD37-3-SMCC-DM1 or huCD37-3-PEG4-mal-DM1 conjugates, respectively. In contrast, the non-binding isotype control conjugates reduced viability with an EC50 of greater than 30 nM for both huIgG-SMCC-DM1 or huIgG-PEG4-mal-DM1. The huCD37-3-SMCC-DM1 conjugate also showed potency against the FL cell line DOHH-2 as well as CLL cell lines such as JVM-2 and JVM-3 (FIG. 32B).

Treatment with huCD37-3 conjugates completely reduced Raji cell viability at the highest concentration tested with an EC50 of 0.071 nM or 0.045 nM for huCD37-3-SMCC-DM1 or huCD37-3-PEG4-mal-DM1 conjugates, respectively. In contrast, the non-binding isotype control conjugates reduced viability with an EC50 of 24 nM or 47 nM for huIgG-SMCC-DM1 or huIgG-PEG4-mal-DM1, respectively. Next, the same conjugates were tested in a vincristine-resistant Raji clone termed Raji-VCR. As seen for the parental Raji cell, both conjugates showed specific cell killing. Treatment with huCD37-3 conjugates completely reduced Raji-VCR cell viability at the highest concentration tested with an EC50 of 0.11 nM or 0.037 nM for huCD37-3-SMCC-DM1 or huCD37-3-PEG4-mal-DM1 conjugates, respectively. In contrast, the non-binding isotype control conjugates reduced viability with an EC50 of 46 nM or 100 nM for huIgG-SMCC-DM1 or huIgG-PEG4-mal-DM1, respectively.

Treatment with huCD37-3 conjugates completely reduced Namalwa cell viability at the highest concentration tested with an EC50 of 0.033 nM or 0.024 nM for huCD37-3-SMCC-DM1 or huCD37-3-PEG4-mal-DM1 conjugates, respectively. In contrast, the non-binding isotype control conjugates reduced viability with an EC50 of 20 nM or greater than 30 nM for huIgG-SMCC-DM1 or huIgG-PEG4-mal-DM1, respectively. Likewise, treatment with huCD37-3 conjugates completely reduced Ramos cell viability at the highest concentration tested with an EC50 of 0.16 nM or 0.069 nM for huCD37-3-SMCC-DM1 or huCD37-3-PEG4-mal-DM1 conjugates, respectively. In contrast, the non-binding isotype control conjugates reduced viability with an EC50 of 20 nM for huIgG-SMCC-DM1 and greater than 30 nM for huIgG-PEG4-mal-DM1.

In Vitro Cytotoxicity of huCD37-3-SMCC-DM1 on Antigen Negative Molt-4 Cells

To further verify the specificity of huCD37-3-SMCC-DM1 cytotoxicity, its activity was compared to a non-specific huIgG-MCC-DM1 conjugate against non-CD37 expressing Molt-4 T-cell acute lymphoblastic leukemia cell line. An increased concentration of both conjugates was used in this experiment to capture the relatively poor non-specific cytotoxicity. HuCD37-3-SMCC-DM1 and the non-specific conjugate showed the same cytotoxicity with an EC50 of 38 nM and 42 nM, respectively.

Summary of In Vitro Cytotoxicity of Anti-CD37 Antibody Maytansinoid Conjugates

Taken these cytotoxicity results together, it is apparent that conjugates made with the isolated anti-CD37 antibodies showed specific cytotoxicity against a panel of CD37-positive lymphoma cell lines (FIG. 32B). In each case tested a good specificity window is observed for each CD37-expressing cell line, suggesting that cytotoxicity is a result of specific anti-CD37 antibody binding to target cells. In addition, huCD37-3-SMCC-DM1 and the non-specific conjugate showed the same poor cytotoxicity against antigen-negative Molt-4 cells. This demonstrates that the cytotoxicity observed for this exemplary conjugate is dependent on CD37 expression. The huCD37-3 antibody was also active against many cell lines including DOHH-2, Granata-519, SU-DHL-4, JVM-2, and JVM-3. In contrast, the anti-CD37 SMIP TRU-016 compound had no direct effect on survival of any of these cell lines. The anti-CD20 antibody showed less direct activity than huCD37-3 in most of these cell lines despite the often higher CD20 expression levels as measured by quantitative flow cytometry (FIG. 32A).

Example 17

In Vivo Efficacy of Anti-CD37 Antibodies and their SMCC-DM1 Conjugates in a BJAB Xenograft Model Anti-CD37 antibodies and their SMCC-DM1 conjugates were tested in an established xenograft model using BJAB lymphoma cells implanted subcutaneous into SCID mice. Animals were randomized by tumor volume into treatment groups when tumors reached a mean tumor volume of approximately 120 $mm^3$ and treated once on day 12 post cell inoculation with either 10 mg/kg of (A) huCD37-3 Ab, huCD37-3-SMCC-DM1, huCD37-50 Ab, huCD37-50-SMCC-DM1 or (B) huCD37-38 Ab, huCD37-38-SMCC-DM1, huCD37-56 Ab, huCD37-56-SMCC-DM1. The mean tumor volume of the different treatment groups is plotted against time post tumor cell inoculation in FIG. 25. It is apparent that treatment with any of the antibodies resulted in a moderate reduction in mean tumor volume, while treatment with any of the SMCC-DM1 conjugates resulted in a more significant reduction in mean tumor volume. In addition, for each treatment a % T/C value was calculated which corresponds to the median tumor volume of each treated group divided by the median tumor volume of the vehicle treated group. A treatment with a % T/C value of below 42% is considered active, while a treatment with a % T/C value of below 12% is considered highly active. Treatment with all SMCC-DM1 conjugates tested resulted in a significant reduction in median tumor volume. The % T/C value on day 29 post cell inoculation corresponded to 20%, 20%, 9% or 4% for huCD37-3-SMCC-DM1, huCD37-50-SMCC-DM1, huCD37-38-SMCC-DM1 or huCD37-56-SMCC-DM1, respectively.

In Vivo Efficacy of huCD37-3 Antibody, Sulfo-Mal-DM4, -SPP-DM1 and SMCC-DM1 Conjugates in a BJAB Xenograft Model In order to evaluate the in vivo efficacy of additional maytansioid conjugates, the sulfo-mal-DM4 and SPP-DM1 conjugates of the exemplary huCD37-3 antibody were compared to SMCC-DM1 conjugates in a xenograft model using BJAB lymphoma cells implanted intravenously into SCID mice.

Animals were randomized by tumor volume into treatment groups when tumors reached a mean tumor volume of approximately 120 $mm^3$ and treated once on day 9 post cell inoculation with either 10 mg/kg of huCD37-3 Ab, huCD37-3-SMCC-DM1, huCD37-3-sulfo-mal-DM4 or 5 mg/kg of huCD37-3-SPP-DM1. The mean tumor volume of the different treatment groups is plotted against time post tumor cell inoculation in FIG. 26. It is apparent that treatment with any of the conjugates resulted in a significant reduction in mean tumor volume. The % T/C value was calculated as described above for each treatment using the median tumor volume for each treatment group. The % T/C value on day 21 post cell inoculation corresponded to 49%, 5%, 7% or 4% for huCD37-3, huCD37-3-SMCC-DM1, huCD37-3-sulfo-mal-DM4 or huCD37-3-SPP-DM1, respectively. At the end of the study on day 121, huCD37-3-sulfo-mal-DM4 treatment resulted in 3 of 8 tumor-free survivors (TFS), while huCD37-3-SPP-DM1 treatment resulted in 1 of 8 TFS. No TFS were observed in the huCD37-3 antibody, huCD37-3-SMCC-DM1 or PBS vehicle control groups. This indicated that maytansinoid conjugates of the huCD37-3 antibody, such as for example SMCC-DM1, sulfo-mal-DM4 or SPP-DM1 conjugates, were highly active in the BJAB model.

In Vivo Efficacy of huCD37-3 Antibody, Sulfo-Mal-DM4, -SPP-DM1 and SMCC-DM1 Conjugates in a SU-DHL-4 Xenograft Model A second xenograft model using SU-DHL-4 diffuse large B-cell lymphoma cells implanted subcutaneous into SCID mice was utilized to evaluate the in vivo efficacy of the sulfo-mal-DM4 and SPP-DM1 conjugates of the exemplary huCD37-3 antibody as compared to SMCC-DM1 conjugates. Animals were randomized by body weight into treatment groups when tumors were established and treated once on day 17 post cell inoculation with either 10 mg/kg of huCD37-3 Ab, huCD37-3-SMCC-DM1, huCD37-3-sulfo-mal-DM4 or 5 mg/kg of huCD37-3-SPP-DM1. The median tumor volume of the different treatment groups is plotted against time post tumor cell inoculation in FIG. 27. It is apparent that treatment with the huCD37-3 antibody resulted in a reduction in median tumor volume, while treatment with any of the conjugates resulted in a more significant reduction in median tumor volume. The % T/C value was calculated as described above for each treatment. The % T/C value on day 37 post cell inoculation corresponded to 32%, 1%, 1% or 3% for huCD37-3, huCD37-3-SMCC-DM1, huCD37-3-sulfo-mal-DM4 or huCD37-3-SPP-DM1, respectively. At the end of the study on day 125, huCD37-3-SMCC-DM1 or huCD37-3-sulfo-mal-DM4 treatment resulted in 8 of 10 tumor-free survivors (TFS), while huCD37-3-SPP-DM1 treatment resulted in 9 of 10 TFS. No TFS were observed in the huCD37-3 antibody or PBS vehicle control groups. This indicated that the huCD37-3 antibody itself was active with a single 10 mg/kg dose in the SU-DHL-4 model. In addition, maytansinoid conjugates, such as for example SMCC-DM1, sulfo-mal-DM4 or SPP-DM1 conjugates, added efficacy to the antibody and result in even greater potency in this model.

In Vivo Efficacy of huCD37-3 Antibody, PEG4-Mal-DM1 and SMCC-DM1 Conjugates in a BJAB Xenograft Model The huCD37-3 antibody and its PEG4-mal-DM1 and SMCC-DM1 conjugates were tested in an established xenograft model using BJAB lymphoma cells implanted subcutaneous into SCID mice. Animals were randomized by tumor volume into treatment groups when tumors reached a mean tumor volume of approximately 120 $mm^3$ and treated once on day 9 post cell inoculation with either 10 mg/kg of huCD37-3 Ab, huCD37-3-SMCC-DM1 or huCD37-3-PEG4-mal-DM1. As seen in FIG. 28, treatment with either conjugate resulted in a significant reduction in mean tumor volume. The % T/C value was calculated as described above for each treatment using the median tumor volume for each treatment group. The % T/C value on day 24 post cell inoculation corresponded to 48%, 16% or 5% for huCD37-3, huCD37-3-SMCC-DM1 or huCD37-3-PEG4-mal-DM1, respectively. On day 74 post cell inoculation, huCD37-3-SMCC-DM1 treatment resulted in 1 of 9 tumor-free survivors (TFS), while huCD37-PEG4-mal-DM1 treatment resulted in 1 of 9 TFS. No TFS were observed in the huCD37-3 antibody or PBS vehicle control groups. In addition, huCD37-3-SMCC-DM1 was also active at a single dose of 5 mg/kg in this model with a % T/C value on day 24 post cell innoculation of 34%. This indicated that maytansinoid conjugates of the huCD37-3 antibody, such as for example SMCC-DM1 or PEG4-mal-DM1 conjugates, were highly active in the BJAB model.

In Vivo Efficacy of huCD37-3 Antibody, PEG4-Mal-DM1 and SMCC-DM1 Conjugates in a SU-DHL-4 Xenograft Model The huCD37-3 antibody and its PEG4-mal-DM1 and SMCC-DM1 conjugates were tested in an established xenograft model using SU-DHL-4 diffuse large B-cell lymphoma cells implanted subcutaneous into SCID mice. Animals were randomized by body weight into treatment groups and treated once on day 15 post cell inoculation with either 10 mg/kg of huCD37-3 Ab, huCD37-3-SMCC-DM1 or huCD37-3-PEG4-mal-DM1. The mean tumor volume of the different treatment groups is plotted against time post tumor cell inoculation FIG. 29. It is apparent that treatment with the huCD37-3 antibody resulted in a reduction in mean tumor volume, while treatment with either conjugate resulted in a more significant reduction in mean tumor volume. The % T/C value was calculated as described above for each treatment using the median tumor volume for each treatment group. The % T/C value on day 38 post cell inoculation corresponded to 34%, 4% or 2% for huCD37-3, huCD37-3-SMCC-DM1, or huCD37-3-PEG4-mal-DM1, respectively. On day 74 post cell inoculation, huCD37-3-SMCC-DM1 treatment resulted in 8 of 10 tumor-free survivors (TFS), while huCD37-3-PEG4-mal-DM1 treatment resulted in 10 of 10 TFS. No TFS were observed in the huCD37-3 antibody or PBS vehicle control groups. This indicated that the huCD37-3 antibody itself was active with a single 10 mg/kg dose in the SU-DHL-4 model. In addition, maytansinoid conjugates, such as for example SMCC-DM1 or PEG4-mal-DM1 conjugates, showed enhanced efficacy as compared to the unconjugated antibody efficacy to the antibody and resulted in even greater potency in this model. The huCD37-3-SMCC-DM1 conjugate also showed strong efficacy at single doses of 2.5 or 5 mg/kg in this model with % T/C values on day 37 post cell innoculation of 18% and 6%, respectively.

In Vivo Efficacy of huCD37-3 Antibody, huCD37-3-SMCC-DM1 Conjugate, Rituximab Antibody, and a Regime of Cyclophosphamide, Vincristine, and Prednisone (CVP) in a DoHH2 Xenograft Model The huCD37-3 antibody and its SMCC-DM1 conjugate were tested in an established xenograft model using DoHH2 follicular lymphoma cells implanted subcutaneously into SCID mice. Animals were randomized by tumor volume into treatment groups, and treatments started on day 12 post inoculation with either a single dose of 10 mg/kg of huCD37-3 antibody or huCD37-3-SMCC-DM1 conjugate; six doses of 2 mg/kg of Rituximab twice per week for three weeks; or with a regimen of a single 40 mg/kg dose of cyclophosphamide, and 0.5 mg/kg of vincristine, along with five daily 0.2 mg/kg doses of prednisone (CVP). The median tumor volume of the different treatment groups was plotted against time post tumor cell inoculation in FIG. 30. Treatment with the huCD37-3 antibody resulted in a reduction in median tumor volume, while treatment with huCD37-3-SMCC-DM1 conjugate resulted in a more significant reduction in median tumor volume. The huCD37-3-SMCC-DM1 conjugate resulted in a median tumor reduction similar to treatment with Rituximab and a more durable median tumor reduction as compared to treatment with CVP. The tumor growth delay (T-C value) was defined as the median time (in days), required for the treatment group (T) and the control group (C) tumors to reach a predetermined size and was calculated for each treatment group excluding the tumor free survivors. The T-C value for median treatment tumors to reach 800 $mm^3$ corresponded to 8, 25, 24, and 13 days for huCD37-3, huCD37-3-SMCC-DM1, rituximab and CVP, respectively. At the end of the study, on day 130 post cell inoculation, huCD37-3-SMCC-DM1 treatment resulted in 1 of 9 tumor-free survivors (TFS). No TFS were observed in the huCD37-3 antibody, rituximab, CVP, or PBS vehicle control groups. The SMCC-DM1 conjugate showed comparable tumor growth delay to rituximab and enhanced tumor growth delay as compared to the unconjugated antibody and treatment with CVP in the DoHH2 model.

In Vivo Efficacy of huCD37-3 Antibody, huCD37-3-SMCC-DM1 Conjugate, Ofatumumab Antibody and Bendamustine in a JVM-3 Xenograft Model The huCD37-3 antibody and its huCD37-3-SMCC-DM1 conjugate were tested in an established xenograft model using JVM-3 chronic lymphocytic leukemia cells implanted subcutaneously into SCID mice. Animals were randomized by tumor volume into treatment groups, and treatments started on day 7 post inoculation with either a single dose of 10 mg/kg of huCD37-3 antibody, a 5 or a 10 mg/kg dose of huCD37-3-SMCC-DM1 conjugate, six doses of 5 mg/kg of ofatumumab twice per week for three weeks, or a single 50 mg/kg dose of bendamustine. The median tumor volume of the different treatment groups was plotted against time post tumor cell inoculation in FIG. 31. Treatment with the huCD37-3 antibody resulted in a reduction in median tumor volume, while treatment with huCD37-3-SMCC-DM1 conjugate resulted in a more significant reduction in median tumor volume. The % T/C value was calculated as described above for each treatment using the median tumor volume for each treatment group. The % T/C value on day 20 post cell inoculation corresponded to 31%, 19%, 10%, 35%, and 38% for huCD37-3, 5 mg/kg huCD37-3-SMCC-DM1, 10 mg/kg huCD37-3-SMCC-DM1, ofatumumab, and bendamustine, respectively. At the end of the study, on day 76 post cell inoculation, huCD37 and ofatumumab antibody treatments both resulted in 1 of 10 tumor-free survivors (TFS), while huCD37-3-SMCC-DM1 at 5 and 10 mg/kg resulted in 1 and 2 out of 10 TFS, respectively. No TFS were observed in the bendamustine or PBS vehicle control groups. This indicated that the huCD37-3 antibody itself was active at a single 10 mg/kg dose in the JVM-3 model. The maytansinoid conjugate, huCD37-3-SMCC-DM1, showed enhanced efficacy as compared to the unconjugated antibody. In addition, treatment with the huCD37-3-SMCC-DM1 maytansinoid conjugate resulted in even greater potency than ofatumumab or bendamustine treatment in this model.

Summary of In Vivo Efficacy of Anti-CD37 Antibody Conjugates

CD37 has not been evaluated as a target for maytansinoid immunoconjugates, however CD20 has. CD37 is structurally similar to CD20 as both antigens are cell surface proteins that contain 4 transmembrane domains and one small and one large extracellular loop. Antibodies against either antigen have been shown to be internalized slowly and have a slow to moderate rate of intracellular metabolism (Press et al. 1989, Cancer Res. 49(17):4906-12, and Press et al. 1994, Blood. 83(5):1390-7). Immunoconjugates of CD20 antibodies have been evaluated previously. In one case, non-cleavable MCC-DM1 conjugates of an anti-CD20 antibody showed the same efficacy as the unconjugated antibody, while a cleavable SPP-DM1 conjugate of the same antibody showed improved efficacy in a Granta-519 xenograft model in SCID mice (Polson A G, Cancer Res 2009; 69:2358-64). Similarly, calicheamicin conjugates of rituximab made with an acid-stable amide linker were did not show improved in vivo efficacy in a Ramos xenograft model in nude mice. Only calicheamicin conjugates of rituximab made with an acid-labile dimethyl hydrazide Ac-But linker showed improved in vivo efficacy in this study (DiJoseph J F, Cancer Immunol Immunotherapy 2007; 56:1107-1117).

In striking contrast non-cleavable SMCC-DM1 conjugates of several isolated anti-CD37 antibodies of this invention show dramatically improved in vivo efficacy in BJAB, SU-DHL-4, DoHH2 and JVM-3 xenograft model as compared to the unconjugated antibody. This suggests that the isolated antibodies have unique properties that allow them to be more efficacious as maytansinoid conjugates, such as for example SMCC-DM1 conjugates, in vivo.

It is to be appreciated that the Detailed Description section, and not the Summary and Abstract sections, is intended to be used to interpret the claims. The Summary and Abstract sections sets forth one or more, but not all, exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An isolated antibody or antigen binding fragment thereof that specifically binds to CD37, wherein said antibody or antigen binding fragment thereof comprises:

i) the VH polypeptide sequence of SEQ ID NO: 57; and the VL-CDR1, VL-CDR2, and VL-CDR3 polypeptide sequences of SEQ ID NOs: 28, 29, and 30 respectively; or ii) the VH-CDR1, VH-CDR2, and VH-CDR3 polypeptide sequences of SEQ ID NOs: 4, 5, and 6 respectively; and the VL polypeptide sequence of SEQ ID NO: 74.

2. An isolated antibody thereof that specifically binds to CD37, wherein said antibody comprises the polypeptide sequences of SEQ ID NO:57 and SEQ ID NO:74, and wherein the antibody comprises an IgG1 constant region and/or a human IgG1 constant region.

3. An immunoconjugate having the formula (A)-(L)-(C), wherein:

(A) is the isolated antibody or antigen binding fragment thereof of claim 1;

(L) is a linker; and (C) is a cytotoxic agent; and wherein said linker (L) links (A) to (C).

4. The immunoconjugate of claim 3, wherein said cytotoxic agent is N(2')-deacetyl-N(2')-(3-mercapto-1-oxopropyl)-maytansine (DM1).

5. An immunoconjugate having the formula (A)-(L)-(C), wherein:

(A) is the isolated antibody of claim 2;

(L) is a linker; and (C) is a cytotoxic agent; and wherein said linker (L) links (A) to (C).

6. The immunoconjugate of claim 5, wherein said cytotoxic agent is N(2')-deacetyl-N(2')-(3-mercapto-1-oxopropyl)-maytansine (DM1).

7. A pharmaceutical composition comprising the immunoconjugate of claim 3 and a pharmaceutically acceptable carrier.

8. The pharmaceutical composition of claim 7, wherein the immunoconjugates have an average of about 3 to about 4 (C) per (A).

9. A pharmaceutical composition comprising the immunoconjugate of claim 5 and a pharmaceutically acceptable carrier.

10. The pharmaceutical composition of claim 9, wherein the immunoconjugates have an average of about 3 to about 4 (C) per (A).

11. An isolated cell producing the isolated antibody or antigen binding fragment thereof of claim 1.

12. A method of making an anti-CD37 antibody or antigen-binding fragment thereof comprising (a) culturing the cell of claim 11; and (b) isolating said antibody or antigen-binding fragment thereof from said cultured cell.

13. An isolated cell producing the isolated antibody of claim 2.

14. A method of making an anti-CD37 antibody comprising (a) culturing the cell of claim 13; and (b) isolating said antibody from said cultured cell.

15. A method for inhibiting the growth of a cell expressing CD37 comprising contacting the cell with the immunoconjugate of claim 3.

16. A method for treating a patient having cancer comprising administering to said patient a therapeutically effective amount of the immunoconjugate of claim 3, wherein said cancer is characterized by CD37 expression.

17. A method for inhibiting the growth of a cell expressing CD37 comprising contacting the cell with the immunoconjugate of claim 5.

18. A method for treating a patient having cancer comprising administering to said patient a therapeutically effective amount of the immunoconjugate of claim 1, wherein said cancer is characterized by CD37 expression.

19. An antibody or antigen-binding fragment thereof produced by the method of claim 12.

20. An antibody or antigen-binding fragment thereof produced by the method of claim 14.

* * * * *

SEQUENCE LISTING

```
Sequence total quantity: 196
SEQ ID NO: 1            moltype = AA  length = 280
FEATURE                 Location/Qualifiers
source                  1..280
                        mol_type = protein
                        note = CD37
                        organism = Homo sapiens
SEQUENCE: 1
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRAQLERSLR  120
DVVEKTIQKY GTNPEETAAE ESWDYVQFQL RCCGWHYPQD WFQVLILRGN GSEAHRVPCS  180
CYNLSATNDS TILDKVILPQ LSRLGHLARS RHSADICAVP AESHIYREGC AQGLQKWLHN  240
NLISIVGICL GVGLLELGFM TLSIFLCRNL DHVYNRLAYR                       280

SEQ ID NO: 2            moltype = AA  length = 281
FEATURE                 Location/Qualifiers
source                  1..281
                        mol_type = protein
                        note = CD37
                        organism = Macaca mulatta
SEQUENCE: 2
MSAQESCLSL IKYFLFVFNL FFFVILGSLI FCFGIWILID KTSFVSFVGL AFVPLQIWSK  60
VLAISGVFTM GLALLGCVGA LKELRCLLGL YFGMLLLLFA TQITLGILIS TQRAQLERSL  120
QDIVEKTIQR YHTNPEETAA EESWDYVQFQ LRCCGWHSPQ DWFQVLTLRG NGSEAHRVPC  180
SCYNLSATND STILDKVILP QLSRLGQLAR SRHSTDICAV PANSHIYREG CARSLQKWLH  240
NNLISIVGIC LGVGLLELGF MTLSIFLCRN LDHVYNRLRY R                     281

SEQ ID NO: 3            moltype = AA  length = 281
FEATURE                 Location/Qualifiers
source                  1..281
                        mol_type = protein
                        note = CD37
                        organism = Mus musculus
SEQUENCE: 3
MSAQESCLSL IKYFLFVFNL FFFVLGGLIF CFGTWILIDK TSFVSFVGLS FVPLQTWSKV  60
LAVSGVLTMA LALLGCVGAL KELRCLLGLY FGMLLLLFAT QITLGILIST QRVRLERRVQ  120
ELVLRTIQSY RTNPDETAAE ESWDYAQFQL RCCGWQSPRD WNKAQMLKAN ESEEPFVPCS  180
CYNSTATNDS TVFDKLFFSQ LSRLGPRAKL RQTADICALP AKAHIYREGC AQSLQKWLHN  240
NIISIVGICL GVGLLELGFM TLSIFLCRNL DHVYDRLARY R                     281

SEQ ID NO: 4            moltype = AA  length = 5
FEATURE                 Location/Qualifiers
source                  1..5
                        mol_type = protein
                        note = Variable heavy chain CDR amino acid sequence;
                         Antibody CD37-3, VH-CDR1
                        organism = synthetic construct
SEQUENCE: 4
TSGVS                                                             5

SEQ ID NO: 5            moltype = AA  length = 9
FEATURE                 Location/Qualifiers
source                  1..9
                        mol_type = protein
                        note = Variable heavy chain CDR amino acid sequence;
                         Antibody CD37-3, VH-CDR2
                        organism = synthetic construct
SEQUENCE: 5
VIWGDGSTN                                                         9

SEQ ID NO: 6            moltype = AA  length = 7
FEATURE                 Location/Qualifiers
source                  1..7
                        mol_type = protein
                        note = Variable heavy chain CDR amino acid sequence;
                         Antibody CD37-3, VH-CDR3
                        organism = synthetic construct
SEQUENCE: 6
GGYSLAH                                                           7

SEQ ID NO: 7            moltype = AA  length = 5
FEATURE                 Location/Qualifiers
source                  1..5
                        mol_type = protein
                        note = Variable heavy chain CDR amino acid sequence;
                         Antibody CD37-12, VH-CDR1
                        organism = synthetic construct
SEQUENCE: 7
```

-continued

```
KYGMN                                                      5

SEQ ID NO: 8              moltype = AA  length = 10
FEATURE                   Location/Qualifiers
source                    1..10
                          mol_type = protein
                          note = Variable heavy chain CDR amino acid sequence;
                           Antibody CD37-12, VH-CDR2
                          organism = synthetic construct
SEQUENCE: 8
WINTNTGESR                                                 10

SEQ ID NO: 9              moltype = AA  length = 6
FEATURE                   Location/Qualifiers
source                    1..6
                          mol_type = protein
                          note = Variable heavy chain CDR amino acid sequence;
                           Antibody CD37-12, VH-CDR3
                          organism = synthetic construct
SEQUENCE: 9
GTVVAD                                                     6

SEQ ID NO: 10             moltype = AA  length = 6
FEATURE                   Location/Qualifiers
source                    1..6
                          mol_type = protein
                          note = Variable heavy chain CDR amino acid sequence;
                           Antibody CD37-38, VH-CDR1
                          organism = synthetic construct
SEQUENCE: 10
SGFGWH                                                     6

SEQ ID NO: 11             moltype = AA  length = 9
FEATURE                   Location/Qualifiers
source                    1..9
                          mol_type = protein
                          note = Variable heavy chain CDR amino acid sequence;
                           Antibody CD37-38, VH-CDR2
                          organism = synthetic construct
SEQUENCE: 11
YILYSGGTD                                                  9

SEQ ID NO: 12             moltype = AA  length = 11
FEATURE                   Location/Qualifiers
source                    1..11
                          mol_type = protein
                          note = Variable heavy chain CDR amino acid sequence;
                           Antibody CD37-38, VH-CDR3
                          organism = synthetic construct
SEQUENCE: 12
GYYGYGAWFV Y                                               11

SEQ ID NO: 13             moltype = AA  length = 6
FEATURE                   Location/Qualifiers
source                    1..6
                          mol_type = protein
                          note = Variable heavy chain CDR amino acid sequence;
                           Antibody CD37-50, VH-CDR1
                          organism = synthetic construct
SEQUENCE: 13
SGFAWH                                                     6

SEQ ID NO: 14             moltype = AA  length = 9
FEATURE                   Location/Qualifiers
source                    1..9
                          mol_type = protein
                          note = Variable heavy chain CDR amino acid sequence;
                           Antibody CD37-50, VH-CDR2
                          organism = synthetic construct
SEQUENCE: 14
YILYSGSTV                                                  9

SEQ ID NO: 15             moltype = AA  length = 11
FEATURE                   Location/Qualifiers
source                    1..11
                          mol_type = protein
                          note = Variable heavy chain CDR amino acid sequence;
                           Antibody CD37-50, VH-CDR3
                          organism = synthetic construct
```

-continued

```
SEQUENCE: 15
GYYGYGAWFA Y                                                        11

SEQ ID NO: 16          moltype = AA  length = 6
FEATURE                Location/Qualifiers
source                 1..6
                       mol_type = protein
                       note = Variable heavy chain CDR amino acid sequence;
                        Antibody CD37-51, VH-CDR1
                       organism = synthetic construct
SEQUENCE: 16
SGFAWH                                                              6

SEQ ID NO: 17          moltype = AA  length = 9
FEATURE                Location/Qualifiers
source                 1..9
                       mol_type = protein
                       note = Variable heavy chain CDR amino acid sequence;
                        Antibody CD37-51, VH-CDR2
                       organism = synthetic construct
SEQUENCE: 17
YIHYSGSTN                                                           9

SEQ ID NO: 18          moltype = AA  length = 11
FEATURE                Location/Qualifiers
source                 1..11
                       mol_type = protein
                       note = Variable heavy chain CDR amino acid sequence;
                        Antibody CD37-51, VH-CDR3
                       organism = synthetic construct
SEQUENCE: 18
GYYGFGAWFV Y                                                        11

SEQ ID NO: 19          moltype = AA  length = 6
FEATURE                Location/Qualifiers
source                 1..6
                       mol_type = protein
                       note = Variable heavy chain CDR amino acid sequence;
                        Antibody CD37-56, VH-CDR1
                       organism = synthetic construct
SEQUENCE: 19
SGFAWH                                                              6

SEQ ID NO: 20          moltype = AA  length = 9
FEATURE                Location/Qualifiers
source                 1..9
                       mol_type = protein
                       note = Variable heavy chain CDR amino acid sequence;
                        Antibody CD37-56, VH-CDR2
                       organism = synthetic construct
SEQUENCE: 20
YIHYSGGTN                                                           9

SEQ ID NO: 21          moltype = AA  length = 11
FEATURE                Location/Qualifiers
source                 1..11
                       mol_type = protein
                       note = Variable heavy chain CDR amino acid sequence;
                        Antibody CD37-56, VH-CDR3
                       organism = synthetic construct
SEQUENCE: 21
GYYGFGAWFA Y                                                        11

SEQ ID NO: 22          moltype = AA  length = 6
FEATURE                Location/Qualifiers
source                 1..6
                       mol_type = protein
                       note = Variable heavy chain CDR amino acid sequence;
                        Antibody CD37-57, VH-CDR1
                       organism = synthetic construct
SEQUENCE: 22
SGFAWH                                                              6

SEQ ID NO: 23          moltype = AA  length = 9
FEATURE                Location/Qualifiers
source                 1..9
                       mol_type = protein
                       note = Variable heavy chain CDR amino acid sequence;
                        Antibody CD37-57, VH-CDR2
```

```
                        organism = synthetic construct
SEQUENCE: 23
YILYSGSTV                                                             9

SEQ ID NO: 24           moltype = AA  length = 11
FEATURE                 Location/Qualifiers
source                  1..11
                        mol_type = protein
                        organism = synthetic construct
SEQUENCE: 24
GYYGYGAWFA Y                                                          11

SEQ ID NO: 25           moltype = AA  length = 6
FEATURE                 Location/Qualifiers
VARIANT                 4
                        note = Wherein X is A or G
source                  1..6
                        mol_type = protein
                        note = Variable heavy chain CDR amino acid sequence;
                         Consensus, VH-CDR1
                        organism = synthetic construct
SEQUENCE: 25
SGFXWH                                                                6

SEQ ID NO: 26           moltype = AA  length = 9
FEATURE                 Location/Qualifiers
VARIANT                 3
                        note = Wherein X is L or H
VARIANT                 7
                        note = Wherein X is G or S
VARIANT                 9
                        note = Wherein X is D, V or N
source                  1..9
                        mol_type = protein
                        note = Variable heavy chain CDR amino acid sequence;
                         Consensus, VH-CDR2
                        organism = synthetic construct
SEQUENCE: 26
YIXYSGXTX                                                             9

SEQ ID NO: 27           moltype = AA  length = 11
FEATURE                 Location/Qualifiers
VARIANT                 5
                        note = Wherein X is Y or F
VARIANT                 10
                        note = Wherein X is V or A
source                  1..11
                        mol_type = protein
                        note = Variable heavy chain CDR amino acid sequence;
                         Consensus, VH-CDR3
                        organism = synthetic construct
SEQUENCE: 27
GYYGXGAWFX Y                                                          11

SEQ ID NO: 28           moltype = AA  length = 11
FEATURE                 Location/Qualifiers
source                  1..11
                        mol_type = protein
                        note = Variable light chain CDR amino acid sequence;
                         CD37-3, VL-CDR1
                        organism = synthetic construct
SEQUENCE: 28
RASENIRSNL A                                                          11

SEQ ID NO: 29           moltype = AA  length = 7
FEATURE                 Location/Qualifiers
source                  1..7
                        mol_type = protein
                        note = Variable light chain CDR amino acid sequence;
                         CD37-3, VL-CDR2
                        organism = synthetic construct
SEQUENCE: 29
VATNLAD                                                               7

SEQ ID NO: 30           moltype = AA  length = 9
FEATURE                 Location/Qualifiers
source                  1..9
                        mol_type = protein
                        note = Variable light chain CDR amino acid sequence;
```

```
                      CD37-3, VL-CDR3
                     organism = synthetic construct
SEQUENCE: 30
QHYWGTTWT                                                                 9

SEQ ID NO: 31        moltype = AA  length = 15
FEATURE              Location/Qualifiers
source               1..15
                     mol_type = protein
                     note = Variable light chain CDR amino acid sequence;
                      CD37-12, VL-CDR1
                     organism = synthetic construct
SEQUENCE: 31
RASQSVSTSS YSYLY                                                          15

SEQ ID NO: 32        moltype = AA  length = 7
FEATURE              Location/Qualifiers
source               1..7
                     mol_type = protein
                     note = Variable light chain CDR amino acid sequence;
                      CD37-12, VL-CDR2
                     organism = synthetic construct
SEQUENCE: 32
YASNLAS                                                                   7

SEQ ID NO: 33        moltype = AA  length = 9
FEATURE              Location/Qualifiers
source               1..9
                     mol_type = protein
                     note = Variable light chain CDR amino acid sequence;
                      CD37-12, VL-CDR3
                     organism = synthetic construct
SEQUENCE: 33
QHSWEIPYT                                                                 9

SEQ ID NO: 34        moltype = AA  length = 10
FEATURE              Location/Qualifiers
source               1..10
                     mol_type = protein
                     note = Variable light chain CDR amino acid sequence;
                      CD37-38, VL-CDR1
                     organism = synthetic construct
SEQUENCE: 34
SASSSVTYMH                                                                10

SEQ ID NO: 35        moltype = AA  length = 7
FEATURE              Location/Qualifiers
source               1..7
                     mol_type = protein
                     note = Variable light chain CDR amino acid sequence;
                      CD37-38, VL-CDR2
                     organism = synthetic construct
SEQUENCE: 35
DTSKLAS                                                                   7

SEQ ID NO: 36        moltype = AA  length = 9
FEATURE              Location/Qualifiers
source               1..9
                     mol_type = protein
                     note = Variable light chain CDR amino acid sequence;
                      CD37-38, VL-CDR3
                     organism = synthetic construct
SEQUENCE: 36
QQWISNPPT                                                                 9

SEQ ID NO: 37        moltype = AA  length = 10
FEATURE              Location/Qualifiers
source               1..10
                     mol_type = protein
                     note = Variable light chain CDR amino acid sequence;
                      CD37-50, VL-CDR1
                     organism = synthetic construct
SEQUENCE: 37
SATSSVTYMH                                                                10

SEQ ID NO: 38        moltype = AA  length = 7
FEATURE              Location/Qualifiers
source               1..7
                     mol_type = protein
```

```
                         note = Variable light chain CDR amino acid sequence;
                          CD37-50, VL-CDR2
                         organism = synthetic construct
SEQUENCE: 38
DTSKLPY                                                                    7

SEQ ID NO: 39            moltype = AA  length = 9
FEATURE                  Location/Qualifiers
source                   1..9
                         mol_type = protein
                         note = Variable light chain CDR amino acid sequence;
                          CD37-50, VL-CDR3
                         organism = synthetic construct
SEQUENCE: 39
QQWSDNPPT                                                                  9

SEQ ID NO: 40            moltype = AA  length = 7
FEATURE                  Location/Qualifiers
source                   1..7
                         mol_type = protein
                         note = Variable light chain CDR amino acid sequence;
                          CD37-50, VL-CDR2, Humanized
                         organism = synthetic construct
SEQUENCE: 40
DTSNLPY                                                                    7

SEQ ID NO: 41            moltype = AA  length = 10
FEATURE                  Location/Qualifiers
source                   1..10
                         mol_type = protein
                         note = Variable light chain CDR amino acid sequence;
                          CD37-51, VL-CDR1
                         organism = synthetic construct
SEQUENCE: 41
SATSSVTYMH                                                                 10

SEQ ID NO: 42            moltype = AA  length = 7
FEATURE                  Location/Qualifiers
source                   1..7
                         mol_type = protein
                         note = Variable light chain CDR amino acid sequence;
                          CD37-51, VL-CDR2
                         organism = synthetic construct
SEQUENCE: 42
DTSKLAS                                                                    7

SEQ ID NO: 43            moltype = AA  length = 9
FEATURE                  Location/Qualifiers
source                   1..9
                         mol_type = protein
                         note = Variable light chain CDR amino acid sequence;
                          CD37-51, VL-CDR3
                         organism = synthetic construct
SEQUENCE: 43
QQWSSNPPT                                                                  9

SEQ ID NO: 44            moltype = AA  length = 10
FEATURE                  Location/Qualifiers
source                   1..10
                         mol_type = protein
                         note = Variable light chain CDR amino acid sequence;
                          CD37-56, VL-CDR1
                         organism = synthetic construct
SEQUENCE: 44
SASSSVTYMH                                                                 10

SEQ ID NO: 45            moltype = AA  length = 7
FEATURE                  Location/Qualifiers
source                   1..7
                         mol_type = protein
                         note = Variable light chain CDR amino acid sequence;
                          CD37-56, VL-CDR2
                         organism = synthetic construct
SEQUENCE: 45
DTSKLAS                                                                    7

SEQ ID NO: 46            moltype = AA  length = 9
FEATURE                  Location/Qualifiers
source                   1..9
```

```
                    mol_type = protein
                    note = Variable light chain CDR amino acid sequence;
                     CD37-56, VL-CDR3
                    organism = synthetic construct
SEQUENCE: 46
QQWISDPPT                                                 9

SEQ ID NO: 47       moltype = AA  length = 7
FEATURE             Location/Qualifiers
source              1..7
                    mol_type = protein
                    note = Variable light chain CDR amino acid sequence;
                     CD37-56, VL-CDR2, Humanized
                    organism = synthetic construct
SEQUENCE: 47
DTSNLAS                                                   7

SEQ ID NO: 48       moltype = AA  length = 10
FEATURE             Location/Qualifiers
source              1..10
                    mol_type = protein
                    note = Variable light chain CDR amino acid sequence;
                     CD37-57, VL-CDR1
                    organism = synthetic construct
SEQUENCE: 48
SATSSVTYMH                                                10

SEQ ID NO: 49       moltype = AA  length = 7
FEATURE             Location/Qualifiers
source              1..7
                    mol_type = protein
                    note = Variable light chain CDR amino acid sequence;
                     CD37-57, VL-CDR2
                    organism = synthetic construct
SEQUENCE: 49
DTSKLAS                                                   7

SEQ ID NO: 50       moltype = AA  length = 9
FEATURE             Location/Qualifiers
source              1..9
                    mol_type = protein
                    note = Variable light chain CDR amino acid sequence;
                     CD37-57, VL-CDR3
                    organism = synthetic construct
SEQUENCE: 50
QQWSDNPPT                                                 9

SEQ ID NO: 51       moltype = AA  length = 7
FEATURE             Location/Qualifiers
source              1..7
                    mol_type = protein
                    note = Variable light chain CDR amino acid sequence;
                     CD37-57, VL-CDR2, Humanized
                    organism = synthetic construct
SEQUENCE: 51
DTSNLAS                                                   7

SEQ ID NO: 52       moltype = AA  length = 10
FEATURE             Location/Qualifiers
VARIANT             3
                    note = Wherein X is T or S
source              1..10
                    mol_type = protein
                    note = Variable light chain CDR amino acid sequence;
                     Consensus, VL-CDR1
                    organism = synthetic construct
SEQUENCE: 52
SAXSSVTYMH                                                10

SEQ ID NO: 53       moltype = AA  length = 7
FEATURE             Location/Qualifiers
VARIANT             4
                    note = Wherein X is K or N
VARIANT             6
                    note = Wherein X is A or P
VARIANT             7
                    note = Wherein X is S or Y
source              1..7
                    mol_type = protein
```

-continued

```
                         note = Variable light chain CDR amino acid sequence;
                          Consensus, VL-CDR2
                         organism = synthetic construct
SEQUENCE: 53
DTSXLXX                                                             7

SEQ ID NO: 54            moltype = AA  length = 9
FEATURE                  Location/Qualifiers
VARIANT                  4
                         note = Wherein X is I or S
VARIANT                  5
                         note = Wherein X is S or D
VARIANT                  6
                         note = Wherein X is N or D
source                   1..9
                         mol_type = protein
                         note = Variable light chain CDR amino acid sequence;
                          Consensus, VL-CDR3
                         organism = synthetic construct
SEQUENCE: 54
QQWXXXPPT                                                           9

SEQ ID NO: 55            moltype = AA  length = 115
FEATURE                  Location/Qualifiers
source                   1..115
                         mol_type = protein
                         note = Variable heavy chain amino acid sequences; muCD37-3
                          antibody
                         organism = synthetic construct
SEQUENCE: 55
QVQVKESGPG LVAPSQSLSI TCTVSGFSLT TSGVSWVRQP PGKGLEWLGV IWGDGSTNYH  60
SALKSRLSIK KDHSKSQVFL KLNSLQTDDT ATYYCAKGGY SLAHWGQGTL VTVSA       115

SEQ ID NO: 56            moltype = AA  length = 115
FEATURE                  Location/Qualifiers
source                   1..115
                         mol_type = protein
                         note = Variable heavy chain amino acid sequences; chCD37-3
                          antibody
                         organism = synthetic construct
SEQUENCE: 56
QVQVKESGPG LVAPSQSLSI TCTVSGFSLT TSGVSWVRQP PGKGLEWLGV IWGDGSTNYH  60
SALKSRLSIK KDHSKSQVFL KLNSLQTDDT ATYYCAKGGY SLAHWGQGTL VTVSA       115

SEQ ID NO: 57            moltype = AA  length = 115
FEATURE                  Location/Qualifiers
source                   1..115
                         mol_type = protein
                         note = Variable heavy chain amino acid sequences;
                          huCD37-3v1.0 antibody
                         organism = synthetic construct
SEQUENCE: 57
QVQVQESGPG LVAPSQTLSI TCTVSGFSLT TSGVSWVRQP PGKGLEWLGV IWGDGSTNYH  60
PSLKSRLSIK KDHSKSQVFL KLNSLTAADT ATYYCAKGGY SLAHWGQGTL VTVSS       115

SEQ ID NO: 58            moltype = AA  length = 115
FEATURE                  Location/Qualifiers
source                   1..115
                         mol_type = protein
                         note = Variable heavy chain amino acid sequences;
                          huCD37-3v1.1 antibody
                         organism = synthetic construct
SEQUENCE: 58
QVQVQESGPG LVAPSQTLSI TCTVSGFSLT TSGVSWVRQP PGKGLEWLGV IWGDGSTNYH  60
SSLKSRLSIK KDHSKSQVFL KLNSLTAADT ATYYCAKGGY SLAHWGQGTL VTVSS       115

SEQ ID NO: 59            moltype = AA  length = 115
FEATURE                  Location/Qualifiers
source                   1..115
                         mol_type = protein
                         note = Variable heavy chain amino acid sequences; muCD37-12
                          antibody
                         organism = synthetic construct
SEQUENCE: 59
QIQLVQSGPE LKKPGETVKI SCKASGYTFT KYGMNWVKQA QGKGLKWMGW INTNTGESRN  60
AEEFKGRFAF SLETSASTAY LQINNLKYED TATYFCGRGT VVADWGQGTT LTVSS       115

SEQ ID NO: 60            moltype = AA  length = 115
FEATURE                  Location/Qualifiers
```

-continued

```
source                 1..115
                       mol_type = protein
                       note = Variable heavy chain amino acid sequences; chCD37-12
                        antibody
                       organism = synthetic construct
SEQUENCE: 60
QIQLVQSGPE LKKPGETVKI SCKASGYTFT KYGMNWVKQA QGKGLKWMGW INTNTGESRN  60
AEEFKGRFAF SLETSASTAY LQINNLKYED TATYFCGRGT VVADWGQGTT LTVSS       115

SEQ ID NO: 61          moltype = AA  length = 120
FEATURE                Location/Qualifiers
source                 1..120
                       mol_type = protein
                       note = Variable heavy chain amino acid sequences; muCD37-38
                        antibody
                       organism = synthetic construct
SEQUENCE: 61
DVQLQESGPD LVKPSQSLSL TCTVTGYSIT SGFGWHWIRQ FPGNKLEWMA YILYSGGTDY  60
NPSLKSRISI TRDTSKNQFF LRLSSVTTED TATYYCARGY YGYGAWFVYW GQGTLVTVSA  120

SEQ ID NO: 62          moltype = AA  length = 120
FEATURE                Location/Qualifiers
source                 1..120
                       mol_type = protein
                       note = Variable heavy chain amino acid sequences; chCD37-38
                        antibody
                       organism = synthetic construct
SEQUENCE: 62
QVQLQESGPD LVKPSQSLSL TCTVTGYSIT SGFGWHWIRQ FPGNKLEWMA YILYSGGTDY  60
NPSLKSRISI TRDTSKNQFF LRLSSVTTED TATYYCARGY YGYGAWFVYW GQGTLVTVSA  120

SEQ ID NO: 63          moltype = AA  length = 120
FEATURE                Location/Qualifiers
source                 1..120
                       mol_type = protein
                       note = Variable heavy chain amino acid sequences; huCD37-38
                        antibody
                       organism = synthetic construct
SEQUENCE: 63
QVQLQESGPG LVKPSQSLSL TCTVSGYSIT SGFGWHWIRQ FPGKGLEWMA YILYSGGTDY  60
NPSLKSRISI TRDTSKNQFF LRLSSVTAAD TATYYCARGY YGYGAWFVYW GQGTLVTVSS  120

SEQ ID NO: 64          moltype = AA  length = 120
FEATURE                Location/Qualifiers
source                 1..120
                       mol_type = protein
                       note = Variable heavy chain amino acid sequences; muCD37-50
                        antibody
                       organism = synthetic construct
SEQUENCE: 64
DVQLQESGPD LLKPSQSLSL TCTVTGYSIT SGFAWHWIRQ FPGNKLEWMG YILYSGSTVY  60
SPSLKSRISI TRDTSKNHFF LQLNSVTTED TATYYCARGY YGYGAWFAYW GQGTLVTVSA  120

SEQ ID NO: 65          moltype = AA  length = 120
FEATURE                Location/Qualifiers
source                 1..120
                       mol_type = protein
                       note = Variable heavy chain amino acid sequences; huCD37-50
                        antibody
                       organism = synthetic construct
SEQUENCE: 65
QVQLQESGPG LLKPSQSLSL TCTVSGYSIT SGFAWHWIRQ HPGNKLEWMG YILYSGSTVY  60
SPSLKSRISI TRDTSKNHFF LQLNSVTAAD TATYYCARGY YGYGAWFAYW GQGTLVTVSA  120

SEQ ID NO: 66          moltype = AA  length = 120
FEATURE                Location/Qualifiers
source                 1..120
                       mol_type = protein
                       note = Variable heavy chain amino acid sequences; muCD37-51
                        antibody
                       organism = synthetic construct
SEQUENCE: 66
DVQLQESGPD LLKPSQSLSL TCTVTGYSIS SGFAWHWIRQ FPGNKLEWMG YIHYSGSTNY  60
SPSLKSRISI TRDSSKNQFF LQLNSVTTED TATYYCARGY YGFGAWFVYW GQGTLVTVSA  120

SEQ ID NO: 67          moltype = AA  length = 120
FEATURE                Location/Qualifiers
source                 1..120
                       mol_type = protein
```

```
                        note = Variable heavy chain amino acid sequences; huCD37-51
                         antibody
                        organism = synthetic construct
SEQUENCE: 67
EVQLVESGPE VLKPGESLSL TCTVSGYSIS SGFAWHWIRQ FPGKGLEWMG YIHYSGSTNY  60
SPSLQGRISI TRDSSINQFF LQLNSVTASD TATYYCARGY YGFGAWFVYW GQGTLVTVSA  120

SEQ ID NO: 68           moltype = AA  length = 120
FEATURE                 Location/Qualifiers
source                  1..120
                        mol_type = protein
                        note = Variable heavy chain amino acid sequences; muCD37-56
                         antibody
                        organism = synthetic construct
SEQUENCE: 68
DVQLQESGPD LVKPSQSLSL TCTVTGYSIT SGFAWHWIRQ FPGNKLEWMG YIHYSGGTNY  60
NPSLKSRVSI TRDTSKNQFF LQLNSVTTED TATYYCARGY YGFGAWFAYW GQGTLVPVSA  120

SEQ ID NO: 69           moltype = AA  length = 120
FEATURE                 Location/Qualifiers
source                  1..120
                        mol_type = protein
                        note = Variable heavy chain amino acid sequences; huCD37-56
                         antibody
                        organism = synthetic construct
SEQUENCE: 69
QVQLQESGPG LVKPSQSLSL TCTVSGYSIT SGFAWHWIRQ FPGKGLEWMG YIHYSGGTNY  60
NPSLKSRVSI TRDTSKNQFF LQLNSVTAAD TATYYCARGY YGFGAWFAYW GQGTLVPVSA  120

SEQ ID NO: 70           moltype = AA  length = 120
FEATURE                 Location/Qualifiers
source                  1..120
                        mol_type = protein
                        note = Variable heavy chain amino acid sequences; muCD37-57
                         antibody
                        organism = synthetic construct
SEQUENCE: 70
DVQLQESGPD LLKPSQSLSL TCTVTGYSIT SGFAWHWIRQ FPGNKLEWMG YILYSGSTVY  60
SPSLKSRISI TRDTSKNQFF LQLNSVTTED TATYYCARGY YGYGAWFAYW GQGTLVTVSA  120

SEQ ID NO: 71           moltype = AA  length = 120
FEATURE                 Location/Qualifiers
source                  1..120
                        mol_type = protein
                        note = Variable heavy chain amino acid sequences; huCD37-57
                         antibody
                        organism = synthetic construct
SEQUENCE: 71
QVQLQESGPG LLKPSQSLSL TCTVSGYSIT SGFAWHWIRQ FPGKGLEWMG YILYSGSTVY  60
SPSLKSRISI TRDTSKNQFF LQLNSVTAAD TATYYCARGY YGYGAWFAYW GQGTLVTVSA  120

SEQ ID NO: 72           moltype = AA  length = 108
FEATURE                 Location/Qualifiers
source                  1..108
                        mol_type = protein
                        note = Variable light chain amino acid sequences; muCD37-3
                         antibody
                        organism = synthetic construct
SEQUENCE: 72
DIQMTQSPAS LSVSVGETVT ITCRASENIR SNLAWYQQKQ GKSPQLLVNV ATNLADGVPS  60
RFSGSGSGTQ YSLKINSLQS EDFGTYYCQH YWGTTWTFGG GTKLEIKR               108

SEQ ID NO: 73           moltype = AA  length = 108
FEATURE                 Location/Qualifiers
source                  1..108
                        mol_type = protein
                        note = Variable light chain amino acid sequences; chCD37-3
                         antibody
                        organism = synthetic construct
SEQUENCE: 73
DIQMTQSPAS LSVSVGETVT ITCRASENIR SNLAWYQQKQ GKSPQLLVNV ATNLADGVPS  60
RFSGSGSGTQ YSLKINSLQS EDFGTYYCQH YWGTTWTFGG GTKLEIKR               108

SEQ ID NO: 74           moltype = AA  length = 108
FEATURE                 Location/Qualifiers
source                  1..108
                        mol_type = protein
                        note = Variable light chain amino acid sequences;
                         huCD37-3v1.0 and  huCD37-3v1.1 antibody
```

```
                         organism = synthetic construct
SEQUENCE: 74
DIQMTQSPSS LSVSVGERVT ITCRASENIR SNLAWYQQKP GKSPKLLVNV ATNLADGVPS  60
RFSGSGSGTD YSLKINSLQP EDFGTYYCQH YWGTTWTFGQ GTKLEIKR               108

SEQ ID NO: 75            moltype = AA  length = 112
FEATURE                  Location/Qualifiers
source                   1..112
                         mol_type = protein
                         note = Variable light chain amino acid sequences; muCD37-12
                          antibody
                         organism = synthetic construct
SEQUENCE: 75
DIVLTQSPAS LAVSLGQRAT ISCRASQSVS TSSYSYLYWF QQKPGQPPKL LIKYASNLAS  60
GVPARFSGSG SGTDFTLNIH PVEEEDTATY YCQHSWEIPY TFGGGTKLEI KR          112

SEQ ID NO: 76            moltype = AA  length = 112
FEATURE                  Location/Qualifiers
source                   1..112
                         mol_type = protein
                         note = Variable light chain amino acid sequences; chCD37-12
                          antibody
                         organism = synthetic construct
SEQUENCE: 76
DIVLTQSPAS LAVSLGQRAT ISCRASQSVS TSSYSYLYWF QQKPGQPPKL LIKYASNLAS  60
GVPARFSGSG SGTDFTLNIH PVEEEDTATY YCQHSWEIPY TFGGGTKLEI KR          112

SEQ ID NO: 77            moltype = AA  length = 107
FEATURE                  Location/Qualifiers
source                   1..107
                         mol_type = protein
                         note = Variable light chain amino acid sequences; muCD37-38
                          antibody
                         organism = synthetic construct
SEQUENCE: 77
QIVLTQSPAI MSASPGEKVT MTCSASSSVT YMHWYQQKSG TSPKRWIYDT SKLASGVPAR  60
FSGGGSGTSY SLTISSMEAE DAATYYCQQW ISNPPTFGGG TKLEIKR                107

SEQ ID NO: 78            moltype = AA  length = 107
FEATURE                  Location/Qualifiers
source                   1..107
                         mol_type = protein
                         note = Variable light chain amino acid sequences; chCD37-38
                          antibody
                         organism = synthetic construct
SEQUENCE: 78
QIVLTQSPAI MSASPGEKVT MTCSASSSVT YMHWYQQKSG TSPKRWIYDT SKLASGVPAR  60
FSGGGSGTSY SLTISSMEAE DAATYYCQQW ISNPPTFGGG TKLEIKR                107

SEQ ID NO: 79            moltype = AA  length = 107
FEATURE                  Location/Qualifiers
source                   1..107
                         mol_type = protein
                         note = Variable light chain amino acid sequences; huCD37-38
                          antibody
                         organism = synthetic construct
SEQUENCE: 79
DIVLTQSPAS MSASPGERVT MTCSASSSVT YMHWYQQKPG TSPKRWIYDT SKLASGVPAR  60
FSGSGSGTSY SLTISSMEAE DAATYYCQQW ISNPPTFGGG TKLEIKR                107

SEQ ID NO: 80            moltype = AA  length = 107
FEATURE                  Location/Qualifiers
source                   1..107
                         mol_type = protein
                         note = Variable light chain amino acid sequences; muCD37-50
                          antibody
                         organism = synthetic construct
SEQUENCE: 80
QIVLTQSPAI MSASPGEKVT MTCSATSSVT YMHWYQQKSG TSPKRWIYDT SKLPYGVPGR  60
FSGSGSGTSY SLTISSMEAE DAATYYCQQW SDNPPTFGSG TKLEIKR                107

SEQ ID NO: 81            moltype = AA  length = 107
FEATURE                  Location/Qualifiers
source                   1..107
                         mol_type = protein
                         note = Variable light chain amino acid sequences; huCD37-50
                          antibody
                         organism = synthetic construct
SEQUENCE: 81
```

-continued

```
EIVLTQSPAT MSASPGERVT MTCSATSSVT YMHWYQQKPG QSPKRWIYDT SNLPYGVPAR  60
FSGSGSGTSY SLTISSMEAE DAATYYCQQW SDNPPTFGQG TKLEIKR                107

SEQ ID NO: 82          moltype = AA  length = 107
FEATURE                Location/Qualifiers
source                 1..107
                       mol_type = protein
                       note = Variable light chain amino acid sequences; muCD37-51
                        antibody
                       organism = synthetic construct
SEQUENCE: 82
QIVLTQSPAI MSASPGEKVT MTCSATSSVT YMHWYQQKSG TSPKRWIYDT SKLASGVPAR  60
FSGSGSGTSY SLTISNMEAE DAATYYCQQW SSNPPTFGSG TKLEIKR                107

SEQ ID NO: 83          moltype = AA  length = 107
FEATURE                Location/Qualifiers
source                 1..107
                       mol_type = protein
                       note = Variable light chain amino acid sequences; huCD37-51
                        antibody
                       organism = synthetic construct
SEQUENCE: 83
EIVLTQSPAT MSASPGERVT MTCSATSSVT YMHWYQQKPG QSPKRWIYDT SKLASGVPAR  60
FSGSGSGTSY SLTISSMEAE DAATYYCQQW SSNPPTFGQG TKLEIKR                107

SEQ ID NO: 84          moltype = AA  length = 107
FEATURE                Location/Qualifiers
source                 1..107
                       mol_type = protein
                       note = Variable light chain amino acid sequences; muCD37-56
                        antibody
                       organism = synthetic construct
SEQUENCE: 84
QIVLTQSPAF MSASPGDKVT MTCSASSSVT YMHWYQQKSG TSPKRWIYDT SKLASGVPAR  60
FSGGGSGTSY SLTISTMEAE DAATYYCQQW ISDPPTFGGG TKLEIKR                107

SEQ ID NO: 85          moltype = AA  length = 107
FEATURE                Location/Qualifiers
source                 1..107
                       mol_type = protein
                       note = Variable light chain amino acid sequences; huCD37-56
                        antibody
                       organism = synthetic construct
SEQUENCE: 85
DIVLTQSPAF MSASPGEKVT MTCSASSSVT YMHWYQQKPD QSPKRWIYDT SNLASGVPSR  60
FSGGGSGTDY SLTISSMEAE DAATYYCQQW ISDPPTFGQG TKLEIKR                107

SEQ ID NO: 86          moltype = AA  length = 107
FEATURE                Location/Qualifiers
source                 1..107
                       mol_type = protein
                       note = Variable light chain amino acid sequences; muCD37-57
                        antibody
                       organism = synthetic construct
SEQUENCE: 86
QIVLTQSPAI MSASPGEKVT MTCSATSSVT YMHWYQQKSG TSPKRWIYDT SKLASGVPAR  60
FSGSGSGTSY SLTISSMEAE DAATYYCQQW SDNPPTFGSG TKLEIKR                107

SEQ ID NO: 87          moltype = AA  length = 107
FEATURE                Location/Qualifiers
source                 1..107
                       mol_type = protein
                       note = Variable light chain amino acid sequences; huCD37-57
                        antibody
                       organism = synthetic construct
SEQUENCE: 87
EIVLTQSPAT MSASPGERVT MTCSATSSVT YMHWYQQKPG QSPRRWIYDT SNLASGVPAR  60
FSGSGSGTSY SLTISSMEAE DAATYYCQQW SDNPPTFGQG TKLEIKR                107

SEQ ID NO: 88          moltype = AA  length = 445
FEATURE                Location/Qualifiers
source                 1..445
                       mol_type = protein
                       note = Full-length heavy chain amino acid sequences;
                        muCD37-3 antibody
                       organism = synthetic construct
SEQUENCE: 88
QVQVKESGPG LVAPSQSLSI TCTVSGFSLT TSGVSWVRQP PGKGLEWLGV IWGDGSTNYH  60
SALKSRLSIK KDHSKSQVFL KLNSLQTDDT ATYYCAKGGY SLAHWGQGTL VTVSAAKTTA  120
```

-continued

```
PSVYPLAPVC GDTTGSSVTL GCLVKGYFPE PVTLTWNSGS LSSGVHTFPA VLQSDLYTLS  180
SSVTVTSSTW PSQSITCNVA HPASSTKVDK KIEPRGPTIK PCPPCKCPAP NLLGGPSVFI  240
FPPKIKDVLM ISLSPIVTCV VVDVSEDDPD VQISWFVNNV EVHTAQTQTH REDYNSTLRV  300
VSALPIQHQD WMSGKEFKCK VNNKDLPAPI ERTISKPKGS VRAPQVYVLP PPEEEMTKKQ  360
VTLTCMVTDF MPEDIYVEWT NNGKTELNYK NTEPVLDSDG SYFMYSKLRV EKKNWVERNS  420
YSCSVVHEGL HNHHTTKSFS RTPGK                                        445

SEQ ID NO: 89           moltype = AA  length = 445
FEATURE                 Location/Qualifiers
source                  1..445
                        mol_type = protein
                        note = Full-length heavy chain amino acid sequences;
                         chCD37-3 antibody
                        organism = synthetic construct
SEQUENCE: 89
QVQVKESGPG LVAPSQSLSI TCTVSGFSLT TSGVSWVRQP PGKGLEWLGV IWGDGSTNYH  60
SALKSRLSIK KDHSKSQVFL KLNSLQTDDT ATYYCAKGGY SLAHWGQGTL VTVSAASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                        445

SEQ ID NO: 90           moltype = AA  length = 444
FEATURE                 Location/Qualifiers
source                  1..444
                        mol_type = protein
                        note = Full-length heavy chain amino acid sequences;
                         huCD37-3v1.0 antibody
                        organism = synthetic construct
SEQUENCE: 90
QVQVQESGPG LVAPSQTLSI TCTVSGFSLT TSGVSWVRQP PGKGLEWLGV IWGDGSTNYH  60
PSLKSRLSIK KDHSKSQVFL KLNSLTAADT ATYYCAKGGY SLAHWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 91           moltype = AA  length = 444
FEATURE                 Location/Qualifiers
source                  1..444
                        mol_type = protein
                        note = Full-length heavy chain amino acid sequences;
                         huCD37-3v1.1 antibody
                        organism = synthetic construct
SEQUENCE: 91
QVQVQESGPG LVAPSQTLSI TCTVSGFSLT TSGVSWVRQP PGKGLEWLGV IWGDGSTNYH  60
SSLKSRLSIK KDHSKSQVFL KLNSLTAADT ATYYCAKGGY SLAHWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 92           moltype = AA  length = 445
FEATURE                 Location/Qualifiers
source                  1..445
                        mol_type = protein
                        note = Full-length heavy chain amino acid sequences;
                         muCD37-12 antibody
                        organism = synthetic construct
SEQUENCE: 92
QIQLVQSGPE LKKPGETVKI SCKASGYTFT KYGMNWVKQA QGKGLKWMGW INTNTGESRN  60
AEEFKGRFAF SLETSASTAY LQINNLKYED TATYFCGRGT VVADWGQGTT LTVSSAKTTA  120
PSVYPLAPVC GDTTGSSVTL GCLVKGYFPE PVTLTWNSGS LSSGVHTFPA VLQSDLYTLS  180
SSVTVTSSTW PSQSITCNVA HPASSTKVDK KIEPRGPTIK PCPPCKCPAP NLLGGPSVFI  240
FPPKIKDVLM ISLSPIVTCV VVDVSEDDPD VQISWFVNNV EVHTAQTQTH REDYNSTLRV  300
VSALPIQHQD WMSGKEFKCK VNNKDLPAPI ERTISKPKGS VRAPQVYVLP PPEEEMTKKQ  360
VTLTCMVTDF MPEDIYVEWT NNGKTELNYK NTEPVLDSDG SYFMYSKLRV EKKNWVERNS  420
YSCSVVHEGL HNHHTTKSFS RTPGK                                        445

SEQ ID NO: 93           moltype = AA  length = 445
FEATURE                 Location/Qualifiers
source                  1..445
                        mol_type = protein
```

```
                        note = Full-length heavy chain amino acid sequences;
                         chCD37-12 antibody
                        organism = synthetic construct
SEQUENCE: 93
QIQLVQSGPE LKKPGETVKI SCKASGYTFT KYGMNWVKQA QGKGLKWMGW INTNTGESRN  60
AEEFKGRFAF SLETSASTAY LQINNLKYED TATYFCGRGT VVADWGQGTT LTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                       445

SEQ ID NO: 94           moltype = AA  length = 444
FEATURE                 Location/Qualifiers
source                  1..444
                        mol_type = protein
                        note = Full-length heavy chain amino acid sequences;
                         muCD37-38 antibody
                        organism = synthetic construct
SEQUENCE: 94
DVQLQESGPD LVKPSQSLSL TCTVTGYSIT SGFGWHWIRQ FPGNKLEWMA YILYSGGTDY  60
NPSLKSRISI TRDTSKNQFF LRLSSVTTED TATYYCARGY YGYGAWFVYW GQGTLVTVSA  120
AKTTPPSVYP LAPGSAAQTN SMVTLGCLVK GYFPEPVTVT WNSGSLSSGV HTFPAVLESD  180
LYTLSSSVTV PSSMRPSETV TCNVAHPASS TKVDKKIVPR DCGCKPCICT VPEVSSVFIF  240
PPKPKDVLTI TLTPKVTCVV VDISKDDPEV QFSWFVDDVE VHTAQTQPRE EQFNSTFRSV  300
SELPIMHQDW LNGKEFKCRV NSAAFPAPIE KTISKTKGRP KAPQVYTIPP PKEQMAKDKV  360
SLTCMITDFF PEDITVEWQW NGQPAENYKN TQPIMNTNGS YFVYSKLNVQ KSNWEAGNTF  420
TCSVLHEGLH NHHTEKSLSH SPGK                                        444

SEQ ID NO: 95           moltype = AA  length = 449
FEATURE                 Location/Qualifiers
source                  1..449
                        mol_type = protein
                        note = Full-length heavy chain amino acid sequences;
                         chCD37-38 antibody
                        organism = synthetic construct
SEQUENCE: 95
QVQLQESGPD LVKPSQSLSL TCTVTGYSIT SGFGWHWIRQ FPGNKLEWMA YILYSGGTDY  60
NPSLKSRISI TRDTSKNQFF LRLSSVTTED TATYYCARGY YGYGAWFVYW GQGTLVTVSA  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 96           moltype = AA  length = 449
FEATURE                 Location/Qualifiers
source                  1..449
                        mol_type = protein
                        note = Full-length heavy chain amino acid sequences;
                         huCD37-38 antibody
                        organism = synthetic construct
SEQUENCE: 96
QVQLQESGPG LVKPSQSLSL TCTVSGYSIT SGFGWHWIRQ FPGKGLEWMA YILYSGGTDY  60
NPSLKSRISI TRDTSKNQFF LRLSSVTAAD TATYYCARGY YGYGAWFVYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 97           moltype = AA  length = 450
FEATURE                 Location/Qualifiers
source                  1..450
                        mol_type = protein
                        note = Full-length heavy chain amino acid sequences;
                         muCD37-50 antibody
                        organism = synthetic construct
SEQUENCE: 97
DVQLQESGPD LLKPSQSLSL TCTVTGYSIT SGFAWHWIRQ FPGNKLEWMG YILYSGSTVY  60
SPSLKSRISI TRDTSKNHFF LQLNSVTTED TATYYCARGY YGYGAWFAYW GQGTLVTVSA  120
AKTTAPSVYP LAPVCGDTTG SSVTLGCLVK GYFPEPVTLT WNSGSLSSGV HTFPAVLQSD  180
LYTLSSSVTV TSSTWPSQSI TCNVAHPASS TKVDKKIEPR GPTIKPCPPC KCPAPNLLGG  240
PSVFIFPPKI KDVLMISLSP IVTCVVVDVS EDDPDVQISW FVNNVEVHTA QTQTHREDYN  300
STLRVVSALP IQHQDWMSGK EFKCKVNNKD LPAPIERTIS KPKGSVRAPQ VYVLPPPEEE  360
MTKKQVTLTC MVTDFMPEDI YVEWTNNGKT ELNYKNTEPV LDSDGSYFMY SKLRVEKKNW  420
```

-continued

```
VERNSYSCSV VHEGLHNHHT TKSFSRTPGK                                 450

SEQ ID NO: 98          moltype = AA  length = 449
FEATURE                Location/Qualifiers
source                 1..449
                       mol_type = protein
                       note = Full-length heavy chain amino acid sequences;
                        huCD37-50 antibody
                       organism = synthetic construct
SEQUENCE: 98
QVQLQESGPG LLKPSQSLSL TCTVSGYSIT SGFAWHWIRQ HPGNKLEWMG YILYSGSTVY  60
SPSLKSRISI TRDTSKNHFF LQLNSVTAAD TATYYCARGY YGYGAWFAYW GQGTLVTVSA  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449

SEQ ID NO: 99          moltype = AA  length = 450
FEATURE                Location/Qualifiers
source                 1..450
                       mol_type = protein
                       note = Full-length heavy chain amino acid sequences;
                        muCD37-51 antibody
                       organism = synthetic construct
SEQUENCE: 99
DVQLQESGPD LLKPSQSLSL TCTVTGYSIS SGFAWHWIRQ FPGNKLEWMG YIHYSGSTNY  60
SPSLKSRISI TRDSSKNQFF LQLNSVTTED TATYYCARGY YGFGAWFVYW GQGTLVTVSA  120
AKTTAPSVYP LAPVCGDTTG SSVTLGCLVK GYFPEPVTLT WNSGSLSSGV HTFPAVLQSD  180
LYTLSSSVTV TSSTWPSQSI TCNVAHPASS TKVDKKIEPR GPTIKPCPPC KCPAPNLLGG  240
PSVFIFPPKI KDVLMISLSP IVTCVVVDVS EDDPDVQISW FVNNVEVHTA QTQTHREDYN  300
STLRVVSALP IQHQDWMSGK EFKCKVNNKD LPAPIERTIS KPKGSVRAPQ VYVLPPPEEE  360
MTKKQVTLTC MVTDFMPEDI YVEWTNNGKT ELNYKNTEPV LDSDGSYFMY SKLRVEKKNW  420
VERNSYSCSV VHEGLHNHHT TKSFSRTPGK                                 450

SEQ ID NO: 100         moltype = AA  length = 449
FEATURE                Location/Qualifiers
source                 1..449
                       mol_type = protein
                       note = Full-length heavy chain amino acid sequences;
                        huCD37-51 antibody
                       organism = synthetic construct
SEQUENCE: 100
EVQLVESGPE VLKPGESLSL TCTVSGYSIS SGFAWHWIRQ FPGKGLEWMG YIHYSGSTNY  60
SPSLQGRISI TRDSSINQFF LQLNSVTASD TATYYCARGY YGFGAWFVYW GQGTLVTVSA  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449

SEQ ID NO: 101         moltype = AA  length = 444
FEATURE                Location/Qualifiers
source                 1..444
                       mol_type = protein
                       note = Full-length heavy chain amino acid sequences;
                        muCD37-56 antibody
                       organism = synthetic construct
SEQUENCE: 101
DVQLQESGPD LVKPSQSLSL TCTVTGYSIT SGFAWHWIRQ FPGNKLEWMG YIHYSGGTNY  60
NPSLKSRVSI TRDTSKNQFF LQLNSVTTED TATYYCARGY YGFGAWFAYW GQGTLVPVSA  120
AKTTPPSVYP LAPGSAAQTN SMVTLGCLVK GYFPEPVTVT WNSGSLSSGV HTFPAVLESD  180
LYTLSSSVTV PSSMRPSETV TCNVAHPASS TKVDKKIVPR DCGCKPCICT VPEVSSVFIF  240
PPKPKDVLTI TLTPKVTCVV VDISKDDPEV QFSWFVDDVE VHTAQTQPRE EQFNSTFRSV  300
SELPIMHQDW LNGKEFKCRV NSAAFPAPIE KTISKTKGRP KAPQVYTIPP PKEQMAKDKV  360
SLTCMITDFF PEDITVEWQW NGQPAENYKN TQPIMNTNGS YFVYSKLNVQ KSNWEAGNTF  420
TCSVLHEGLH NHHTEKSLSH SPGK                                       444

SEQ ID NO: 102         moltype = AA  length = 449
FEATURE                Location/Qualifiers
source                 1..449
                       mol_type = protein
                       note = Full-length heavy chain amino acid sequences;
                        huCD37-56 antibody
                       organism = synthetic construct
SEQUENCE: 102
QVQLQESGPG LVKPSQSLSL TCTVSGYSIT SGFAWHWIRQ FPGKGLEWMG YIHYSGGTNY  60
```

-continued

```
NPSLKSRVSI TRDTSKNQFF LQLNSVTAAD TATYYCARGY YGFGAWFAYW GQGTLVPVSA  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 103          moltype = AA  length = 450
FEATURE                 Location/Qualifiers
source                  1..450
                        mol_type = protein
                        note = Full-length heavy chain amino acid sequences;
                         muCD37-57 antibody
                        organism = synthetic construct
SEQUENCE: 103
DVQLQESGPD LLKPSQSLSL TCTVTGYSIT SGFAWHWIRQ FPGNKLEWMG YILYSGSTVY  60
SPSLKSRISI TRDTSKNQFF LQLNSVTTED TATYYCARGY YGYGAWFAYW GQGTLVTVSA  120
AKTTAPSVYP LAPVCGDTTG SSVTLGCLVK GYFPEPVTLT WNSGSLSSGV HTFPAVLQSD  180
LYTLSSSVTV TSSTWPSQSI TCNVAHPASS TKVDKKIEPR GPTIKPCPPC KCPAPNLLGG  240
PSVFIFPPKI KDVLMISLSP IVTCVVVDVS EDDPDVQISW FVNNVEVHTA QTQTHREDYN  300
STLRVVSALP IQHQDWMSGK EFKCKVNNKD LPAPIERTIS KPKGSVRAPQ VYVLPPPEEE  360
MTKKQVTLTC MVTDFMPEDI YVEWTNNGKT ELNYKNTEPV LDSDGSYFMY SKLRVEKKNW  420
VERNSYSCSV VHEGLHNHHT TKSFSRTPGK                                  450

SEQ ID NO: 104          moltype = AA  length = 449
FEATURE                 Location/Qualifiers
source                  1..449
                        mol_type = protein
                        note = Full-length heavy chain amino acid sequences;
                         huCD37-57 antibody
                        organism = synthetic construct
SEQUENCE: 104
QVQLQESGPG LLKPSQSLSL TCTVSGYSIT SGFAWHWIRQ FPGKGLEWMG YILYSGSTVY  60
SPSLKSRISI TRDTSKNQFF LQLNSVTAAD TATYYCARGY YGYGAWFAYW GQGTLVTVSA  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 105          moltype = AA  length = 214
FEATURE                 Location/Qualifiers
source                  1..214
                        mol_type = protein
                        note = Full-length light chain amino acid sequences;
                         muCD37-3 antibody
                        organism = synthetic construct
SEQUENCE: 105
DIQMTQSPAS LSVSVGETVT ITCRASENIR SNLAWYQQKQ GKSPQLLVNV ATNLADGVPS  60
RFSGSGSGTQ YSLKINSLQS EDFGTYYCQH YWGTTWTFGG GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 106          moltype = AA  length = 214
FEATURE                 Location/Qualifiers
source                  1..214
                        mol_type = protein
                        note = Full-length light chain amino acid sequences;
                         chCD37-3 antibody
                        organism = synthetic construct
SEQUENCE: 106
DIQMTQSPAS LSVSVGETVT ITCRASENIR SNLAWYQQKQ GKSPQLLVNV ATNLADGVPS  60
RFSGSGSGTQ YSLKINSLQS EDFGTYYCQH YWGTTWTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 107          moltype = AA  length = 214
FEATURE                 Location/Qualifiers
source                  1..214
                        mol_type = protein
                        note = Full-length light chain amino acid sequences;
                         huCD37-3v1.0 and huCD37-3v1.1 antibody
                        organism = synthetic construct
SEQUENCE: 107
DIQMTQSPSS LSVSVGERVT ITCRASENIR SNLAWYQQKP GKSPKLLVNV ATNLADGVPS  60
RFSGSGSGTD YSLKINSLQP EDFGTYYCQH YWGTTWTFGQ GTKLEIKRTV AAPSVFIFPP  120
SDEQLKSGTA SVVCLLNNFY PREAKVQWKV DNALQSGNSQ ESVTEQDSKD STYSLSSTLT  180
```

```
LSKADYEKHK VYACEVTHQG LSSPVTKSFN RGEC                              214

SEQ ID NO: 108         moltype = AA  length = 218
FEATURE                Location/Qualifiers
source                 1..218
                       mol_type = protein
                       note = Full-length light chain amino acid sequences;
                        muCD37-12 antibody
                       organism = synthetic construct
SEQUENCE: 108
DIVLTQSPAS LAVSLGQRAT ISCRASQSVS TSSYSYLYWF QQKPGQPPKL LIKYASNLAS  60
GVPARFSGSG SGTDFTLNIH PVEEEDTATY YCQHSWEIPY TFGGGTKLEI KRADAAPTVS  120
IFPPSSEQLT SGGASVVCFL NNFYPKDINV KWKIDGSERQ NGVLNSWTDQ DSKDSTYSMS  180
STLTLTKDEY ERHNSYTCEA THKTSTSPIV KSFNRNEC                          218

SEQ ID NO: 109         moltype = AA  length = 218
FEATURE                Location/Qualifiers
source                 1..218
                       mol_type = protein
                       note = Full-length light chain amino acid sequences;
                        chCD37-12 antibody
                       organism = synthetic construct
SEQUENCE: 109
DIVLTQSPAS LAVSLGQRAT ISCRASQSVS TSSYSYLYWF QQKPGQPPKL LIKYASNLAS  60
GVPARFSGSG SGTDFTLNIH PVEEEDTATY YCQHSWEIPY TFGGGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 110         moltype = AA  length = 213
FEATURE                Location/Qualifiers
source                 1..213
                       mol_type = protein
                       note = Full-length light chain amino acid sequences;
                        muCD37-38 antibody
                       organism = synthetic construct
SEQUENCE: 110
QIVLTQSPAI MSASPGEKVT MTCSASSSVT YMHWYQQKSG TSPKRWIYDT SKLASGVPAR  60
FSGGGSGTSY SLTISSMEAE DAATYYCQQW ISNPPTFGGG TKLEIKRADA APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                               213

SEQ ID NO: 111         moltype = AA  length = 213
FEATURE                Location/Qualifiers
source                 1..213
                       mol_type = protein
                       note = Full-length light chain amino acid sequences;
                        chCD37-38 antibody
                       organism = synthetic construct
SEQUENCE: 111
QIVLTQSPAI MSASPGEKVT MTCSASSSVT YMHWYQQKSG TSPKRWIYDT SKLASGVPAR  60
FSGGGSGTSY SLTISSMEAE DAATYYCQQW ISNPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 112         moltype = AA  length = 213
FEATURE                Location/Qualifiers
source                 1..213
                       mol_type = protein
                       note = Full-length light chain amino acid sequences;
                        huCD37-38 antibody
                       organism = synthetic construct
SEQUENCE: 112
DIVLTQSPAS MSASPGERVT MTCSASSSVT YMHWYQQKPG TSPKRWIYDT SKLASGVPAR  60
FSGSGSGTSY SLTISSMEAE DAATYYCQQW ISNPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 113         moltype = AA  length = 213
FEATURE                Location/Qualifiers
source                 1..213
                       mol_type = protein
                       note = Full-length light chain amino acid sequences;
                        muCD37-50 antibody
                       organism = synthetic construct
SEQUENCE: 113
QIVLTQSPAI MSASPGEKVT MTCSATSSVT YMHWYQQKSG TSPKRWIYDT SKLPYGVPGR  60
FSGSGSGTSY SLTISSMEAE DAATYYCQQW SDNPPTFGSG TKLEIKRADA APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                               213
```

-continued

```
SEQ ID NO: 114          moltype = AA  length = 213
FEATURE                 Location/Qualifiers
source                  1..213
                        mol_type = protein
                        note = Full-length light chain amino acid sequences;
                         huCD37-50 antibody
                        organism = synthetic construct
SEQUENCE: 114
EIVLTQSPAT MSASPGERVT MTCSATSSVT YMHWYQQKPG QSPKRWIYDT SNLPYGVPAR  60
FSGSGSGTSY SLTISSMEAE DAATYYCQQW SDNPPTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 115          moltype = AA  length = 213
FEATURE                 Location/Qualifiers
source                  1..213
                        mol_type = protein
                        note = Full-length light chain amino acid sequences;
                         muCD37-51 antibody
                        organism = synthetic construct
SEQUENCE: 115
QIVLTQSPAI MSASPGEKVT MTCSATSSVT YMHWYQQKSG TSPKRWIYDT SKLASGVPAR  60
FSGSGSGTSY SLTISNMEAE DAATYYCQQW SSNPPTFGSG TKLEIKRADA APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                              213

SEQ ID NO: 116          moltype = AA  length = 213
FEATURE                 Location/Qualifiers
source                  1..213
                        mol_type = protein
                        note = Full-length light chain amino acid sequences;
                         huCD37-51 antibody
                        organism = synthetic construct
SEQUENCE: 116
EIVLTQSPAT MSASPGERVT MTCSATSSVT YMHWYQQKPG QSPKRWIYDT SKLASGVPAR  60
FSGSGSGTSY SLTISSMEAE DAATYYCQQW SSNPPTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 117          moltype = AA  length = 213
FEATURE                 Location/Qualifiers
source                  1..213
                        mol_type = protein
                        note = Full-length light chain amino acid sequences;
                         muCD37-56 antibody
                        organism = synthetic construct
SEQUENCE: 117
QIVLTQSPAF MSASPGDKVT MTCSASSSVT YMHWYQQKSG TSPKRWIYDT SKLASGVPAR  60
FSGGGSGTSY SLTISTMEAE DAATYYCQQW ISDPPTFGGG TKLEIKRADA APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                              213

SEQ ID NO: 118          moltype = AA  length = 213
FEATURE                 Location/Qualifiers
source                  1..213
                        mol_type = protein
                        note = Full-length light chain amino acid sequences;
                         huCD37-56 antibody
                        organism = synthetic construct
SEQUENCE: 118
DIVLTQSPAF MSASPGEKVT MTCSASSSVT YMHWYQQKPD QSPKRWIYDT SNLASGVPSR  60
FSGGGSGTDY SLTISSMEAE DAATYYCQQW ISDPPTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 119          moltype = AA  length = 213
FEATURE                 Location/Qualifiers
source                  1..213
                        mol_type = protein
                        note = Full-length light chain amino acid sequences;
                         muCD37-57 antibody
                        organism = synthetic construct
SEQUENCE: 119
QIVLTQSPAI MSASPGEKVT MTCSATSSVT YMHWYQQKSG TSPKRWIYDT SKLASGVPAR  60
FSGSGSGTSY SLTISSMEAE DAATYYCQQW SDNPPTFGSG TKLEIKRADA APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                              213
```

-continued

```
SEQ ID NO: 120         moltype = AA  length = 213
FEATURE                Location/Qualifiers
source                 1..213
                       mol_type = protein
                       note = Full-length light chain amino acid sequences;
                        huCD37-57 antibody
                       organism = synthetic construct
SEQUENCE: 120
EIVLTQSPAT MSASPGERVT MTCSATSSVT YMHWYQQKPG QSPRRWIYDT SNLASGVPAR  60
FSGSGSGTSY SLTISSMEAE DAATYYCQQW SDNPPTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                             213

SEQ ID NO: 121         moltype = DNA  length = 345
FEATURE                Location/Qualifiers
source                 1..345
                       mol_type = other DNA
                       note = Variable heavy chain polynucleotide sequences;
                        muCD37-3 antibody
                       organism = synthetic construct
SEQUENCE: 121
caggtgcagg tgaaggagtc aggacctggc ctggtggcgc cctcacagag cctgtccatt  60
acatgcactg tctcagggtt ctcattaacc acctctggtg taagctgggt tcgccagcct  120
ccaggaaagg gtctggagtg gctgggagta atatggggtg acgggagcac aaactatcat  180
tcagctctca aatccagact gagcatcaag aaggatcact ccaagagcca agttttctta  240
aaactgaaca gtctgcaaac tgatgacaca gccacgtact actgtgccaa aggaggctac  300
tcgttggctc actggggcca agggactctg gtcacagtct ctgca                 345

SEQ ID NO: 122         moltype = DNA  length = 431
FEATURE                Location/Qualifiers
source                 1..431
                       mol_type = other DNA
                       note = Variable heavy chain polynucleotide sequences;
                        chCD37-3 antibody
                       organism = synthetic construct
SEQUENCE: 122
aagcttgcca ccatggctgt cctggcactg ctcctctgcc tggtgacata cccaagctgt  60
gtcctatcac aggtgcaggt gaaggagtca ggacctggcc tggtggcgcc ctcacagagc  120
ctgtccatta catgcactgt ctcagggttc tcattaacca cctctggtgt aagctgggtt  180
cgccagcctc caggaaaggg tctggagtgg ctgggagtaa tatggggtga cgggagcaca  240
aactatcatt cagctctcaa atccagactg agcatcaaga aggatcactc caagagccaa  300
gttttcttaa aactgaacag tctgcaaact gatgacacag ccacgtacta ctgtgccaaa  360
ggaggctact cgttggctca ctggggccaa gggactctgg tcacagtctc tgcagcctct  420
acgaagggcc c                                                     431

SEQ ID NO: 123         moltype = DNA  length = 431
FEATURE                Location/Qualifiers
source                 1..431
                       mol_type = other DNA
                       note = Variable heavy chain polynucleotide sequences;
                        huCD37-3v1.0 antibody
                       organism = synthetic construct
SEQUENCE: 123
aagcttgcca ccatgggttg gagctgcatt attctgtttc tggtggccac cgccaccggt  60
gtgcactcac aagtccaagt ccaagaatct ggtccaggtc tggtggcccc ttcccaaact  120
ctgagcatca cctgtaccgt ttctggtttt agccttacca cctctggtgt gagttgggta  180
cgccaaccac ccggtaaggg tctcgaatgg ctgggtgtaa tctggggtga tggttccaca  240
aattaccatc cttccctcaa gtcccgcctt agcatcaaaa aggatcacag caaaagtcaa  300
gttttcctga aactgaatag tctgacagca gccgatacag ccacctacta ttgcgccaag  360
ggtggttata gtcttgcaca ctggggtcaa ggtaccctcg ttaccgtctc ctcagctagt  420
accaagggcc c                                                     431

SEQ ID NO: 124         moltype = DNA  length = 431
FEATURE                Location/Qualifiers
source                 1..431
                       mol_type = other DNA
                       note = Variable heavy chain polynucleotide sequences;
                        huCD37-3v1.1 antibody
                       organism = synthetic construct
SEQUENCE: 124
aagcttgcca ccatgggctg gagctgtatc attctgtttc tggtggcgac agctactggg  60
gtccactccc aagtgcaggt acaagagtcc gggcctggat tggtcgcacc aagccagacc  120
ctctctatca cttgtaccgt tagcgggttc tctctgacaa ccagtggagt gagttgggtg  180
aggcagccac caggaaaggg actggagtgg ctgggggtga tttggggcga cggcagcaca  240
aactatcatt ccagtcttaa atctcggttg tccattaaaa aagaccatag taaatctcaa  300
gttttcctga aactcaatag cctgacagcc gcagacactg ctacgtatta ctgcgccaaa  360
ggaggataca gtctggctca ctggggacag gggaccctgg tgaccgtgtc atccgcatca  420
acaaagggcc c                                                     431
```

```
SEQ ID NO: 125          moltype = DNA  length = 345
FEATURE                 Location/Qualifiers
source                  1..345
                        mol_type = other DNA
                        note = Variable heavy chain polynucleotide sequences;
                         muCD37-12 antibody
                        organism = synthetic construct
SEQUENCE: 125
cagatccagt tggtgcagtc tggacctgag ctgaagaagc ctggagagac agtcaagatc  60
tcctgcaagg cttctgggta taccttcaca aagtatggaa tgaactgggt gaagcaggct  120
caaggaaagg gtttaaagtg gatgggctgg ataaacacca acactggaga gtcaagaaat  180
gctgaagaat tcaagggacg gtttgccttc tctttggaaa cctctgccag cactgcctat  240
ttgcagatca acaacctcaa atatgaggac acggctacat atttctgtgg aaggggcacg  300
gtagtagcgg actggggcca aggcaccact ctcacagtct cctca                 345

SEQ ID NO: 126          moltype = DNA  length = 431
FEATURE                 Location/Qualifiers
source                  1..431
                        mol_type = other DNA
                        note = Variable heavy chain polynucleotide sequences;
                         chCD37-12 antibody
                        organism = synthetic construct
SEQUENCE: 126
aagcttgcca ccatggggtg gtcatgcata atcctctttc tggtcgctac tgctaccggt  60
gtgcactcac agattcagct ggttcaaagt ggcccagagc tgaaaaagcc aggggaaaca  120
gtgaaaataa gttgcaaggc atccggttac actttcacaa agtacggcat gaactgggtc  180
aagcaggccc agggcaaggg gctcaaatgg atgggttgga tcaataccaa cactggcgag  240
tctaggaatg ctgaggagtt taagggccgg tttgccttca gcctggagac aagtgccagc  300
acagcttacc tgcaaatcaa caatctgaag tatgaggata cagcaaccta tttctgcggc  360
cgcggcactg tcgttgcaga ctggggacaa ggtaccacct tgactgtatc cagtgccagc  420
actaagggcc c                                                      431

SEQ ID NO: 127          moltype = DNA  length = 360
FEATURE                 Location/Qualifiers
source                  1..360
                        mol_type = other DNA
                        note = Variable heavy chain polynucleotide sequences;
                         muCD37-38 antibody
                        organism = synthetic construct
SEQUENCE: 127
gatgtgcagc ttcaggagtc aggacctgac ctggtgaaac cttctcagtc actttcactc  60
acctgcactg tcactggcta ctccatcacc agtggttttg gctggcactg gatccggcag  120
tttccaggaa acaagctgga atggatggcc tacatactct acagtggtgg cactgactac  180
aacccatctc tcaaaagtcg aatctctatc actcgagaca cttccaagaa ccagttcttc  240
ctgcggttga gttctgtgac tactgaggac acagccacat attactgtgc aagaggctac  300
tatggttacg gggcctggtt tgtttactgg ggccaaggga ctctggtcac tgtctctgca  360

SEQ ID NO: 128          moltype = DNA  length = 446
FEATURE                 Location/Qualifiers
source                  1..446
                        mol_type = other DNA
                        note = Variable heavy chain polynucleotide sequences;
                         chCD37-38 antibody
                        organism = synthetic construct
SEQUENCE: 128
aagcttgcca ccatgggctg gagttgtatc attctgtttt tggtggccac cgccactgga  60
gtccattccc aagtgcaact ccaggaatct ggccctgacc tggttaagcc atctcagagc  120
ctctccctga cctgcactgt tacaggatac tcaatcacat caggctttgg ctggcactgg  180
atcagacaat ttcccgggaa caagttggaa tggatggctt acattctgta tagcgggggt  240
accgattaca atccttccct caagagccga atctctatca ccagggatac aagcaagaac  300
caatttttc tccgcctcag ctctgtgact accgaagata ccgctactta ctattgtgcc  360
aggggctact atggatatgg tgcatggttc gtctattggg gccagggaac cctggtgact  420
gtgagcgctg cctctaccaa gggccc                                      446

SEQ ID NO: 129          moltype = DNA  length = 446
FEATURE                 Location/Qualifiers
source                  1..446
                        mol_type = other DNA
                        note = Variable heavy chain polynucleotide sequences;
                         huCD37-38 antibody
                        organism = synthetic construct
SEQUENCE: 129
aagcttgcca ccatgggttg gagctgcatc attcttttcc tggtcgctac tgcaactgga  60
gtccactcac aggtccagct gcaagagtcc ggtcctgggc ttgtgaaacc cagccagtcc  120
ctcagtctca cctgtactgt ctctggctac tctattacca gtgggttcgg ctggcattgg  180
attaggcagt ttcccggtaa ggggctggag tggatggcat atatcctgta cagcggagga  240
accgattaca acccaagtct gaagagcagg atcagcatta cccgggacac aagcaaaaac  300
cagtttttcc ttcggctgtc tagtgttaca gctgcagaca ccgctactta ctattgtgct  360
cggggttact atggctatgg ggcttggttt gtgtattggg gacaaggcac tcttgtgacc  420
```

```
gtgagcagcg cctcaacaaa gggccc                                       446

SEQ ID NO: 130         moltype = DNA  length = 360
FEATURE                Location/Qualifiers
source                 1..360
                       mol_type = other DNA
                       note = Variable heavy chain polynucleotide sequences;
                        muCD37-50 antibody
                       organism = synthetic construct
SEQUENCE: 130
gatgtgcagc ttcaggagtc aggacctgac ctgttgaaac cttctcagtc actttcactc  60
acctgcactg tcactggcta ctccatcacc agtggttttg cctggcactg gatccggcag  120
tttccaggaa acaaactgga atggatgggc tacatactct acagtggtag cactgtctac  180
agcccatctc tcaaaagtcg aatctctatc actcgagaca catccaagaa ccacttcttc  240
ctgcagttga attctgtgac tactgaggac acagccacat attactgtgc aagagggtac  300
tatggttacg gcgcctggtt tgcttactgg ggccaaggga ctctggtcac tgtctctgca  360

SEQ ID NO: 131         moltype = DNA  length = 360
FEATURE                Location/Qualifiers
source                 1..360
                       mol_type = other DNA
                       note = Variable heavy chain polynucleotide sequences;
                        muCD37-51 antibody
                       organism = synthetic construct
SEQUENCE: 131
gatgtgcagc ttcaggagtc aggacctgac ctgttgaaac cttctcagtc actttcactc  60
acctgcactg tcactggcta ctccatctcc agtggttttg cctggcactg gatccggcag  120
tttccaggaa acaaactgga atggatgggc tacatacact acagtggtag cactaactac  180
agcccatctc tcaaaagtcg aatctctatc actcgagact catccaagaa ccagttcttc  240
ctgcagttga attctgtgac tactgaggac acagccacat attactgtgc aagaggatac  300
tatggtttcg gcgcctggtt tgtttactgg ggccaaggga ctctggtcac tgtctctgca  360

SEQ ID NO: 132         moltype = DNA  length = 360
FEATURE                Location/Qualifiers
source                 1..360
                       mol_type = other DNA
                       note = Variable heavy chain polynucleotide sequences;
                        muCD37-56 antibody
                       organism = synthetic construct
SEQUENCE: 132
gatgtgcagc ttcaggagtc aggacctgac ctggtgaaac cttctcagtc actttcactc  60
acctgcactg tcactggcta ctccatcacc agtggttttg cctggcactg gatccggcag  120
tttccaggaa acaaactgga atggatgggc tacatacact acagtggtgg cactaactac  180
aacccatctc tcaaaagtcg agtctctatc actcgagaca catccaagaa ccagttcttc  240
ctgcagttga attctgtgac tactgaggac acagccacat attactgtgc aagaggctac  300
tatggtttcg gggcctggtt tgcttactgg ggccaaggga ctctggtccc tgtctctgca  360

SEQ ID NO: 133         moltype = DNA  length = 446
FEATURE                Location/Qualifiers
source                 1..446
                       mol_type = other DNA
                       note = Variable heavy chain polynucleotide sequences;
                        huCD37-56 antibody
                       organism = synthetic construct
SEQUENCE: 133
aagcttgcca ccatggggtg gagctgcatt atcctgttcc tcgtcgccac cgcaaccggc  60
gtccactccc aggtgcagct gcaagaaagc gggccaggat tggtaaaacc ttcccagtct  120
ctgagtctta cttgtaccgt atctggatac agtatcacat ctggcttcgc ctggcattgg  180
attcgccagt ttcccggcaa ggggcttgag tggatggggt atattcatta ttctggaggt  240
accaactaca acccttccct gaagagtcga gtctcaatta ccagggacac ttccaagaac  300
caattctttt tgcagcttaa ttcagtgacc gctgccgaca ccgctactta ctactgcgcc  360
cggggctact atgggtttgg tgcctggttc gcctactggg gccaggggac cctggtgccc  420
gtgtctgctg cctccacaaa gggccc                                       446

SEQ ID NO: 134         moltype = DNA  length = 360
FEATURE                Location/Qualifiers
source                 1..360
                       mol_type = other DNA
                       note = Variable heavy chain polynucleotide sequences;
                        muCD37-57 antibody
                       organism = synthetic construct
SEQUENCE: 134
gatgtgcagc ttcaggagtc aggacctgac ctgttgaaac cttctcagtc actttcactc  60
acctgcactg tcactggcta ctccatcacc agtggttttg cctggcactg gatccggcag  120
tttccaggaa acaaactgga atggatgggc tacatactct acagtggtag cactgtctac  180
agcccatctc tcaaaagtcg aatctctatc actcgagaca catccaagaa ccagttcttc  240
ctgcagttga attctgtgac tactgaggac acagccacat attactgtgc aagagggtac  300
tatggttacg gcgcctggtt tgcttactgg ggccaaggga ctctggtcac tgtctctgca  360
```

```
SEQ ID NO: 135         moltype = DNA  length = 446
FEATURE                Location/Qualifiers
source                 1..446
                       mol_type = other DNA
                       note = Variable heavy chain polynucleotide sequences;
                        huCD37-57 antibody
                       organism = synthetic construct
SEQUENCE: 135
aagcttgcca ccatgggctg gagctgcatc attctgtttc tggtggccac agcaactggc  60
gttcacagtc aagtccaact gcaggagagc ggccccggac tcctgaaacc atctcagtca  120
ctcagtctga catgtactgt gagcggctac agcattacct caggcttcgc ttggcattgg  180
atcaggcagt tccccggaaa aggtctggag tggatggggt acattctgta cagcggcagt  240
acagtgtatt caccctcctt gaaatctagg atatcaatca cacgtgatac aagcaaaaat  300
cagttcttcc tccagctgaa ctccgtcacc gccgcagaca cagcaaccta ttattgtgct  360
cgcggatact acggatatgg cgcatggttc gcctattggg gccaggggac actcgtgacc  420
gtttccgccg cctccacaaa gggccc                                       446

SEQ ID NO: 136         moltype = DNA  length = 324
FEATURE                Location/Qualifiers
source                 1..324
                       mol_type = other DNA
                       note = Variable light chain polynucleotide sequences;
                        muCD37-3 antibody
                       organism = synthetic construct
SEQUENCE: 136
gacatccaga tgactcagtc tccagcctcc ctttctgtat ctgtgggaga aactgtcacc  60
atcacatgtc gagcaagtga gaatattcgc agtaatttag catggtatca gcagaaacag  120
ggaaaatctc ctcagctcct ggtcaatgtt gcaacaaact tagcagatgg tgtgccatca  180
aggttcagtg gcagtggatc aggcacacag tattccctca agatcaacag cctgcagtct  240
gaagattttg ggacttatta ctgtcaacat tattggggta ctacgtggac gttcggtgga  300
ggcaccaagc tggaaatcaa acgt                                         324

SEQ ID NO: 137         moltype = DNA  length = 399
FEATURE                Location/Qualifiers
source                 1..399
                       mol_type = other DNA
                       note = Variable light chain polynucleotide sequences;
                        chCD37-3 antibody
                       organism = synthetic construct
SEQUENCE: 137
gaattcgcca ccatgagtgt gcccactcag gtcctggggt tgctgctgct gtggcttaca  60
gatgccagat gtgacatcca gatgactcag tctccagcct ccctttctgt atctgtggga  120
gaaactgtca ccatcacatg tcgagcaagt gagaatattc gcagtaattt agcatggtat  180
cagcagaaac agggaaaatc tcctcagctc ctggtcaatg ttgcaacaaa cttagcagat  240
ggtgtgccat caaggttcag tggcagtgga tcaggcacac agtattccct caagatcaac  300
agcctgcagt ctgaagattt tgggacttat tactgtcaac attattgggg tactacgtgg  360
acgttcggtg gaggcaccaa gctggaaatc aaacgtacg                          399

SEQ ID NO: 138         moltype = DNA  length = 396
FEATURE                Location/Qualifiers
source                 1..396
                       mol_type = other DNA
                       note = Variable light chain polynucleotide sequences;
                        huCD37-3v1.0 and huCD37-3v1.1 antibody
                       organism = synthetic construct
SEQUENCE: 138
gaattcgcca ccatgggttg gtcctgcatc atcttgtttc tcgtggccac agccaccggt  60
gttcactctg atatacaaat gactcaaagc ccttccagtt tgagcgtaag tgtgggtgaa  120
cgcgtaacaa tcacctgtag agctagtgaa aacatccgca gtaatctcgc atggtaccaa  180
caaaagccag gtaagtcacc taagctcctc gtgaatgttg ctaccaacct cgctgatggt  240
gtgccttcac gattctctgg ttcaggttcc ggtaccgatt attcacttaa gatcaactca  300
ctccaaccag aagatttcgg tacatattac tgtcaacact actggggtac gacctggaca  360
ttcggtcaag gtactaagct ggaaatcaag cgtacg                             396

SEQ ID NO: 139         moltype = DNA  length = 336
FEATURE                Location/Qualifiers
source                 1..336
                       mol_type = other DNA
                       note = Variable light chain polynucleotide sequences;
                        muCD37-12 antibody
                       organism = synthetic construct
SEQUENCE: 139
gacattgtgc taacacagtc tcctgcttcc ttagctgtat ctctggggca gagggccacc  60
atctcatgca gggccagcca aagtgtcagt acatctagct atagttattt gtactggttc  120
cagcagaaac caggacagcc acccaaactc ctcatcaagt atgcatccaa cctagcatct  180
ggggtccctg ccaggttcag tggcagtggg tctgggacag acttcaccct caacatccat  240
cctgtggagg aggaggatac tgcaacatat tactgtcaac acagttggga gattccgtac  300
acgttcggag gggggaccaa actggaaata aaacgg                             336
```

-continued

```
SEQ ID NO: 140          moltype = DNA  length = 408
FEATURE                 Location/Qualifiers
source                  1..408
                        mol_type = other DNA
                        note = Variable light chain polynucleotide sequences;
                         chCD37-12 antibody
                        organism = synthetic construct
SEQUENCE: 140
gaattcgcca ccatgggttg gtcctgtata atcctgttct tggtggccac cgctactggc  60
gttcatagtg atattgtact cactcagtca ccagccagtc tggcagtgtc cctgggccag  120
cgtgccacca tctcctgccg ggcctcacag tccgtgagca ctagctctta ttcctatctc  180
tactggtttc aacagaagcc aggacagccc cctaagctgc tgatcaagta cgcctccaac  240
ctcgccagcg gcgttcccgc tagattctct ggttccggta gcggaactga tttcactttg  300
aacatccacc ccgttgagga agaggatacc gccacttact attgtcaaca ctcttgggag  360
attccttaca cctttggagg aggaacaaag ctcgaaatta agcgtacg             408

SEQ ID NO: 141          moltype = DNA  length = 321
FEATURE                 Location/Qualifiers
source                  1..321
                        mol_type = other DNA
                        note = Variable light chain polynucleotide sequences;
                         muCD37-38 antibody
                        organism = synthetic construct
SEQUENCE: 141
caaattgttc tcacccagtc tccagcaatc atgtctgcat ctccagggga gaaggtcacc  60
atgacctgca gtgccagctc aagtgtaact tacatgcact ggtaccagca gaagtcaggc  120
acctcccccaa aaagatggat ttatgacaca tccaaactgg cttctggagt ccctgctcgc  180
ttcagtggcg gtgggtctgg gacctcttac tctctcacaa tcagcagcat ggaggctgaa  240
gatgctgcca cttattactg ccagcagtgg attagtaacc cacccacgtt cggaggggggg  300
accaagctgg aaattaaacg g                                          321

SEQ ID NO: 142          moltype = DNA  length = 393
FEATURE                 Location/Qualifiers
source                  1..393
                        mol_type = other DNA
                        note = Variable light chain polynucleotide sequences;
                         chCD37-38 antibody
                        organism = synthetic construct
SEQUENCE: 142
gaattcgcca ccatgggctg gtcctgtatc atcctgtttc tcgtggccac agctacaggt  60
gttcattctc agattgtgct gacccaatca ccagctatta tgtccgctag ccccggcgag  120
aaagtgacaa tgacatgtag cgctagctct tctgtgactt acatgcattg gtatcaacag  180
aagtcaggta ccagtcccaa gcgttggatc tacgacacat ccaaactggc ctccggagtc  240
cctgccaggt tcagcggagg tgggtccggc accagttatt cactgaccat atcctctatg  300
gaagctgaag atgctgctac ttattattgt caacaatgga tttctaaccc ccccaccttt  360
ggtggcggaa caaagctgga gatcaagcgt acg                             393

SEQ ID NO: 143          moltype = DNA  length = 393
FEATURE                 Location/Qualifiers
source                  1..393
                        mol_type = other DNA
                        note = Variable light chain polynucleotide sequences;
                         huCD37-38 antibody
                        organism = synthetic construct
SEQUENCE: 143
gaattcgcca ccatgggatg gtcctgcatt attctgttct tggtcgccac tgctactggc  60
gttcactctg acattgtgct cacacagtct ccagcctcaa tgtctgcttc cccccggtgag  120
cgggtgacca tgacatgctc tgccagttcc tccgtgacat atatgcattg gtatcagcaa  180
aaacccggta cctctccaaa aagatggatc tacgacactt caaagcttgc atcaggcgtt  240
cctgccagat tttccgggtc tgggtctggc acttcataca gtctgaccat tagttccatg  300
gaagctgaag atgcagccac ctattactgt cagcagtgga tttcaaatcc tcctaccttc  360
ggcggcggaa ccaaactgga gataaagcgt acg                             393

SEQ ID NO: 144          moltype = DNA  length = 321
FEATURE                 Location/Qualifiers
source                  1..321
                        mol_type = other DNA
                        note = Variable light chain polynucleotide sequences;
                         muCD37-50 antibody
                        organism = synthetic construct
SEQUENCE: 144
caaattgttc tcacccagtc tccagcaatc atgtctgcat ctccagggga gaaggtcacc  60
atgacctgca gtgccacctc aagtgtgact tacatgcact ggtaccagca gaagtcaggc  120
acctccccca aaagatggat ttatgacaca tccaaactgc cttatggagt ccctggtcgt  180
ttcagtggta gtgggtctgg gacctcttac tctctcacaa tcagcagcat ggaggctgaa  240
gatgctgcca cttattactg ccagcagtgg agtgataacc cacccacgtt cggctcgggg  300
acaaagttgg aaataaagcg g                                          321

SEQ ID NO: 145          moltype = DNA  length = 393
```

```
FEATURE                Location/Qualifiers
source                 1..393
                       mol_type = other DNA
                       note = Variable light chain polynucleotide sequences;
                        huCD37-50 antibody
                       organism = synthetic construct
SEQUENCE: 145
gaattcgcca ccatgggttg gtcatgcatt attctgttcc tggttgctac cgcaacagga  60
gtacatagtg agatagtcct cacccaaagt cctgctacta tgtctgccag cccaggagag  120
cgtgtgacca tgacttgctc tgcaacctca agtgtgacat acatgcattg gtatcagcaa  180
aagcctggcc aatcccctaa aaggtggatc tacgatactt ctaatctgcc atacggtgtg  240
cccgcaaggt tctccgggag tggcagtggc accagttata gtctgaccat cagttcaatg  300
gaagcagagg atgcagcaac ctattattgt cagcagtggt ccgataatcc ccctactttt  360
ggtcagggta caaagctgga gattaagcgt acg                               393

SEQ ID NO: 146         moltype = DNA  length = 321
FEATURE                Location/Qualifiers
source                 1..321
                       mol_type = other DNA
                       note = Variable light chain polynucleotide sequences;
                        muCD37-51 antibody
                       organism = synthetic construct
SEQUENCE: 146
caaattgttc tcacccagtc tccagcaatc atgtctgcat ctccagggga gaaggtcacc  60
atgacctgca gtgccacctc aagtgtgact tacatgcact ggtaccagca gaagtcaggc  120
acctccccca aaagatggat ttatgacaca tccaaactgg cttctggagt ccctgctcgc  180
ttcagtggca gtgggtctgg gacctcttac tctctcacaa tcagcaacat ggaggctgaa  240
gatgctgcca cttattactg ccagcagtgg agtagtaacc cacccacgtt cggctcgggg  300
acaaagttgg aaataaagcg g                                            321

SEQ ID NO: 147         moltype = DNA  length = 393
FEATURE                Location/Qualifiers
source                 1..393
                       mol_type = other DNA
                       note = Variable light chain polynucleotide sequences;
                        huCD37-51 antibody
                       organism = synthetic construct
SEQUENCE: 147
gaattcgcca ccatgggatg gagctgtatt attctgttcc tggttgctac tgctactggc  60
gtccattccg agatagtcct cacccagagc cccgcaacca tgagtgcctc ccctggggag  120
cgagtgacta tgacttgttc cgccacttct tcagttacct atatgcattg gtatcagcag  180
aaacctggac agtctccaaa gcgttggatt tacgacacct ccaacctggc ttcaggagtt  240
cctgctaggt tcagcggatc tgggtctggc acaagttatt cactcaccat tagttccatg  300
gaggccgaag atgccgctac ttactactgt cagcagtgga gcagcaaccc ccctacattc  360
gggcagggaa ctaagctgga gatcaaacgt acg                               393

SEQ ID NO: 148         moltype = DNA  length = 321
FEATURE                Location/Qualifiers
source                 1..321
                       mol_type = other DNA
                       note = Variable light chain polynucleotide sequences;
                        muCD37-56 antibody
                       organism = synthetic construct
SEQUENCE: 148
caaattgttc tcacccagtc tccagcattc atgtctgcat ctccagggga taaggtcacc  60
atgacctgca gtgccagttc aagtgttact tacatgcact ggtatcagca gaagtcaggc  120
acctccccca aaagatggat ttatgacaca tccaaactgg cttctggagt ccctgctcgc  180
ttcagtggcg gtgggtctgg gacctcttac tctctcacaa tcagcaccat ggaggctgaa  240
gatgctgcca cttattactg ccagcagtgg attagtgacc cacccacgtt cggagggggg  300
accaagctgg aaataaaacg g                                            321

SEQ ID NO: 149         moltype = DNA  length = 393
FEATURE                Location/Qualifiers
source                 1..393
                       mol_type = other DNA
                       note = Variable light chain polynucleotide sequences;
                        huCD37-56 antibody
                       organism = synthetic construct
SEQUENCE: 149
gaattcgcca ccatgggctg gtcctgtatc atcctgtttc tggtggcaac cgctactggg  60
gttcactctg atattgtcct gacacagagt ccagccttca tgagtgcttc tcccggagaa  120
aaggtcacaa tgacttgttc agcttcctcc tccgtcacat acatgcattg gtaccagcag  180
aagcctgacc agagtcctaa gaggtggatc tatgatacaa gcaatctggc ttccggtgtc  240
ccctcccgct tttcaggcgg cggaagcgga actgactata gccttaccat ctcctcaatg  300
gaagccgagg acgctgctac atattactgc cagcaatgga tcagcgaccc tcctactttc  360
ggacagggaa caaaattgga aattaagcgt acg                               393

SEQ ID NO: 150         moltype = DNA  length = 321
FEATURE                Location/Qualifiers
```

```
source                 1..321
                       mol_type = other DNA
                       note = Variable light chain polynucleotide sequences;
                        muCD37-57 antibody
                       organism = synthetic construct
SEQUENCE: 150
caaattgttc tcacccagtc tccagcaatc atgtctgcat ctccagggga gaaggtcacc  60
atgacctgca gtgccacctc aagtgtgact tacatgcact ggtaccagca gaagtcaggc  120
acctccccca aaagatggat ttatgacaca tccaaactgg cttctggagt ccctgctcgc  180
ttcagtggca gtgggtctgg gacctcttac tctctcacaa tcagcagcat ggaggctgaa  240
gatgctgcca cttattactg ccagcagtgg agtgataacc cacccacgtt cggctcgggg  300
acaaagttgg aaataaagcg g                                           321

SEQ ID NO: 151         moltype = DNA  length = 393
FEATURE                Location/Qualifiers
source                 1..393
                       mol_type = other DNA
                       note = Variable light chain polynucleotide sequences;
                        huCD37-57 antibody
                       organism = synthetic construct
SEQUENCE: 151
gaattcgcca ccatggggtg gtcctgtatt atcctgttcc tggtcgcaac cgccacaggc  60
gttcactccg agatcgtgtt gactcagagc ccagccacca tgtccgcttc ccccggggag  120
agagtgacaa tgacttgttc cgccacaagt tctgtaacct acatgcattg gtaccagcaa  180
aaaccaggac agagtccccg tcgttggatt tatgatacct ctaacctggc ttcaggcgtt  240
cctgcccgct ttctggtag tggatctggg acttcctata gccttaccat aagctctatg  300
gaagccgagg acgccgctac atactactgc cagcagtgga gtgataaccc ccccaccttc  360
gggcagggaa ccaaattgga gatcaaacgt acg                              393

SEQ ID NO: 152         moltype = DNA  length = 1410
FEATURE                Location/Qualifiers
source                 1..1410
                       mol_type = other DNA
                       note = Full-length heavy chain polynucleotide sequences;
                        chCD37-3 antibody
                       organism = synthetic construct
SEQUENCE: 152
aagcttgcca ccatggctgt cctggcactg ctcctctgcc tggtgacata cccaagctgt  60
gtcctatcac aggtgcaggt gaaggagtca ggacctggcc tggtggcgcc ctcacagagc  120
ctgtccatta catgcactgt ctcagggttc tcattaacca cctctggtgt aagctgggtt  180
cgccagcctc caggaaaggg tctggagtgg ctgggagtaa tatggggtga cgggagcaca  240
aactatcatt cagctctcaa atccagactg agcatcaaga aggatcactc caagagccaa  300
gttttcttaa aactgaacag tctgcaaact gatgacacag ccacgtacta ctgtgccaaa  360
ggaggctact cgttggctca ctggggccaa gggactctgg tcacagtctc tgcagcctct  420
acgaagggcc catcagtttt ccccttggct ccaagttcta aatccacaag cggtggaaca  480
gctgcactgg gatgcctcgt taaagattat ttccctgagc ctgtgacagt gagctggaat  540
agcggagcat tgacttcagg tgtgcacact tttcccgctg tgttgcagtc ctccggtctg  600
tactcactgt ccagtgtcgt aaccgtccct tctagcagct tgggaaccca gacctacatc  660
tgtaacgtca accataaacc atccaacaca aaggtggata agaaggttga accaaagagc  720
tgtgataaga cacatacatg ccctccttgt cctgcaccag agctcctcgg aggtccatct  780
gtgttcctgt ttccccccaa acccaaggac actcttatga tctctcgtac tccagaggtc  840
acctgtgttg ttgtcgacgt gagccatgaa gatcccgagg ttaaattcaa ctggtacgtg  900
gatggagtcg aggttcacaa tgccaagacc aagcccaggg aggagcaata taattctaca  960
tatcgggtag tgagcgttct gaccgtgctc caccaagatt ggctcaatgg aaaagagtac  1020
aagtgcaagg tgtccaacaa ggctcttccc gctcccattg agaaaactat ctccaaagcc  1080
aaggggcagc cacgggaacc ccaggtgtat acattgcccc catctagaga cgagctgacc  1140
aagaaccagg tgagtctcac ttgtctggtc aaggggtttt acccttctga cattgctgta  1200
gagtgggagt ctaacggaca gccagaaaac aactacaaga caactccccc agtgctggac  1260
agcgacggga gcttcttcct ctactccaag ttgactgtag acaagtctag atggcagcaa  1320
ggaaacgttt tctcctgctc agtaatgcat gaggctctgc acaatcacta tacccagaaa  1380
tcactgtccc ttagcccagg gtgactcgag                                  1410

SEQ ID NO: 153         moltype = DNA  length = 1410
FEATURE                Location/Qualifiers
source                 1..1410
                       mol_type = other DNA
                       note = Full-length heavy chain polynucleotide sequences;
                        huCD37-3v1.0 antibody
                       organism = synthetic construct
SEQUENCE: 153
aagcttgcca ccatgggttg gagctgcatt attctgtttc tggtggccac cgccaccggt  60
gtgcactcac aagtccaagt ccaagaatct ggtccaggtc tggtggcccc ttcccaaact  120
ctgagcatca cctgtaccgt ttctggtttt agccttacca cctctggtgt gagttgggta  180
cgccaaccac ccggtaaggg tctcgaatgg ctgggtgtaa tctggggtga tggttccaca  240
aattaccatc cttccctcaa gtcccgcctt agcatcaaaa aggatcacag caaaagtcaa  300
gttttcctga aactgaatag tctgacagca gccgatacag ccacctacta ttgcgccaag  360
ggtggttata gtcttgcaca ctggggtcaa ggtaccctcg ttaccgtctc ctcagctagt  420
accaagggcc catcagtttt ccccttggct ccaagttcta aatccacaag cggtggaaca  480
gctgcactgg gatgcctcgt taaagattat ttccctgagc ctgtgacagt gagctggaat  540
```

-continued

```
agcggagcat tgacttcagg tgtgcacact tttcccgctg tgttgcagtc ctccggtctg  600
tactcactgt ccagtgtcgt aaccgtccct tctagcagct tgggaaccca gacctacatc  660
tgtaacgtca accataaacc atccaacaca aaggtggata agaaggttga accaaagagc  720
tgtgataaga cacatacatg ccctccttgt cctgcaccag agctcctcgg aggtccatct  780
gtgttcctgt ttcccccaa acccaaggac actcttatga tctctcgtac tccagaggtc  840
acctgtgttg ttgtcgacgt gagccatgaa gatcccgagg ttaaattcaa ctggtacgtg  900
gatggagtcg aggttcacaa tgccaagacc aagcccaggg aggagcaata taattctaca  960
tatcgggtag tgagcgttct gaccgtgctc caccaagatt ggctcaatgg aaaagagtac  1020
aagtgcaagg tgtccaacaa ggctcttccc gctcccattg agaaaactat ctccaaagcc  1080
aaggggcagc cacgggaacc ccaggtgtat acattgcccc catctagaga cgagctgacc  1140
aagaaccagg tgagtctcac ttgtctggtc aaggggtttt acccttctga cattgctgta  1200
gagtgggagt ctaacggaca gccagaaaac aactacaaga caactccccc agtgctggac  1260
agcgacggga gcttcttcct ctactccaag ttgactgtag acaagtctag atggcagcaa  1320
ggaaacgttt tctcctgctc agtaatgcat gaggctctgc acaatcacta tacccagaaa  1380
tcactgtccc ttagcccagg gtgactcgag                                  1410
```

```
SEQ ID NO: 154         moltype = DNA  length = 1410
FEATURE                Location/Qualifiers
source                 1..1410
                       mol_type = other DNA
                       note = Full-length heavy chain polynucleotide sequences;
                        huCD37-3v1.1 antibody
                       organism = synthetic construct
SEQUENCE: 154
aagcttgcca ccatgggctg gagctgtatc attctgtttc tggtggcgac agctactggg  60
gtccactccc aagtgcaggt acaagagtcc gggcctggat tggtcgcacc aagccagacc  120
ctctctatca cttgtaccgt tagcgggttc tctctgacaa ccagtggagt gagttgggtg  180
aggcagccac caggaaaggg actggagtgg ctgggggtga tttggggcga cggcagcaca  240
aactatcatt ccagtcttaa atctcggttg tccattaaaa aagaccatag taaatctcaa  300
gttttcctga aactcaatag cctgacagcc gcagacactg ctacgtatta ctgcgccaaa  360
ggaggataca gtctggctca ctggggacag gggaccctgg tgaccgtgtc atccgcatca  420
acaaagggcc catcagtttt ccccttggct ccaagttcta aatccacaag cggtggaaca  480
gctgcactgg gatgcctcgt taaagattat ttccctgagc ctgtgacagt gagctggaat  540
agcggagcat tgacttcagg tgtgcacact tttcccgctg tgttgcagtc ctccggtctg  600
tactcactgt ccagtgtcgt aaccgtccct tctagcagct tgggaaccca gacctacatc  660
tgtaacgtca accataaacc atccaacaca aaggtggata agaaggttga accaaagagc  720
tgtgataaga cacatacatg ccctccttgt cctgcaccag agctcctcgg aggtccatct  780
gtgttcctgt ttcccccaa acccaaggac actcttatga tctctcgtac tccagaggtc  840
acctgtgttg ttgtcgacgt gagccatgaa gatcccgagg ttaaattcaa ctggtacgtg  900
gatggagtcg aggttcacaa tgccaagacc aagcccaggg aggagcaata taattctaca  960
tatcgggtag tgagcgttct gaccgtgctc caccaagatt ggctcaatgg aaaagagtac  1020
aagtgcaagg tgtccaacaa ggctcttccc gctcccattg agaaaactat ctccaaagcc  1080
aaggggcagc cacgggaacc ccaggtgtat acattgcccc catctagaga cgagctgacc  1140
aagaaccagg tgagtctcac ttgtctggtc aaggggtttt acccttctga cattgctgta  1200
gagtgggagt ctaacggaca gccagaaaac aactacaaga caactccccc agtgctggac  1260
agcgacggga gcttcttcct ctactccaag ttgactgtag acaagtctag atggcagcaa  1320
ggaaacgttt tctcctgctc agtaatgcat gaggctctgc acaatcacta tacccagaaa  1380
tcactgtccc ttagcccagg gtgactcgag                                  1410
```

```
SEQ ID NO: 155         moltype = DNA  length = 1410
FEATURE                Location/Qualifiers
source                 1..1410
                       mol_type = other DNA
                       note = Full-length heavy chain polynucleotide sequences;
                        chCD37-12 antibody
                       organism = synthetic construct
SEQUENCE: 155
aagcttgcca ccatggggtg gtcatgcata atcctctttc tggtcgctac tgctaccggt  60
gtgcactcac agattcagct ggttcaaagt ggcccagagc tgaaaaagcc aggggaaaca  120
gtgaaaataa gttgcaaggc atccggttac actttcacaa agtacggcat gaactgggtc  180
aagcaggccc agggcaaggg gctcaaatgg atgggttgga tcaataccaa cactggcgag  240
tctaggaatg ctgaggagtt taagggccgg tttgccttca gcctggagac aagtgccagc  300
acagcttacc tgcaaatcaa caatctgaag tatgaggata cagcaaccta tttctgcggc  360
cgcggcactg tcgttgcaga ctggggacaa ggtaccacct tgactgtatc cagtgccagc  420
actaagggcc catcagtttt ccccttggct ccaagttcta aatccacaag cggtggaaca  480
gctgcactgg gatgcctcgt taaagattat ttccctgagc ctgtgacagt gagctggaat  540
agcggagcat tgacttcagg tgtgcacact tttcccgctg tgttgcagtc ctccggtctg  600
tactcactgt ccagtgtcgt aaccgtccct tctagcagct tgggaaccca gacctacatc  660
tgtaacgtca accataaacc atccaacaca aaggtggata agaaggttga accaaagagc  720
tgtgataaga cacatacatg ccctccttgt cctgcaccag agctcctcgg aggtccatct  780
gtgttcctgt ttcccccaa acccaaggac actcttatga tctctcgtac tccagaggtc  840
acctgtgttg ttgtcgacgt gagccatgaa gatcccgagg ttaaattcaa ctggtacgtg  900
gatggagtcg aggttcacaa tgccaagacc aagcccaggg aggagcaata taattctaca  960
tatcgggtag tgagcgttct gaccgtgctc caccaagatt ggctcaatgg aaaagagtac  1020
aagtgcaagg tgtccaacaa ggctcttccc gctcccattg agaaaactat ctccaaagcc  1080
aaggggcagc cacgggaacc ccaggtgtat acattgcccc catctagaga cgagctgacc  1140
aagaaccagg tgagtctcac ttgtctggtc aaggggtttt acccttctga cattgctgta  1200
gagtgggagt ctaacggaca gccagaaaac aactacaaga caactccccc agtgctggac  1260
agcgacggga gcttcttcct ctactccaag ttgactgtag acaagtctag atggcagcaa  1320
```

```
ggaaacgttt tctcctgctc agtaatgcat gaggctctgc acaatcacta tacccagaaa  1380
tcactgtccc ttagcccagg gtgactcgag                                   1410

SEQ ID NO: 156         moltype = DNA  length = 1425
FEATURE                Location/Qualifiers
source                 1..1425
                       mol_type = other DNA
                       note = Full-length heavy chain polynucleotide sequences;
                        chCD37-38 antibody
                       organism = synthetic construct
SEQUENCE: 156
aagcttgcca ccatgggctg gagttgtatc attctgtttt tggtggccac cgccactgga  60
gtccattccc aagtgcaact ccaggaatct ggccctgacc tggttaagcc atctcagagc  120
ctctccctga cctgcactgt tacaggatac tcaatcacat caggctttgg ctggcactgg  180
atcagacaat ttcccgggaa caagttggaa tggatggctt acattctgta tagcgggggt  240
accgattaca atccttccct caagagccga atctctatca ccagggatac aagcaagaac  300
caatttttc tccgcctcag ctctgtgact accgaagata ccgctactta ctattgtgcc  360
aggggctact atggatatgg tgcatggttc gtctattggg gccagggaac cctggtgact  420
gtgagcgctg cctctaccaa gggcccatca gttttcccct tggctccaag ttctaaatcc  480
acaagcggtg gaacagctgc actgggatgc ctcgttaaag attatttccc tgagcctgtg  540
acagtgagct ggaatagcgg agcattgact tcaggtgtgc acacttttcc cgctgtgttg  600
cagtcctccg gtctgtactc actgtccagt gtcgtaaccg tcccttctag cagcttggga  660
acccagacct acatctgtaa cgtcaaccat aaaccatcca acacaaaggt ggataagaag  720
gttgaaccaa agagctgtga taagacacat acatgccctc cttgtcctgc accagagctc  780
ctcggaggtc catctgtgtt cctgtttccc cccaaaccca aggacactct tatgatctct  840
cgtactccag aggtcacctg tgttgttgtc gacgtgagcc atgaagatcc cgaggttaaa  900
ttcaactggt acgtggatgg agtcgaggtt cacaatgcca agaccaagcc cagggaggag  960
caatataatt ctacatatcg ggtagtgagc gttctgaccg tgctccacca agattggctc  1020
aatggaaaag agtacaagtg caaggtgtcc aacaaggctc ttcccgctcc cattgagaaa  1080
actatctcca aagccaaggg gcagccacgg gaaccccagg tgtatacatt gcccccatct  1140
agagacgagc tgaccaagaa ccaggtgagt ctcacttgtc tggtcaaggg gttttaccct  1200
tctgacattg ctgtagagtg ggagtctaac ggacagccag aaaacaacta caagacaact  1260
cccccagtgc tggacagcga cgggagcttc ttcctctact ccaagttgac tgtagacaag  1320
tctagatggc agcaaggaaa cgttttctcc tgctcagtaa tgcatgaggc tctgcacaat  1380
cactataccc agaaatcact gtcccttagc ccagggtgac tcgag                  1425

SEQ ID NO: 157         moltype = DNA  length = 1425
FEATURE                Location/Qualifiers
source                 1..1425
                       mol_type = other DNA
                       note = Full-length heavy chain polynucleotide sequences;
                        huCD37-38 antibody
                       organism = synthetic construct
SEQUENCE: 157
aagcttgcca ccatgggttg gagctgcatc attcttttcc tggtcgctac tgcaactgga  60
gtccactcac aggtccagct gcaagagtcc ggtcctgggc ttgtgaaacc cagccagtcc  120
ctcagtctca cctgtactgt ctctggctac tctattacca gtgggttcgg ctggcattgg  180
attaggcagt ttcccggtaa ggggctggag tggatggcat atatcctgta cagcggagga  240
accgattaca acccaagtct gaagagcagg atcagcatta cccgggacac aagcaaaaac  300
cagtttttcc ttcggctgtc tagtgttaca gctgcagaca ccgctactta ctattgtgct  360
cggggttact atggctatgg ggcttggttt gtgtattggg gacaaggcac tcttgtgacc  420
gtgagcagcg cctcaacaaa gggcccatca gttttcccct tggctccaag ttctaaatcc  480
acaagcggtg gaacagctgc actgggatgc ctcgttaaag attatttccc tgagcctgtg  540
acagtgagct ggaatagcgg agcattgact tcaggtgtgc acacttttcc cgctgtgttg  600
cagtcctccg gtctgtactc actgtccagt gtcgtaaccg tcccttctag cagcttggga  660
acccagacct acatctgtaa cgtcaaccat aaaccatcca acacaaaggt ggataagaag  720
gttgaaccaa agagctgtga taagacacat acatgccctc cttgtcctgc accagagctc  780
ctcggaggtc catctgtgtt cctgtttccc cccaaaccca aggacactct tatgatctct  840
cgtactccag aggtcacctg tgttgttgtc gacgtgagcc atgaagatcc cgaggttaaa  900
ttcaactggt acgtggatgg agtcgaggtt cacaatgcca agaccaagcc cagggaggag  960
caatataatt ctacatatcg ggtagtgagc gttctgaccg tgctccacca agattggctc  1020
aatggaaaag agtacaagtg caaggtgtcc aacaaggctc ttcccgctcc cattgagaaa  1080
actatctcca aagccaaggg gcagccacgg gaaccccagg tgtatacatt gcccccatct  1140
agagacgagc tgaccaagaa ccaggtgagt ctcacttgtc tggtcaaggg gttttaccct  1200
tctgacattg ctgtagagtg ggagtctaac ggacagccag aaaacaacta caagacaact  1260
cccccagtgc tggacagcga cgggagcttc ttcctctact ccaagttgac tgtagacaag  1320
tctagatggc agcaaggaaa cgttttctcc tgctcagtaa tgcatgaggc tctgcacaat  1380
cactataccc agaaatcact gtcccttagc ccagggtgac tcgag                  1425

SEQ ID NO: 158         moltype = DNA  length = 1425
FEATURE                Location/Qualifiers
source                 1..1425
                       mol_type = other DNA
                       note = Full-length heavy chain polynucleotide sequences;
                        huCD37-50 antibody
                       organism = synthetic construct
SEQUENCE: 158
aagcttgcca ccatggggtg gtcctgcata atccttttcc tggttgctac tgctaccgga  60
gtccattcac aggtgcagct gcaggagtcc ggccccggcc tgctcaagcc ttctcagagt  120
```

```
ctgagtctga cttgtactgt ttctggctac agcataacca gcggtttcgc ttggcactgg  180
atcagacagc atcccggcaa caaactggag tggatgggat acatactgta ctcaggctca  240
actgtctatt cccccctccct gaaatcccgg atcagtatta cccgtgacac ttctaagaac  300
catttttttc tgcagctgaa cagcgttacc gcagctgaca ctgcaaccta ctactgtgcc  360
cggggatatt atggatacgg agcttggttc gcttactggg gccaaggcac cctcgtaact  420
gtgagtgctg cttccaccaa gggcccatca gttttcccct tggctccaag ttctaaatcc  480
acaagcggtg gaacagctgc actgggatgc ctcgttaaag attatttccc tgagcctgtg  540
acagtgagct ggaatagcgg agcattgact tcaggtgtgc acacttttcc cgctgtgttg  600
cagtcctccg gtctgtactc actgtccagt gtcgtaaccg tcccttctag cagcttggga  660
acccagacct acatctgtaa cgtcaaccat aaaccatcca acacaaaggt ggataagaag  720
gttgaaccaa agagctgtga taagacacat acatgccctc cttgtcctgc accagagctc  780
ctcggaggtc catctgtgtt cctgtttccc cccaaaccca aggacactct tatgatctct  840
cgtactccag aggtcacctg tgttgttgtc gacgtgagcc atgaagatcc cgaggttaaa  900
ttcaactggt acgtggatgg agtcgaggtt cacaatgcca agaccaagcc cagggaggag  960
caatataatt ctacatatcg ggtagtgagc gttctgaccg tgctccacca agattggctc  1020
aatggaaaag agtacaagtg caaggtgtcc aacaaggctc ttcccgctcc cattgagaaa  1080
actatctcca aagccaaggg gcagccacgg gaaccccagg tgtatacatt gcccccatct  1140
agagacgagc tgaccaagaa ccaggtgagt ctcacttgtc tggtcaaggg gttttaccct  1200
tctgacattg ctgtagagtg ggagtctaac ggacagccag aaaacaacta caagacaact  1260
cccccagtgc tggacagcga cgggagcttc ttcctctact ccaagttgac tgtagacaag  1320
tctagatggc agcaaggaaa cgttttctcc tgctcagtaa tgcatgaggc tctgcacaat  1380
cactataccc agaaatcact gtcccttagc ccagggtgac tcgag                 1425

SEQ ID NO: 159         moltype = DNA  length = 1425
FEATURE                Location/Qualifiers
source                 1..1425
                       mol_type = other DNA
                       note = Full-length heavy chain polynucleotide sequences;
                        huCD37-51 antibody
                       organism = synthetic construct
SEQUENCE: 159
aagcttgcca ccatgggttg gtcttgcatc atcctgttcc tggtggccac tgccactggc  60
gtgcattcag aagttcagtt ggtggagtcc ggcccagaag tgctgaaacc cggcgaatca  120
ctgtccctga cttgtaccgt gtcaggttat agcatcagca gcggctttgc ttggcactgg  180
attcggcagt ttccaggcaa gggactggaa tggatgggct acatccatta cagtggctca  240
accaattaca gccctagcct gcagggccga atctctatta ccagggatag ttctattaac  300
cagtttttcc tgcagcttaa ttccgtgact gcctctgaca cagcaactta ctattgcgcc  360
cgtggctact acgggttcgg agcctggttt gtatactggg gtcagggcac cctggtcact  420
gtctcagccg cctctaccaa gggcccatca gttttcccct tggctccaag ttctaaatcc  480
acaagcggtg gaacagctgc actgggatgc ctcgttaaag attatttccc tgagcctgtg  540
acagtgagct ggaatagcgg agcattgact tcaggtgtgc acacttttcc cgctgtgttg  600
cagtcctccg gtctgtactc actgtccagt gtcgtaaccg tcccttctag cagcttggga  660
acccagacct acatctgtaa cgtcaaccat aaaccatcca acacaaaggt ggataagaag  720
gttgaaccaa agagctgtga taagacacat acatgccctc cttgtcctgc accagagctc  780
ctcggaggtc catctgtgtt cctgtttccc cccaaaccca aggacactct tatgatctct  840
cgtactccag aggtcacctg tgttgttgtc gacgtgagcc atgaagatcc cgaggttaaa  900
ttcaactggt acgtggatgg agtcgaggtt cacaatgcca agaccaagcc cagggaggag  960
caatataatt ctacatatcg ggtagtgagc gttctgaccg tgctccacca agattggctc  1020
aatggaaaag agtacaagtg caaggtgtcc aacaaggctc ttcccgctcc cattgagaaa  1080
actatctcca aagccaaggg gcagccacgg gaaccccagg tgtatacatt gcccccatct  1140
agagacgagc tgaccaagaa ccaggtgagt ctcacttgtc tggtcaaggg gttttaccct  1200
tctgacattg ctgtagagtg ggagtctaac ggacagccag aaaacaacta caagacaact  1260
cccccagtgc tggacagcga cgggagcttc ttcctctact ccaagttgac tgtagacaag  1320
tctagatggc agcaaggaaa cgttttctcc tgctcagtaa tgcatgaggc tctgcacaat  1380
cactataccc agaaatcact gtcccttagc ccagggtgac tcgag                 1425

SEQ ID NO: 160         moltype = DNA  length = 1425
FEATURE                Location/Qualifiers
source                 1..1425
                       mol_type = other DNA
                       note = Full-length heavy chain polynucleotide sequences;
                        huCD37-56 antibody
                       organism = synthetic construct
SEQUENCE: 160
aagcttgcca ccatggggtg gagctgcatt atcctgttcc tcgtcgccac cgcaaccggc  60
gtccactccc aggtgcagct gcaagaaagc gggccaggat tggtaaaacc ttcccagtct  120
ctgagtctta cttgtaccgt atctggatac agtatcacat ctggcttcgc ctggcattgg  180
attcgccagt ttcccggcaa ggggcttgag tggatggggt atattcatta ttctggaggt  240
accaactaca acccttccct gaagagtcga gtctcaatta ccagggacac ttccaagaac  300
caattctttt tgcagcttaa ttcagtgacc gctgccgaca ccgctactta ctactgcgcc  360
cggggctact atgggtttgg tgcctggttc gcctactggg gccaggggac cctggtgccc  420
gtgtctgctg cctccacaaa gggcccatca gttttcccct tggctccaag ttctaaatcc  480
acaagcggtg gaacagctgc actgggatgc ctcgttaaag attatttccc tgagcctgtg  540
acagtgagct ggaatagcgg agcattgact tcaggtgtgc acacttttcc cgctgtgttg  600
cagtcctccg gtctgtactc actgtccagt gtcgtaaccg tcccttctag cagcttggga  660
acccagacct acatctgtaa cgtcaaccat aaaccatcca acacaaaggt ggataagaag  720
gttgaaccaa agagctgtga taagacacat acatgccctc cttgtcctgc accagagctc  780
ctcggaggtc catctgtgtt cctgtttccc cccaaaccca aggacactct tatgatctct  840
cgtactccag aggtcacctg tgttgttgtc gacgtgagcc atgaagatcc cgaggttaaa  900
```

-continued

```
ttcaactggt acgtggatgg agtcgaggtt cacaatgcca agaccaagcc cagggaggag  960
caatataatt ctacatatcg ggtagtgagc gttctgaccg tgctccacca agattggctc  1020
aatggaaaag agtacaagtg caaggtgtcc aacaaggctc ttcccgctcc cattgagaaa  1080
actatctcca aagccaaggg gcagccacgg gaaccccagg tgtatacatt gcccccatct  1140
agagacgagc tgaccaagaa ccaggtgagt ctcacttgtc tggtcaaggg gttttaccct  1200
tctgacattg ctgtagagtg ggagtctaac ggacagccag aaaacaacta caagacaact  1260
cccccagtgc tggacagcga cgggagcttc ttcctctact ccaagttgac tgtagacaag  1320
tctagatggc agcaaggaaa cgttttctcc tgctcagtaa tgcatgaggc tctgcacaat  1380
cactataccc agaaatcact gtcccttagc ccagggtgac tcgag                  1425

SEQ ID NO: 161          moltype = DNA  length = 1425
FEATURE                 Location/Qualifiers
source                  1..1425
                        mol_type = other DNA
                        note = Full-length heavy chain polynucleotide sequences;
                         huCD37-57 antibody
                        organism = synthetic construct
SEQUENCE: 161
aagcttgcca ccatgggctg gagctgcatc attctgtttc tggtggccac agcaactggc  60
gttcacagtc aagtccaact gcaggagagc ggccccggac tcctgaaacc atctcagtca  120
ctcagtctga catgtactgt gagcggctac agcattacct caggcttcgc ttggcattgg  180
atcaggcagt tccccggaaa aggtctggag tggatggggt acattctgta cagcggcagt  240
acagtgtatt caccctcctt gaaatctagg atatcaatca cacgtgatac aagcaaaaat  300
cagttcttcc tccagctgaa ctccgtcacc gccgcagaca cagcaaccta ttattgtgct  360
cgcggatact acggatatgg cgcatggttc gcctattggg gccaggggac actcgtgacc  420
gtttccgccg cctccacaaa gggcccatca gttttcccct tggctccaag ttctaaatcc  480
acaagcggtg gaacagctgc actgggatgc ctcgttaaag attatttccc tgagcctgtg  540
acagtgagct ggaatagcgg agcattgact tcaggtgtgc acacttttcc cgctgtgttg  600
cagtcctccg gtctgtactc actgtccagt gtcgtaaccg tcccttctag cagcttggga  660
acccagacct acatctgtaa cgtcaaccat aaaccatcca acacaaaggt ggataagaag  720
gttgaaccaa agagctgtga taagacacat acatgccctc cttgtcctgc accagagctc  780
ctcggaggtc catctgtgtt cctgtttccc cccaaaccca aggacactct tatgatctct  840
cgtactccag aggtcacctg tgttgttgtc gacgtgagcc atgaagatcc cgaggttaaa  900
ttcaactggt acgtggatgg agtcgaggtt cacaatgcca agaccaagcc cagggaggag  960
caatataatt ctacatatcg ggtagtgagc gttctgaccg tgctccacca agattggctc  1020
aatggaaaag agtacaagtg caaggtgtcc aacaaggctc ttcccgctcc cattgagaaa  1080
actatctcca aagccaaggg gcagccacgg gaaccccagg tgtatacatt gcccccatct  1140
agagacgagc tgaccaagaa ccaggtgagt ctcacttgtc tggtcaaggg gttttaccct  1200
tctgacattg ctgtagagtg ggagtctaac ggacagccag aaaacaacta caagacaact  1260
cccccagtgc tggacagcga cgggagcttc ttcctctact ccaagttgac tgtagacaag  1320
tctagatggc agcaaggaaa cgttttctcc tgctcagtaa tgcatgaggc tctgcacaat  1380
cactataccc agaaatcact gtcccttagc ccagggtgac tcgag                  1425

SEQ ID NO: 162          moltype = DNA  length = 717
FEATURE                 Location/Qualifiers
source                  1..717
                        mol_type = other DNA
                        note = Full-length light chain polynucleotide sequences;
                         chCD37-3 antibody
                        organism = synthetic construct
SEQUENCE: 162
gaattcgcca ccatgagtgt gcccactcag gtcctggggt tgctgctgct gtggcttaca  60
gatgccagat gtgacatcca gatgactcag tctccagcct ccctttctgt atctgtggga  120
gaaactgtca ccatcacatg tcgagcaagt gagaatattc gcagtaattt agcatggtat  180
cagcagaaac agggaaaatc tcctcagctc ctggtcaatg ttgcaacaaa cttagcagat  240
ggtgtgccat caaggttcag tggcagtgga tcaggcacac agtattccct caagatcaac  300
agcctgcagt ctgaagattt tgggacttat tactgtcaac attattgggg tactacgtgg  360
acgttcggtg gaggcaccaa gctggaaatc aaacgtacgg tggctgcacc atctgtcttc  420
atcttcccgc catctgatga gcagttgaaa tctggaactg cctctgttgt gtgcctgctg  480
aataacttct atcccagaga ggccaaagta cagtggaagg tggataacgc cctccaatcg  540
ggtaactccc aggagagtgt cacagagcag gacagcaagg acagcaccta cagcctcagc  600
agcaccctga cgctgagcaa agcagactac gagaaacaca aagtctacgc ctgcgaagtc  660
acccatcagg gcctgagctc gcccgtcaca aagagcttca acaggggaga gtgttag     717

SEQ ID NO: 163          moltype = DNA  length = 714
FEATURE                 Location/Qualifiers
source                  1..714
                        mol_type = other DNA
                        note = Full-length light chain polynucleotide sequences;
                         huCD37-3v1.0 and huCD37-3v1.1 antibody
                        organism = synthetic construct
SEQUENCE: 163
gaattcgcca ccatgggttg gtcctgcatc atcttgtttc tcgtggccac agccaccggt  60
gttcactctg atatacaaat gactcaaagc ccttccagtt tgagcgtaag tgtgggtgaa  120
cgcgtaacaa tcacctgtag agctagtgaa aacatccgca gtaatctcgc atggtaccaa  180
caaaagccag gtaagtcacc taagctcctc gtgaatgttg ctaccaacct cgctgatggt  240
gtgccttcac gattctctgg ttcaggttcc ggtaccgatt attcacttaa gatcaactca  300
ctccaaccag aagatttcgg tacatattac tgtcaacact actggggtac gacctggaca  360
ttcggtcaag gtactaagct ggaaatcaag cgtacggtgg ctgcaccatc tgtcttcatc  420
```

-continued

```
ttcccgccat ctgatgagca gttgaaatct ggaactgcct ctgttgtgtg cctgctgaat  480
aacttctatc ccagagaggc caaagtacag tggaaggtgg ataacgccct ccaatcgggt  540
aactcccagg agagtgtcac agagcaggac agcaaggaca gcacctacag cctcagcagc  600
accctgacgc tgagcaaagc agactacgag aaacacaaag tctacgcctg cgaagtcacc  660
catcagggcc tgagctcgcc cgtcacaaag agcttcaaca ggggagagtg ttag        714

SEQ ID NO: 164         moltype = DNA  length = 726
FEATURE                Location/Qualifiers
source                 1..726
                       mol_type = other DNA
                       note = Full-length light chain polynucleotide sequences;
                        chCD37-12 antibody
                       organism = synthetic construct
SEQUENCE: 164
gaattcgcca ccatgggttg gtcctgtata atcctgttct tggtggccac cgctactggc  60
gttcatagtg atattgtact cactcagtca ccagccagtc tggcagtgtc cctgggccag  120
cgtgccacca tctcctgccg ggcctcacag tccgtgagca ctagctctta ttcctatctc  180
tactggtttc aacagaagcc aggacagccc cctaagctgc tgatcaagta cgcctccaac  240
ctcgccagcg gcgttcccgc tagattctct ggttccggta gcggaactga tttcactttg  300
aacatccacc ccgttgagga agaggatacc gccacttact attgtcaaca ctcttgggag  360
attccttaca cctttggagg aggaacaaag ctcgaaatta agcgtacggt ggctgcacca  420
tctgtcttca tcttcccgcc atctgatgag cagttgaaat ctggaactgc ctctgttgtg  480
tgcctgctga ataacttcta tcccagagag gccaaagtac agtggaaggt ggataacgcc  540
ctccaatcgg gtaactccca ggagagtgtc acagagcagg acagcaagga cagcacctac  600
agcctcagca gcaccctgac gctgagcaaa gcagactacg agaaacacaa agtctacgcc  660
tgcgaagtca cccatcaggg cctgagctcg cccgtcacaa agagcttcaa caggggagag  720
tgttag                                                             726

SEQ ID NO: 165         moltype = DNA  length = 711
FEATURE                Location/Qualifiers
source                 1..711
                       mol_type = other DNA
                       note = Full-length light chain polynucleotide sequences;
                        chCD37-38 antibody
                       organism = synthetic construct
SEQUENCE: 165
gaattcgcca ccatgggctg gtcctgtatc atcctgtttc tcgtggccac agctacaggt  60
gttcattctc agattgtgct gacccaatca ccagctatta tgtccgctag ccccggcgag  120
aaagtgacaa tgacatgtag cgctagctct tctgtgactt acatgcattg gtatcaacag  180
aagtcaggta ccagtcccaa gcgttggatc tacgacacat ccaaactggc ctccggagtc  240
cctgccaggt tcagcggagg tgggtccggc accagttatt cactgaccat atcctctatg  300
gaagctgaag atgctgctac ttattattgt caacaatgga tttctaaccc ccccaccttt  360
ggtggcggaa caaagctgga gatcaagcgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgtta g           711

SEQ ID NO: 166         moltype = DNA  length = 711
FEATURE                Location/Qualifiers
source                 1..711
                       mol_type = other DNA
                       note = Full-length light chain polynucleotide sequences;
                        huCD37-38 antibody
                       organism = synthetic construct
SEQUENCE: 166
gaattcgcca ccatgggatg gtcctgcatt attctgttct tggtcgccac tgctactggc  60
gttcactctg acattgtgct cacacagtct ccagcctcaa tgtctgcttc ccccggtgag  120
cgggtgacca tgacatgctc tgccagttcc tccgtgacat atatgcattg gtatcagcaa  180
aaacccggta cctctccaaa aagatggatc tacgacactt caaagcttgc atcaggcgtt  240
cctgccagat tttccgggtc tgggtctggc acttcataca gtctgaccat tagttccatg  300
gaagctgaag atgcagccac ctattactgt cagcagtgga tttcaaatcc tcctaccttc  360
ggcggcggaa ccaaactgga gataaagcgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgtta g           711

SEQ ID NO: 167         moltype = DNA  length = 711
FEATURE                Location/Qualifiers
source                 1..711
                       mol_type = other DNA
                       note = Full-length light chain polynucleotide sequences;
                        huCD37-50 antibody
                       organism = synthetic construct
SEQUENCE: 167
gaattcgcca ccatgggttg gtcatgcatt attctgttcc tggttgctac cgcaacagga  60
```

-continued

```
gtacatagtg agatagtcct cacccaaagt cctgctacta tgtctgccag cccaggagag  120
cgtgtgacca tgacttgctc tgcaacctca agtgtgacat acatgcattg gtatcagcaa  180
aagcctggcc aatcccctaa aaggtggatc tacgatactt ctaatctgcc atacggtgtg  240
cccgcaaggt tctccgggag tggcagtggc accagttata gtctgaccat cagttcaatg  300
gaagcagagg atgcagcaac ctattattgt cagcagtggt ccgataatcc ccctactttt  360
ggtcagggta caaagctgga gattaagcgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgtta g           711

SEQ ID NO: 168          moltype = DNA  length = 711
FEATURE                 Location/Qualifiers
source                  1..711
                        mol_type = other DNA
                        note = Full-length light chain polynucleotide sequences;
                         huCD37-51 antibody
                        organism = synthetic construct
SEQUENCE: 168
gaattcgcca ccatgggatg gagctgtatt attctgttcc tggttgctac tgctactggc  60
gtccattccg agatagtcct cacccagagc cccgcaacca tgagtgcctc ccctggggag  120
cgagtgacta tgacttgttc cgccacttct tcagttacct atatgcattg gtatcagcag  180
aaacctggac agtctccaaa gcgttggatt tacgacacct ccaacctggc ttcaggagtt  240
cctgctaggt tcagcggatc tgggtctggc acaagttatt cactcaccat tagttccatg  300
gaggccgaag atgccgctac ttactactgt cagcagtgga gcagcaaccc ccctacattc  360
gggcagggaa ctaagctgga gatcaaacgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgtta g           711

SEQ ID NO: 169          moltype = DNA  length = 711
FEATURE                 Location/Qualifiers
source                  1..711
                        mol_type = other DNA
                        note = Full-length light chain polynucleotide sequences;
                         huCD37-56 antibody
                        organism = synthetic construct
SEQUENCE: 169
gaattcgcca ccatgggctg gtcctgtatc atcctgtttc tggtggcaac cgctactggg  60
gttcactctg atattgtcct gacacagagt ccagccttca tgagtgcttc tcccggagaa  120
aaggtcacaa tgacttgttc agcttcctcc tccgtcacat acatgcattg gtaccagcag  180
aagcctgacc agagtcctaa gaggtggatc tatgatacaa gcaatctggc ttccggtgtc  240
ccctcccgct tttcaggcgg cggaagcgga actgactata gccttaccat ctcctcaatg  300
gaagccgagg acgctgctac atattactgc cagcaatgga tcagcgaccc tcctactttc  360
ggacagggaa caaaattgga aattaagcgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgtta g           711

SEQ ID NO: 170          moltype = DNA  length = 711
FEATURE                 Location/Qualifiers
source                  1..711
                        mol_type = other DNA
                        note = Full-length light chain polynucleotide sequences;
                         huCD37-57 antibody
                        organism = synthetic construct
SEQUENCE: 170
gaattcgcca ccatggggtg gtcctgtatt atcctgttcc tggtcgcaac cgccacaggc  60
gttcactccg agatcgtgtt gactcagagc ccagccacca tgtccgcttc cccggggag  120
agagtgacaa tgacttgttc cgccacaagt tctgtaacct acatgcattg gtaccagcaa  180
aaaccaggac agagtccccg tcgttggatt tatgatacct ctaacctggc ttcaggcgtt  240
cctgcccgct tttctggtag tggatctggg acttcctata gccttaccat aagctctatg  300
gaagccgagg acgccgctac atactactgc cagcagtgga gtgataaccc ccccaccttc  360
gggcagggaa ccaaattgga gatcaaacgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgtta g           711

SEQ ID NO: 171          moltype = DNA  length = 32
FEATURE                 Location/Qualifiers
source                  1..32
                        mol_type = other DNA
```

```
                      note = Degenerate primer EcoMH1
                      organism = synthetic construct
SEQUENCE: 171
cttccggaat tcsargtnma gctgsagsag tc                               32

SEQ ID NO: 172        moltype = DNA  length = 35
FEATURE               Location/Qualifiers
source                1..35
                      mol_type = other DNA
                      note = Degenerate primer EcoMH2
                      organism = synthetic construct
SEQUENCE: 172
cttccggaat tcsargtnma gctgsagsag tcwgg                            35

SEQ ID NO: 173        moltype = DNA  length = 36
FEATURE               Location/Qualifiers
source                1..36
                      mol_type = other DNA
                      note = Degenerate primer BamIgG1
                      organism = synthetic construct
SEQUENCE: 173
ggaggatcca tagacagatg ggggtgtcgt tttggc                           36

SEQ ID NO: 174        moltype = DNA  length = 31
FEATURE               Location/Qualifiers
source                1..31
                      mol_type = other DNA
                      note = Degenerate primer SacIMK
                      organism = synthetic construct
SEQUENCE: 174
ggagctcgay attgtgmtsa cmcarwctmc a                                31

SEQ ID NO: 175        moltype = DNA  length = 46
FEATURE               Location/Qualifiers
source                1..46
                      mol_type = other DNA
                      note = Degenerate primer HindKL
                      organism = synthetic construct
SEQUENCE: 175
tatagagctc aagcttggat ggtgggaaga tggatacagt tggtgc                46

SEQ ID NO: 176        moltype = AA  length = 16
FEATURE               Location/Qualifiers
REGION                10..16
                      note = Portion of the Kabat heavy chain CDR2 not considered
                       a CDR forresurfacing
source                1..16
                      mol_type = protein
                      note = Kabat Defined CD37-3 HC CDR2 for Murine
                      organism = synthetic construct
SEQUENCE: 176
VIWGDGSTNY HSALKS                                                 16

SEQ ID NO: 177        moltype = AA  length = 16
FEATURE               Location/Qualifiers
REGION                10..16
                      note = Portion of the Kabat heavy chain CDR2 not considered
                       a CDR forresurfacing
source                1..16
                      mol_type = protein
                      note = Kabat Defined CD37-3 HC CDR2 for Human
                      organism = synthetic construct
SEQUENCE: 177
VIWGDGSTNY HPSLKS                                                 16

SEQ ID NO: 178        moltype = AA  length = 16
FEATURE               Location/Qualifiers
REGION                10..16
                      note = Portion of the Kabat heavy chain CDR2 not considered
                       a CDR forresurfacing
source                1..16
                      mol_type = protein
                      note = Kabat Defined CD37-50 HC CDR2 for Murine
                      organism = synthetic construct
SEQUENCE: 178
YILYSGSTVY SPSLKS                                                 16

SEQ ID NO: 179        moltype = AA  length = 16
FEATURE               Location/Qualifiers
```

```
REGION                  10..16
                        note = Portion of the Kabat heavy chain CDR2 not considered
                         a CDR forresurfacing
source                  1..16
                        mol_type = protein
                        note = Kabat Defined CD37-50 HC CDR2 for Human
                        organism = synthetic construct
SEQUENCE: 179
YILYSGSTVY SPSLKS                                                  16

SEQ ID NO: 180          moltype = AA  length = 281
FEATURE                 Location/Qualifiers
source                  1..281
                        mol_type = protein
                        note = hCD37-M1
                        organism = synthetic construct
SEQUENCE: 180
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRVRLERRVQ  120
ELVLRTIQSY RTNPDETAAE ESWDYVQFQL RCCGWHYPQD WFQVLILRGN GSEAHRVPCS  180
CYNLSATNDS TILDKVILPQ LSRLGHLARS RHSADICAVP AESHIYREGC AQGLQKWLHN  240
NLISIVGICL GVGLLELGFM TLSIFLCRNL DHVYNRLARY R                      281

SEQ ID NO: 181          moltype = AA  length = 281
FEATURE                 Location/Qualifiers
source                  1..281
                        mol_type = protein
                        note = hCD37-M2
                        organism = synthetic construct
SEQUENCE: 181
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRAQLERSLR  120
DVVEKTIQKY GTNPEETAAE ESWDYAQFQL RCCGWQSPRD WNKAQMLKAN ESEEPRVPCS  180
CYNLSATNDS TILDKVILPQ LSRLGHLARS RHSADICAVP AESHIYREGC AQGLQKWLHN  240
NLISIVGICL GVGLLELGFM TLSIFLCRNL DHVYNRLARY R                      281

SEQ ID NO: 182          moltype = AA  length = 281
FEATURE                 Location/Qualifiers
source                  1..281
                        mol_type = protein
                        note = hCD37-M3
                        organism = synthetic construct
SEQUENCE: 182
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRAQLERSLR  120
DVVEKTIQKY GTNPEETAAE ESWDYVQFQL RCCGWHYPQD WFQVLILRGN GSEAHRVPCS  180
CYNSTATNDS TVFDKLFFSQ LSRLGHLARS RHSADICAVP AESHIYREGC AQGLQKWLHN  240
NLISIVGICL GVGLLELGFM TLSIFLCRNL DHVYNRLARY R                      281

SEQ ID NO: 183          moltype = AA  length = 281
FEATURE                 Location/Qualifiers
source                  1..281
                        mol_type = protein
                        note = hCD37-M45
                        organism = synthetic construct
SEQUENCE: 183
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRAQLERSLR  120
DVVEKTIQKY GTNPEETAAE ESWDYVQFQL RCCGWHYPQD WFQVLILRGN GSEAHRVPCS  180
CYNLSATNDS TILDKVILPQ LSRLGPRAKL RQTADICALP AKAHIYREGC AQSLQKWLHN  240
NLISIVGICL GVGLLELGFM TLSIFLCRNL DHVYNRLARY R                      281

SEQ ID NO: 184          moltype = AA  length = 128
FEATURE                 Location/Qualifiers
source                  1..128
                        mol_type = protein
                        note = muCD37-R176
                        organism = synthetic construct
SEQUENCE: 184
ISTQRVRLER RVQELVLRTI QSYRTNPDET AAEESWDYAQ FQLRCCGWQS PRDWNKAQML  60
KANESEEPRV PCSCYNSTAT NDSTVFDKLF FSQLSRLGPR AKLRQTADIC ALPAKAHIYR  120
EGCAQSLQ                                                           128

SEQ ID NO: 185          moltype = AA  length = 280
FEATURE                 Location/Qualifiers
source                  1..280
                        mol_type = protein
                        note = hCD37mECD-H1
                        organism = synthetic construct
```

-continued

```
SEQUENCE: 185
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRAQLERSLR  120
DVVEKTIQKY GTNPEETAAE ESWDYAQFQL RCCGWQSPRD WNKAQMLKAN ESEEPRVPCS  180
CYNSTATNDS TVFDKLFFSQ LSRLGPRAKL RQTADICALP AKAHIYREGC AQSLQKWLHN  240
NLISIVGICL GVGLLELGFM TLSIFLCRNL DHVYNRLARY                       280

SEQ ID NO: 186         moltype = AA  length = 281
FEATURE                Location/Qualifiers
source                 1..281
                       mol_type = protein
                       note = hCD37mECD-H2
                       organism = synthetic construct
SEQUENCE: 186
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRVRLERRVQ  120
ELVLRTIQSY RTNPDETAAE ESWDYVQFQL RCCGWHYPQD WFQVLILRGN GSEAHRVPCS  180
CYNSTATNDS TVFDKLFFSQ LSRLGPRAKL RQTADICALP AKAHIYREGC AQSLQKWLHN  240
NLISIVGICL GVGLLELGFM TLSIFLCRNL DHVYNRLARY R                     281

SEQ ID NO: 187         moltype = AA  length = 281
FEATURE                Location/Qualifiers
source                 1..281
                       mol_type = protein
                       note = hCD37mECD-H3
                       organism = synthetic construct
SEQUENCE: 187
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRVRLERRVQ  120
ELVLRTIQSY RTNPDETAAE ESWDYAQFQL RCCGWQSPRD WNKAQMLKAN ESEEPRVPCS  180
CYNLSATNDS TILDKVILPQ LSRLGPRAKL RQTADICALP AKAHIYREGC AQSLQKWLHN  240
NLISIVGICL GVGLLELGFM TLSIFLCRNL DHVYNRLARY R                     281

SEQ ID NO: 188         moltype = AA  length = 281
FEATURE                Location/Qualifiers
source                 1..281
                       mol_type = protein
                       note = hCD37mECD-H4
                       organism = synthetic construct
SEQUENCE: 188
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRVRLERRVQ  120
ELVLRTIQSY RTNPDETAAE ESWDYAQFQL RCCGWQSPRD WNKAQMLKAN ESEEPRVPCS  180
CYNSTATNDS TVFDKLFFSQ LSRLGHLARS RHSADICALP AKAHIYREGC AQSLQKWLHN  240
NLISIVGICL GVGLLELGFM TLSIFLCRNL DHVYNRLARY R                     281

SEQ ID NO: 189         moltype = AA  length = 281
FEATURE                Location/Qualifiers
source                 1..281
                       mol_type = protein
                       note = hCD37mECD-H5
                       organism = synthetic construct
SEQUENCE: 189
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRVRLERRVQ  120
ELVLRTIQSY RTNPDETAAE ESWDYAQFQL RCCGWQSPRD WNKAQMLKAN ESEEPRVPCS  180
CYNSTATNDS TVFDKLFFSQ LSRLGPRAKL RQTADICAVP AESHIYREGC AQGLQKWLHN  240
NLISIVGICL GVGLLELGFM TLSIFLCRNL DHVYNRLARY R                     281

SEQ ID NO: 190         moltype = AA  length = 281
FEATURE                Location/Qualifiers
source                 1..281
                       mol_type = protein
                       note = hCD37mECD-H45
                       organism = synthetic construct
SEQUENCE: 190
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRVRLERRVQ  120
ELVLRTIQSY RTNPDETAAE ESWDYAQFQL RCCGWQSPRD WNKAQMLKAN ESEEPRVPCS  180
CYNSTATNDS TVFDKLFFSQ LSRLGHLARS RHSADICAVP AESHIYREGC AQGLQKWLHN  240
NLISIVGICL GVGLLELGFM TLSIFLCRNL DHVYNRLARY R                     281

SEQ ID NO: 191         moltype = AA  length = 281
FEATURE                Location/Qualifiers
source                 1..281
                       mol_type = protein
                       note = hCD37-Mac12
                       organism = synthetic construct
SEQUENCE: 191
```

-continued

```
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRAQLERSLQ  120
DIVEKTIQRY HTNPEETAAE ESWDYVQFQL RCCGWHSPQD WFQVLTLRGN GSEAHRVPCS  180
CYNLSATNDS TILDKVILPQ LSRLGHLARS RHSADICAVP AESHIYREGC AQGLQKWLHN  240
NLISIVGICL GVGLLELGFM TLSIFLCRNL DHVYNRLARY R                     281

SEQ ID NO: 192         moltype = AA  length = 281
FEATURE                Location/Qualifiers
source                 1..281
                       mol_type = protein
                       note = hCD37-Mac4
                       organism = synthetic construct
SEQUENCE: 192
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRAQLERSLR  120
DVVEKTIQKY GTNPEETAAE ESWDYVQFQL RCCGWHYPQD WFQVLILRGN GSEAHRVPCS  180
CYNLSATNDS TILDKVILPQ LSRLGQLARS RHSTDICAVP AESHIYREGC AQGLQKWLHN  240
NLISIVGICL GVGLLELGFM TLSIFLCRNL DHVYNRLARY R                     281

SEQ ID NO: 193         moltype = AA  length = 281
FEATURE                Location/Qualifiers
source                 1..281
                       mol_type = protein
                       note = hCD37-Mac5
                       organism = synthetic construct
SEQUENCE: 193
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRAQLERSLR  120
DVVEKTIQKY GTNPEETAAE ESWDYVQFQL RCCGWHYPQD WFQVLILRGN GSEAHRVPCS  180
CYNLSATNDS TILDKVILPQ LSRLGHLARS RHSADICAVP ANSHIYREGC ARSLQKWLHN  240
NLISIVGICL GVGLLELGFM TLSIFLCRNL DHVYNRLARY R                     281

SEQ ID NO: 194         moltype = AA  length = 280
FEATURE                Location/Qualifiers
source                 1..280
                       mol_type = protein
                       note = hCD37-Mac45
                       organism = synthetic construct
SEQUENCE: 194
MSAQESCLSL IKYFLFVFNL FFFVLGSLIF CFGIWILIDK TSFVSFVGLA FVPLQIWSKV  60
LAISGIFTMG IALLGCVGAL KELRCLLGLY FGMLLLLFAT QITLGILIST QRAQLERSLR  120
DVVEKTIQKY GTNPEETAAE ESWDYVQFQL RCCGWHYPQD WFQVLILRGN GSEAHRVPCS  180
CYNLSATNDS TILDKVILPQ LSRLGQLARS RHSTDICAVP ANSHIYREGC ARSLQKWLHN  240
NLISIVGICL GVGLLELGFM TLSIFLCRNL DHVYNRLARY                       280

SEQ ID NO: 195         moltype = DNA  length = 446
FEATURE                Location/Qualifiers
source                 1..446
                       mol_type = other DNA
                       note = Variable heavy chain polynucleotide sequences;
                        huCD37-50 antibody
                       organism = synthetic construct
SEQUENCE: 195
aagcttgcca ccatggggtg gtcctgcata atcctttttcc tggttgctac tgctaccgga  60
gtccattcac aggtgcagct gcaggagtcc ggccccggcc tgctcaagcc ttctcagagt  120
ctgagtctga cttgtactgt ttctggctac agcataacca gcggtttcgc ttggcactgg  180
atcagacagc atcccggcaa caaactggag tggatgggat acatactgta ctcaggctca  240
actgtctatt ccccctccct gaaatcccgg atcagtatta cccgtgacac ttctaagaac  300
cattttttc tgcagctgaa cagcgttacc gcagctgaca ctgcaaccta ctactgtgcc  360
cggggatatt atggatacgg agcttggttc gcttactggg gccaaggcac cctcgtaact  420
gtgagtgctg cttccaccaa gggccc                                     446

SEQ ID NO: 196         moltype = DNA  length = 446
FEATURE                Location/Qualifiers
source                 1..446
                       mol_type = other DNA
                       note = Variable heavy chain polynucleotide sequences;
                        huCD37-51 antibody
                       organism = synthetic construct
SEQUENCE: 196
aagcttgcca ccatgggttg gtcttgcatc atcctgttcc tggtggccac tgccactggc  60
gtgcattcag aagttcagtt ggtggagtcc ggcccagaag tgctgaaacc cggcgaatca  120
ctgtccctga cttgtaccgt gtcaggttat agcatcagca gcggctttgc ttggcactgg  180
attcggcagt ttccaggcaa gggactggaa tggatgggct acatccatta cagtggctca  240
accaattaca gccctagcct gcagggccga atctctatta ccagggatag ttctattaac  300
cagtttttcc tgcagcttaa ttccgtgact gcctctgaca cagcaactta ctattgcgcc  360
cgtggctact acgggttcgg agcctggttt gtatactggg gtcagggcac cctggtcact  420
gtctcagccg cctctaccaa gggccc                                     446
```